(12) United States Patent
Funasaka et al.

(10) Patent No.: US 8,933,099 B2
(45) Date of Patent: Jan. 13, 2015

(54) MONOCYCLIC PYRIDINE DERIVATIVE

(71) Applicant: Eisai R&D Management Co., Ltd., Tokyo (JP)

(72) Inventors: Setsuo Funasaka, Tsukuba (JP); Toshimi Okada, Tsukuba (JP); Keigo Tanaka, Tsukuba (JP); Satoshi Nagao, Tsukuba (JP); Isao Ohashi, Tsukuba (JP); Yoshinobu Yamane, Tsukuba (JP); Yusuke Nakatani, Tsukuba (JP); Yuki Karoji, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/183,864

(22) Filed: Feb. 19, 2014

(65) Prior Publication Data

US 2014/0235614 A1 Aug. 21, 2014

Related U.S. Application Data

(60) Provisional application No. 61/766,922, filed on Feb. 20, 2013.

(51) Int. Cl.
*A61K 31/445* (2006.01)
*C07D 401/14* (2006.01)
*C07D 409/14* (2006.01)
*C07D 401/12* (2006.01)

(52) U.S. Cl.
CPC ............ *C07D 409/14* (2013.01); *C07D 401/12* (2013.01); *C07D 401/14* (2013.01)
USPC ................. 514/318; 514/210.21; 514/253.09; 514/339; 546/194; 546/278.1

(58) Field of Classification Search
CPC ............................ C07D 401/12; C07D 401/14
USPC ........ 514/210.21, 253.09, 318, 339; 546/194, 546/278.1
See application file for complete search history.

(56) References Cited

U.S. PATENT DOCUMENTS

| | | | |
|---|---|---|---|
| 6,831,175 B2 * | 12/2004 | Li et al. .......................... | 546/187 |
| 8,131,527 B1 | 3/2012 | Saxty et al. ..................... | 703/11 |
| 8,614,216 B2 * | 12/2013 | Okhamafe et al. ....... | 514/253.07 |
| 2004/0053908 A1 | 3/2004 | Funahashi et al. | |
| 2004/0122029 A1 | 6/2004 | Liu et al. .................. | 514/264.11 |
| 2004/0204427 A1 | 10/2004 | Chen et al. | |
| 2005/0187236 A1 | 8/2005 | Tsuruoka et al. | |
| 2005/0256154 A1 | 11/2005 | Luk et al. ....................... | 514/301 |
| 2008/0108648 A1 | 5/2008 | Alcouffe et al. | |
| 2011/0060215 A1 | 3/2011 | Tupin, Jr. et al. ............. | 600/425 |
| 2012/0270918 A1 | 10/2012 | Abecassis et al. | |
| 2013/0338134 A1 | 12/2013 | Wu et al. .................. | 514/210.18 |
| 2014/0142084 A1 | 5/2014 | Kameda et al. | |

FOREIGN PATENT DOCUMENTS

| | | |
|---|---|---|
| EP | 2657233 | 8/2014 |
| JP | 2006-522756 | 10/2006 |
| JP | 2008-533111 | 8/2008 |
| WO | WO 02/32872 | 4/2002 |
| WO | WO 2004/020434 | 3/2004 |
| WO | WO 2006/000420 | 1/2006 |
| WO | WO 2006/097625 | 9/2006 |
| WO | WO 2007/071752 | 6/2007 |
| WO | WO 2008/008747 | 1/2008 |
| WO | WO 2008/012690 | 1/2008 |
| WO | WO 2008/075068 | 6/2008 |
| WO | WO 2008/078091 | 7/2008 |

(Continued)

OTHER PUBLICATIONS

Li et al. "Preparation of heteroaryls . . . " CA139:323437 (2003).*

(Continued)

*Primary Examiner* — Celia Chang
(74) *Attorney, Agent, or Firm* — Fish & Richardson P.C.

(57) ABSTRACT

The present invention provides a novel compound having FGFR inhibitory activity or a pharmaceutically acceptable salt thereof, and a pharmaceutical composition containing the same. Specifically, the present invention provides a compound represented by the following formula (I) or a pharmaceutically acceptable salt thereof:

(I)

wherein n represents 0 to 2; A represents an arylene group or a heteroarylene group; G represents a single bond, an oxygen atom or —$CH_2$—; E represents a nitrogen-containing non-aromatic heterocycle; $R^1$ represents an alkoxy group or the like; $R^2$ represents a hydrogen atom or the like; and $R^3$ represents a hydrogen atom, an alkyl group, an alkoxy group or the like, with the proviso that when E represents an azetidine ring and $R^2$ or $R^3$ is present on a nitrogen atom on the azetidine ring, the $R^2$ or $R^3$ does not represent a hydrogen atom.

25 Claims, No Drawings

(56) References Cited

FOREIGN PATENT DOCUMENTS

| WO | WO 2008/078100 | 7/2008 |
|---|---|---|
| WO | WO 2009/001070 | 12/2008 |
| WO | WO 2009/019518 | 2/2009 |
| WO | WO 2009/047506 | 4/2009 |
| WO | WO 2009/047522 | 4/2009 |
| WO | WO 2009/056886 | 5/2009 |
| WO | WO2009076602 * | 6/2009 |
| WO | WO 2009/141386 | 11/2009 |
| WO | WO 2009/150240 | 12/2009 |
| WO | WO 2009/153592 | 12/2009 |
| WO | WO 2010/078421 | 7/2010 |
| WO | WO 2010/078427 | 7/2010 |
| WO | WO 2010/078430 | 7/2010 |
| WO | WO 2010/119284 | 10/2010 |
| WO | WO 2010/119285 | 10/2010 |
| WO | WO 2011/001122 | 1/2011 |
| WO | WO 2011/016528 | 2/2011 |
| WO | WO 2011/051425 | 5/2011 |
| WO | WO 2011/001413 | 6/2011 |
| WO | WO 2011/071821 | 6/2011 |
| WO | WO 2011/135376 | 11/2011 |
| WO | WO 2012/004732 | 1/2012 |
| WO | WO 2012/073017 | 6/2012 |
| WO | WO 2012/088266 | 6/2012 |
| WO | WO 2013/010380 | 1/2013 |
| WO | WO 2013/061074 | 5/2013 |
| WO | WO 2013/061077 | 5/2013 |
| WO | WO 2013/061080 | 5/2013 |
| WO | WO 2013/061081 | 5/2013 |
| WO | WO 2013/087744 | 6/2013 |
| WO | WO 2013/108809 | 7/2013 |
| WO | WO 2013/129369 | 9/2013 |
| WO | WO 2013/179034 | 12/2013 |
| WO | WO 2014/011900 | 1/2014 |
| WO | WO 2014/026125 | 2/2014 |
| WO | WO 2014/044846 | 3/2014 |
| WO | WO 2014/048878 | 3/2014 |
| WO | WO 2014/051022 | 3/2014 |
| WO | WO2014/162039 | 10/2014 |

OTHER PUBLICATIONS

Patani et al. "Bioisosterism:, . . . " Chem. Rev. v.96, 3147-3176 (1996).*

Rubini et al. "Synthesis of isosteric . . . " Tetrhedron v.42921) 6039-45 (1986).*

NCI "Cancer classification" p. 1-3 from internet (2008).*

Applicant's unpublished experimental data, 2014, 1 page.

Bono et al., "Inhibition of Tumor Angiogenesis and Growth by a Small-Molecule Multi-FGF Receptor Blocker with Allosteric Properties," Cancer Cell, 2013, 23:477-488.

Bucci et al., "Circadian Rhythms: channels contribute," Nature Chem Bio., Jun. 2013, 9:349.

Cancer Genome Atlas Research Network, "Comprehensive genomic characterization of squamous cell lung cancers," Nature, 2012, 489(7417):519-525.

Chen et al., "Inhibition of endogenous SPARC enhances pancreatic cancer cell growth: modulation by FGFRI-III isoform expression," Br J Cancer, 2010, 102:188-195.

Daniele et al., "FGF Receptor Inhibitors: Role in Cancer Therapy," Curr Oncol Rep., 2012, 14:111-119.

French et al., "Targeting FGFR4 Inhibits Hepatocellular Carcinoma in Preclinical Mouse Models," PLoS One., 2012, 7:1-12.

Gavine et al., "AZD4547: An Orally Bioavailable, Potent, and Selective Inhitor of the Fibroblast Growth Factor Receptor Tyrosine Kinase Family," Cancer Res., 2012, 72:2045-2056.

Guagnano et al., "Discovery of 3-(2,6-Dichloro-3,5-dimethoxyphenyl)-1 -{6-[4-( 4-ethyl-piperazin-1-yl)-phenylamino ]-pyrimidin-4-yl}-1-methyl-urea (NVP-BGJ398), A Potent and Selective Inhibitor of the Fibroblast Growth Factor Receptor Family of Receptor Tyrosine Kinase," J Med Chem., 2011, 54(20):7066-83.

Guagnano et al., "FGFR Genetic Alterations Predict for Sensitivity to NVP-BGJ398, a Selective Pan-FGFR Inhibitor," Cancer Discovery, 2012, 2:1118-1133.

Harbinski et al., "Rescue Screens with Secreted Proteins Reveal Compensatory Potential of Receptor Tyrosine Kinases in Driving Cancer Growth," Cancer Discovery, 2012, 2:948-958.

Ishiwata et al., "Enhanced Expression of Fibroblast Growth Factor Receptor 2 IIIc Promotes Human Pancreatic Cancer Cell Proliferation," Am J Pathol., 2012, 180(50:1928-1941.

Logie et al., "Activating mutations of the tyrosine kinase receptor FGFR3 are associated with benign skin tumors in mice and humans," Hum Mol Genet., 2005, 14(9):1153-1160.

Mohammadi et al., "Crystal structure of anangiogenesis inhibitor bound to the FGF receptor tyrosine kinase domain," EMBO J., 1998,17(20):5896-5904.

Nicholas and Grose, "Fibroblast growth factor signalling: from development to cancer," Nature Reviews Cancer, 2010, 10:116-129.

Norman et al., "Protein-Ligand Crystal Structures Can Guide the Design of Selective Inhibitors of the FGFR Tyrosine Kinase," J Med Chem., May 21, 2012, 55:5003-5012.

Sasaki et al., "Increased FGFRI copy number in lung squamous cell carcinomas," Mol Med Report., 2012, 5:725-728.

St. Bernard et al., "Fibroblast Growth Factor Receptors as Molecular Targets in Thyroid Carcinoma," Endocrinology, 2005, 146(3):1145-1153.

Tsimafeyeu et al., "Overexpression of fibroblast growth factor receptors FGFR1 and FGFR2 in renal cell carcinoma," Scand J Urol Nephrol., 2011, 45:190-195.

Weiss et al., "Frequent and Focal FGFR1 Amplification Associates with Therapeutically Tractable FGFR1 Dependency in Squamous Cell Lung Cancer," Sci Transl Med., Dec. 15, 2010, 62(2):62ra93, pp. 1-7.

Wesche et al, "Fibroblast growth factors and their receptors in cancer," Biochem J., 2011, 437:199-213.

Zhang et al., "Translating the Therapeutic Potential of AZD4547 in FGFRI-Amplified Non-Small Cell Lung Cancer through the Use of Patient-Derived Tumor Xenograft Models," Clin Cancer Res., 2012, 18:6657-6667.

International Search Report in International Application No. PCT/JP2014/053819, dated Apr. 15, 2014, 9 pages.

Written Amendment in JP App. Ser. No. 2014-526292, dated May 30, 2014, 14 pages (with English translation).

* cited by examiner

MONOCYCLIC PYRIDINE DERIVATIVE

CROSS-REFERENCE TO RELATED APPLICATION

This application claims the benefit of U.S. provisional application No. 61/766,922 filed on Feb. 20, 2013, the disclosure of which is herein incorporated by reference in its entirety.

TECHNICAL FIELD

1. Field of the Invention

The present invention relates to a monocyclic pyridine derivative having an FGFR inhibitory action or a pharmaceutically acceptable salt thereof, and a medical use thereof.

All references cited herein are hereby incorporated by reference in their entireties.

2. Related Background Art

An FGF (fibroblast growth factor) is known as a growth factor for controlling a variety of physiological functions such as cell growth, cell migration, cellular infiltration, cell survival, differential induction, wound healing and angiogenesis.

The FGF controls the various physiological functions via FGF receptors (FGFRs: FGFR1, FGFR2, FGFR3 and FGFR4), that is, receptor tyrosine kinases. Each FGFR includes three types of domains of an extracellular domain, a transmembrane domain and an intracellular tyrosine kinase domain. When an FGF binds to the extracellular domain of an FGFR, a dimer of the receptor is formed. Thereafter, the intracellular tyrosine kinase is activated, and then, an intracellular signal is transmitted mainly via a MAPK (mitogen-activated protein kinase)/ERK (extracellular signal-regulated kinase) pathway or a PI3K (phosphatidylinositol 3-kinase)/Akt pathway.

Meanwhile, it has been reported that various cancers such as breast cancer, bladder cancer, EMS (8p11 myeloproliferative syndrome), stomach cancer, endometrial cancer and prostatic cancer are caused as a result of induction of FGF/FGFR signal abnormality accompanying FGF production enhancement, FGFR gene amplification, FGFR overexpression, FGFR fusion protein production, FGFR mutation and the like (Non Patent Literature 1). Furthermore, the following have been reported as cancers accompanied by the FGF/FGFR signal abnormality: Non-small-cell lung carcinoma, small-cell lung carcinoma, ovarian cancer, sarcoma, colon cancer, melanoma, glioblastoma, astrocytoma, and head and neck cancer (Non Patent Literatures 2 and 3), thyroid cancer (Non Patent Literature 4), pancreatic cancer (Non Patent Literatures 5 and 6), liver cancer (Non Patent Literature 7), skin cancer (Non Patent Literature 8), kidney cancer (Non Patent Literature 9), and lung squamous cell carcinoma (Non Patent Literatures 10, 11, and 12).

Besides, the FGF/FGFR signal is one of main angiogenic signals in endothelial cells along with a VEGF (vascular endothelial growth factor)/KDR (kinase-insert domain-containing receptor) signal, and is reported to be involved in the interaction between cancer stromal cells (fibroblasts) and cancer cells (Non Patent Literature 1).

Accordingly, an FGFR inhibitor targeting an FGF/FGFR signal is expected to work as an antitumor drug, against cancers accompanied by the FGF/FGFR signal abnormality, based on its inhibitory action against the signal abnormality and its inhibitory action against the angiogenic signal. Recently, a selective FGFR inhibitor regarded to be unsusceptible to be affected by a confronting effect of another signal, such as a selective FGFR inhibitor against FGFR1, FGFR2 or FGFR3, which is obviously different in the structure from a compound of the present invention, has been reported. In the development as an antitumor drug for humans, however, the selective FGFR inhibitor falls behind an antitumor drug simultaneously targeting both the FGF/FGFR signal and the VEGF/KDR signal, and has not been put on the market yet (Non Patent Literatures 13 and 14; Patent Literatures 1 and 2). Patent Literature 3 discloses pyrimidine derivatives but does not disclose an inhibitory action against the signal abnormality of the FGF/FGFR signal. Patent Literature 4 discloses pyridine derivatives or pyrimidine derivatives that inhibit angiogenesis induced by the VEGF and the FGF. None of these literatures, however, discloses the compounds of the present invention.

CITATION LIST

Patent Literature

[Patent Literature 1] International Publication No. WO 2008/075068

[Patent Literature 2] International Publication No. WO 2006/000420

[Patent Literature 3] International Publication No. WO 2002/032872

[Patent Literature 4] International Publication No. WO 2004/020434

Non Patent Literature

[Non Patent Literature 1] Nicholas et al., "Fibroblast growth factor signalling: from development to cancer", Nature Reviews Cancer. 2010; 10: 116-129

[Non Patent Literature 2] Jorgen WESCHE et al., Fibroblast growth factors and their receptors in cancer, Biochem J. 2011: 437; 199-213

[Non Patent Literature 3] Gennaro Daniele et al., FGF Receptor Inhibitors: Role in Cancer Therapy, Curr Oncol Rep. 2012; 14:111-119

[Non Patent Literature 4] Rosanne St. Bernard et al., Fibroblast Growth Factor Receptors as Molecular Targets in Thyroid Carcinoma, Endocrinology. 2005; 146: 1145-1153

[Non Patent Literature 5] Toshiyuki Isbiwata et at, Enhanced Expression of Fibroblast Growth Factor Receptor 2 Bic Promotes Human Pancreatic Cancer Cell Proliferation, Am J Pathol. 2012; 180: 1928-1941

[Non Patent Literature 6] G Chen et al., Inhibition of endogenous SPARC enhances pancreatic cancer cell growth: modulation by FGFR1-III isoform expression, Br J Cancer. 2010; 102: 188-195

[Non Patent Literature 7] Dorothy M. French et at, Targeting FGFR4 Inhibits Hepatocellular Carcinoma in Preclinical Mouse Models, PLoS One. 2012; 7: e36713

[Non Patent Literature 8] Annelle Logic et al., Activating mutations of the tyrosine kinase receptor FGFR3 are associated with benign skin tumors in mice and humans, Hum Mol Genet. 2005; 14: 1153-1160

[Non Patent Literature 9] Tsimafeyeu I et al., Overexpression of fibroblast growth factor receptors FGFR1 and FGFR2 in renal cell carcinoma, Scand J Urol Nephrol 2011; 45: 190-195

[Non Patent Literature 10] Jonathan Weiss et at, Frequent and Focal FGFR1 Amplification Associates with Therapeutically Tractable FGFR1 Dependency in Squamous Cell Lung Cancer, Sci Transl Med. 2010; 2: issue 62 62-93

[Non Patent Literature 11] Hidefitmi Sasaki et al., Increased FGFR1 copy number in lung squamous cell carcinomas, Mol Med. Report. 2012; 5: 725-728

[Non Patent Literature 12] The Cancer Genome Atlas Research Network, Comprehensive genomic characterization of squamous cell lung cancers, Nature 2012; 489: 519-525

[Non Patent Literature 13] Paul R Lavine et al, AZD4547: An Orally Bioavailable, Potent, and Selective Inhibitor of the Fibroblast Growth Factor Receptor Tyrosine Kinase Family, Cancer Res. 2012; 72: 2045-2056

[Non Patent Literature 14] Vito Guagnano et at, Discovery of 3-(2,6-Dichloro-3,5-dimethoxy-phenyl)-1-{6-[4-(4-ethyl-piperazin-1-yl)-phenylamino]pyrimidin-4-yl}-1-methyl-urea (NVP-BGJ398), A Potent and Selective Inhibitor of the Fibroblast Growth Factor Receptor Family of Receptor Tyrosine Kinase, J Med. Chem. 2011; 54: 7066-7083

SUMMARY OF THE INVENTION

Under these circumstances, an object of the present invention is to provide a novel compound having an FGFR inhibitory action or a pharmaceutically acceptable salt thereof, and a pharmaceutical composition containing the same.

The present inventors have made earnest studies in consideration of the aforementioned circumstances, and as a result, have succeeded in synthesizing a novel monocycle pyridine derivative represented by the following formula (I) (hereinafter referred to as the compound (I) of the present invention), and have found that such a compound has an FGFR1 inhibitory action, an FGFR2 inhibitory action and an FGFR3 inhibitory action, and thus, have accomplished the present invention. Furthermore, the present inventors have found that the compound (I) of the present invention has an action to selectively inhibit an FGF/FGFR signal against a VEGFXDR signal, particularly, a selective FGFR1, FGFR2 or FGFR3 inhibitory action.

[Chemical Formula 1]

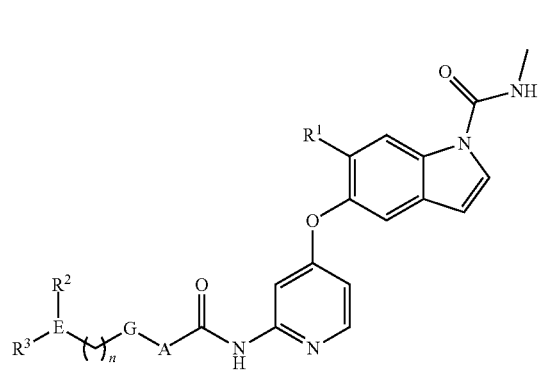

(I)

Specifically, the present invention provides the following [1] to [28].

[1] A compound represented by the following formula (I) or a pharmaceutically acceptable salt thereof:

[Chemical Formula 2]

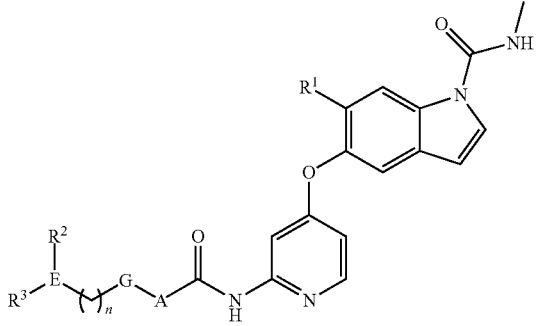

(I)

wherein
n represents 0 to 2;
A represents a $C_{6-10}$ arylene group or a $C_{3-5}$ heteroarylene group;
G represents a single bond, an oxygen atom or —$CH_2$—;
E represents a $C_{3-5}$ nitrogen-containing non-aromatic heterocycle;
$R^1$ represents a $C_{1-6}$ alkoxy group optionally substituted by 1 to 3 halogen atoms, or a $C_{1-6}$ alkoxy $C_{1-6}$ alkoxy group optionally substituted by 1 to 3 halogen atoms;
$R^2$ represents a hydrogen atom, a halogen atom, a hydroxyl group, a $C_{1-6}$ alkyl group optionally substituted by 1 to 3 halogen atoms, a hydroxy $C_{1-6}$ alkyl group optionally substituted by 1 to 3 halogen atoms, or a $C_{3-5}$ nitrogen-containing non-aromatic heterocyclic group; and
$R^3$ represents a hydrogen atom, a $C_{1-6}$ alkyl group optionally substituted by 1 to 3 halogen atoms, or a $C_{1-6}$ alkoxy group optionally substituted by 1 to 3 halogen atoms, with the proviso that when E represents an azetidine ring and $R^2$ or $R^3$ is present on a nitrogen atom on the azetidine ring, the $R^2$ or $R^3$ does not represent a hydrogen atom.

[2] The compound or the pharmaceutically acceptable salt thereof according to [1], wherein A represents a $C_{6-10}$ arylene group.

[3] The compound or the pharmaceutically acceptable salt thereof according to [1] or [2], wherein G represents a single bond or an oxygen atom.

[4] The compound or the pharmaceutically acceptable salt thereof according to [1], wherein
A represents a phenylene group, a thienylene group, a pyrazolylene group or a pyridylene group; and
E represents an azetidine ring, a pyrrolidine ring, a piperidine ring or a piperazine ring.

[5] The compound or the pharmaceutically acceptable salt thereof according to [1], wherein
A represents a phenylene group; and
E represents an azetidine ring or a piperidine ring.

[6] The compound or the pharmaceutically acceptable salt thereof according to [1], wherein
A represents a phenylene group; and
E represents a piperidine ring.

[7] The compound or the pharmaceutically acceptable salt thereof according to any one of [4] to [6], wherein
n represents 0; and
G represents a single bond.

[8] The compound or the pharmaceutically acceptable salt thereof according to any one of [1] to [7], wherein
$R^1$ represents a $C_{1-6}$ alkoxy group or a $C_{1-6}$ alkoxy $C_{1-6}$ alkoxy group;

$R^2$ represents a hydrogen atom, a hydroxyl group, a $C_{1-6}$ alkyl group or a hydroxy $C_{1-6}$ alkyl group; and $R^3$ represents a hydrogen atom.

[9] The compound or the pharmaceutically acceptable salt thereof according to any one of [1] to [8], wherein $R^1$ represents a $C_{1-6}$ alkoxy $C_{1-6}$ alkoxy group.

[10] The compound or the pharmaceutically acceptable salt thereof according to [1], represented by the following formula (II):

[Chemical Formula 3]

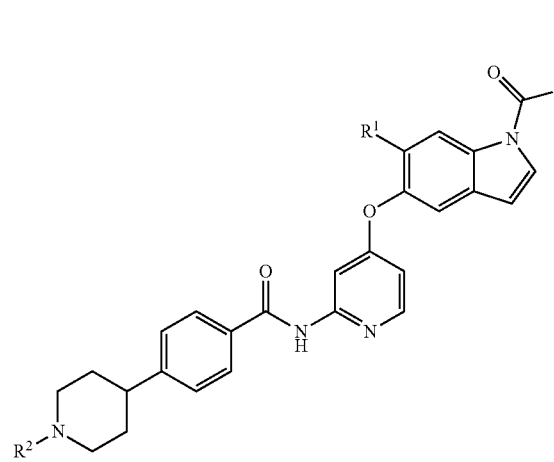

(II)

wherein $R^1$ represents a $C_{1-6}$ alkoxy $C_{1-6}$ alkoxy group; and $R^2$ represents a hydrogen atom, a $C_{1-6}$ alkyl group or a hydroxy $C_{2-6}$ alkyl group.

[11] The compound or the pharmaceutically acceptable salt thereof according to [1], represented by the following formula (III):

[Chemical Formula 4]

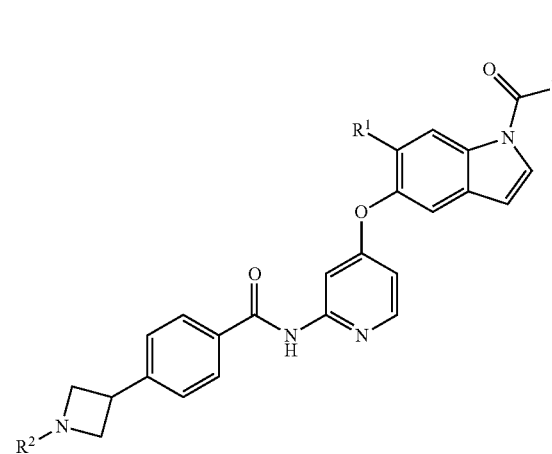

(III)

wherein $R^1$ represents a $C_{1-4}$ alkoxy $C_{1-6}$ alkoxy group; and $R^2$ represents a $C_{1-6}$ alkyl group or a hydroxy $C_{2-6}$ alkyl group.

[12] 5-((2-(4-(1-Ethylpiperidin-4-yl)benzamide)pyridin-4-yl)oxy)-6-methoxy-N-methyl-1H-indole-1-carboxamide represented by the following structural formula, or a pharmaceutically acceptable salt thereof:

[Chemical Formula 5]

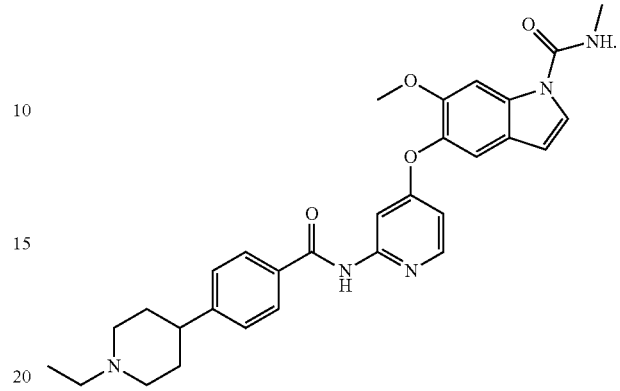

[13] 6-(2-Methoxyethoxy)-N-methyl-5-((2-(4-(1-methylpiperidin-4-yl)benzamide)pyridin-4-yl)oxy)-1H-indole-1-carboxamide represented by the following structural formula, or a pharmaceutically acceptable salt thereof:

[Chemical Formula 6]

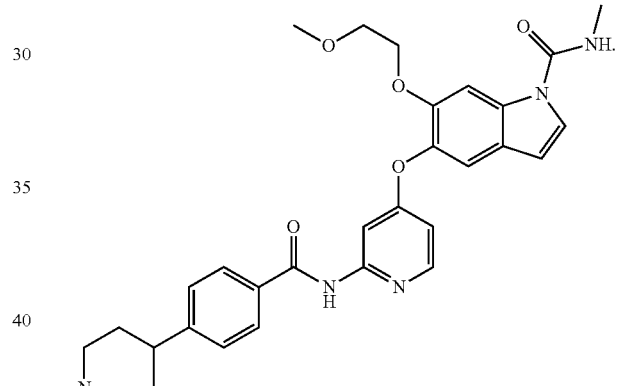

[14] 5-((2-(4-(1-(2-Hydroxyethyl)piperidin-4-yl)benzamide)pyridin-4-yl)oxy)-6-(2-methoxyethoxy)-N-methyl-1H-indole-1-carboxamide represented by the following structural formula, or a pharmaceutically acceptable salt thereof:

[Chemical Formula 7]

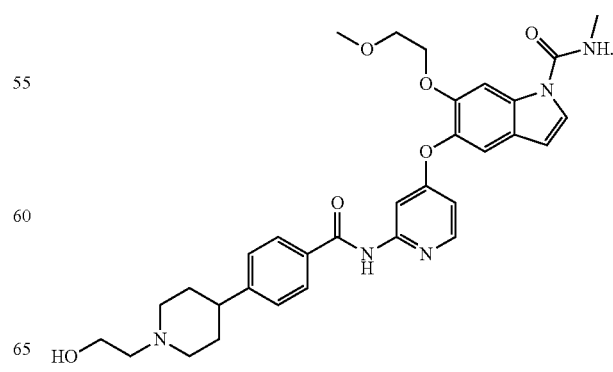

[15] 6-(2-Ethoxyethoxy)-5-((2-(4-(1-(2-hydroxyethyl)piperidin-4-yl)benzamide)pyridin-4-yl)oxy)-N-methyl-1H-indole-1-carboxamide represented by the following structural formula, or a pharmaceutically acceptable salt thereof:

[Chemical Formula 8]

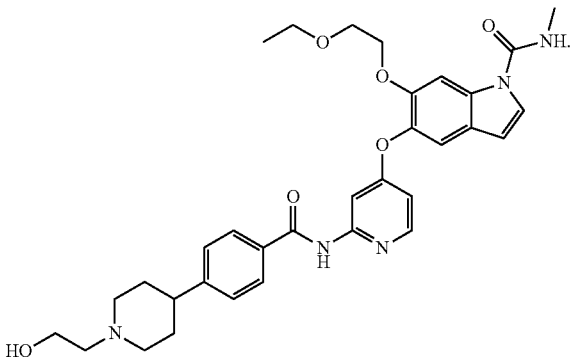

[16] 6-(2-Ethoxyethoxy)-5-((2-(4-(1-ethylazetidin-3-yl)benzamide)pyridin-4-yl)oxy)-N-methyl-1H-indole-1-carboxamide represented by the following structural formula, or a pharmaceutically acceptable salt thereof:

[Chemical Formula 9]

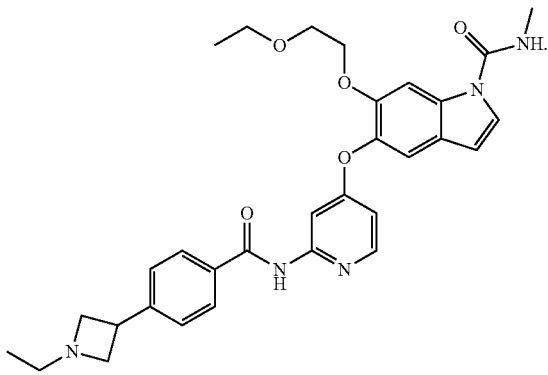

[17] A pharmaceutical composition comprising the compound or the pharmaceutically acceptable salt thereof according to any one of [1] to [16].
[18] A therapeutic agent for stomach cancer or non-small-cell lung carcinoma comprising the compound or the pharmaceutically acceptable salt thereof according to any one of [1] to [16] as an active ingredient,
[19] A method for treating stomach cancer or non-small-cell lung carcinoma comprising administering a pharmacologically effective dose of the compound or the pharmaceutically acceptable salt thereof according to any one of [1] to [16].
[20] A method for treating bladder cancer or endometrial cancer comprising administering a pharmacologically effective dose of the compound or the pharmaceutically acceptable salt thereof according to any one of [1] to [16].
[21] A therapeutic agent for non-small-cell lung carcinoma comprising the compound or the pharmaceutically acceptable salt thereof according to any one of [1] to [16] as an active ingredient.
[22] A therapeutic agent for lung squamous cell carcinoma comprising the compound or the pharmaceutically acceptable salt thereof according to any one of [1] to [16] as an active ingredient.
[23] A therapeutic agent for bladder cancer or endometrial cancer comprising the compound or the pharmaceutically acceptable salt thereof according to any one of [1] to [16] as an active ingredient.
[24] An FGFR inhibitor for treating non-small-cell lung carcinoma comprising the compound or the pharmaceutically acceptable salt thereof according to any one of [1] to [16] as an active ingredient.
[25] The compound or the pharmaceutically acceptable salt thereof according to any one of [1] to [16], for use as a therapeutic agent for stomach cancer or non-small-cell lung carcinoma.
[26] The compound or the pharmaceutically acceptable salt thereof according to any one of [1] to [16], for use as a therapeutic agent for bladder cancer or endometrial cancer.
[27] A use of the compound or the pharmaceutically acceptable salt thereof according to any one of [1] to [16], for manufacturing a therapeutic agent for stomach cancer or non-small-cell lung carcinoma.
[28] A use of the compound or the pharmaceutically acceptable salt thereof according to any one of [1] to [16], for manufacturing a therapeutic agent for bladder cancer or endometrial cancer.

The compound (I) of the present invention or the pharmaceutically acceptable salt thereof has FGFR1, FGFR2 and FGFR3 inhibitory actions as shown in activity data obtained in pharmacological test examples described later. Furthermore, the compound (I) of the present invention or the pharmaceutically acceptable salt thereof has a selective FGFR1, FGFR2 or FGFR3 inhibitory action as opposed to a KDR or HUVEC inhibitory action. Accordingly, the compound (I) of the present invention or a pharmaceutically acceptable salt thereof has a potential use for a therapeutic agent for stomach cancer, non-small-cell lung carcinoma including lung squamous cell carcinoma, bladder cancer or endometrial cancer.

DESCRIPTION OF THE PREFERRED EMBODIMENTS

Now, the present invention is described in details by defining symbols and terms used herein and describing embodiments and the like of the present invention.

Herein, a structural formula of a compound may represent a given isomer for convenience, but the compound of the present invention includes isomers, such as all geometric isomers structurally formed from the compound, optical isomers based on asymmetric carbon, stereoisomers, rotamers and tautomers, and mixtures of these isomers, and hence is not limited to the formula given for convenience but may be any one of the isomers and mixtures. Accordingly, the compound of the present invention may have asymmetric carbon atom(s) in the molecule, and there may be an optically active substance and a racemate, and the present invention is not limited but includes all of these. It is understood, however, that some isomers, racemates and mixtures of isomers may show stronger activity than the others. Furthermore, there may exist crystal polymorphism, which also does not limit the present invention, and the compound of the present invention may be in any of single crystal forms or a mixture of two or more crystal forms, and the compound of the present invention includes an amorphous form, and embraces an anhydride and a solvate such as a hydrate.

The present invention includes an isotope-labeled compound of the compound (I) of the present invention and a pharmaceutically acceptable salt thereof. The isotope-labeled compound is equivalent to the compound represented by formula (I) except that one or more of atom(s) are replaced by atom(s) having an atomic mass or a mass number different from those usually found in nature. Examples of an isotope that can be incorporated into the compound of the present invention include isotopes of hydrogen, carbon, nitrogen, oxygen, phosphorus, fluorine, iodine, bromine and chlorine, such as $^{2}H$, $^{3}H$, $^{11}C$, $^{13}C$, $^{14}C$, $^{18}F$, $^{35}S$, $^{123}I$ and $^{125}I$.

The isotope-labeled compound, such as a compound into which a radioactive isotope of, for example, $^{3}H$ and/or $^{14}C$ is incorporated, is useful for a tissue distribution assay for a medicine and/or a matrix. The isotopes $^{3}H$ and $^{14}C$ are regarded to be useful because these isotopes can be easily prepared and detected. The isotopes $^{11}C$ and $^{18}F$ are regarded to be useful in PET (positron emission tomography), the isotope $^{125}I$ is regarded to be useful in SPECT (single photon emission computed tomography), and can be useful in brain imaging. Replacement by a heavier isotope such as $^{2}H$ causes, because of its higher metabolic stability, some advantages, in a treatment, of, for example, extension of half-life in vivo or reduction of a necessary dose, and therefore, is regarded useful under given circumstances. The isotope-labeled compound can be similarly prepared by using a readily available isotope-labeled reagent instead of a nonisotope-labeled reagent and by performing processes disclosed in schemes and/or examples described below.

The compound (I) of the present invention can be used as a chemical probe for capturing a target protein of a biologically active low molecular weight compound. Specifically, the compound of the present invention can be transformed into an affinity chromatography probe, a photoaffinity probe or the like by introducing a labeling group, a linker or the like into a moiety other than a structural moiety indispensable to activity expression of the compound by a method described in J. Mass Spectrum. Soc. Jpn. Vol. 51, No. 5, 2003, p. 492-498, WO2007/139149 or the like.

Examples of the labeling group, the linker or the like used in such a chemical probe include groups belonging to the following groups (1) to (5).

(1) Protein labeling groups such as photoaffinity labeling groups (such as a benzoyl group, a benzophenone group, an azide group, a carbonyl azide group, a diaziridine group, an enone group, a diazo group and a nitro group), and chemical affinity groups (such as a ketone group in which an alpha carbon atom is substituted by a halogen atom, a carbamoyl group, an ester group, an alkylthio group, a Michael receptor of α,β-unsaturated ketone, ester or the like, and an oxirane group);

(2) cleavable linkers such as —S—S—, —O—Si—O—, a monosaccharide (such as a glucose group or a galactose group) and a disaccharide (such as lactose), and oligopeptide linkers that can be cleaved by an enzyme reaction;

(3) fishing tag groups such as biotin and a 3-(4,4-difluoro-5,7-dimethyl-4H-3a,4a-diaza-4-bora-s-indacene-3-yl)propionyl group;

(4) radioactive labeling groups such as $^{125}I$, $^{32}P$, $^{3}H$ and $^{14}C$; fluorescence labeling groups such as fluorescein, rhodamine, dansyl, umbelliferone, 7-nitrofurazanyl, and a 3-(4,4-difluoro-5,7-dimethyl-4H-3a,4a-diaza-4-bora-s-indacene-3-yl) propionyl group; chemiluminescent groups such as luciferin and luminol; and markers capable of detecting heavy metal ions such as lanthanoid metal ions and radium ions; and (5) groups to be bonded to a solid phase carrier such as glass beads, a glass bed, a microliter plate, agarose beads, an agarose bed, polystyrene beads, a polystyrene bed, nylon beads and a nylon bed.

A probe prepared by introducing, into the compound of the present invention, a labeling group or the like selected from the above-described groups (1) to (5) by the method described in any of the aforementioned literatures or the like can be used as a chemical probe for identifying a marker protein useful for research of a novel potential drug target.

A "halogen atom" used herein means a fluorine atom, a chlorine atom, a bromine atom or an iodine atom.

A "hetero atom" used herein means a nitrogen atom, a sulfur atom or an oxygen atom.

A "$C_{1-6}$ alkyl group" used herein means a linear or branched alkyl group having 1 to 6 carbon atoms that is a monovalent group induced by removing one arbitrary hydrogen atom from an aliphatic hydrocarbon having 1 to 6 carbon atoms, Examples of such a group include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a neopentyl group, a 1-methylbutyl group, a 2-methylbutyl group, a 1,1-dimethylpropyl group, a 1,2-dimethylpropyl group, a n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group and the like. More specifically, it is a methyl group, an ethyl group, a n-propyl group, an isopropyl group, a n-butyl group, an isobutyl group, a sec-butyl group, a tert-butyl group or the like, and is preferably a methyl group, an ethyl group or an isopropyl group.

A "$C_{1-6}$ alkyl group optionally substituted by 1 to 3 halogen atoms" used herein means the above-described $C_{1-6}$ alkyl group in which arbitrary 1 to 3 hydrogen atoms may be substituted by a halogen atom. The position to be substituted by a halogen atom is not especially limited, and specific examples of such a group include a monofluoromethyl group, a difluoromethyl group, a trifluoromethyl group, a 2-fluoroethyl group, a 2,2-difluoroethyl group, a 2,2,2-trifluoroethyl group, a monochloromethyl group, a dichloromethyl group, a trichloromethyl group, a 2-chloroethyl group, a 2,2-dichloroethyl group, a 2,2,2-trichloroethyl group, a 3-fluoropropyl group and the like. As the halogen atom used for the substitution, specifically, for example, a fluorine atom, a chlorine atom or the like is preferably used, and a fluorine atom is more preferably used.

A "hydroxy $C_{1-6}$ alkyl group" used herein means the above-described $C_{1-6}$ alkyl group in which one arbitrary hydrogen atom is substituted by a hydroxyl group. The position to be substituted by a hydroxyl group is not especially limited, and specific examples of such a group include a hydroxymethyl group, a 2-hydroxyethyl group, a 1-hydroxyethyl group, a 3-hydroxypropyl group, a 2-hydroxypropyl group, a 1-hydroxypropyl group, a 2-hydroxy-2,2-dimethylethyl group and the like. It is preferably a 2-hydroxyethyl group, a 2-hydroxypropyl group or a 2-hydroxy-2,2-dimethylethyl group.

A "hydroxy $C_{2-6}$ alkyl group" used herein means a linear or branched alkyl group having 2 to 6 carbon atoms that is a monovalent group induced by removing one arbitrary hydrogen atom from an aliphatic hydrocarbon having 2 to 6 carbon atoms, in which one arbitrary hydrogen atom is substituted by a hydroxyl group. The position to be substituted by a hydroxyl group is not especially limited, and specific examples of such a group include a 2-hydroxyethyl group, a 1-hydroxyethyl group, a 3-hydroxypropyl group, a 2-hydroxypropyl group, a 1-hydroxypropyl group, a 2-hydroxy-2,2-dimethylethyl group and the like. It is preferably a 2-hydroxyethyl group, a 2-hydroxypropyl group or a 2-hydroxy-2,2-dimethylethyl group.

A "hydroxy $C_{1-6}$ alkyl group optionally substituted by 1 to 3 halogen atoms" used herein means the above-described hydroxy $C_{1-6}$ alkyl group in which arbitrary 1 to 3 hydrogen atoms may be substituted by a halogen atom. The position to be substituted by a halogen atom is not especially limited. As the halogen atom to be used for the substitution, specifically, for example, a fluorine atom, a chlorine atom or the like is preferably used, and a fluorine atom is more preferably used.

A "$C_{1-6}$ alkoxy group" used herein means the above defined "$C_{1-6}$ alkyl group" having an oxygen atom bonded to a terminal thereof, and examples of such a group include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a neopentyloxy group, a 1-methylbutoxy group, a 2-methylbutoxy group, a 1,1-dimethylpropoxy group, a 1,2-dimethylpropoxy group, a n-hexyloxy group, an isohexyloxy group, a 1-methylpentyloxy group, a 2-methylpentyloxy group, a 3-methylpentyloxy group, a 1,1-dimethylbutoxy group, a 1,2-dimethylbutoxy group, a 2,2-dimethylbutoxy group, a 1,3-dimethylbutoxy group, a 2,3-dimethylbutoxy group, a 3,3-dimethylbutoxy group, a 1-ethylbutoxy group, a 2-ethylbutoxy group, a 1,1,2-trimethylpropoxy group, a 1,2,2-trimethylpropoxy group, a 1-ethyl-1-methylpropoxy group, a 1-ethyl-2-methylpropoxy group and the like, and more specifically, it is a methoxy group, an ethoxy group, a n-propoxy group, an isopropoxy group, a n-butoxy group, an isobutoxy group, a sec-butoxy group, a n-pentyloxy group, an isopentyloxy group, a n-hexyloxy group, an isohexyloxy group or the like, and is preferably a methoxy group, an ethoxy group or an isopropoxy group.

A "$C_{1-6}$ alkoxy group optionally substituted by 1 to 3 halogen atoms" used herein means the above-described $C_{1-6}$ alkoxy group in which arbitrary 1 to 3 hydrogen atoms are substituted by a halogen atom. The position to be substituted by a halogen atom is not especially limited, and specific examples of such a group include a monofluoromethoxy group, a difluoromethoxy group, a trifluoromethoxy group, a 2-fluoroethoxy group, a 2,2-difluoroethoxy group, a 2,2,2-ixifluoroethoxy group, a monochloromethoxy group, a dichloromethoxy group, a nichloromethoxy group, a 2-chloroethoxy group, a 2,2-dichloroethoxy group, a 2,2,2-tichloroethoxy group, a 3-fluoropropoxy group and the like.

A "$C_{1-6}$ alkoxy $C_{1-6}$ alkoxy group" used herein means the above defined "$C_{1-6}$ alkoxy group" in which one arbitrary hydrogen atom is substituted by the above defined "$C_{1-6}$ alkoxy group", and specific examples of such a group include a methoxymethoxy group, an ethoxymethoxy group, a n-propoxymethoxy group, a 2-methoxyethoxy group, a 2-ethoxyethoxy group, a 3-methoxypropoxy group and the like. Preferably, it is a 2-methoxyethoxy group, a 2-ethoxyethoxy group or a 3-methoxypropoxy group.

A "$C_{1-6}$ alkoxy $C_{1-6}$ alkoxy group optionally substituted by 1 to 3 halogen atoms" used herein means the above-described "$C_{1-6}$ alkoxy $C_{1-6}$ alkoxy group" in which arbitrary 1 to 3 hydrogen atoms may be substituted by a halogen atom. The position to be substituted by a halogen atom is not especially limited, and specific examples of such a group include a monofluoromethoxymethoxy group, a difluoromethoxymethoxy group, a monofluoroethoxymethoxy group, a difluoroethoxymethoxy group, a monofluoromethoxyethoxy group, a trifluoromethoxyethoxy group, a difluoromethoxyethoxy group, a monofluoroethoxyethoxy group, a difluoroethoxyethoxy group and the like.

A "$C_{3-5}$ heteroarylene group" used herein means a bivalent group having 3 to 5 carbon atoms forming a ring that is induced by removing arbitrary 2 hydrogen atoms from a hetero aromatic compound having 1 to 2 hetero atoms as atoms forming the ring, and specific examples of such a group include a furylene group, a thienylene group, a pyrrolylene group, an imidazolylene group, a thiazolylene group, a pyrazolylene group, an oxazolylene group, an isooxazolylene group, an isothiazolylene group, a furazanylene group, a pyridylene group, a pyrazinylene group, a pyridazinylene group, a pyrimidinylene group and the like, and it is preferably a pyridylene group, a pyrazolylene group or a thienylene group.

A "$C_{3-5}$ nitrogen-containing non-aromatic heterocyclic group" used herein means a monovalent non-aromatic cyclic group having 3 to 5 carbon atoms forming a ring and having 1 to 2 nitrogen atoms among atoms forming the ring, and specific examples of such a group include an azetidinyl group, a pynolidinyl group, a pyrazolidinyl group, an imidazolidinyl group, a piperidinyl group, a piperazinyl group, an isooxazolidinyl group, an isothiazolidinyl group, a morpholinyl group, a thiomorpholinyl group and the like.

A "$C_{3-5}$ nitrogen-containing non-aromatic heterocycle" used herein means a non-aromatic ring having 3 to 5 carbon atoms forming the ring and having 1 to 2 nitrogen atoms among atoms forming the ring, and specific examples of such a group include an anticline ring, a pynolidine ring, a pyrazolidine ring, an imidazolidine ring, a piperidine ring, a piperazine ring, an isooxazolidine ring, an isothiazolidine ring, a morpholine ring, a thiomorpholine ring and the like.

A "$C_{6-10}$ arylene group" used herein means a bivalent group induced by removing arbitrary two hydrogen atoms from an aromatic hydrocarbon having 6 to 10 carbon atoms, and specific examples of such a group include a phenylene group, a naphthylene group, an indenylene group, an azulenylene group, a heptalenylene group and the like, and it is preferably a phenylene group.

In formula used herein, n represents 0 to 2. Preferably, n is 0 or 1, and more preferably, n is 0.

In formula used herein, A represents a $C_{6-10}$ arylene group or a $C_{3-5}$ heteroarylene group, preferably a phenylene group, a thienylene group, a pyridylene group or a pyrazolylene group, and more preferably, a phenylene group.

In formula used herein, G represents a single bond, an oxygen atom or preferably a single bond or an oxygen atom, and more preferably a single bond.

In formula used herein, E represents the $C_{3-5}$ nitrogen-containing non-aromatic heterocycle described above, and specifically, for example, an azetidine ring, a pyrrolidine ring, a piperidine ring or a piperazine ring, preferably an azetidine ring or a piperidine ring, and more preferably a piperidine ring.

In formula used herein, $R^1$ represents a $C_{1-4}$ alkoxy group optionally substituted by 1 to 3 halogen atoms, or a $C_{1-6}$ alkoxy $C_{1-4}$ alkoxy group optionally substituted by 1 to 3 halogen atoms. It is preferably a $C_{1-6}$ alkoxy group or a $C_{1-6}$ alkoxy $C_{1-4}$ alkoxy group. Specific examples of $R^1$ include a methoxy group, an ethoxy group, a n-propoxy group, an isopropoxy group, a n-butoxy group, an isobutoxy group, a sec-butoxy group, a n-pentyloxy group, an isopentyloxy group, a n-hexyloxy group, an isohexyloxy group, a monofluoromethoxy group, a difluoromethoxy group, a trifluoromethoxy group, a 2-fluoroethoxy group, a 2,2-difluoroethoxy group, a 3-fluoropropoxy group, an ethoxymethoxy group, a n-propoxymethoxy group, a 2-methoxyethoxy group, a 2-ethoxyethoxy group, a 3-methoxypropoxy group, a monofluoromethoxymethoxy group, a difluoromethoxymethoxy group, a monofluoroethoxyrnethoxy group, a difluoroethoxymethoxy group, a monofluoromethoxyethoxy group, a difluoromethoxyethoxy group, a trifluormethoxyethoxy group, a monofluoroethoxyethoxy group, a difluoroethoxyethoxy group and the like. Preferable examples include a methoxy group, an ethoxy group, an isopropoxy group, a 3-fluoropropoxy group, a 2-methoxyethoxy group, a 2-ethoxyethoxy group and a 3-methoxypropoxy group, among which a methoxy group, a 2-methoxyethoxy group, a 2-ethoxyethoxy group and the like are preferred, and a 2-methoxyethoxy group and a 2-ethoxyethoxy group are more preferred.

In formula used herein, $R^2$ represents a hydrogen atom, a halogen atom, a hydroxyl group, a $C_{1-6}$ alkyl group optionally substituted by 1 to 3 halogen atoms, a hydroxy $C_{1-6}$ alkyl group optionally substituted by 1 to 3 halogen atoms, or a $C_{3-5}$ nitrogen-containing non-aromatic heterocyclic group. Preferably, it is a hydrogen atom, a halogen atom, a hydroxyl group, a $C_{1-6}$ alkyl group or a hydroxy $C_{1-6}$ alkyl group, and more preferably, it is a hydrogen atom, a hydroxyl group, a $C_{1-6}$ alkyl group or a hydroxy $C_{1-6}$ alkyl group. Specific examples of $R^2$ include a hydrogen atom, a fluorine atom, a chlorine atom, a bromine atom, an iodine atom, a hydroxyl group, a methyl group, an ethyl group, a n-propyl group, an isopropyl group, a n-butyl group, an isobutyl group, a sec-butyl group, a tert-butyl group, a monofluoromethyl group, a difluoromethyl group, a trifluoromethyl group, a 2-fluoroethyl group, a 2,2-difluoroethyl group, a 2,2,2-trifluoroethyl group, a monochloromethyl group, a dichloromethyl group, a trichloromethyl group, a 2-chloroethyl group, a 2,2-dichloroethyl group, a 2,2,2-trichloroethyl group, a 3-fluoropropyl group, a hydroxymethyl group, a 2-hydroxyethyl group, a 1-hydroxyethyl group, a 3-hydroxypropyl group, a 2-hydroxypropyl group, a 1-hydroxypropyl group, a 2-hydroxy-2,2-dimethylethyl group, an azetidinyl group, a pyrrolidinyl group, a piperidinyl group, a piperazinyl group and the like. Preferably, it is a hydrogen atom, a fluorine atom, a hydroxyl group, a methyl group, an ethyl group, a n-propyl group, an isopropyl group, a hydroxymethyl group, a 2-hydroxyethyl group, a 1-hydroxyethyl group, a 3-hydroxypropyl group, a 2-hydroxypropyl group, a 1-hydroxypropyl group, a 2-hydroxy-2,2-dimethylethyl group, an azetidinyl group, a pyrrolidinyl group, a piperidinyl group or the like, and more preferably, it is a methyl group, an ethyl group or a 2-hydroxyethyl group.

In formula used herein, $R^3$ represents a hydrogen atom, a $C_{1-6}$ alkyl group optionally substituted by 1 to 3 halogen atoms, or a $C_{1-6}$ alkoxy group optionally substituted by 1 to 3 halogen atoms. Preferably, it is a hydrogen atom, a $C_{1-6}$ alkyl group or a $C_{1-6}$ alkoxy group. Specifically, it is preferably a hydrogen atom, a methyl group or an ethyl group, and more preferably a hydrogen atom.

However, if E represents an azetidine ring and $R^2$ or $R^3$ is present on a nitrogen atom of the azetidine ring, this $R^2$ or $R^3$ does not represent a hydrogen atom. Besides, each of $R^2$ and $R^3$ is an atom or a group substituted in an arbitrary position on E, namely, in an arbitrary position on the $C_{3-5}$ nitrogen-containing non-aromatic heterocycle.

In the following formula (I),

[Chemical Formula 10]

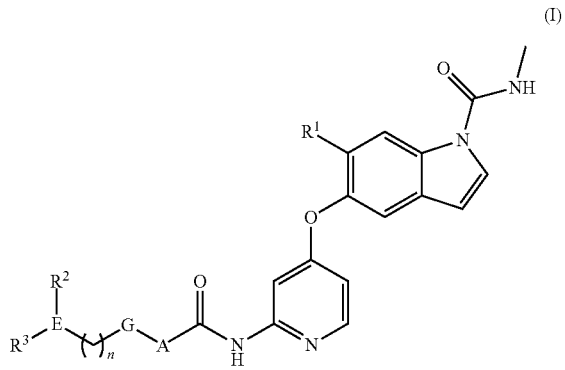

(I)

a partial structure represented by the following formula (IV) is preferably a partial structure represented by the following formula (V) or (VI), and more preferably a partial structure presented by formula (V).

[Chemical Formula 11]

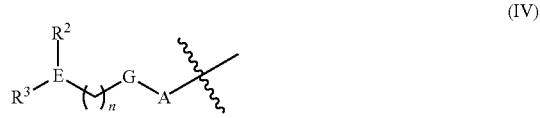

(IV)

[Chemical Formula 12]

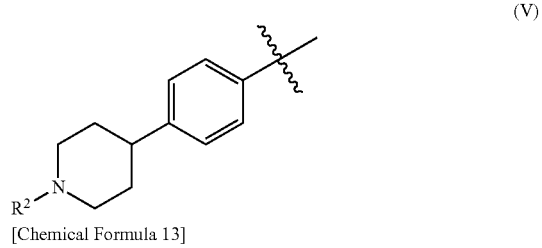

(V)

[Chemical Formula 13]

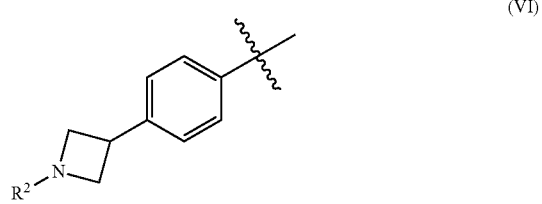

(VI)

In formula (V), $R^2$ represents a hydrogen atom, a $C_{1-6}$ alkyl group or a hydroxy alkyl group, and specific examples include a hydrogen atom, a methyl group, an ethyl group, a propyl group, an isopropyl group, a 2-hydroxyethyl group, a 3-hydroxypropyl group, a 2-hydroxypropyl group, a 2-hydroxy-2,2-dimethylethyl group and the like. It is preferably a methyl group, an ethyl group, a 2-hydroxyethyl group, a 2-hydroxypropyl group or a 2-hydroxy-2,2-dimethylethyl group.

In formula (VI), $R^2$ represents a $C_{1-6}$ alkyl group or a hydroxy $C_{2-6}$ alkyl group, and specific examples include a methyl group, an ethyl group, a propyl group, an isopropyl group, a 2-hydroxyethyl group, a 3-hydroxypropyl group, a 2-hydroxypropyl group, a 2-hydroxy-2,2-dimethylethyl group and the like. It is preferably a methyl group, an ethyl group, a 2-hydroxyethyl group, a 2-hydroxypropyl group or a 2-hydroxy-2,2-dimethylethyl group.

A compound of the present invention is preferably any one of the following compounds or the like or pharmaceutically acceptable salts thereof:

5-((2-(4-(1-Ethylpiperidin-4-yl)benzamide)pyridin-4-yl) oxy)-6-methoxy-N-methyl-1H-indole-1-carboxamide;
6-(2-Methoxyethoxy)-N-methyl-5-((2-(4-(1-methylpiperidin-4-yl)benzamide)pyridin-4-yl)oxy)-1H-indole-1-carboxamide;
5-((2-(4-(1-(2-Hydroxyethyl)piperidin-4-yl)benzamide)pyridin-4-yl)oxy)-6-(2-methoxyethoxy)-N-methyl-1H-indole-1-carboxamide;
6-(2-Ethoxyethoxy)-5-((2-(4-(1-(2-hydroxyethyl)piperidin-4-yl)benzamide)pyridin-4-yl)oxy)-N-methyl-1H-indole-1-carboxamide;
6-(2-Ethoxyethoxy)-5-((2-(4-(1-ethylazetidin-3-yl)benzamide)pyridin-4-yl)oxy)-N-methyl-1H-indole-1-carboxamide.

Examples of a "salt" used herein include salts with inorganic acids, salts with organic acids, and salts with acidic amino acids, and in particular, pharmaceutically acceptable salts are preferred. Besides, a salt of the compound of the present invention embraces an anhydride of a pharmaceutically acceptable salt thereof and a solvate, such as a hydrate, of the pharmaceutically acceptable salt.

Preferable examples of a salt with an inorganic acid include salts with hydrochloric acid, hydrobromic acid, sulfuric acid, nitric acid, phosphoric acid and the like, and preferable examples of a salt with an organic acid include salts with acetic acid, succinic acid, fumaric acid, maleic acid, tartaric acid, citric acid, lactic acid, stearic acid, benzoic acid, methanesulfonic acid, ethanesulfonic acid, p-toluenesulfonic acid and the like.

Preferable examples of a salt with an acidic amino acid include salts with aspartic acid and glutamic acid and the like.

The compound (I) of the present invention or the pharmaceutically acceptable salt thereof can be formulated by a general method, and the dosage form can be, for example, an oral formulation (such as a tablet, a granule, a powder, a capsule, a syrup or the like), an injection formulation (for intravenous administration, intramuscular administration, subcutaneous administration, intraperitoneal administration or the like), or an external formulation (such as a transdermal absorbable drug (including an ointment, a patch and the like), an eye dropper, nasal drops, a suppository or the like).

For producing an oral solid formulation, a vehicle, a binder, a disintegrator, a lubricant, a colorant and the like can be added, if necessary, to the compound (I) of the present invention or the pharmaceutically acceptable salt thereof, and the resulting mixture can be prepared by a conventional method into tablets, granulates, powders, or capsules. Furthermore, the tablets, granulates, powders, capsules or the like can be coated with a film if necessary.

Examples of the vehicle include lactose, corn starch, crystalline cellulose and the like, examples of the binder include hydroxypropyl cellulose, hydroxypropyl methyl cellulose and the like, examples of the disintegrator include calcium carboxymethylcellulose, sodium croscarmellose and the like, examples of the lubricant include magnesium stearate, calcium stearate and the like, an example of the colorant includes titanium oxide and the like, and examples of a film-coating agent include hydroxypropyl cellulose, hydroxypropyl methyl cellulose, methyl cellulose and the like, but these components are not limited to the aforementioned examples.

The solid formulation such as a tablet, a capsule, a granule or a powder may contain the compound (I) of the present invention or the pharmaceutically acceptable salt thereof in a content of generally 0.001 to 99.5% by weight, and specifically 0.001 to 90% by weight.

For producing an injection formulation (for intravenous administration, intramuscular administration, subcutaneous administration, intraperitoneal administration or the like), a pH adjuster, a buffer, a suspending agent, a solubilizing agent, an antioxidant, a preservative (an antiseptic agent), a tonicity adjusting agent and the like are added, if necessary, to the compound (I) of the present invention or the pharmaceutically acceptable salt thereof, and the resulting mixture can be prepared into an injection formulation by a conventional method. Furthermore, the resultant can be freeze-dried to be used as a lyophilized product to be dissolved before use.

Examples of the pH adjuster and the buffer include organic acids or inorganic acids and/or pharmaceutically acceptable salts thereof; examples of the suspending agent include methyl cellulose, Polysorbate 80, sodium carboxymethylcellulose and the like, examples of the solubilizing agent include Polysorbate 80, polyoxyethylene sorbitan monolaurate and the like, an example of the antioxidant includes α-tocopherol and the like, examples of the preservative include methyl paraoxybenzoate, ethyl paraoxybenzoate and the like, and examples of the tonicity adjusting agent include grape sugar, sodium chloride, mannitol and the like, but these components are not limited to the aforementioned examples.

Such an injection formulation may contain the compound (I) of the present invention or the pharmaceutically acceptable salt thereof in a content of generally 0.000001 to 99.5% by weight, and specifically 0.00001 to 90% by weight.

For producing an external formulation, a base material is added to the compound (I) of the present invention or the pharmaceutically acceptable salt thereof, and if necessary, for example, a preservative, a stabilizer, a pH adjuster, an antioxidant, a colorant and the like described above are further added thereto, and the resulting mixture is prepared by a conventional method into, for example, a transdermal absorbable drug (such as an ointment or a patch), an eye dropper, nasal drops, a suppository or the like.

As the base material to be used, various materials usually used for, for example, medicines, quasi-drugs and cosmetics can be used. Specific examples of the material include animal and vegetable oils, mineral oils, ester oils, waxes, emulsifiers, higher alcohols, fatty acids, silicone oils, surfactants, phospholipids, alcohols, polyhydric alcohols, water soluble polymers, clay minerals, purified water and the like.

Such an external formulation can contain the compound (I) of the present invention or the pharmaceutically acceptable salt thereof in a content of generally 0.000001 to 99.5% by weight, and specifically 0.00001 to 90% by weight.

A dose of the compound (I) of the present invention or the pharmaceutically acceptable salt thereof depends upon the level of symptom severity, the patient's age, sex and weight, the administration form and the kind of salt, a specific kind of disease and the like, and is not especially limited unless it exceeds the maximum dose of the medicine that can be given without causing an unacceptable adverse reaction, and in an adult patient, it is administered, once or dividedly several times per day, at a dose for oral administration of generally approximately 30 μg to 10 g, specifically 100 μg to 5 g and more specifically 100 μg to 1 g, or a dose for injection administration of generally approximately 30 μg to 1 g, specifically 100 μg to 500 mg, and more specifically 100 μg to 300 mg.

[General Synthesis Method]

A production method for the compound (I) of the present invention will now be described. The compound (I) of the present invention can be synthesized by using general organic synthesizing means, and some examples of the compound (I) of the present invention, for example, compounds (1-1), (1-2), (1-3), (1-4) and (1-5) can be synthesized by methods described in [Production Method 1] or the like described below. If a protective group is used in production methods described herein, known protective groups, for example, as those described in Green's PROTECTIVE GROUP IN ORGANIC CHEMISTRY, fourth edition, JOHN WILEY & SONS, INC. are appropriately selected and introduced, and deprotection can be appropriately performed by a known method.

[Production Method 1] Representative production method for compound (I) of the present invention

[Chemical Formula 14]

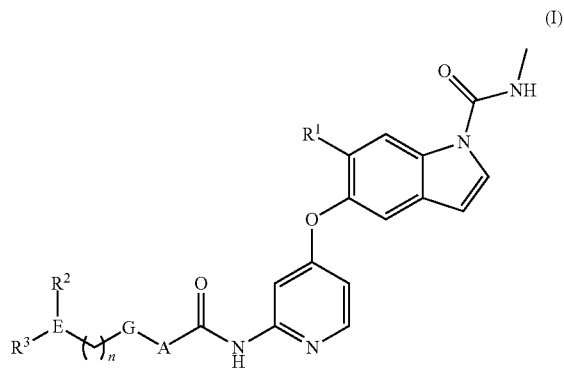

wherein $R^1$, $R^2$, $R^3$, A, E, G and n represent the same as defined above.

[Production Method 1-1] Production Method for Compound (1-1), (1-2) or (1-3)

[Chemical Formula 15]

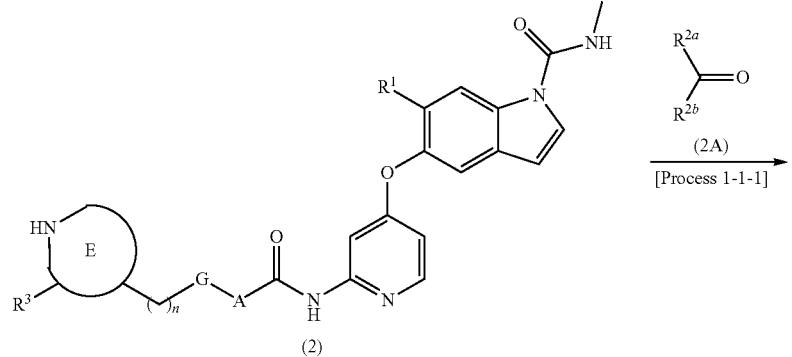

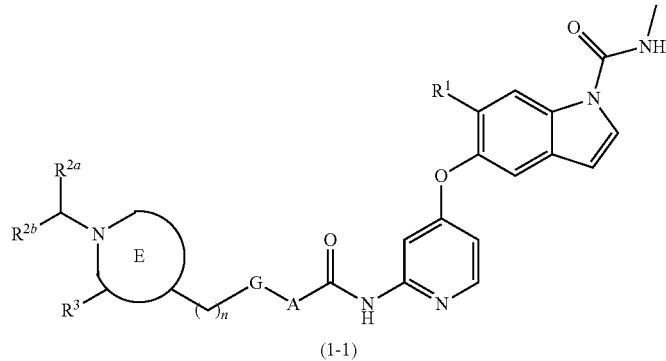

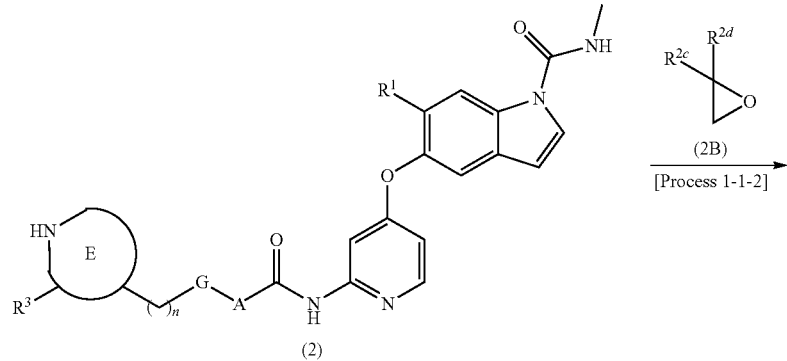

-continued

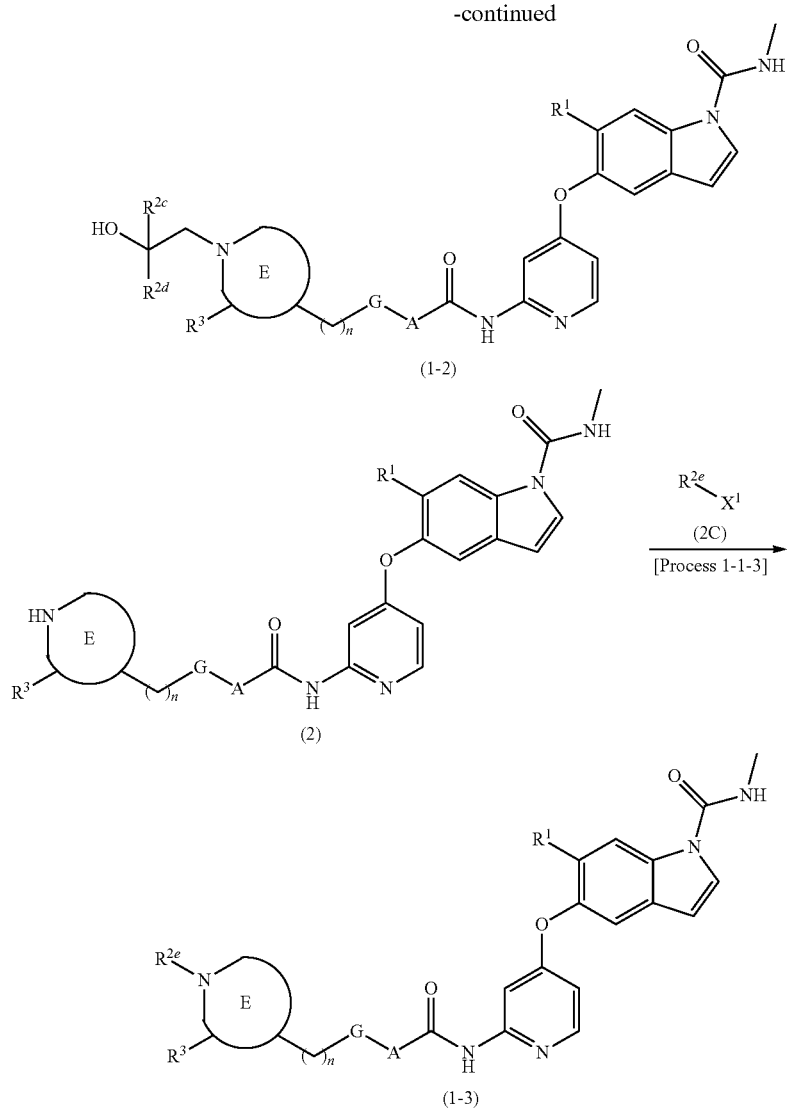

In the above formula, $R^1$, $R^3$, A, E, G and n represent the same as defined above; $R^{2a}$ and $R^{2b}$ each represent a hydrogen atom, a $C_{1-5}$ alkyl group optionally substituted by 1 to 3 halogen atoms, or a hydroxy $C_{1-5}$ alkyl group optionally substituted by 1 to 3 halogen atoms; $R^{2c}$ and $R^{2d}$ each represent a hydrogen atom or a $C_{1-4}$ alkyl group optionally substituted by 1 to 3 halogen atoms; $R^{2e}$ represents a $C_{1-6}$ alkyl group optionally substituted by 1 to 3 halogen atoms, or a hydroxy $C_{1-6}$ alkyl group optionally substituted by 1 to 3 halogen atoms, if $R^{2e}$ has a hydroxyl group, the hydroxyl group may be protected by a known suitable protective group; and $X^1$ represents a halogen atom such as a chlorine atom, a bromine atom, or an iodine atom, or a leaving group of sulfonate such as methanesulfonate or p-toluenesulfonate A compound (2) can be also produced by a method described in a production example in any of examples described below, [Production Method 2] or the like.

Compounds (2A), (2B) and (2C) can be commercially available products, or can be produced from commercially available products by known methods. Alternatively, these compounds can be produced by methods described in production examples in any of the examples described below or the like. The compound (2A) can be in any form ranging a dimer to a multimer.

[Process 1-1-1]

In this process, the compound (2) and the compound (2A) are reacted with each other in the presence of a reducing agent to give a compound (1-1). A solvent used in this reaction is not especially limited as long as it dissolves a starting material to some extent and does not inhibit the reaction, and for example, an ether solvent such as tetrahydrofuran, an alcohol solvent such as ethanol, a nitrile solvent such as acetonitrile, carboxylic acid solvent such as acetic acid, an aromatic hydrocarbon solvent such as benzene or toluene, an amide solvent such as N,N-dimethylformamide or N-methylpyrrolidinone, a halogenated hydrocarbon solvent such as dichloromethane or chloroform, water, or a mixed solvent of these can be used. As the reducing agent used in this reaction, a metal hydrogen complex compound such as sodium borohydride, sodium cyanoborohydride or sodium niacetoxyborohydride, or substituted borane such as diborane or a pyridine-borane complex can be used. Besides, a catalytic reduction catalyst such as palladium-carbon can be used under a hydrogen atmosphere. The compound (2A) can be used in an amount of 1 to 10 equivalents to the compound (2), and is preferably used in an amount of 1 to 2 equivalents. The reducing agent can be used in an amount of 1 equivalent or more to the compound (2), and is preferably used in an amount of 1 to 5 equivalents. In this reaction, an acid such as acetic acid can be added in an amount of 0 to 10 equivalents. The reaction temperature is from −20° C. to reflux temperature, and the reaction time is from 10 minutes to 24 hours.

[Process 1-1-2]

In this process, the compound (2) and the compound (2B) are reacted with each other to give a compound (1-2). A solvent used in this reaction is not especially limited as long as it dissolves a starting material to some extent and does not inhibit the reaction, and for example, an ether solvent such as tetrahydrofuran, an alcohol solvent such as ethanol, an amide solvent such as N,N-dimethylformamide or N-methylpyrrolidinone, a nitrile solvent such as acetonitrile, an aromatic hydrocarbon solvent such as toluene, a halogenated hydrocarbon solvent such as dichloromethane or chloroform, or a mixed solvent of these can be used. In this reaction, alkyl amine such as triethyl amine, aromatic amine such as pyridine, or an inorganic base such as potassium carbonate can be used as a base. The compound (2B) can be used in an amount of 1 equivalent or more to the compound (2), and is preferably used in an amount of 1 to 10 equivalents. The base can be used in an amount of 0 to 10 equivalents to the compound (2). The reaction temperature is from 0° C. to 200° C., and the reaction time is from 10 minutes to 24 hours.

[Process 1-1-3]

In this process, the compound (2) and the compound (2C) are reacted with each other to give a compound (1-3). A solvent used in this reaction is not especially limited as long as it dissolves a starting material to some extent and does not inhibit the reaction, and for example, an ether solvent such as tetrahydrofuran, a nitrile solvent such as acetonitrile, an aromatic hydrocarbon solvent such as toluene, a halogenated hydrocarbon solvent such as dichloromethane or chloroform, an amide solvent such as N,N-dimethylformamide or N-methylpyrrolidinone, dimethylsulfoxide, or a mixed solvent of these can be used. In this reaction, alkyl amine such as triethyl amine, aromatic amine such as pyridine, or an inorganic base such as sodium hydrogen carbonate, potassium carbonate or cesium carbonate can be used as a base. The compound (2C) can be used in an amount of 1 equivalent or more to the compound (2), and is preferably used in an amount of 1 to 3 equivalents. The base can be used in an amount of 1 to 10 equivalents to the compound (2). The reaction temperature is from 0° C. to reflux temperature, and the reaction time is from 10 minutes to 24 hours. If the hydroxyl group of $R^{2e}$ is protected, it can be deprotected by a known method.

[Production Method 1-2] Production Method for Compound (1-4)

[Chemical Formula 16]

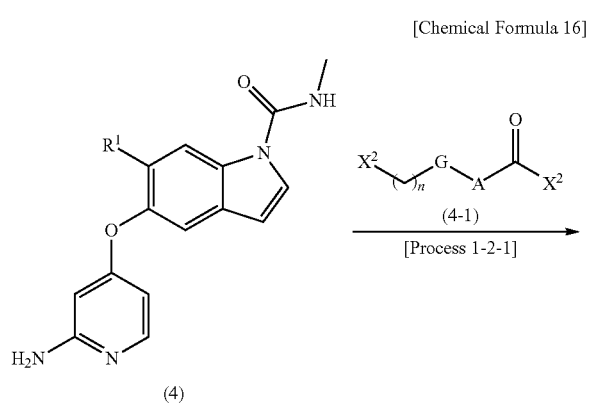

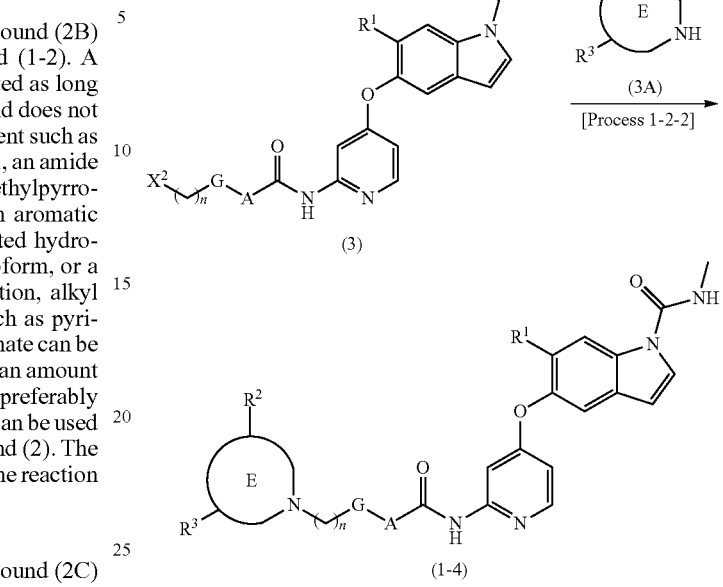

In the above formula, $R^1$, $R^2$, $R^3$, A, E, G and n represent the same as defined above; and $X^2$ represents a halogen atom such as a chorine atom or a bromine atom, or a leaving group of sulfonate such as methanesulfonate or a p-toluenesulfonate.

Compounds (3) and (4) can be also produced by methods described in [Production Method 3], production examples of any of the examples described below or the like.

Compounds (3A) and (4-1) can be commercially available products, or can be produced from commercially available products by known methods. Alternatively, these compounds can be produced by methods described in [Production Method 6], production examples of any of the examples described below or the like.

[Process 1-2-1]

In this process, the compound (4) and the compound (4-1) are reacted with each other to give the compound (3). A solvent used in this reaction is not especially limited as long as it dissolves a starting material to some extent and does not inhibit the reaction, and for example, an ether solvent such as tetrahydrofuran, an ester solvent such as ethyl acetate, a nitrile solvent such as acetonitrile, an aromatic hydrocarbon solvent such as toluene, a halogenated hydrocarbon solvent such as dichloromethane or chloroform, an amide solvent such as N,N-dimethylformamide or N-methylpynolidinone, or a mixed solvent of these can be used. In this reaction, alkyl amine such as triethyl amine or N,N-diisopropylethylamine, aromatic amine such as 4-ditnethylaminopyridine, or an inorganic base such as potassium carbonate or cesium carbonate can be used as a base, or a combination of these bases can be used. The compound (4-1) can be used in an amount of 1 equivalent or more to the compound (4), and is preferably used in an amount of 2 to 3 equivalents. The base can be used in an amount of 1 to 10 equivalents to the compound (4). The reaction temperature is from 0° C. to reflux temperature, and the reaction time is from 10 minutes to 24 hours. In this process, a diacyl form resulting from a reaction of 2 equivalents of the compound (4-1) may be produced, but this can be directly used in the following reaction.

[Process 1-2-2]

In this process, the compound (3) and the compound (3A) are reacted with each other to give a compound (1-4). A solvent used in this reaction is not especially limited as long as it dissolves a starting material to some extent and does not inhibit the reaction, and for example, an ether solvent such as tetrahydrofuran, an aromatic hydrocarbon solvent such as toluene, a halogenated hydrocarbon solvent such as dichloromethane or chloroform, an amide solvent such as N,N-dimethylformamide or N-methylpyrrolidinone, dimethylsulfoxide, or a mixed solvent of these can be used. In this reaction, alkyl amine such as triethyl amine or N,N-diisopropylethylamine, or an inorganic base such as potassium carbonate or cesium carbonate can be used as a base. The compound (3A) can be used in an amount of 1 equivalent or more to the compound (3), and is preferably used in an amount of 1 to 10 equivalents. The base can be used in an amount of 1 to 10 equivalents to the compound (3). The reaction temperature is from 0° C. to reflux temperature, and the reaction time is from 10 minutes to 24 hours.

[Production Method 1-3] Production Method for Compound (1) or (1-5)

[Chemical Formula 17]

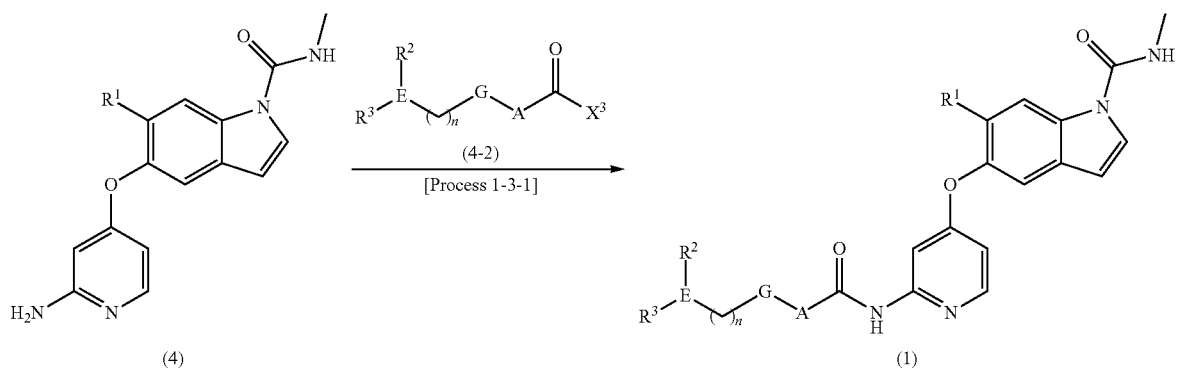

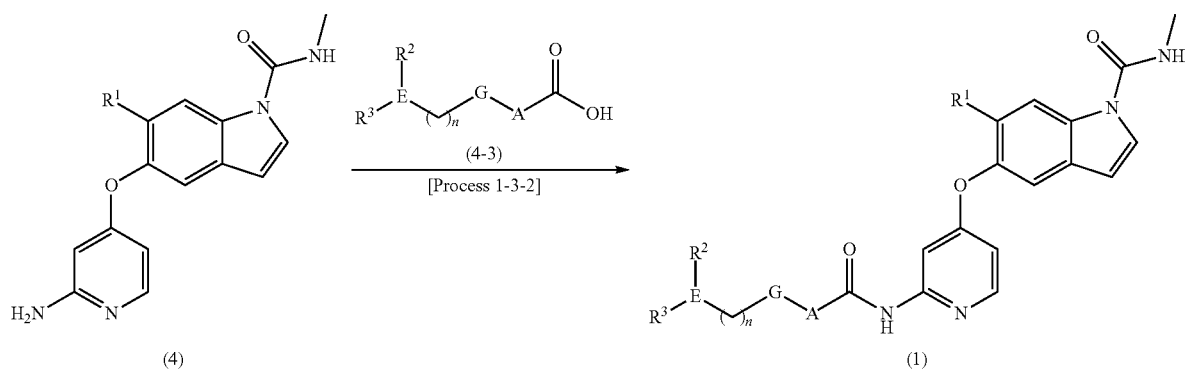

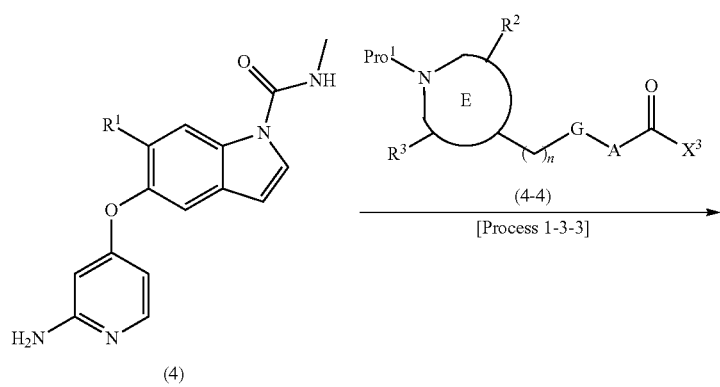

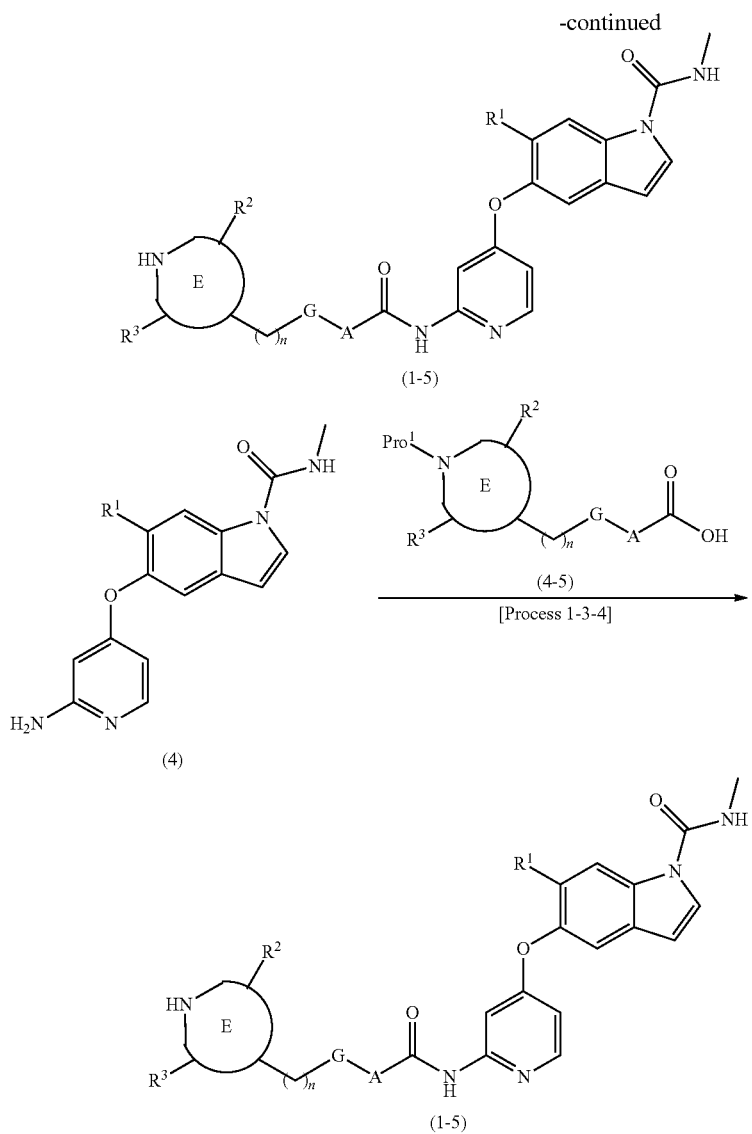

In the above formula, $R^1$, $R^2$, $R^3$, A, E, G and n represent the same as defined above; $X^3$ represents a halogen atom such as a chlorine atom or a bromine atom; and $Pro^1$ represents a known protective group for a nitrogen atom such as a tert-butoxycarbonyl group.

The compound (4) can be produced by a method described in a production example of any of the examples described below, [Production Method 3] or the like.

Compounds (4-2), (4-3), (4-4) and (4-5) can be commercially available products, or can be produced from commercially available products by known methods. These compounds can be also produced by methods described in [Production Method 5], production examples of any of the examples described below or the like.

[Process 1-3-1 or 1-3-3]

In this process, the compound (4) and the compound (4-2) or (4-4) are reacted with each other to give the compound (1) or (1-5) respectively. A solvent used in this reaction is not especially limited as long as it dissolves a starting material to some extent and does not inhibit the reaction, and for example, an ether solvent such as tetrahydrofuran, an ester solvent such as ethyl acetate, a nitrile solvent such as acetonitrile, an aromatic hydrocarbon solvent such as toluene, a halogenated hydrocarbon solvent such as dichloromethane or chloroform, an amide solvent such as N,N-dimethylformamide or N-methylpyrrolidinone, or a mixed solvent of these can be used. In this reaction, alkyl amine such as triethyl amine or N,N-diisopropylethylamine, aromatic amine such as 4-dimethylaminopyridine, or an inorganic base such as potassium carbonate or cesium carbonate can be used as a base, or a combination of these bases can be used. The compound (4-2) or (4-4) can be used in an amount of 1 equivalent or more to the compound (4), and is preferably used in an amount of 2 to 3 equivalents. The base can be used in an amount of 1 to 10 equivalents to the compound (4). The reaction temperature is from 0° C. to reflux temperature, and the reaction time is from 10 minutes to 24 hours. In this process, a diacyl form resulting from a reaction of 2 equivalents of the compound (4-2) or (4-4) may be produced. In this case, the diacyl form can be changed into a desired monoacyl form by a treatment with ammonia or primary or secondary alkyl amine such as methyl amine or piperidine.

In process 1-3-3, a protective group for a nitrogen atom can be subsequently removed by a known method. If $Pro^1$ is, for example, a tert-butoxycarbonyl group, the deprotection can be performed by using a solvent not inhibiting the reaction, for example, a halogenated hydrocarbon solvent such as dichloromethane, an ester solvent such as ethyl acetate, an alcohol solvent such as methanol, or a mixed solvent of these, and by using an acid such as trifluoroacetic acid or hydrochloric acid.

[Process 1-3-2 or 1-3-4]

In this process, the compound (4) and the compound (4-3) or (4-5) are reacted with each other by using a condensation agent to give the compound (I) or (1-5). A solvent used in this reaction is not especially limited as long as it dissolves a starting material to some extent and does not inhibit the reaction, and for example, an ether solvent such as tetrahydrofuran, an ester solvent such as ethyl acetate, a nitrile solvent such as acetonitrile, an aromatic hydrocarbon solvent such as toluene, a halogenated hydrocarbon solvent such as dichloromethane or chloroform, an amide solvent such as N,N-dimethylformamide or N-methylpyrrolidinone, dimethylsulfoxide, or a mixed solvent of these can be used. In this reaction, a condensation agent such as O-(7-azabenzotriazole-1-yl)-N,N,N',N'-tetramethyluronium hexafluorophosphate or 1-ethyl-3-(3-dimethylaminopropyl) carbodiimide hydrochloride can be used. Furthermore, 1-hydroxybenzotriazole or the like can be used as an additive. In this reaction, alkyl amine such as triethyl amine or N,N-diisopropylethylamine, aromatic amine such as 4-dimethylaminopyridine, or an inorganic base such as potassium carbonate or cesium carbonate can be used as a base, or a combination of these bases can be used. The compound (4-3) or (4-5) can be used in an amount of 1 equivalent or more to the compound (4), and is preferably used in an amount of 2 to 3 equivalents. The condensation agent can be used in an amount of the same equivalents as the compound (4-3) or (4-5), and the base can be used in an amount of 1 to 10 equivalents to the compound (4). The reaction temperature is from 0° C. to reflux temperature, and the reaction time is from 10 minutes to 24 hours. In this process, a diacyl form resulting from a reaction of 2 equivalents of the compound (4-3) or (4-5) may be produced. In this case, the diacyl form can be changed into a desired monoacyl form by a treatment with ammonia or primary or secondary alkyl amine such as methyl amine or piperidine.

In process 1-3-4, a protective group for a nitrogen atom can be subsequently removed by a known method. If Pro$^1$ is, for example, a tert-butoxycarbonyl group, the deprotection can be performed by using a solvent not inhibiting the reaction, for example, a halogenated hydrocarbon solvent such as dichloromethane, an ester solvent such as ethyl acetate, an alcohol solvent such as methanol, or a mixed solvent of these, and by using an acid such as trifluoroacetic acid or hydrochloric acid.

[Production Method 2] Production Method for Compound (2)

[Chemical Formula 18]

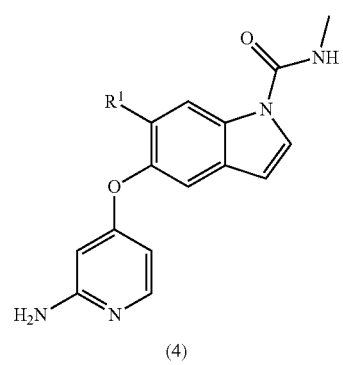

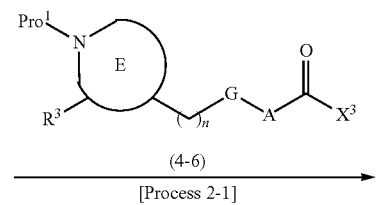

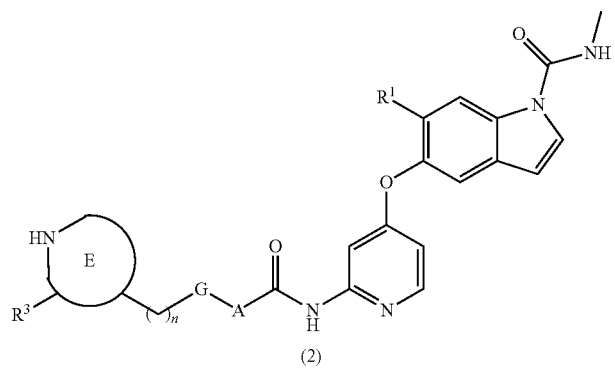

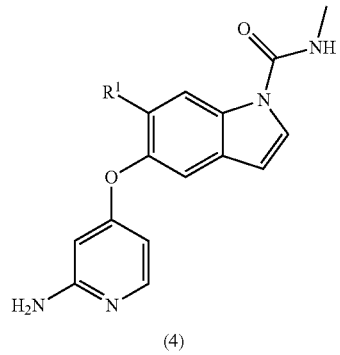

(4)

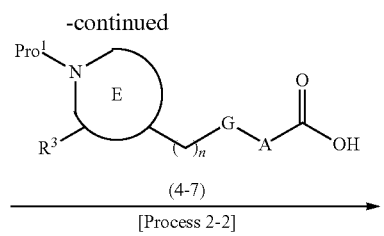

-continued (4-7)

[Process 2-2]

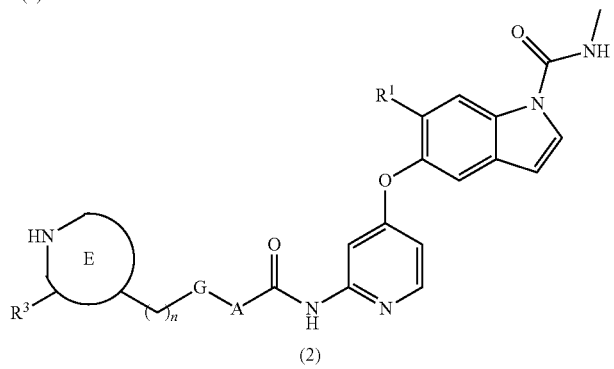

(2)

In the above formula, $R^1$, $R^3$, A, E, G and n represent the same as defined above; $X^3$ represents a halogen atom such as a chlorine atom or a bromine atom; and $Pro^1$ represents a known protective group for a nitrogen atom such as a tert-butoxycarbonyl group.

Compounds (4-6) and (4-7) can be commercially available products, or can be produced from commercially available products by known methods. These compounds can be also produced by methods described in production examples of any of the examples described below or the like. Compound (4-6) can be also produced by methods described in [Production Method 5] or the like.

[Process 2-1]

In this process, the compound (4) and the compound (4-6) are reacted with each other to give the compound (2). A solvent used in this reaction is not especially limited as long as it dissolves a starting material to some extent and does not inhibit the reaction, and for example, an ether solvent such as tetrahydrofuran, an ester solvent such as ethyl acetate, a nitrite solvent such as acetonitrile, an aromatic hydrocarbon solvent such as toluene, a halogenated hydrocarbon solvent such as dichloromethane or chloroform, an amide solvent such as N,N-dimethylformamide or N-methylpyrrolidinone, or a mixed solvent of these can be used. In this reaction, alkyl amine such as triethyl amine or N,N-diisopropylethylamine, aromatic amine such as 4-dimethylaminopyridine, or an inorganic base such as potassium carbonate or cesium carbonate can be used as a base, or a combination of these bases can be used. The compound (4-6) can be used in an amount of 1 equivalent or more to the compound (4), and is preferably used in an amount of 2 to 3 equivalents. The base can be used in an amount of 1 to 10 equivalents to the compound (4). The reaction temperature is from 0° C. to reflux temperature, and the reaction time is from 10 minutes to 24 hours. In this process, a diacyl form resulting from a reaction of 2 equivalents of the compound (4-6) may be produced. In this case, the diacyl form can be changed into a desired monoacyl form by a treatment with ammonia or primary or secondary alkyl amine such as methyl amine or piperidine. A protective group for a nitrogen atom can be subsequently removed by a known method. If $Pro^1$ is, for example, a tert-butoxycarbonyl group, the deprotection can be performed by using a solvent not inhibiting the reaction, for example, a halogenated hydrocarbon solvent such as dichloromethane, an ester solvent such as ethyl acetate, an alcohol solvent such as methanol, or a mixed solvent of these, and by using an acid such as trifluoroacetic acid or hydrochloric acid.

[Process 2-2]

In this process, the compound (4) and the compound (4-7) are reacted with each other to give the compound (2). A solvent used in this reaction is not especially limited as long as it dissolves a starting material to some extent and does not inhibit the reaction, and for example, an ether solvent such as tetrahydrofuran, an ester solvent such as ethyl acetate, a nitrile solvent such as acetonitrile, an aromatic hydrocarbon solvent such as toluene, a halogenated hydrocarbon solvent such as dichloromethane or chloroform, an amide solvent such as N,N-dimethylformamide or N-methylpyrrolidinone, dimethylsulfoxide, or a mixed solvent of these can be used. In this reaction, a condensation agent such as O-(7-azabenzotriazole-1-yl)-N,N,N',N'-tetramethyluronium hexafluorophosphate or 1-ethyl-3-(3-dimethylaminopropyl)carbodiimide hydrochloride can be used. Furthermore, 1-hydroxybenzotriazole or the like can be used as an additive. In this reaction, alkyl amine such as triethyl amine or N,N-diisopropylethylamine, aromatic amine such as 4-dimethylaminopyridine, or an inorganic base such as potassium carbonate or cesium carbonate can be used as a base, or a combination of these bases can be used. The compound (4-7) can be used in an amount of 1 equivalent or more to the compound (4), and is preferably used in an amount of 2 to 3 equivalents. The base can be used in an amount of 1 to 10 equivalents to the compound (4). The reaction temperature is from 0° C. to reflux temperature, and the reaction time is from 10 minutes to 24 hours. In this process, a diacyl form resulting from a reaction of 2 equivalents of the compound (4-7) may be produced. In this case, the diacyl form can be changed into a desired monoacyl form by a treatment with ammonia or primary or secondary alkyl amine such as methyl amine or piperidine. A protective group for a nitrogen atom can be subsequently removed by a known method. If $Pro^1$ is, for example, a tert-butoxycarbonyl group, the deprotection can be performed by using a solvent not inhibiting the reaction, for example, a halogenated hydrocarbon solvent such as dichloromethane, an ester solvent such as ethyl acetate, an alcohol solvent such as methanol, or a mixed solvent of these, and by using an acid such as trifluoroacetic acid or hydrochloric acid.

[Production Method 3] Production Method for Compound (4)

In the above formula, $R^1$ represents the same as defined above; $Pro^2$ represents a protective group for a nitrogen atom, such as an acetyl group; $Pro^3$ represents a protective group for a phenolic oxygen atom, such as a benzyl group; and $X^3$ represents a halogen atom such as a chlorine atom or a bromine atom.

Compounds (7), (8), (9), (10) and (11) can be commercially available products, or can be produced from commercially available products by known methods. These compounds can be also produced by methods described in production examples of any of the examples described below. Compounds (5) and (6) can be also produced by methods described in production examples of any of the examples described below or the like.

Compounds (5A), (6A) and (11A) can be commercially available products, or can be produced from commercially available products by known methods. Alternatively, these

[Chemical Formula 19]

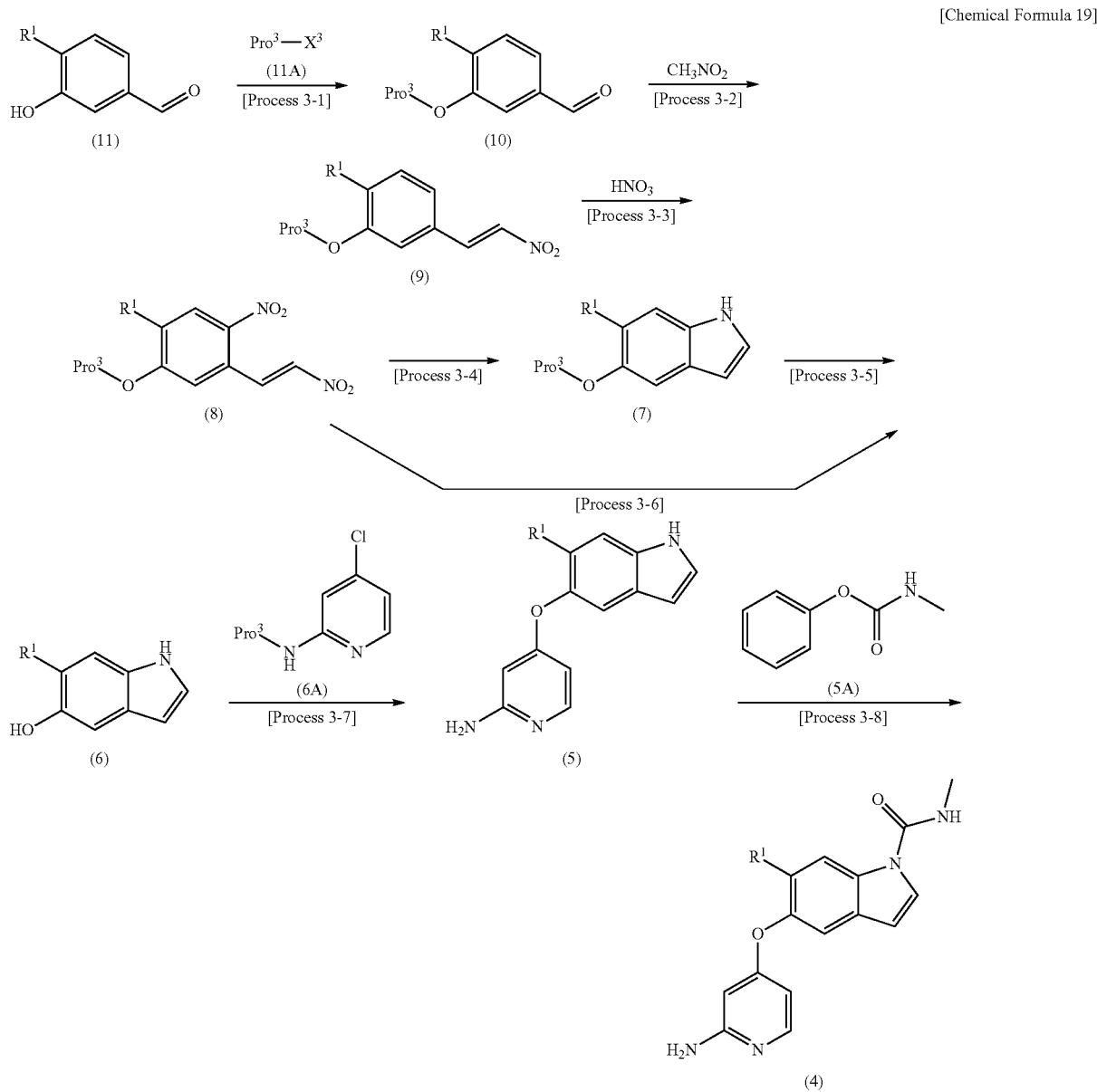

compounds can be produced by methods described in production examples of any of the examples described below or the like.

[Process 3-1]

In this process, the compound (11) and the compound (11A) are reacted with each other to give the compound (10). A solvent used in this reaction is not especially limited as long as it dissolves a starting material to some extent and does not inhibit the reaction, and for example, an ether solvent such as tetrahydrofuran, an alcohol solvent such as ethanol, a nitrite solvent such as acetonitrile, a ketone solvent such as acetone, a halogenated hydrocarbon solvent such as dichloromethane, an amide solvent such as N,N-dimethylformamide or N-methylpyrrolidinone, dimethylsulfoxide, or a mixed solvent of these can be used. In this reaction, the compound (11A) is used in an amount of 1 to 5 equivalents to the compound (11), and 1 to 5 equivalents of a base, such as sodium hydrogen carbonate, potassium carbonate, sodium methoxide, sodium hydride or diisopropylethylamine can be added. Besides, sodium iodide or potassium iodide can be added as an additive. The reaction temperature is from −20° C. to reflux temperature, and the reaction time is from 10 minutes to 24 hours.

[Process 3-2]

In this process, the compound (10) and nitromethane are reacted with each other to give the compound (9). A solvent used in this reaction is not especially limited as long as it dissolves a starting material to some extent and does not inhibit the reaction, and for example, an alcohol solvent such as methanol, an organic acid solvent such as acetic acid, or a mixed solvent of these can be used. In this reaction, nitromethane is used in an amount of 1 to 10 equivalents, and 0.1 to 10 equivalents of ammonium acetate, ethylenediamine-N,N-diacetic acid or the like can be added as an additive. The reaction temperature is from 0° C. to reflux temperature, and the reaction time is from 10 minutes to 100 hours.

[Process 3-3]

In this process, the compound (9) is nitrated to give the compound (8). A solvent used in this reaction is not especially limited as long as it dissolves a starting material to some extent and does not inhibit the reaction, and for example, a halogenated hydrocarbon solvent such as dichloromethane, an organic acid solvent such as acetic acid, sulfuric acid, or a mixed solvent of these can be used. In this reaction, fuming nitric acid, concentrated nitric acid or nitric acid is used, and acetic anhydride or the like can be added as an additive. The nitric acid or the like used in this reaction may be in an amount of 1 to 100 equivalents to the compound (9). The reaction temperature is from −20° C. to reflux temperature, and the reaction time is from 10 minutes to 100 hours.

[Process 3-4]

In this process, the compound (8) is cyclized to give the compound (7). A solvent used in this reaction is not especially limited as long as it dissolves a starting material to some extent and does not inhibit the reaction, and for example, an ether solvent such as tetrahydrofuran, an alcohol solvent such as ethanol, an aromatic hydrocarbon solvent such as benzene or toluene, a hydrocarbon solvent such as cyclohexane, water, or a mixed solvent of these can be used. In this reaction, a heavy metal such as iron or zinc is used, and an acid such as acetic acid, a salt such as ammonium chloride, a base such as sodium hydroxide, an inorganic compound such as silica gel or a mixture of these can be added as an additive. The heavy metal such as iron used in this reaction may be in an amount of 5 to 20 equivalents to the compound (8). The reaction temperature is from 0° C. to reflux temperature, and the reaction time is from 10 minutes to 24 hours.

[Process 3-5]

In this process, $Pro^3$ of the compound (7) is deprotected to give the compound (6). $Pro^3$ can be deprotected by a known method, and if $Pro^3$ is benzyl, a solvent used in this reaction is not especially limited as long as it dissolves a starting material to some extent and does not inhibit the reaction, and for example, an ether solvent such as tetrahydrofuran, an alcohol solvent such as ethanol, an aromatic hydrocarbon solvent such as benzene or toluene, acetic acid, water, or a mixed solvent of these can be used. This reaction can be performed under a hydrogen atmosphere with a catalytic reduction catalyst such as palladium-carbon used as a catalyst. The pressure of the hydrogen can be from normal pressure to 20 atm, and the catalyst can be used in an amount of 0.001 to 1 equivalent to the compound (7). Besides, an acid such as hydrochloric acid can be added. The reaction temperature is from 0° C. to reflux temperature, and the reaction time is from 10 minutes to 24 hours.

[Process 3-6]

In this process, the compound (8) is cyclized to give the compound (6). A solvent used in this reaction is not especially limited as long as it dissolves a starting material to some extent and does not inhibit the reaction, and for example, an ether solvent such as tetrahydrofuran, an alcohol solvent such as methanol, an aromatic hydrocarbon solvent such as benzene or toluene, acetic acid, water, or a mixed solvent of these can be used. This reaction can be performed under a hydrogen atmosphere with a catalytic reduction catalyst such as palladium-carbon used as a catalyst. The pressure of the hydrogen can be from normal pressure to 20 atm, and the catalyst can be used in an amount of 0.001 to 1 equivalent to the compound (8). An acid such as hydrochloric acid can be added as an additive. The reaction temperature is from 0° C. to reflux temperature, and the reaction time is from 10 minutes to 24 hours.

[Process 3-7]

In this process, the compound (6) and the compound (6A) are reacted with each other to give the compound (5). A solvent used in this reaction is not especially limited as long as it dissolves a starting material to some extent and does not inhibit the reaction, and for example, an amide solvent such as N,N-dimethylformamide or N-methylpynolidinone, dimethylsulfoxide, or a mixed solvent of these can be used. In this reaction, a base such as potassium carbonate, cesium carbonate or potassium tert-butoxide can be used as a base. The base can be used in an amount of 1 to 10 equivalents to the compound (6), and is preferably used in an amount of 1 to 2 equivalents. The reaction temperature is from 0° C. to reflux temperature, and the reaction time is from 10 minutes to 24 hours. $Pro^2$ can be deprotected by a known method, and if $Pro^2$ is an acetyl group, it can be deprotected by using a solvent not inhibiting the reaction, such as an alcohol solvent like methanol, and by using a base such as potassium carbonate, sodium hydroxide or sodium methoxide, or it can be deprotected by using a solvent not inhibiting the reaction, such as an ether solvent like 1,4-dioxane, and by using an acid such as hydrochloric acid. Alternatively, this process can be performed by using a compound not protected by $Pro^2$ as the compound (6A).

[Process 3-8]

In this process, the compound (5) and the compound (5A) are reacted with each other to give the compound (4). A solvent used in this reaction is not especially limited as long as it dissolves a starting material to some extent and does not inhibit the reaction, and for example, an ether solvent such as tetrahydrofuran, an amide solvent such as N,N-dimethylformamide or N-methylpyrrolidinone, dimethylsulfoxide, or a mixed solvent of these can be used. In this reaction, a base such as sodium hydroxide or potassium tert-butoxide can be used as a base. The compound (5A) can be used in an amount of 1 equivalent or more to the compound (5), and is preferably used in an amount of 1 to 2 equivalents. The base can be used in an amount of 1 to 2 equivalents to the compound (5). The reaction temperature is from −20° C. to reflux temperature, and the reaction time is from 10 minutes to 24 hours.

[Production Method 4] Production Method for Compound (11-1)

[Chemical formula 20]

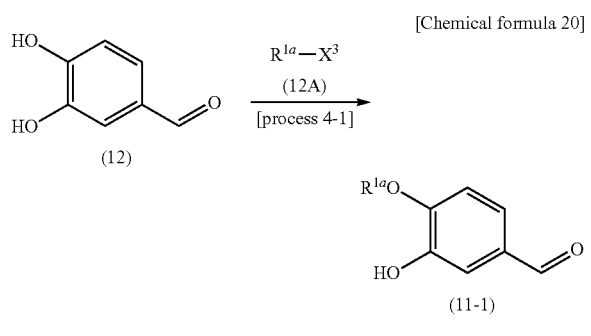

In the above formula, $R^{1a}$ represents a $C_{1-6}$ alkyl group optionally substituted by 1 to 3 halogen atoms, or a $C_{1-6}$ alkoxy $C_{1-6}$ alkyl group optionally substituted by 1 to 3 halogen atoms; and $X^3$ represents a leaving group of a halogen atom such as a bromine atom or an iodine atom.

A compound (12) can be a commercially available product, or can be produced from a commercially available product by a known method.

A compound (12A) can be a commercially available product, or can be produced from a commercially available product by a known method.

[Process 4-1]

In this process, the compound (12) and the compound (12A) are reacted with each other to give a compound (11-1). A solvent used in this reaction is not especially limited as long as it dissolves a starting material to some extent and does not inhibit the reaction, and for example, an ether solvent such as tetrahydrofuran, an alcohol solvent such as ethanol, a nitrile solvent such as acetonitrile, an amide solvent such as N,N-dimethylformamide or N-methylpyrrolidinone, dimethylsulfoxide, or a mixed solvent of these can be used. In this reaction, the compound (12A) is used in an amount of 0.5 to 1.5 equivalents to the compound (12), and 0.5 to 1.5 equivalents of a base such as sodium hydrogen carbonate, potassium carbonate, sodium methoxide or sodium hydride can be added as an additive. The reaction temperature is from 0° C. to reflux temperature, and the reaction time is from 10 minutes to 100 hours.

[Production Method 5] Production Method for Compound (4-2), (4.4) or (4-6)

[Chemical Formula 21]

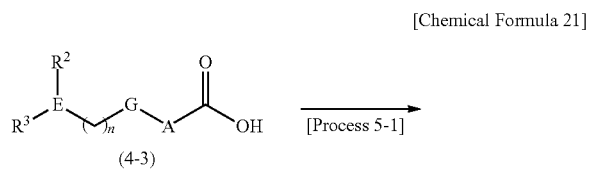

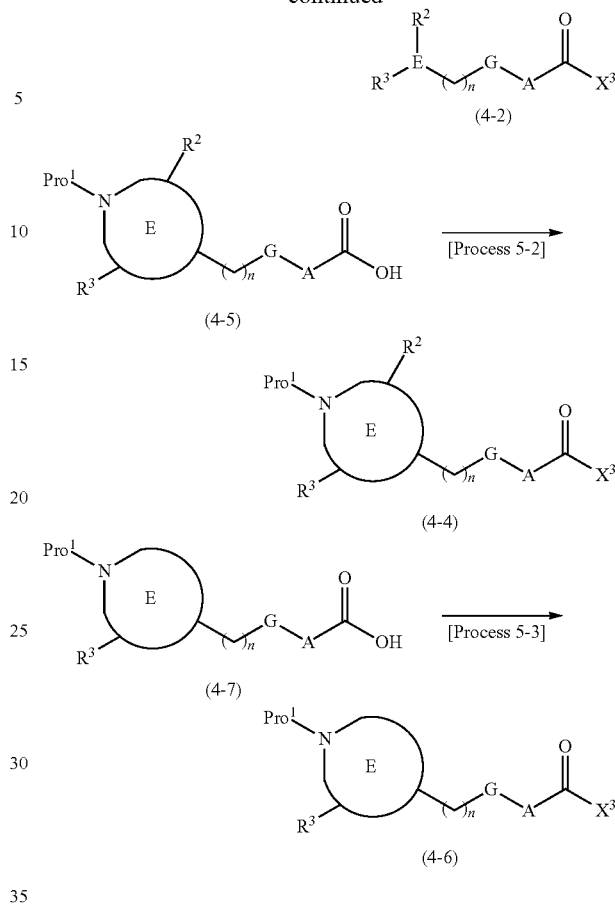

In the above formula, $R^2$, $R^3$, A, E, G and n represent the same as defined above; $X^3$ represents a halogen atom such as a chlorine atom or a bromine atom; and $Pro^1$ represents a known protective group for a nitrogen atom such as a tert-butoxycarbonyl group.

Compounds (4-3), (4-5) and (4-7) can be commercially available products, or can be produced from commercially available products by known methods. Alternatively, these compounds can be also produced by methods described in production examples in any of the examples described below or a method described in [Production Method 7], [Production Method 9] or the like.

[Process 5-1, 5-2 or 5-3]

In this process, the compound (4-3), (4-5) or (4-7) is reacted to give the compound (4-2), (4-4) or (4-6) respectively. A solvent used in this reaction is not especially limited as long as it dissolves a starting material to some extent and does not inhibit the reaction, and for example, a halogenated hydrocarbon solvent such as dichloromethane, an ether solvent such as tetrahydrofuran, a nitrile solvent such as acetonitrile, or a mixed solvent of these can be used. In this reaction, an acid halide such as oxalyl chloride or an inorganic halogen compound such as thionyl chloride is used in an amount of 1 to 10 equivalents to the compound (4-3), (4-5) or (4-7), and 1 to 10 equivalents of a base such as benzotriazole can be added as an additive. Furthermore, a catalytic amount of N,N-dimethylformamide, N-methylpyrrolidinone or the like can be added. The reaction temperature is from −20° C. to reflux temperature, and the reaction time is from 10 minutes to 24 hours.

[Production Method 6] Production Method for Compound (4-1)

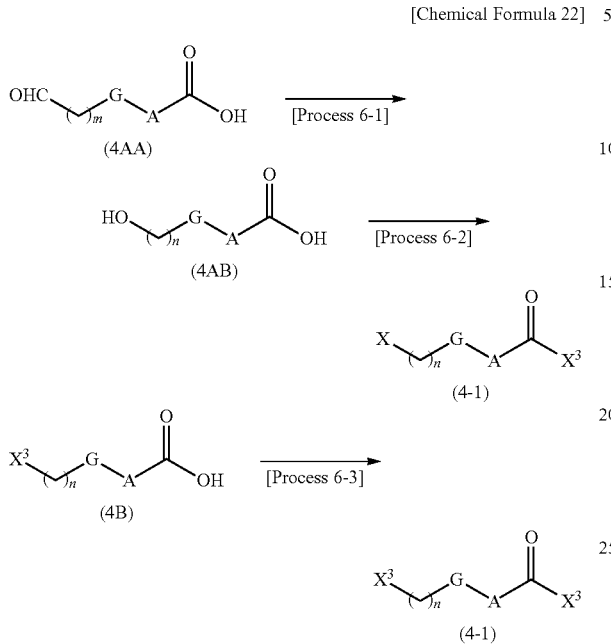

[Production Method 7] Production Method for Compound (4-3g)

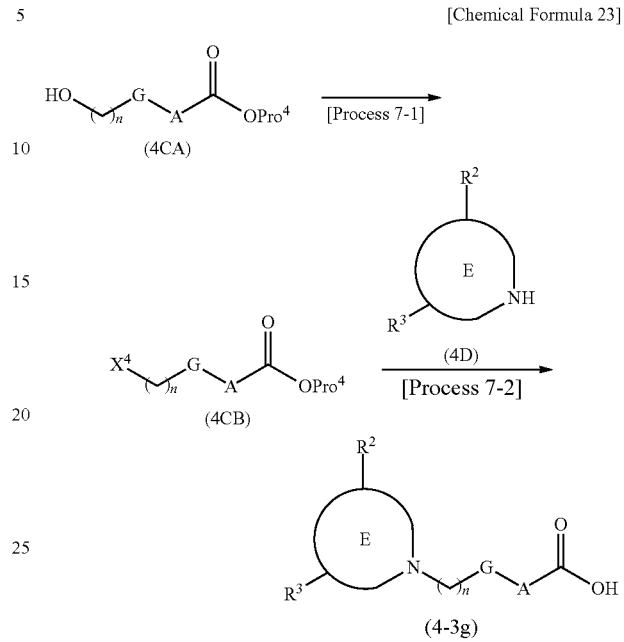

In the above formula, A, G and n represent the same as defined above; m represents 0 or 1; and $X^3$ represents a halogen atom such as a chlorine atom or a bromine atom.

Compounds (4AA), (4AB) and (4B) can be commercially available products, or can be produced from commercially available products by known methods. Alternatively, these compounds can be produced by methods described in production examples in any of the examples described below or the like.

[Process 6-1]

In this process, the compound (4AA) is reacted to give the compound (4AB). A solvent used in this reaction is not especially limited as long as it dissolves a starting material to some extent and does not inhibit the reaction, and for example, an ether solvent such as tetrahydrofuran, an alcohol solvent such as ethanol, or a mixed solvent of these can be used. In this reaction, a reducing reagent such as sodium borohydride can be used in an amount of 1 to 10 equivalents to the compound (4AA). The reaction temperature is from −20° C. to reflux temperature, and the reaction time is from 10 minutes to 24 hours.

[Process 6-2 or 6-3]

In this process, the compound (4AB) or (4B) is reacted to give the compound (4-1). A solvent used in this reaction is not especially limited as long as it dissolves a starting material to some extent and does not inhibit the reaction, and for example, a halogenated hydrocarbon solvent such as dichloromethane, an ether solvent such as tetrahydrofuran, a nitrite solvent such as acetonitrile, or a mixed solvent of these can be used. In this reaction, an acid halide such as oxalyl chloride or an inorganic halogen compound such as thionyl chloride can be used in an amount of 1 to 10 equivalents to the compound (4AB) or (4B), and a catalytic amount of N,N-dimethylfoimamide, N-methylpyrrolidinone or the like can be added as an additive. The reaction temperature is from 0° C. to reflux temperature, and the reaction time is from 10 minutes to 24 hours.

In the above formula, $R^2$, $R^3$, A, E, G and n represent the same as defined above; $X^4$ represents a halogen atom such as a chlorine atom, a bromine atom or an iodine atom, or a leaving group of sulfonate such as methanesulfonate, p-toluenesulfonate or trifluoromethanesulfonate; and $Pro^4$ represents a known protective group for carboxylic acid such as an ethyl group.

A compound (4CB) can be a commercially available product, or can be produced from a commercially available product by a known method. Alternatively, it can be produced by a method described in a production example in any of the examples described below or the like.

A compound (4CA) or (4D) can be a commercially available product, or can be produced from a commercially available product by a known method.

[Process 7-1]

In this process, the compound (4CA) is reacted with a halogenating reagent to give the compound (4CB) or reacted with a sulfonating reagent to give the compound (4CB). A solvent used in this reaction is not especially limited as long as it dissolves a starting material to some extent and does not inhibit the reaction, and for example, an ether solvent such as tetrahydrofuran, a nitrile solvent such as acetonitrile, a halogenated hydrocarbon solvent such as dichloromethane, an amide solvent such as N,N-dimethylformamide or N-methylpyrrolidinone, water, or a mixed solvent of these can be used. In the halogenation reaction, an excessive amount of hydrohalic acid such as hydrochloric acid or hydrobromic acid can be used. In this case, an inorganic chloride such as zinc chloride or lithium bromide, a phase transfer catalyst or the like can be used. Besides, this reaction can be performed by using, as the halogenating reagent, a halogenated phosphorus compound such as phosphorus trichloride. In this case, N,N-dimethylformamide can be acted to be used as an iminium salt. Alternatively, a combination of an organic phosphorus compound, such as triphenylphosphine, and a carbon tetrahalide can be used as the halogenating reagent.

Alternatively, a halogenating reagent such as thionyl chloride can be used. In this case, a base such as pyridine can be used as an additive. The halogenating reagent can be used in an amount of 1 to 10 equivalents. In the sulfonation reaction, a sulfonating reagent such as p-toluenesulfonylchloride can be used in an amount of 1 to 10 equivalents, and a base such as triethylamine or pyridine can be used in an amount of 1 to 10 equivalents as an additive. The reaction temperature is from 0° C. to reflux temperature, and the reaction time is from 10 minutes to 24 hours.

[Process 7-2]

In this process, the compound (4CB) is reacted with the compound (4D) to give the compound (4-3g). A solvent used in this reaction is not especially limited as long as it dissolves a starting material to some extent and does not inhibit the reaction, and for example, an ether solvent such as tetrahydrofuran, an amide solvent such as N,N-dimethylformamide or N-methylpyrrolidinone, dimethylsulfoxide, or a mixed solvent of these can be used. In this reaction, an organic base such as triethylamine or an inorganic base such as cesium carbonate can be used for condensation. The compound (4D) is used in an amount of 1 to 10 equivalents to the compound (4-CB), and the base can be added in an amount of 0 to 10 equivalents. The reaction temperature is from 0° C. to reflux temperature, and the reaction time is from 10 minutes to 24 hours. $Pro^4$ can be deprotected by a known deprotection method for carboxylic acid.

[Production Method 8] Production Method for Compound (4CB-1)

[Chemical Formula 24]

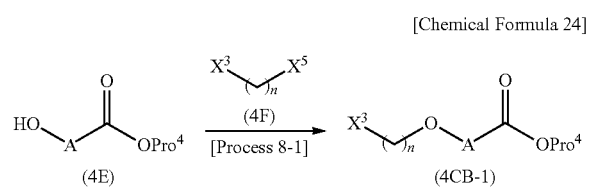

In the above formula, A and n represent the same as defined above; $X^3$ represents a halogen atom such as a chorine atom or a bromine atom; $X^5$ represents a halogen atom such as a bromine atom or an iodine atom; and $Pro^4$ represents a known protective group for carboxylic acid such as an ethyl group.

Compounds (4E) and (4F) can be commercially available products, or can be produced from commercially available products by known methods.

[Process 8-1]

In this process, the compound (4E) is reacted with the compound (4F) to give the compound (4CB-1). A solvent used in this reaction is not especially limited as long as it dissolves a starting material to some extent and does not inhibit the reaction, and for example, an ether solvent such as tetrahydrofuran, an amide solvent such as N,N-dimethylformamide or N-methylpyrrolidinone, dimethylsulfoxide, or a mixed solvent of these can be used. In this reaction, an organic base such as triethylamine or an inorganic base such as potassium carbonate can be used for condensation. The compound (4F) is used in an amount of 1 to 10 equivalents to the compound (4E), and the base can be added in an amount of 1 to 10 equivalents. The reaction temperature is from 0° C. to reflux temperature, and the reaction time is from 10 minutes to 24 hours. $Pro^4$ can be also deprotected by a known deprotection method for carboxylic acid.

[Production Method 9] Production Method for Compound (4-3b), (4-5a), (4-5b), (4-5c), (4-5d), (4-5e) or (4-5f)

[Production Method 9-1] Production Method for Compound (4-3b)

[Chemical Formula 25]

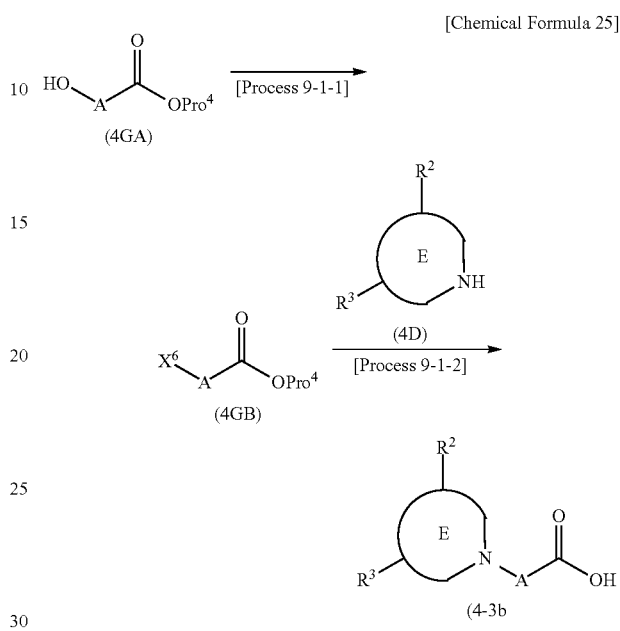

In the above formula, $R^2$, $R^3$, A and E represent the same as defined above; $X^6$ represents a halogen atom such as a chlorine atom, a bromine atom or an iodine atom, or a leaving group of sulfonate such as trifluoromethanesulfonate; and $Pro^4$ represents a known protective group for carboxylic acid such as an ethyl group.

Compounds (4GA) and (4GB) can be commercially available products, or can be produced from commercially available products by known methods. Alternatively, the compound (4GB) can be produced by a method described in a production example in any of the examples described below or the like.

[Process 9-1-1]

In this process, the compound (4GA) is reacted with a halogenating reagent to give the compound (4GB) or reacted with a sulfonating reagent to give the compound (4GB). A solvent used in this reaction is not especially limited as long as it dissolves a starting material to some extent and does not inhibit the reaction, and for example, an ether solvent such as tetrahydrofuran, a halogenated hydrocarbon solvent such as dichloromethane, an amide solvent such as N,N-dimethylformamide or N-methylpyrrolidinone, a nitrile solvent such as acetonitrile, or a mixed solvent of these can be used. In the halogenation reaction, a phosphorus halide such as phosphorus pentabromide or a halogenating reagent such as triphenylphosphinedibromide can be used in an amount of 1 to 5 equivalents. In the sulfonation reaction, a sulfonating reagent such as trifluoromethanesolfonic anhydride can be used in an amount of 1 to 5 equivalents, and a base such as triethylamine or pyridine can be used, as an additive, in an amount of 1 to 10 equivalents. The reaction temperature is from 20° C. to reflux temperature, and the reaction time is from 10 minutes to 24 hours.

[Process 9-1-2]

In this process, the compound (4GB) is reacted with the compound (4D) to give a compound (4-3b). A solvent used in this reaction is not especially limited as long as it dissolves a starting material to some extent and does not inhibit the reaction, and for example, an ether solvent such as tetrahydrofuran, an amide solvent such as N,N-dimethylformamide or N-methylpyrrolidinone, dimethylsulfoxide, or a mixed solvent of these can be used. In this reaction, an organic base such as triethylamine or an inorganic base such as cesium carbonate can be used for condensation. The compound (4D) can be used in an amount of 1 to 10 equivalents to the compound (4GB), and the base can be added in an amount of 0 to 10 equivalents. The reaction temperature is from 0° C. to reflux temperature, and the reaction time is from 10 minutes to 24 hours. Furthermore, in this reaction, a heavy metal such as copper can be added, and an organometallic catalyst containing palladium and an organophosphorus ligand can be also added. $Pro^4$ can be deprotected by a known deprotection method for carboxylic acid.

[Production method 9-2] Production Method for Compound (4-5a)

[Chemical Formula 26]

In the above formula, $R^2$, $R^3$, A, E and n represent the same as defined above; $Pro^1$ represents a known protective group for a nitrogen atom such as a tert-butoxycarbonyl group; and $Pro^s$ represents a known protective group for carboxylic acid such as an ethyl group or a benzyl group.

Compounds (4H) and (4I) can be commercially available products, or can be produced from commercially available products by known methods.

[Process 9-2-1]

In this process, the compound (4H) and the compound (4I) are reacted with each other to give a compound (4-5a). A solvent used in this reaction is not especially limited as long as it dissolves a starting material to some extent and does not inhibit the reaction, and for example, an ether solvent such as tetrahydrofuran, an aromatic hydrocarbon solvent such as toluene, a halogenated hydrocarbon solvent such as dichloromethane, an ester solvent such as ethyl acetate, or a mixed solvent of these can be used. In this reaction, the compound (4H) can be used in an amount of 0.5 to 2 equivalents to the compound (4I). In this reaction, azodicarboxylate such as diisopropyl azodicarboxylate, and triphenylphosphine can be used in an amount of 1 to 5 equivalents respectively to the compounds (4H) and (4I). The reaction temperature is from −20° C. to reflux temperature, and the reaction time is from 10 minutes to 24 hours. $Pro^5$ can be deprotected by a known deprotection method for carboxylic acid.

Production Method 9-31 Production Method for Compound (4-5b) or (4-5c)

[Chemical Formula 27]

In the above formula, $R^2$, $R^3$, A and E represent the same as defined above; $X^5$ represents a halogen atom such as a bromine atom or an iodine atom; $X^7$ represents a halogen atom such as a bromine atom or an iodine atom, or a leaving group of sulfonate such as methanesulfonate or trifluoromethanesulfonate; M represents a leaving group of borate ester or the like; $Pro^1$ represents a known protective group for a nitrogen atom such as a tert-butoxycarbonyl group; and $Pro^5$ represents a known protective group for carboxylic acid such as an ethyl group or a benzyl group, and carboxylic acid may be or may not be protected in this reaction.

Compounds (4J), (4K) and (4L) can be commercially available products, or can be produced from commercially available products by known methods.

[Process 9-3-1]

In this process, the compound (4J) and the compound (4K) are reacted with each other to give a compound (4-5b). A solvent used in this reaction is not especially limited as long as it dissolves a starting material to some extent and does not inhibit the reaction, and for example, an ether solvent such as tetrahydrofuran, an aromatic hydrocarbon solvent such as toluene, an amide solvent such as N,N-dimethylformamide or N-methylpynolidinone, or a mixed solvent of these can be used. In this reaction, the compound (4K) can be used in an amount of 0.5 to 2 equivalents to the compound (4J). In this reaction, a palladium complex compound containing an organic phosphorus compound as a ligand can be used as a catalyst. The catalyst can be prepared within the reaction system. In this reaction, a zinc powder can be used in an amount of 0.5 to 2 equivalents to the compound (4J). Besides, a copper halide, a dehalogenated alkyl compound, a halogenated organic silicon compound or the like can be added as an additive. The reaction temperature is from 0° C. to reflux temperature, and the reaction time is from 10 minutes to 24 hours. $Pro^5$ can be deprotected by a known deprotection method for carboxylic acid.

[Process 9-3-2]

In this process, the compound (4J) and the compound (4L) are reacted with each other to give a compound (4-5c). A solvent used in this reaction is not especially limited as long as it dissolves a starting material to some extent and does not inhibit the reaction, and for example, an ether solvent such as 1,4-dioxane, an aromatic hydrocarbon solvent such as toluene, an alcohol solvent such as ethanol, an amide solvent such as N,N-dimethylformamide or N-methylpyrrolidinone, or a mixed solvent of these can be used. In this reaction, the compound (4L) can be used in an amount of 0.5 to 2 equivalents to the compound (4J). In this reaction, a palladium complex compound containing an organic phosphorus compound as a ligand can be used as a catalyst. The catalyst can be prepared within the reaction system. In this reaction, a base such as sodium carbonate can be used in an amount of 1 to 10 equivalents to the compound (4J). The reaction temperature is from 0° C. to reflux temperature, and the reaction time is from 10 minutes to 24 hours.

[Process 9-3-3]

In this process, the compound (4-5c) is reduced and deprotected to give the compound (4-5b). A solvent used in this reaction is not especially limited as long as it dissolves a starting material to some extent and does not inhibit the reaction, and for example, an ether solvent such as tetrahydrofuran, an ester solvent such as ethyl acetate, an alcohol solvent such as ethanol, an amide solvent such as N,N-dimethylformamide or N-methylpyrrolidinone, or a mixed solvent of these can be used. In this reaction, a catalytic reduction catalyst such as palladium-carbon can be used in an amount of 0.001 to 1 equivalent to the compound (4-5c).

Besides, the reaction can be performed in a hydrogen atmosphere at a pressure ranging from normal pressure to 20 atm. The reaction temperature is from 0° C. to reflux temperature, and the reaction time is from 10 minutes to 24 hours. $Pro^5$ can be deprotected by a known deprotection method for carboxylic acid.

[Production Method 9-4] Production Method for Compound (4-5d) or (4-5e)

[Chemical Formula 28]

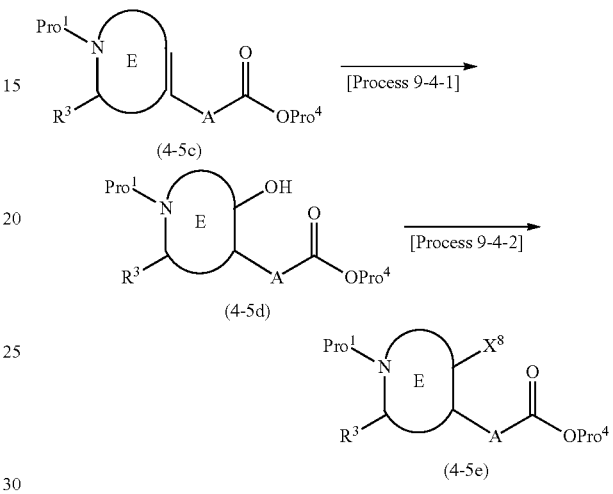

In the above formula, $R^3$, A and E represent the same as defined above; $X^8$ represents a halogen atom such as a fluorine atom; $Pro^1$ represents a known protective group for a nitrogen atom such as a tert-butoxycarbonyl group; and $Pro^4$ represents a known protective group for carboxylic acid such as an ethyl group, and in this reaction, carboxylic acid may be or may not be protected.

The compound (4-5c) can be a commercially available product, or can be produced from a commercially available product by a known method. Alternatively, it can be produced by a method described in a production example in any of the examples described below or the like.

[Process 9-4-1]

In this process, the compound (4-5c) is reacted to give a compound (4-5d). A solvent used in this reaction is not especially limited as long as it dissolves a starting material to some extent and does not inhibit the reaction, and for example, an ether solvent such as tetrahydrofuran can be used. In this reaction, a borane complex compound such as a borane-methyl sulfide complex can be used in an amount of 1 to 2 equivalents to the compound (4-5c). The reaction temperature is from −20° C. to reflux temperature, and the reaction time is from 10 minutes to 24 hours. Subsequently, by using a sodium hydroxide aqueous solution in an amount of 1 to 10 equivalents and a hydrogen peroxide solution in an amount of 1 to 10 equivalents, a hydroxyl group can be obtained. The reaction temperature is from 0° C. to reflux temperature, and the reaction time is from 10 minutes to 24 hours.

[Process 9-4-2]

In this process, the hydroxyl group of the compound (4-5d) is substituted by halogen to give a compound (4-5e). A solvent used in this reaction is not especially limited as long as it dissolves a starting material to some extent and does not inhibit the reaction, and for example, a halogenated hydrocarbon solvent such as a dichloromethane, an ether solvent such as tetrahydrofuran, an ester solvent such as ethyl acetate, an amide solvent such as N,N-dimethylformamide or N-methylpyrrolidinone, or a mixed solvent of these can be used. In this reaction, a halogenating reagent such as [bis-(2-methoxyethyl)-amino]sulfur trifluoride can be used in an amount of 1 to 10 equivalents to the compound (4-5d). The reaction temperature is from 0° C. to reflux temperature, and the reaction time is from 10 minutes to 24 hours. Pro⁴ can be deprotected by a known deprotection method for carboxylic acid,

[Production Method 9-5] Production Method for Compound (4-5f)

[Chemical Formula 29]

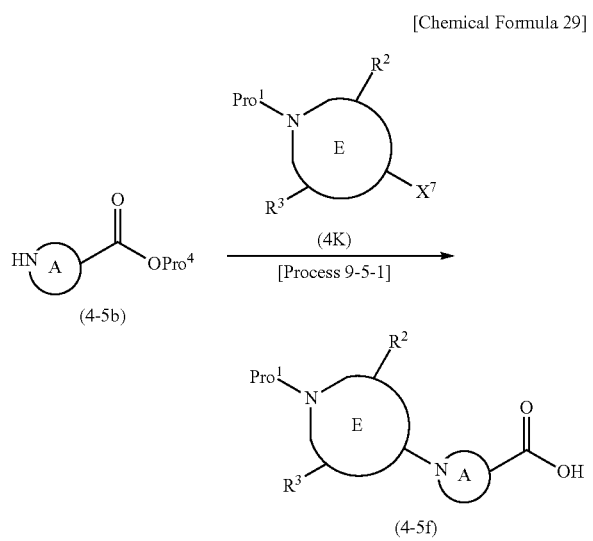

In the above formula, $R^2$, $R^3$, A and E represent the same as defined above; $X^7$ represents a halogen atom such as a bromine atom or an iodine atom, or a leaving group of sultanate such as methanesulfonate or trifluoromethanesulfonate; Pro¹ represents a known protective group for a nitrogen atom such as a tert-butoxycarbonyl group; and Pro⁴ represents a known protective group for carboxylic acid such as an ethyl group, and in this reaction, carboxylic acid may be or may not be protected.

The compounds (4-5b) and (4K) can be commercially available products, or can be produced from commercially available products by known methods. Alternatively, these compounds can be produced by methods described in production examples in any of the examples described below or the like.

[Process 9-5-1]

In this process, the compound (4-5b) and the compound (4K) are reacted with each other to give a compound (4-5f). A solvent used in this reaction is not especially limited as long as it dissolves a starting material to some extent and does not inhibit the reaction, and for example, an ether solvent such as tetrahydrofuran, an amide solvent such as N,N-dimethylformamide or N-methylpyrrolidinone, or a mixed solvent of these can be used. In this reaction, the compound (4K) can be used in an amount of 0.5 to 2 equivalents to the compound (4-5b). Besides, a base such as a sodium hydride or potassium tert-butoxide can be used in an amount of 1 to 5 equivalents to the compound (4-5b). The reaction temperature is from −20° C. to reflux temperature, and the reaction time is from 10 minutes to 24 hours. Pro⁴ can be deprotected by a known deprotection method for carboxylic acid.

[Production Method 10] Production Method for Compound (4K)

[Chemical Formula 30]

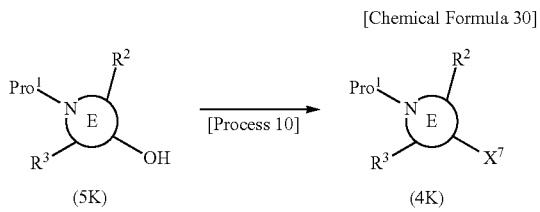

In the above formula, $R^2$, $R^3$ and E represent the same as defined above; $X^7$ represents a halogen atom such as a bromine atom or an iodine atom, or a leaving group of sulfonate such as methanesulfonate or trifluoromethanesulfonate; and Pro¹ represents a known protective group for a nitrogen atom such as a tert-butoxycarbonyl group.

A compound (5K) can be a commercially available product, or can be produced from a commercially available product by a known method.

[Process 10]

In this process, the compound (5K) is reacted with a halogenating reagent to give the compound (4K), or reacted with a sulfonating reagent to give the compound (4K). A solvent used in this reaction is not especially limited as long as it dissolves a starting material to some extent and does not inhibit the reaction, and for example, an ether solvent such as tetrahydrofuran, a halogenated hydrocarbon solvent such as dichloromethane, an amide solvent such as N,N-dimethylformamide or N-methylpyrrolidinone, a nitrile solvent such as acetonitrile, or a mixed solvent of these can be used. In the halogenation reaction, a phosphorus halide such as phosphorus pentabromide or a halogenating reagent such as triphenylphosphinedibromide can be used in an amount of 1 to 5 equivalents. In the sulfonation reaction, a sulfonating reagent such as methanesulfonyl chloride or trifluoromethanesulfonic anhydride can be used in an amount of 1 to 5 equivalents, and a base such as triethylamine or pyridine can be used, as an additive, in an amount of 1 to 10 equivalents. The reaction temperature is from −20° C. to reflux temperature, and the reaction time is from 10 minutes to 24 hours.

EXAMPLES

Compounds according to the present invention can be produced by methods described in Production Examples and Examples described below, for example. However, these methods are mere examples, and therefore the compounds according to the present invention are not limited to those produced by specific examples described below in any cases.

In Production Examples and Examples, Silica gel 60 (Kanto Chemicals) or Presep Silica Gel (WAKO) was used as a purification silica gel used for silica gel column chromatography unless otherwise stated. In addition, NH silica gel (Fuji Silysia Chemical LTD.) or Hi-Hash Column Amino (YAMAZENE CORPORATION) was used as a purification silica gel used for NH silica gel column chromatography, and TLC Plates NH (20 cm×20 cm, Fuji Silysia Chemical LTD.) was used as a thin-layer plate used for NH silica gel TLC (Thin Layer Chromatography).

Varian Mercury 400, Varian Mercury Plus 400, or Varian INOVA 500 was used for the measurement of proton nuclear magnetic resonance spectra, and the proton nuclear magnetic resonance spectra were measured at 400 MHz unless otherwise stated. Chemical shifts of proton nuclear magnetic resonance spectra are recorded in the unit of δ (ppm) with respect to tetramethylsilane and coupling constants are recorded in the unit of Hertz (Hz). Abbreviations for splitting patterns are as follows: s: singlet; d: doublet; I: triplet; q: quartet; quin: quintet; spt: septet; m: multiplet; and brs: broad singlet.

Waters Micromass ZQ 2000, Waters SQ Detector 2, or Thermo Fisher Scientific LCQ was used for the measurement of mass spectra. For the ionization method, an electrospray ionization (ESI) method was used for the measurement.

In Production Examples and Examples, commercially available products were appropriately used as commercially available compounds. In the description below, the term "BOC" refers to tert-butoxycarbonyl.

Example 1

6-Methoxy-N-methyl-5-((2-(4-(piperidin-4-yl)benzamide)pyridin-4-yl)oxy)-1H-indole-1-carboxamide

[Chemical Formula 31]

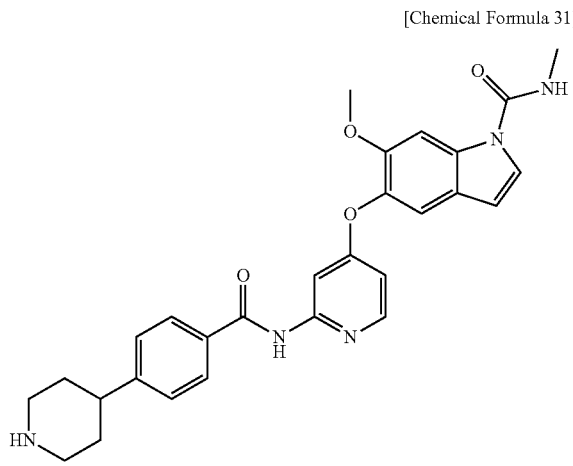

tert-Butyl 4-(4-((4-((6-methoxy-1-(methylcarbamoyl)-1H-indol-5-yl)oxy)pyridin-2-yl)carbamoyl)phenyl)piperidine-1-carboxylate described in Production Example 1-8 (3.42 g, 5.70 mmol) was dissolved in dichloromethane (45 mL), and trifluoroacetic acid (15 mL) was added at 0° C. The mixture was stirred at room temperature for 60 minutes and then concentrated under vacuum, and then the residue was dissolved in dichloromethane-triethylamine, and the resultant was purified with NH silica gel column chromatography (ethyl acetate:methanol=97:3-4:1). The target fraction was concentrated under vacuum and then the precipitate was collected by filtration and washed with diethyl ether and ethyl acetate to obtain the title compound (2.61 g, 92%).

¹H-NMR Spectrum (CDCl₃) δ (ppm): 1.55-1.70 (2H, m), 1.78-1.88 (2H, m), 2.62-2.80 (3H, m), 3.06 (3H, d, J=4.8 Hz), 3.15-3.24 (2H, m), 3.86 (3H, s), 5.52-5.61 (1H, m), 6.54 (1H, d, J=3.3 Hz), 6.60 (1H, dd, J=5.7, 2.4 Hz), 7.23 (1H, d, J=3.7 Hz), 7.28-7.35 (3H, m), 7.80 (2H, d, J=8.4 Hz), 7.91 (1H, d, J=2.2 Hz), 8.03 (1H, s), 8.10 (1H, d, J=5.9 Hz), 8.53 (1H, brs).

The starting material tert-butyl 4-(4-((4-((6-methoxy-1-(methylcarbamoyl)-1H-indol-5-yl)oxy)pyridin-2-yl)carbamoyl)phenyl)piperidine-1-carboxylate was synthesized by the following method.

Production Example 1-1

(E)-2-(Benzyloxy)-1-methoxy-4-(2-nitrovinyl)benzene

[Chemical Formula 32]

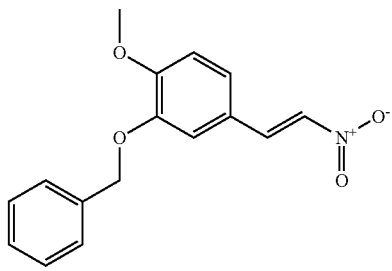

Commercially available 3-benzyloxy-4-methoxybenzaldehyde (30 g, 124 mmol) was dissolved in acetic acid (100 mL), then ammonium acetate (10.8 g, 140 mmol) and nitromethane (16.8 mL, 310 mmol) were added under nitrogen atmosphere at room temperature, and the mixture was heated and stirred at 130° C. for 2 hours and 20 minutes. The mixture was cooled to room temperature, then the precipitate was collected by filtration and washed with ethanol to obtain the title compound (28.5 g, 81%).

¹H-NMR Spectrum (CDCl₃) δ (ppm): 3.95 (3H, s), 5.18 (2H, s), 6.93 (1H, d, J=8.1 Hz), 7.03 (1H, d, J=2.2 Hz), 7.17 (1H, dd, J=8.4, 2.2 Hz), 7.30-7.47 (6H, m), 7.91 (1H, d, J=13.5 Hz).

Production Example 1

(E)-1-(Benzyloxy)-2-methoxy-4-nitro-5-(2-nitrovinyl)benzene

[Chemical Formula 33]

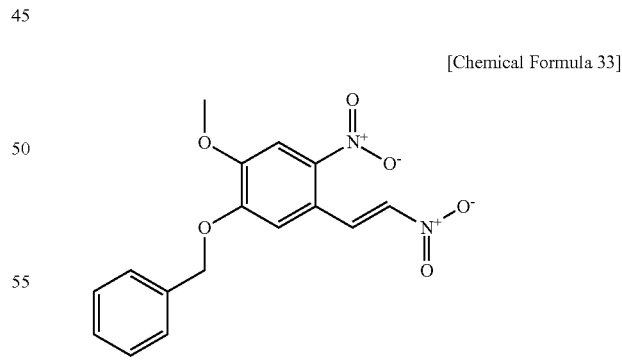

69% Nitric acid (10 mL, 155 mmol) was added to a mixture of (E)-2-(benzyloxy)-1-methoxy-4-(2-nitrovinyl)benzene described in Production Example 1-1 (10 g, 35.1 mmol) and acetic acid (70 mL) under nitrogen atmosphere at 25° C., and the mixture was stirred at 40° C. for 3 hours. The reaction mixture was poured onto ice and the precipitate was collected by filtration and then washed with ethanol to obtain the title compound (10.5 g, 91%).

$^1$H-NMR Spectrum (CDCl$_3$) δ (ppm): 4.02 (3H, s), 5.28 (2H, s), 6.93 (1H, s), 7.22 (1H, d, J=13.5 Hz), 7.35-7.48 (5H, m), 7.75 (1H, s), 8.58 (1H, d, J=13.2 Hz).

Production Example 1-3

6-Methoxy-1H-indol-5-ol

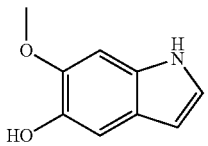

[Chemical Formula 34]

(E)-1-(Benzyloxy)-2-methoxy-4-nitro-5-(2-nitrovinyl) benzene described in Production Example 1-2 (9.4 g, 28.5 mmol) was suspended in methanol (300 mL), then 10% palladium-carbon (water content, 50%) (3.09 g) was added, and the mixture was stirred under hydrogen atmosphere for 3 hours. The catalyst was filtered off with celite and washed with methanol. The filtrate was concentrated under vacuum and the resultant was purified with silica gel column chromatography (n-heptane:ethyl acetate=3:1-3:7). The target fraction was concentrated under vacuum to obtain the title compound (2.12 g, 46%).

$^1$H-NMR Spectrum (CDCl$_3$) δ (ppm): 3.92 (3H, s), 5.45 (1H, s), 6.39-6.44 (1H, m), 6.88 (1H, s), 7.08 (1H, t, J=2.9 Hz), 7.14 (1H, s), 7.95 (1H, brs).

Production Example 1-4

4-((6-Methoxy-1H-indol-5-yl)oxy)pyridin-2-amine

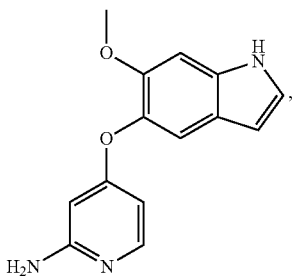

[Chemical Formula 35]

6-Methoxy-1H-indol-5-ol described in Production Example 1-3 (2.86 g, 17.6 mmol), N-(4-chloropyridin-2-yl) acetamide described in Production Example 1-5 (8.98 g, 52.7 mmol), and potassium tert-butoxide (3.94 g, 35.1 mmol) were dissolved in dimethylsulfoxide (45 mL) under nitrogen atmosphere and the mixture was heated and stirred at 160° C. for 12.5 hours. The reaction liquid was cooled to room temperature, and water and ethyl acetate were added for partition. The aqueous layer was extracted with ethyl acetate twice, and the combined organic layer was washed with water twice and then with a saturated saline solution. The organic layer was dried over anhydrous magnesium sulfate. The drying agent was filtered off; then the filtrate was concentrated under vacuum, and the resultant was purified with NH silica gel column chromatography (n-heptane:ethyl acetate=1:1-0:1-ethyl acetate:methanol=99:1-9:1). The mixture fraction was concentrated under vacuum, the resultant was purified with NH silica gel column chromatography (n-heptane:ethyl acetate=1:1-0:1-ethyl acetate:methanol=99:1-9:1), and then the target fraction was concentrated under vacuum to obtain a crude product (3.88 g).

The crude product (3.88 g) was dissolved in methanol (75 mL), 28% sodium methoxide (14 mL, 68.6 mmol) was added under nitrogen atmosphere at room temperature, and then the mixture was heated and stirred at 70° C. for 5.5 hours. The reaction mixture was cooled to room temperature and then water and ethyl acetate were added for partition. The aqueous layer was extracted with ethyl acetate once and the combined organic layer was washed with a saturated saline solution. The organic layer was dried over anhydrous magnesium sulfate. The drying agent was filtered off, the filtrate was concentrated under vacuum, and then the resultant was purified with NH silica gel column chromatography (n-heptane:ethyl acetate=1:3-0:1-ethyl acetate:methanol=99:1-19:1). The target fraction was concentrated under vacuum to obtain the title compound (1.97 g, 44%).

$^1$H-NMR Spectrum (CDCl$_3$) δ (ppm): 3.82 (3H, s), 4.29 (2H, brs), 5.89-5.92 (1H, m), 6.30 (1H, dd, J=5.9, 22 Hz), 6.49 (1H, ddd, J=3.2, 2.2, 0.9 Hz), 7.01 (1H, s), 7.17 (1H, dd, J=3.1, 2.4 Hz), 733 (1H, s), 7.89 (1H, d, J=6.0 Hz), 8.19 (1H, bis).

Production Example 1-5

N-(4-Chloropyridin-2-yl)acetamide

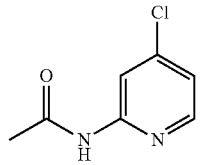

[Chemical Formula 36]

Commercially available 2-amino-4-chloropyridine (50 g, 389 mmol) was dissolved in acetic anhydride (500 mL), triethylamine (271 mL, 1.94 mol) was added at 20° C., and the mixture was stirred at 60° C. for 12 hours. The mixture was cooled to 25° C. and then the solvent was evaporated. The residue was purified with silica gel column chromatography (n-heptane:ethyl acetate=4:1-1:1) and then the target fraction was concentrated under vacuum to obtain the title compound (66 g, 99%).

$^1$H-NMR Spectrum (CDCl$_3$) δ (ppm): 2.21 (3H, s), 7.05 (1H, dd, J=5.4, 1.9 Hz), 8.15 (1H, d, J=5.4 Hz), 8.30 (2H, brs).

Production Example 1-6

5-((2-Aminopyridin-4-yl)oxy)-6-methoxy-N-methyl-1H-indole-1-carboxamide

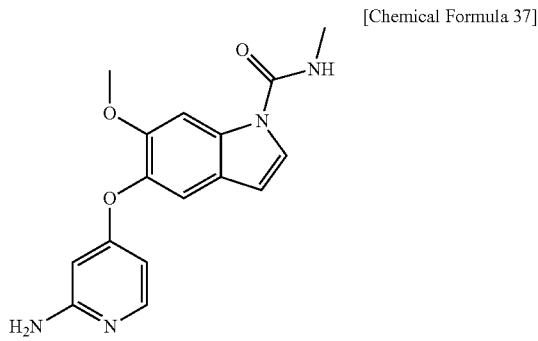 [SMILES: CNC(=O)n1ccc2cc(Oc3ccnc(N)c3)c(OC)cc21]

[Chemical Formula 37]

4-((6-Methoxy-1H-indol-5-yl)oxy)pyridin-2-amine described in Production Example 1-4 (1.7 g, 6.66 mmol) was dissolved in N,N-dimethylformamide (25 mL), 50-72% oily sodium hydride (424 mg) was added under nitrogen atmosphere at 0° C., and then the mixture was stirred at room temperature for 45 minutes. The mixture was cooled to 0° C. again, phenyl methylcarbamate described in Production Example 1-7 (1.64 g, 10.8 mmol) was added, and the resultant was stirred at room temperature for 3 hours. A saturated aqueous ammonium chloride solution, water, and ethyl acetate were added to the reaction mixture for partition. The aqueous layer was extracted with ethyl acetate once and the combined organic layer was washed with water and a saturated saline solution. The organic layer was dried over anhydrous magnesium sulfate. The drying agent was filtered off, then the filtrate was concentrated under vacuum, and then the resultant was purified with NH silica gel column chromatography (n-heptane:ethyl acetate=1:3-0:1-ethyl acetate:methanol=99:1-19:1). The target fraction was concentrated under vacuum and then the precipitate was collected by filtration and washed with ethyl acetate to obtain the title compound (1.37 g, 66%). The mixture fraction was concentrated under vacuum and purified with NH silica gel column chromatography (n-heptane:ethyl acetate=3:7-0:1-ethyl acetate:methanol—99:1-19:1). The target fraction was concentrated under vacuum, and then the precipitate was collected by filtration and washed with ethyl acetate twice to obtain the title compound (387 mg, 19%).

$^1$H-NMR Spectrum (CDCl$_3$) δ (ppm): 3.07 (3H, d, J=4.6 Hz), 3.86 (3H, s), 4.31 (2H, bis), 5.44-5.56 (1H, m), 5.89 (1H, d, J=2.2 Hz), 6.27 (1H, dd, J=5.9, 2.2 Hz), 6.55 (1H, d, J=3.7 Hz), 7.23 (1H, d, J=3.7 Hz), 7.25-7.28 (1H, m), 7.89 (1H, d, J=5.9 Hz), 8.01 (1H, brs).

The reagent phenyl methylcarbamate was synthesized by the following method.

Production Example 1-7

Phenyl methylcarbamate

[Chemical Formula 38]

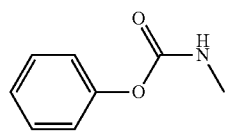

A mixture of commercially available methylamine hydrochloride (50 g, 0.74 mol), pyridine (124 mL, 1.53 mol), and N,N-dimethylformamide (500 mL) was stirred at 5° C., and commercially available phenyl chlorocarbamate (94 mL, 0.75 mol) was added dropwise over 2 hours. After the dripping was complete, the mixture was stirred under nitrogen atmosphere at room temperature for 16 hours. The reaction mixture was added to ice water (2 L) and extracted with ethyl acetate (1.5 L) twice. The organic layer was washed with water (1 L) and a saturated saline solution (300 mL). The organic layer was dried over anhydrous magnesium sulfate and then the solvent was evaporated. n-Heptane and ethyl acetate were added to the concentrated residue and the precipitate was collected by filtration and washed with n-heptane and tert-butyl methyl ether to obtain the title compound (74.2 g, 66%).

$^1$H-NMR Spectrum (CDCl$_3$) δ (ppm): 2.90 (3H, d, J=4.9 Hz), 4.95 (1H, brs), 7.08-7.16 (2H, m), 7.16-7.24 (1H, m), 7.31-7.41 (2H, m)

Production Example 1-8 tert-Butyl 4-(4-((4-((6-methoxy-1-(methylcarbamoyl)-1H-indol-5-yl)oxy)pyridin-2-yl)carbamoyl)phenyl)piperidine-1-carboxylate

[Chemical Formula 39]

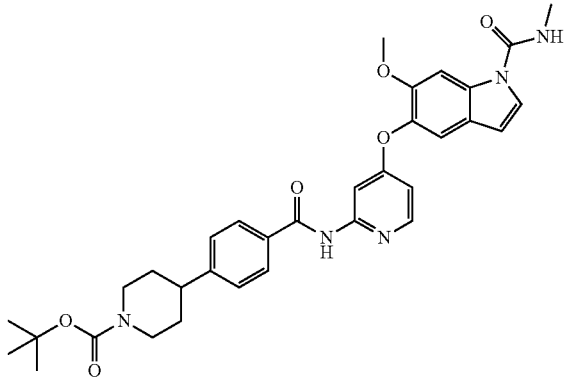

Benzotriazole (2.32 g, 19.5 mmol) was dissolved in dichloromethane (100 mL), thionyl chloride (1.4 mL, 19.2 mmol) was added under nitrogen atmosphere at room temperature, and the mixture was stirred for 5 minutes. 4-(1-(tert-Butoxycarbonyl)piperidin-4-yl)benzoic acid described in Production Example 1-12 (5.4 g, 17.7 mmol) was added to the reaction mixture at mom temperature, and the mixture was stirred for 25 minutes. The reaction mixture was filtered through a glass filter entirely covered with anhydrous sodium sulfate and then washed with dichloromethane, then the filtrate was added to a mixture of 5-((2-aminopyridin-4-yl)oxy)-6-methoxy-N-methyl-1H-indole-1-carboxamide described in Production Example 1-6 (2.5 g, 8.01 mmol), triethylamine (11 mL, 79.4 mmol), and 4-dimethylaminopyridine (101 mg, 0.827 mmol) in tetrahydrofuran (80 mL) at 0° C. The resultant was stirred at mom temperature for 5 hours and then the reaction mixture was concentrated under vacuum. Water and ethyl acetate were added to the residue for partition, and the organic layer was washed with a saturated saline solution, and then dried over anhydrous magnesium sulfate and filtered. The filtrate was concentrated under vacuum, the residue was dissolved in tetrahydrofuran, an excessive quantity of 9.8 M methylamine methanol solution was added at room temperature, and the mixture was stirred for 50 minutes. The reaction mixture was concentrated under vacuum, the residue was dissolved in dichloromethane, and the resultant was purified with NH silica gel column chromatography (n-heptane:ethyl acetate=1:1-1:3-0:1). The target fraction was concentrated under vacuum and the precipitate was collected by filtration and washed with diethyl ether and ethyl acetate to obtain the title compound (3.15 g, 66%). The filtrate was combined with the mixture fraction and the resultant was concentrated under vacuum and dissolved in dichloromethane, and the resultant was purified with NH silica gel column chromatography (n-heptane:ethyl acetate=1:1-1:3-0:1). The target fraction was concentrated under vacuum and the precipitate was collected by filtration and washed with diethyl ether and ethyl acetate to obtain the title compound (264 mg, 5.5%).

$^1$H-NMR Spectrum (CDCl$_3$) δ (ppm): 1.48 (9H, s), 1.55-1.69 (2H, m), 1.77-1.87 (2H, m), 2.64-2.89 (3H, m), 3.02-3.07 (3H, m), 3.86 (3H, s), 4.26 (2H, brs), 5.62 (1H, brs), 6.50-6.55 (1H, m), 6.61 (1H, dd, J=5.9, 2.2 Hz), 7.22 (1H, d, J=3.7 Hz), 7.27-7.33 (3H, m), 7.80 (2H, d, J=8.4 Hz), 7.90 (1H, d, J=2.2 Hz), 8.04 (1H, s), 8.09 (1H, d, J=5.9 Hz), 8.54 (1H, brs).

4-(1-(tert-Butoxycarbonyl)piperidin-4-yl)benzoic acid was synthesized by the following method.

Production Example 1-9

1-(4-Phenylpiperidin-1-yl)ethanone

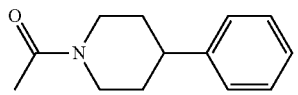

[Chemical Formula 40]

A mixture of commercially available 4-phenylpiperidine (10 g, 62 mmol), pyridine (5.7 mL, 70.5 mmol), and tetrahydrofuran (80 mL) was stirred at 0° C. and a mixture of acetyl chloride (5 mL, 70.3 mmol) and tetrahydrofuran (20 mL) was dripped over 10 minutes. The mixture was stirred under nitrogen atmosphere at 25° C. for 14 hours. Ethyl acetate (100 mL) and water (100 mL) were added to the reaction liquid for separation. The aqueous layer was extracted with ethyl acetate (100 mL), then the organic layers were combined, and the resultant was washed with a saturated aqueous sodium bicarbonate solution (100 mL), water (100 mL), and then a saturated saline solution (50 mL). The organic layer was dried over anhydrous magnesium sulfate and then the solvent was evaporated to obtain the title compound (12.3 g, 98%).

$^1$H-NMR Spectrum (CDCl$_3$) δ (ppm): 1.52-1.78 (2H, m), 1.81-1.99 (2H, m), 2.14 (3H, s), 2.63 (1H, td, J=12.9, 2.7 Hz), 2.74 (1H, tt, J=12.1, 3.7 Hz), 3.17 (1H, td, J=13.2, 2.6 Hz), 3.84-4.02 (1H, m), 4.69-4.89 (1H, m), 7.08-7.43 (5H, m).

Production Example 1-10

4-(1-Acetylpiperidin-4-yl)benzoic acid

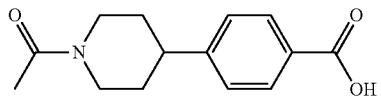

[Chemical Formula 41]

A mixture of aluminum chloride(III) (26 g, 195 mmol) and dichloromethane (200 mL) was stirred at 0° C., and oxalyl chloride (20 mL, 228 mmol) was dripped over 10 minutes. Then a mixture of 1-(4-phenylpiperidin-1-yl)ethanone described in Production Example 1-9 (12.3 g, 60.5 mmol) and dichloromethane (50 mL) was dripped over 30 minutes. The mixture was stirred under nitrogen atmosphere at 25° C. for 14 hours. The reaction liquid was poured onto ice and ethyl acetate (1 L) and water (1 L) were added for separation. The aqueous layer was extracted with ethyl acetate (1 L) twice, then the organic layer was washed with water (1 L) twice and then with a saturated saline solution (500 mL). The organic layer was dried over anhydrous magnesium sulfate and then the solvent was evaporated. Ethyl acetate was added to the concentrated residue and the product was collected by filtration and washed with ethyl acetate to obtain the title compound (9.09 g, 61%).

$^1$H-NMR Spectrum (CDCl$_3$) δ (ppm): 1.49-1.82 (2H, m), 1.92 (2H, t, J=13.2 Hz), 2.15 (3H, s), 2.65 (1H, t, J=11.7 Hz), 2.75-2.94 (1H, m), 3.08-3.30 (1H, m), 3.97 (1H, d, J=13.2 Hz), 4.82 (1H, d, J=12.8 Hz), 7.30 (2H, d, J=8.4 Hz), 8.05 (2H, d, J=8.1 Hz).

Production Example 1-11

4-(Piperidin-4-yl)benzoic acid hydrochloride

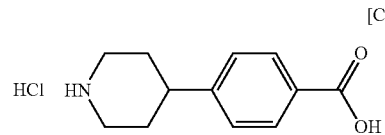

[Chemical Formula 42]

A mixture of 4-(1-acetylpiperidin-4-yl)benzoic acid described in Production Example 1-10 (4.50 g, 18.2 mmol) and 5 M hydrochloric acid (50 mL, 250 mmol) was stirred under nitrogen atmosphere at 140° C. for 18 hours. The mixture was cooled to room temperature and then the product was collected by filtration and washed with water to obtain the title compound (3.77 g, 86%).

$^1$H-NMR Spectrum (DMSO-d$_6$) δ (ppm): 1.60-2.15 (4H, m), 2.76-3.16 (3H, m), 3.27-3.45 (2H, m), 7.36 (2H, d, J=8.1 Hz), 7.92 (2H, d, J=8.1 Hz), 8.65-9.04 (2H, m), 12.89 (1H, brs).

Production Example 1-12

4-(1-(tert-Butoxycarbonyl)piperidin-4-yl)benzoic acid

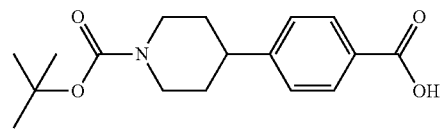

[Chemical Formula 43]

A mixture of 4-(piperidin-4-yl)benzoic acid hydrochloride described in Production Example 1-11 (2.00 g, 8.27 mmol), a 1 M sodium hydroxide solution (25 mL, 25 mmol), and acetone (50 mL) was stirred at 25° C., and a solution of di-tert-butyl dicarbonate (1.9 g, 8.71 mmol) in acetone (25 mL) was added dropwise over 10 minutes. The mixture was stirred under nitrogen atmosphere at 25° C. for 18 hours. 1 M hydrochloric acid (17 mL) was added under cooling at 0° C. The mixture was extracted with ethyl acetate (100 mL) twice. The organic layer was washed with a saturated saline solution (50 mL). The organic layer was dried over anhydrous magnesium sulfate and then concentrated under vacuum. n-Heptane and tert-butyl methyl ether were added to the concentrated residue and the product was collected by filtration and washed with n-heptane to obtain the title compound (2.30 g, 91%).

$^1$H-NMR Spectrum (CDCl$_3$) δ (ppm): 1.49 (9H, s), 1.57-1.76 (2H, m), 1.84 (2H, d, J=135 Hz), 2.62-2.97 (3H, m), 4.27 (2H, brs), 7.28-7.36 (2H, m), 7.98-8.10 (2H, m).

Example 2

5-((2-(4-(1-Ethylpiperidin-4-yl)benzamide)pyridin-4-yl)oxy)-6-methoxy-N-methyl-1H-indole-1-carboxamide

[Chemical Formula 44]

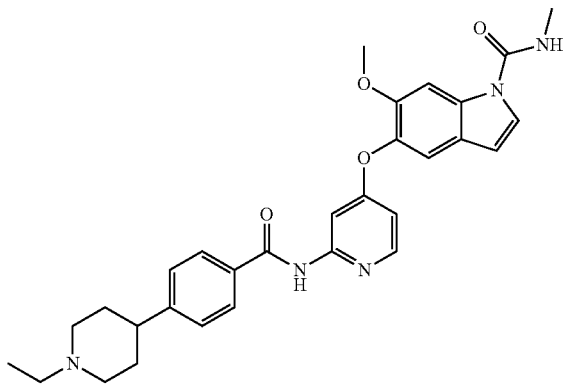

Acetaldehyde (0.677 mL, 12.1 mmol) and sodium triacetoxyborohydride (2.57 g, 12.1 mmol) were added to a mixture of 6-methoxy-N-methyl-5-((2-(4-(piperidin-4-yl)benzamide)pyridin-4-yl)oxy)-1H-indole-1-carboxamide described in Example 1 (3.03 g, 6.06 mmol) and tetrahydrofuran (80 mL), and the mixture was stirred at room temperature for 3 hours. Ethyl acetate, a saturated aqueous sodium bicarbonate solution, and water were added to the reaction mixture for partition. The organic layer was washed with a saturated saline solution, and then dried over anhydrous sodium sulfate and filtered. The solvent was evaporated, the resultant residue was dissolved in dichloromethane, and the resultant was purified with NH silica gel column chromatography (n-heptane:ethyl acetate=1:4-0:1-ethyl acetate:methanol=99:1-9:1). The target fraction was concentrated under vacuum and the residue was collected by filtration and washed with n-heptane and diethyl ether to obtain the title compound (2.61 g, 82%).

$^1$H-NMR Spectrum (CDCl$_3$) δ (ppm): 1.12 (3H, t, J=7.1 Hz), 1.77-1.90 (4H, m), 1.98-2.07 (2H, m), 2.45 (2H, q, J=7.1 Hz), 2.52-2.62 (1H, m), 3.05-3.12 (5H, m), 3.83 (3H, s), 5.50-5.58 (1H, m), 6.55 (1H, d, J=3.7 Hz), 6.60 (1H, dd, J=5.9, 2.4 Hz), 7.23 (1H, d, J=3.7 Hz), 7.30-7.35 (3H, m), 7.79 (2H, d, J=8.2 Hz), 7.91 (1H, d, J=2.4 Hz), 8.03 (1H, s), 8.10 (1H, d, J=5.7 Hz), 8.50 (1H, brs).

Example 3

5-((2-(4-(1-(2-Hydroxyethyl)piperidin-4-yl)benzamide)pyridin-4-yl)oxy)-6-methoxy-N-methyl-1H-indole-1-carboxamide

[Chemical Formula 45]

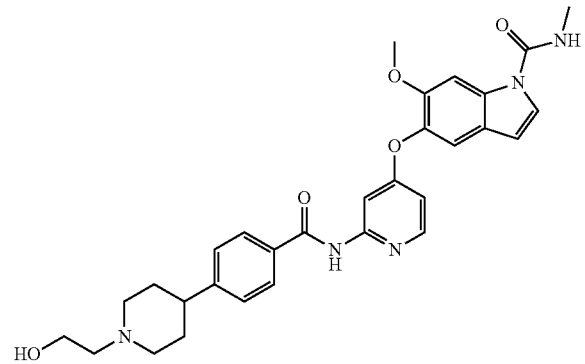

Commercially available 2-hydroxyacetaldehyde (110 mg, 1.83 mmol), sodium triacetoxyborohydride (382 mg, 1.80 mmol), and acetic acid (103 μL, 1.80 mmol) were added to a mixture of 6-methoxy-N-methyl-5-((2-(4-(piperidin-4-yl)benzamide)pyridin-4-yl)oxy)-1H-indole-1-carboxamide described in Example 1 (300 mg, 0.601 mmol) and tetrahydrofuran (15 mL) under nitrogen atmosphere, and the mixture was stirred at room temperature for 15 hours. A saturated aqueous sodium bicarbonate solution and ethyl acetate were added to the reaction mixture for partition. The organic layer was washed with a saturated saline solution, and then dried over anhydrous sodium sulfate and filtered. The solvent was evaporated, the resultant residue was dissolved in dichloromethane, and the resultant was purified with NH silica gel column chromatography (ethyl acetate:methanol 99:1-4:1). The target fraction and the mixture fraction were concentrated under vacuum, then the residue of the mixture fraction was purified with NH silica gel column chromatography (ethyl acetate:methanol=97:3-19:1-23:2). The combined target fraction was concentrated under vacuum and the precipitate was collected by filtration and washed with diethyl ether and ethyl acetate to obtain the title compound (209 mg, 64%).

$^1$H-NMR Spectrum (CDCl$_3$) δ (ppm): 1.70-1.90 (4H, m), 2.14-2.25 (2H, m), 2.53-2.65 (3H, m), 2.97-3.09 (2H, m), 3.06 (3H, d, J=4.4 Hz), 3.63 (2H, t, J=5.3 Hz), 3.86 (3H, s), 5.51-5.60 (1H, m), 6.54 (1H, d, J=3.7 Hz), 6.61 (1H, dd, J=5.7, 2.4 Hz), 7.23 (1H, d, J=3.7 Hz), 7.29-7.35 (3H, m), 7.80 (2H, d, J=8.4 Hz), 7.91 (1H, d, J=2.6 Hz), 8.04 (1H, s), 8.10 (1H, d, J=5.9 Hz), 8.51 (1H, brs).

Example 4

(S)-5-((2-(4-(1-(2-Hydroxypropyl)piperidin-4-yl)benzamide)pyridin-4-yl)oxy)-6-methoxy-N-methyl-1H-indole-1-carboxamide

[Chemical Formula 46]

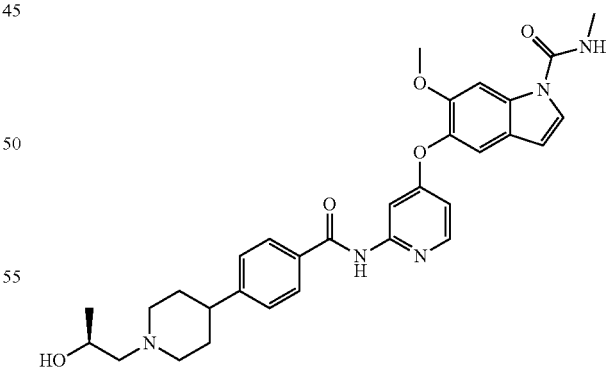

Commercially available (S)-(−)-propylene oxide (233 mg, 4.00 mmol) was added to a mixture of 6-methoxy-N-methyl-5-((2-(4-(piperidin-4-yl)benzamide)pyridin-4-yl)oxy)-1H-indole-1-carboxamide described in Example 1 (400 mg, 0.801 mmol) and ethanol (10 mL), and the mixture was heated and stirred with a sealed tube at 60° C. for 1 hour. The mixture was cooled to room temperature and then tetrahydrofuran (5.0 mL) was added, and the mixture was heated and stirred at 70° C. for 2 hours. The reaction mixture was concentrated under vacuum, the resultant residue was dissolved in dichloromethane, and the resultant was purified with NH silica gel column chromatography (n-heptane:ethyl acetate=1:4-0:1-ethyl acetate:methanol=99:1-19:1). The target fraction was concentrated under vacuum and the precipitate was collected by filteration and washed with diethyl ether and ethyl acetate to obtain the title compound (347 mg, 78%).

$^1$H-NMR Spectrum (CDCl$_3$) δ (ppm): 1.14 (3H, d, J=6.2 Hz), 1.66-1.89 (4H, m), 1.98-2.09 (1H, m), 2.21-2.45 (3H, m), 2.52-2.64 (1H, m), 2.88-2.96 (1H, m), 3.06 (3H, d, J=4.8 Hz), 3.10-3.17 (1H, m), 3.57 (1H, brs), 3.80-3.92 (1H, m), 3.86 (3H, s), 5.52-5.59 (1H, m), 6.54 (1H, d, J=3.7 Hz), 6.60 (1H, dd, J=5.9, 2.6 Hz), 7.23 (1H, d, J=3.7 Hz), 7.29-7.35 (3H, m), 7.78-7.83 (2H, m), 7.91 (1H, d, J=2.6 Hz), 8.03 (1H, s), 8.10 (1H, d, J=5.9 Hz), 8.53 (1H, brs).

Example 5

5-((2-(4-(1-(3-Fluoropropyl)piperidin-4-yl)benzamide)pyridin-4-yl)oxy)-6-methoxy-N-methyl-1H-indole-1-carboxamide

[Chemical Formula 47]

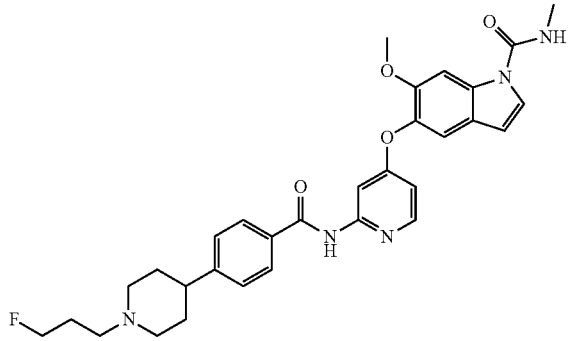

Triethylamine (11.8 μL, 0.085 mmol) and 3-fluoropropyl 4-methylbenzenesulfonate described in Production Example 5-1 (16.1 mg, 0.069 mmol) were added to a mixture of 6-methoxy-N-methyl-5-((2-(4-(piperidin-4-yl)benzamide)pyridin-4-yl)oxy)-1H-indole-1-carboxamide described in Example 1 (14.1 mg, 0.028 mmol) and N,N-dimethylformamide (0.5 mL), and the mixture was heated and stirred at 50° C. for 1 hour and then stirred at room temperature for 13 hours. Triethylamine (11.8 μL, 0.085 mmol) and 3-fluoropropyl 4-methylbenzenesulfonate (16.1 mg, 0.069 mmol) were added to the reaction mixture, and the mixture was heated and stirred at 50° C. for 3 hours. The resultant was cooled to room temperature and then water and ethyl acetate were added for partition. The organic layer was washed with a saturated saline solution, and then dried over anhydrous sodium sulfate and filtered. The solvent was evaporated, the resultant residue was dissolved in dichloromethane, and the resultant was purified with NH silica gel column chromatography (n-heptane:ethyl acetate=2:3-0:1-ethyl acetate:methanol=99:1-19:1-9:1). The target fraction was concentrated under vacuum and the precipitate was collected by filteration and washed with diethyl ether to obtain the title compound (10.2 mg, 65%).

$^1$H-NMR Spectrum (CDCl$_3$) δ (ppm): 1.72-2.00 (6H, m), 2.02-2.13 (2H, m), 2.47-2.62 (3H, m), 3.01-3.09 (2H, m), 3.06 (3H, d, J=4.8 Hz), 3.86 (3H, s), 4.47 (1H, t, J=6.0 Hz), 4.59 (1H, t, J=6.0 Hz), 5.48-5.58 (1H, m), 6.55 (1H, d, J=3.7 Hz), 6.60 (1H, dd, J=5.7, 2.4 Hz), 7.23 (1H, d, J=3.7 Hz), 7.30-7.34 (3H, m), 7.77-7.82 (2H, m), 7.91 (1H, d, J=2.6 Hz), 8.03 (1H, s), 8.10 (1H, d, J=6.2 Hz), 8.50 (1H, brs).

The reagent 3-fluoropropyl 4-methylbenzenesulfonate was synthesized by the following method.

Production Example 5-11

3-Fluoropropyl 4-methylbenzenesulfonate

[Chemical Formula 48]

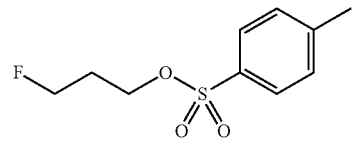

Triethylamine (11 mL, 79.4 mmol), 4-dimethylaminopyridine (390 mg, 3.19 mmol), and p-toluenesulfonyl chloride (13.4 g, 70.4 mmol) were added to a mixture of commercially available 3-fluoropropan-1-ol (5.0 g, 64 mmol) and tetrahydrofuran (120 mL) under nitrogen atmosphere at 0° C., and the mixture was stirred at mom temperature for 90 hours. Water and ethyl acetate were added to the reaction mixture for partition. The organic layer was washed with water and a saturated saline solution, dried over anhydrous magnesium sulfate, and filtered. The solvent was evaporated, the resultant residue was dissolved in dichloromethane and n-heptane, and the resultant was purified with silica gel column chromatography (n-heptane:ethyl acetate=10:1-2:1) to obtain the title compound (12.7 g, 85%).

$^1$H-NMR. Spectrum (CDCl$_3$) δ (ppm): 1.97-2.15 (2H, m), 2.46 (3H, s), 4.16 (2H, t, J=6.2 Hz), 4.49 (2H, dt, J=46.8, 5.6 Hz), 7.36 (2H, dd, J=8.4, 0.6 Hz), 7.75-7.85 (2H, m).

Example 6

5-((2-(4-(3-Fluoropiperidin-4-yl)benzamide)pyridin-4-yl)oxy)-6-methoxy-N-methyl-1H-indole-1-carboxamide

[Chemical Formula 49]

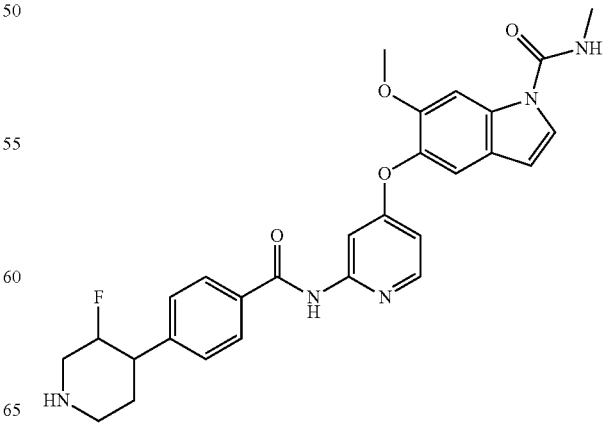

tert-Butyl 3-fluoro-4-(4-((4-((6-methoxy-1-(methylcarbamoyl)-1H-indol-5-yl)oxy)pyridin-2-yl)carbamoyl)phenyl)piperidine-1-carboxylate described in Production Example 6-5 (29.1 mg, 0.047 mmol) was dissolved in dichloromethane (4 mL), trifluoroacetic acid (0.8 mL, 10.4 mmol) was added at room temperature, and then the mixture was stirred for 30 minutes. The solvent was evaporated, the resultant residue was dissolved in dichloromethane (4 mL), and triethylamine was added to neutralize the excessive trifluoroacetic acid. The solvent was evaporated and the resultant residue was purified with NH silica gel column chromatography (n-heptane:ethyl acetate=1:4-0:1-ethyl acetate:methanol=97:3-19:1) to obtain the title compound (16.8 mg, 69%).

$^1$H-NMR Spectrum (500 MHz, CDCl$_3$) δ (ppm): 1.71-1.80 (2H, m), 1.89-1.97 (1H, m), 2.63-2.70 (1H, m), 2.70-2.76 (1H, m), 2.79-2.89 (1H, m), 3.05 (3H, d, J=4.9 Hz), 3.09 (1H, d, J=11.2 Hz), 3.48 (1H, dt, J=11.3, 4.1 Hz), 3.87 (3H, s), 4.58 (1H, dtd, J=50.0, 9.9, 4.6 Hz), 5.58 (1H, q, J=4.7 Hz), 6.54 (1H, d, J=3.4 Hz), 6.61 (1H, dd, J=5.6, 2.2 Hz), 7.22 (1H, d, J=3.9 Hz), 7.32 (1H, s), 7.38 (2H, d, J=8.3 Hz), 7.84 (2H, d, J=8.3 Hz), 7.91 (1H, d, J=2.4 Hz), 8.04 (1H, s), 8.10 (11L d, J=5.9 Hz), 8.57 (1H, s).

The starting material tert-butyl 3-fluoro-4-(4-((4-((6-methoxy-1-(methylcarbamoyl)-1H-indol-5-yl)oxy)pyridin-2-yl)carbamoyl)phenyl)piperidine-1-carboxylate was synthesized by the following method.

Production Example 6-1 tert-Butyl 4-(4-(methoxycarbonyl)phenyl)-5,6-dihydropyridine-1(2H)-carboxylate

[Chemical Formula 50]

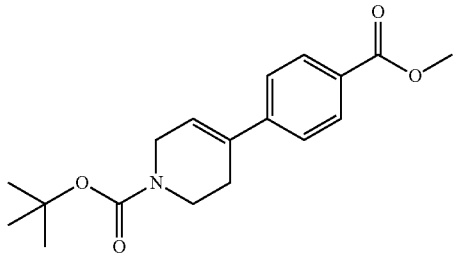

Toluene (20 mL), ethanol (6 mL), and water (2 mL) were added to commercially available 1-N—BOC-4-(4,4,5,5-tetramethyl-[1,3,2]dioxaborolan-2-yl)-3,6-dihydro-2H-pyridine (1.00 g, 3.23 mmol), methyl 4-bromobenzoate (695 mg, 3.23 mmol), 2-dicyclohexylphosphino-2',6'-dimethoxybiphenyl (266 mg, 0.65 mmol), palladium(II) acetate (73 mg, 0.32 mmol), and tripotassium phosphate (2.06 g, 9.70 mmol) under nitrogen atmosphere, and the mixture was stirred at 90° C. for 5 hours. The reaction mixture was cooled to room temperature and a saturated aqueous sodium bicarbonate solution and ethyl acetate were added for partition. The aqueous layer was extracted with ethyl acetate three times and then the organic layer was dried over anhydrous sodium sulfate and filtered. The solvent was evaporated and the resultant residue was purified with silica gel column chromatography (n-heptane:ethyl acetate=19:1-13:7) to obtain the title compound (0.99 g, 96%).

$^1$H-NMR Spectrum (500 MHz, CDCl$_3$) δ (ppm): 1.49 (9H, s), 2.55 (2H, brs), 3.65 (2H, t, J=5.9 Hz), 3.92 (3H, s), 4.10 (2H, brs), 6.16 (1H, brs), 7.43 (2H, d, J=8.3 Hz), 8.00 (2H, d, J=8.8 Hz).

Production Example 6-2 tert-Butyl 3-hydroxy-4-(4-(methoxycarbonyl)phenyl)piperidine-1-carboxylate

[Chemical Formula 51]

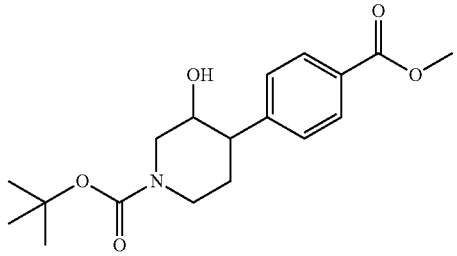

tert-Butyl 4-(4-(methoxycarbonyl)phenyl)-5,6-dihydropyridine-1(2H)-carboxylate described in Production Example 6-1 (776 mg, 2.45 mmol) was dissolved in tetrahydrofuran (10 mL), a solution of borane-methyl sulfide complex (0.269 mL, 2.69 mmol) in tetrahydrofuran (10 mL) was added at room temperature over 3 minutes, and the mixture was stirred for 13 hours. The reaction liquid was cooled to 0° C. and a 1 M sodium hydroxide solution (6.12 mL, 6.12 mmol) was added over 1 minute. 30% Hydrogen peroxide water (0.625 mL, 6.12 mmol) was added, and the mixture was stirred at room temperature for 45 minutes. A saturated aqueous sodium thiosulfate solution (20 mL), water, and ethyl acetate were serially added to the reaction mixture. The aqueous layer was extracted with ethyl acetate three times and then the organic layers were combined, dried over anhydrous magnesium sulfate, and filtered. The solvent was evaporated and the resultant residue was purified with silica gel column chromatography (n-heptane:ethyl acetate=4:1-1:4) to obtain the title compound (518 mg, 63%).

$^1$H-NMR Spectrum (500 MHz, CDCl$_3$) δ (ppm): 1.49 (9H, s), 1.59 (1H, d, J=2.9 Hz), 1.69-1.88 (2H, m), 2.57-2.71 (2H, m), 2.77 (1H, brs), 3.67-3.82 (1H, m), 3.91 (3H, s), 4.22 (1H, brs), 4.42 (1H, brs), 7.34 (2H, d, J=8.3 Hz), 8.02 (2H, d, J=8.3 Hz).

Production Example 6-3 tert-Butyl 3-fluoro-4-(4-(methoxycarbonyl)phenyl)piperidine-1-carboxylate

[Chemical Formula 52]

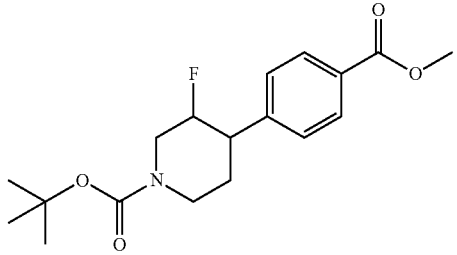

tert-Butyl 3-hydroxy-4-(4-(methoxycarbonyl)phenyl)piperidine-1-carboxylate described in Production Example 6-2 (518 mg, 1.54 mmol) was dissolved in dichloromethane (15 mL), [bis-(2-methoxyethyl)amino]sulfur trifluoride (0.313 mL, 1.70 mmol) was added at −78° C. over 3 minutes, and the mixture was stirred for 1 hour while warming to room temperature. A saturated aqueous sodium bicarbonate solution and ethyl acetate were serially added to the reaction mixture. The aqueous layer was extracted with ethyl acetate three times and then the organic layers were combined, dried over anhydrous sodium sulfate, and filtered. The solvent was evaporated and the resultant residue was purified with silica gel column chromatography (n-heptane:ethyl acetate=19:1-3:2) to obtain the title compound (402 mg, 77%).

$^1$H-NMR Spectrum (500 MHz, CDCl$_3$) δ (ppm): 1.49 (9H, s), 1.64-1.81 (1H, m), 1.86-2.01 (1H, m), 2.72-2.94 (3H, m), 3.91 (3H, s), 4.19 (1H, brs), 4.94-4.66 (2H, m), 7.33 (2H, d, J=8.3 Hz), 8.02 (2H, d, J=8.3 Hz).

Production Example 6-4

4-(1-(tert-Butoxycarbonyl)-3-fluoropiperidin-4-yl)benzoic acid

[Chemical Formula 53]

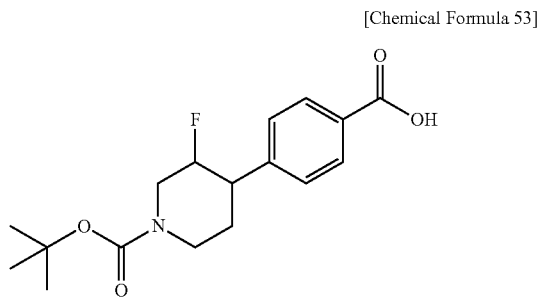 [SMILES: CC(C)(C)OC(=O)N1CCC(c2ccc(C(=O)O)cc2)C(F)C1]

tert-Butyl 3-fluoro-4-(4-(methoxycarbonyl)phenyl)piperidine-1-carboxylate described in Production Example 6-3 (402 mg, 1.19 mmol) was dissolved in tetrahydrofuran (18 mL), methanol (6 mL), and water (4 mL), then a 2 M aqueous lithium hydroxide solution (4.17 mL, 8.34 mmol) was added at room temperature, and then the mixture was stirred for 3 hours. Tetrahydrofuran and methanol were evaporated under vacuum and 1 M hydrochloric acid was added to the residual solution for neutralization. The aqueous layer was extracted with ethyl acetate four times, and the organic layers were combined, dried over anhydrous sodium sulfate, and filtered. The solvent was evaporated and the resultant residue was purified with silica gel column chromatography (n-heptane:ethyl acetate=4:1-1:4) to obtain the title compound (347 mg, 90%).

$^1$H-NMR Spectrum (500 MHz, CDCl$_3$) δ (ppm): 1.50 (9H, s), 1.77 (1H, qd, J=13.0, 3.9 Hz), 1.92 (1H, d, J=14.1 Hz), 2.72-2.95 (3H, m), 4.21 (1H, brs), 4.46-4.67 (2H, m), 7.37 (2H, d, J=8.3 Hz), 8.09 (2H, d, J=8.3 Hz).

Production Example 6-5 tert-Butyl 3-fluoro-4-(4-((4-((6-methoxy-1-(methylcarbamoyl)-1H-indol-5-yl)oxy)pyridin-2-yl)carbamoyl)phenyl)piperidine-1-carboxylate

[Chemical Formula 54]

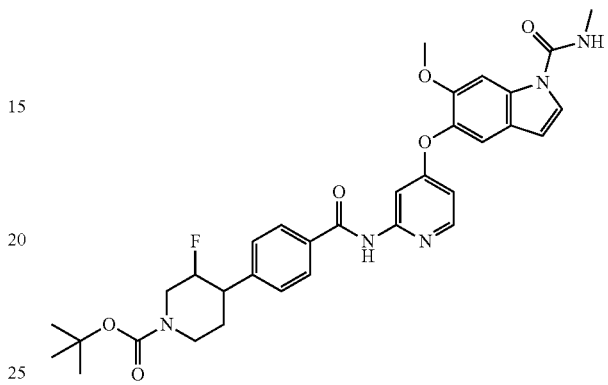

Thionyl chloride (30 μL, 0.319 mmol) was added to a mixture of benzotriazole (49.3 mg, 0.414 mmol) and dichloromethane (4 mL) under nitrogen atmosphere, and the mixture was stirred at room temperature for 5 minutes. 4-(1-(tert-Butoxycarbonyl)-3-fluoropiperidin-4-yl)benzoic acid described in Production Example 6-4 (103 mg, 0.319 mmol) was added, and the mixture was stirred at mom temperature for 30 minutes. The reaction liquid was filtered through anhydrous sodium sulfate and washed with dichloromethane (4 mL) to obtain a dichloromethane solution of the crude product.

A dichloromethane solution of the above-described crude product (4 mL, 0.16 mmol) was added to a mixture of 5-((2-aminopyridin-4-yl)oxy)-6-methoxy-N-methyl-1H-indole-1-carboxamide described in Production Example 1-6 (25.0 mg, 0.080 mmol), triethylamine (56 μL, 0.40 mmol), 4-dimethylaminopyridine (1.0 mg, 0.008 mmol), and dichloromethane (1 mL) at 0° C., then the mixture was stirred at 0° C. for 10 minutes and then at room temperature for 3 hours. A 40% aqueous methylamine solution (138 μL, 1.60 mmol) was added, and the mixture was further stirred at room temperature for 2 hours. A saturated aqueous sodium bicarbonate solution and ethyl acetate were added to the reaction mixture for partition. The aqueous layer was extracted with ethyl acetate three times and then the organic layers were combined, dried over anhydrous sodium sulfate, and filtered. The solvent was evaporated and the resultant residue was purified with NH silica gel column chromatography (n-heptane:ethyl acetate=1:1-0:1) to obtain the title compound (29.1 mg, 59%).

$^1$H-NMR Spectrum (500 MHz, CDCl$_3$) δ (ppm): 1.49 (9H, s), 1.65-1.82 (1H, m), 1.91 (1H, brs), 2.69-2.93 (3H, m), 3.04 (3H, d, J=4.9 Hz), 3.86 (3H, s), 4.18 (1H, brs), 4.42-4.66 (2H, m), 5.65 (1H, q, J=4.4 Hz), 6.53 (1H, d, J=3.4 Hz), 6.62 (1H, dd, J=5.9, 2.4 Hz), 7.23 (1H, d, J=3.9 Hz), 7.31 (1H, s), 7.36

(2H, d, J=8.3 Hz), 7.84 (2H, d, J=8.3 Hz), 7.91 (1H, d, J=2.0 Hz), 8.05 (1H, s), 8.09 (1H, d, J=5.9 Hz), 8.63 (1H, s).

Example 7

5-((2-(4-(4-Fluoropiperidin-4-yl)benzamide)pyridin-4-yl)oxy)-6-methoxy-N-methyl-1H-indole-1-carboxamide

[Chemical Formula 55]

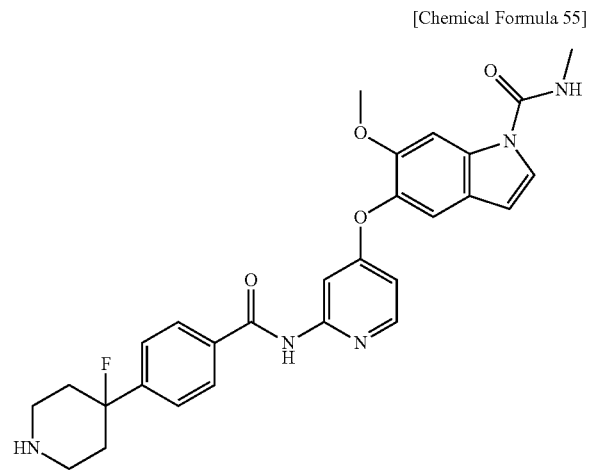 [SMILES: CNC(=O)n1ccc2cc(Oc3ccnc(NC(=O)c4ccc(C5(F)CCNCC5)cc4)c3)c(OC)cc21]

Benzotriazole (33.2 mg, 0.278 mmol) was dissolved in dichloromethane (10 mL) under nitrogen atmosphere, then thionyl chloride (20 µL, 0.278 mmol) was added, and the mixture was stirred at 20° C. for 5 minutes. 4-(1-tert-Butoxycarbonyl)-4-fluoropiperidin-4-yl)benzoic acid described in Production Example 7-4 (60 mg, 0.186 mmol) was added to the reaction mixture, and the mixture was stirred at 20° C. for 2 hours. The reaction mixture was filtered and dichloromethane was evaporated under vacuum until the amount thereof became as small as about 5 ml. 5-((2-Aminopyridin-4-yl)oxy)-6-methoxy-N-methyl-1H-indole-1-carboxamide described in Production Example 1-6 (25 mg, 0.08 mmol), triethylamine (55 µL, 0.40 mmol), and 4-dimethylaminopyridine (1.96 mg, 0.016 mmol) were serially added to the resultant reaction mixture, and the mixture was stirred at room temperature for 2 hours. A 2 M methylamine tetrahydrofuran solution (120 µL, 0.24 mmol) was added to the reaction mixture, then the mixture was stirred at room temperature for 1 hour, and then ethyl acetate and a saturated aqueous sodium bicarbonate solution were added for partition. The organic layer was dried over anhydrous sodium sulfate and filtered. The solvent was evaporated under vacuum and the resultant residue was dissolved in dichloromethane (5 mL), then trifluoroacetic acid (1 mL) was added at 0° C., and then the mixture was stirred at room temperature for 1 hour. The solvent was evaporated under vacuum, an azeotropic mixture of the resultant residue with toluene was formed, and then the mixture was dried under vacuum. The resultant residue was dissolved in a mixed solvent of dichloromethane and triethylamine, and the resultant was purified with NH silica gel column chromatography (ethyl acetate:methanol=1:0-17:3). The target fraction was concentrated under vacuum to obtain the title compound (11.8 mg, 29%).

$^1$H-NMR Spectrum (CDCl$_3$) δ (ppm): 1.73-2.01 (4H, m), 2.91-3.23 (7H, m), 3.86 (3H, s), 5.76-5.91 (1H, m), 6.44-6.52 (1H, m), 6.64 (1H, dd, J=5.9, 2.2 Hz), 7.22 (1H, d, J=3.7 Hz), 7.31 (1H, s), 7.48 (2H, d, J=8.4 Hz) 7.81-7.97 (3H, m), 8.02-8.14 (2H, m), 8.74 (1H, brs).

The starting material 4-(1-tert-butoxycarbonyl)-4-fluoropiperidin-4-yl)benzoic acid was synthesized by the following method.

Production Example 7-1

1-Benzyl-4-(4-(4,4-dimethyl-4,5-dihydrooxazol-2-yl)phenyl)piperidin-4-ol

[Chemical Formula 56]

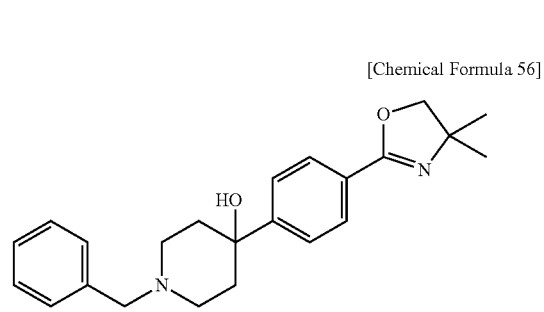 [SMILES: CC1(C)COC(c2ccc(C3(O)CCN(Cc4ccccc4)CC3)cc2)=N1]

Magnesium (3.10 g, 127 mmol), iodine (135 mg, 0.531 mmol), and 2-(4-bromophenyl)-4,5-dihydro-4,4-dimethyloxazole (27 g, 106 mmol) were added to tetrahydrofuran (120 mL), and the mixture was heated under reflux for 1 hour. This reaction mixture was cooled to mom temperature, then 1-benzyl-4-piperidone (21.7 mL, 117 mmol) was added, and the mixture was heated under reflux for 3 hours. The reaction mixture was cooled to room temperature and then a saturated aqueous ammonium chloride solution and ethyl acetate were added for partition. The aqueous layer was extracted with ethyl acetate, and then the organic layers were combined and washed serially with water and a saturated saline solution. The organic layer was dried over anhydrous magnesium sulfate and filtered. The solvent was evaporated under vacuum and the resultant residue was purified with silica gel column chromatography (n-heptane:ethyl acetate=3:1-1:1). The target fraction was concentrated under vacuum to obtain the title compound (13.4 g, 35%).

$^1$H-NMR Spectrum (CDCl$_3$) δ (ppm): 1.37 (6H, s), 1.67-1.76 (2H, m), 2.16 (2H, td, J=13.1, 4.5 Hz), 2.47 (2H, td, J=12.0, 2.5 Hz), 2.79 (2H, d, J=11.4 Hz), 3.58 (2H, s), 4.09 (2H, s), 7.23-7.40 (5H, m), 7.55 (2H, d, J=8.8 Hz), 7.91 (2H, d, J=8.6 Hz).

Production Example 7-2

Ethyl 4-(1-benzyl-4-hydroxypiperidin-4-yl)benzoate

[Chemical Formula 57]

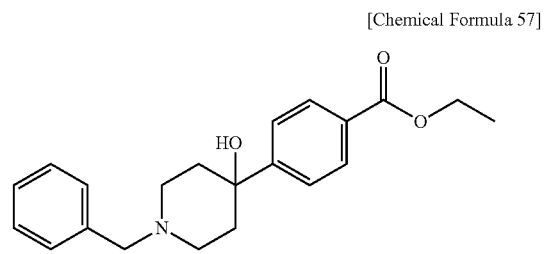 [SMILES: CCOC(=O)c1ccc(C2(O)CCN(Cc3ccccc3)CC2)cc1]

1-Benzyl-4-(4-(4,4-dimethyl-4,5-dihydrooxazol-2-yl)phenyl)piperidin-4-ol described in Production Example 7-1

(13.4 g, 36.8 mmol) was dissolved in ethanol (300 mL), then sulfuric acid was added, and the mixture was stirred at 90° C. for 12 hours. The reaction mixture was cooled to room temperature and then the solvent was evaporated under vacuum. The resultant residue was dissolved in dichloromethane, the resultant was washed with a saturated aqueous sodium bicarbonate solution, and then the organic layer was dried over anhydrous sodium sulfate and filtered. The solvent was evaporated under vacuum and the resultant residue was purified with NH silica gel column chromatography (n-heptane:ethyl acetate=4:1-1:1). The target fraction was concentrated under vacuum to obtain the title compound (7.23 g, 58%).

$^1$H-NMR Spectrum (CDCl$_3$) δ (ppm): 1.39 (3H, t, J=7.1 Hz), 1.59-1.85 (2H, m), 2.17 (2H, td, J=13.1, 4.5 Hz), 2.47 (2H, td, J=12.0, 2.5 Hz), 2.72-2.93 (2H, m), 3.59 (2H, s), 4.37 (2H, q, J=7.0 Hz), 7.14-7.44 (5H, m), 7.59 (2H, d, J=8.4 Hz), 8.02 (2H, d, J=8.4 Hz).

Production Example 7-3 tert-Butyl 4-(4-(ethoxycarbonyl)phenyl)-4-fluoropiperidine-1-carboxylate

[Chemical Formula 58]

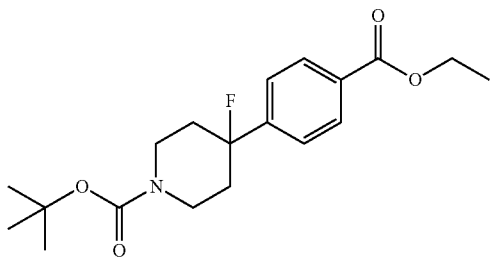

Ethyl 4-(1-benzyl-4-hydroxypiperidin-4-yl)benzoate described in Production Example 7-2 (6.23 g, 18.4 mmol) was dissolved in dichloromethane (200 mL) under nitrogen atmosphere, then diethylaminosulfur trifluoride (2.89 mL, 22.0 mmol) was added at −78° C., and the mixture was stirred at room temperature for 3 hours. Dichloromethane was added to the reaction mixture, and the mixture was washed with water and then dried over anhydrous magnesium sulfate and filtered. The solvent was evaporated under vacuum to obtain a crude product A (6.13 g).

The crude product A (6.13 g) was dissolved in dichloromethane (100 mL) under nitrogen atmosphere, then 1-chloroethyl chloroformate (2.13 mL, 19.8 mmol) was added, and the mixture was stirred at 20° C. for 2 hours. The reaction mixture was concentrated under vacuum, then the resultant residue was dissolved in methanol (100 mL), and the resultant was heated under reflux for 30 minutes. The reaction mixture was concentrated under vacuum, then diethyl ether was added to the resultant residue, the precipitate was collected by fliteration, and then the resultant was washed with diethyl ether to obtain a crude product B (4.72 g).

The crude product B (4.72 g) was dissolved in dichloromethane (50 mL), then triethylamine (5.24 mL, 37.6 mmol) and di-tert-butyl dicarbonate (4.92 g, 22.5 mmol) were added, and the mixture was stirred at room temperature for 1 hour. Water and ethyl acetate were added to the reaction mixture for partition. The aqueous layer was extracted with ethyl acetate again, and then the organic layers were combined and washed with water and then with a saturated saline solution. The organic layer was dried over anhydrous magnesium sulfate and filtered. The solvent was evaporated under vacuum and the resultant residue was purified with silica gel column chromatography (n-heptane:ethyl acetate=9:1-1:1). The target fraction was concentrated under vacuum to obtain the title compound (3.74 g, 58%).

$^1$H-NMR Spectrum (CDCl$_3$) δ (ppm): 1.24-1.34 (1H, m), 1.40 (3H, t, J=7.1 Hz), 1.50 (9H, s), 1.86-2.14 (2H, m), 2.54 (1H, brs), 3.18 (1H, brs), 3.65 (1H, t, J=5.7 Hz), 4.00-4.26 (2H, m), 4.38 (2H, qd, J=7.1, 3.1 Hz), 7.43 (2H, dd, J=8.6, 1.3 Hz), 8.03 (2H, dd, J=18.1, 8.6 Hz).

Production Example 7-4

4-(1-tert-Butoxycarbonyl)-4-fluoropiperidin-4-yl)benzoic acid

[Chemical Formula 59]

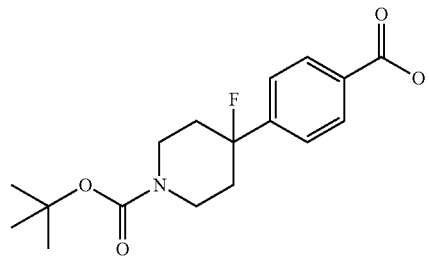

tert-Butyl 4-(4-(ethoxycarbonyl)phenyl)-4-fluoropiperidine-1-carboxylate described in Production Example 7-3 (3.74 g, 10.6 mmol) was dissolved in a mixed solvent of tetrahydrofuran (10 mL) and methanol (5 mL), then a 1 M sodium hydroxide solution (42.6 mL) was added, and the mixture was stirred at 50° C. for 4 hours. 1 M Hydrochloric acid was added to the reaction mixture, the precipitate was collected by filteration and washed with water, and then the resultant was dried by through-flow drying to obtain the title compound (1.33 g, 39%).

$^1$H-NMR Spectrum (DMSO-d$_6$) δ (ppm): 1.43 (9H, s), 1.83-2.15 (4H, m), 3.06 (2H, brs), 3.99 (2H, d, J=10.3 Hz), 7.50 (2H, d, J=8.4 Hz), 7.92 (2H, d, J=8.4 Hz).

Example 8

6-Methoxy-N-methyl-5-((2-(4-(4-(pyrrolidin-1-yl)piperidin-1-yl) benzamide)pyridin-4-yl)oxy)-1H-indole-1-carboxamide

[Chemical Formula 60]

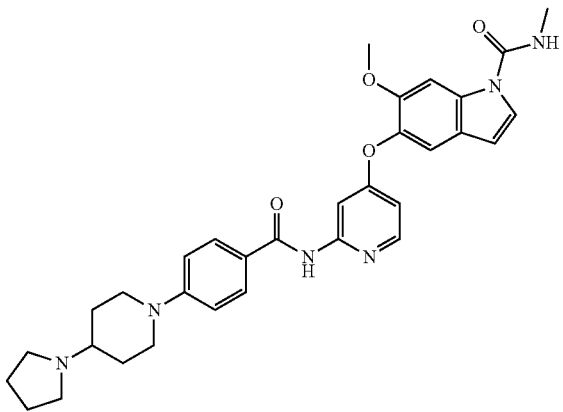

Oxalyl chloride (27 μL, 0.321 mmol) and N,N-dimethylformamide (1.24 μL, 0.016 mmol) were added to a solution of 4-(4-(pyrrolidin-1-yl)piperidin-1-yl)benzoic acid described in Production Example 8-2 (44 mg, 0.16 mmol) in dichloromethane (2 mL) at mom temperature. The reaction liquid mixture was stirred at mom temperature for 1 hour. The reaction liquid mixture was concentrated and triethylamine (112 μL, 0.80 mmol), 5-((2-aminopyridin-4-yl)oxy)-6-methoxy-N-methyl-1H-indole-1-carboxamide described in Production Example 1-6 (50 mg, 0.16 mmol), and 4-dimethylaminopyridine (3.91 mg, 0.032 mmol) were serially added to a solution of the residue in dichloromethane (2 mL) at room temperature. The reaction liquid mixture was stirred at room temperature. A saturated aqueous sodium bicarbonate solution was added to the reaction liquid and then ethyl acetate was added for dilution. The aqueous layer was extracted with ethyl acetate, then the combined organic layer was dried over anhydrous sodium sulfate. The drying agent was separated by filtration and then the filtrate was concentrated under vacuum. The residue was purified with NH silica gel column chromatography (n-heptane:ethyl acetate=1:1-0:1) to obtain the title compound (3.6 mg, 4.0%).

$^1$H-NMR Spectrum (CDCl$_3$) δ (ppm): 1.18-1.38 (2H, m), 1.84 (4H, brs), 1.95-2.11 (2H, m), 2.24-2.38 (1H, m), 2.70 (4H, brs), 2.82-2.96 (2H, m), 3.06 (3H, d, J=4.8 Hz), 3.80-3.91 (5H, m), 552-5.68 (1H, m), 6.54 (1H, d, J=3.3 Hz), 6.61 (1H, dd, J=5.9, 2.2 Hz), 6.89 (2H, d, J=8.8 Hz), 7.23 (1H, d, J=3.7 Hz), 7.32 (1H, s), 7.75 (2H, d, J=8.8 Hz), 7.90 (1H, d, J=2.2 Hz), 8.02 (1H, s), 8.09 (1H, d, J=5.9 Hz), 8.56 (1H, brs).

The starting material 4-(4-(pyrrolidin-1-yl)piperidin-1-yl) benzoic acid was synthesized by the following method.

Production Example 8-1

Methyl 4-(4-(pyrrolidin-1-yl)piperidin-1-yl)benzoate

[Chemical Formula 61]

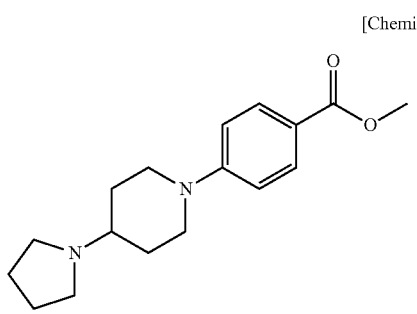

Commercially available methyl 4-fluorobenzoate (1.5 g, 9.73 mmol) was added to a solution of commercially available 4-(1-pyrrolidinyl)piperidine (3.0 g, 19.5 mmol) in dimethylsulfoxide (15 mL) at room temperature and then the mixture was stirred under nitrogen atmosphere and under irradiation with microwave at 150° C. for 4 hours. The reaction liquid was allowed to stand to cool to room temperature and then diluted with water and ethyl acetate. The organic layer was washed with water and then dried by a conventional method. The drying agent was separated by filtration and then the filtrate was concentrated under vacuum. The residue was purified with NH silica gel column chromatography (n-heptane:ethyl acetate=1:1) to obtain the title compound (2.06 g, 73%).

$^1$H-NMR Spectrum (CDCl$_3$) δ (ppm): 1.54-1.70 (2H, m), 1.74-1.88 (4H, m), 1.93-2.06 (2H, m), 2.12-2.26 (1H, m), 2.53-2.65 (4H, m), 2.90 (2H, td, J=12.4, 2.6 Hz), 3.74-3.97 (5H, m), 6.86 (2H, d, J=9.2 Hz), 7.89 (2H, d, J=9.2 Hz).

Production Example 8-2

4-(4-(Pyrrolidin-1-yl)piperidin-1-yl)benzoic acid

[Chemical Formula 62]

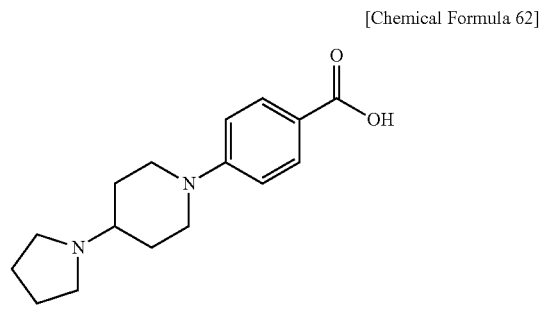 [SMILES: O=C(O)c1ccc(N2CCC(N3CCCC3)CC2)cc1]

A 5 M sodium hydroxide solution (15 mL, 75.0 mmol) was added to a solution of methyl 4-(4-(pyrrolidin-1-yl)piperidin-1-yl)benzoate described in Production Example 8-1 (2.06 g, 7.14 mmol) in tetrahydrofuran (10 mL) and methanol (10 mL). The reaction liquid was stirred at 50° C. for 4 hours. The reaction liquid was cooled to 0° C. and then 5 M hydrochloric acid was dripped until pH reached 1. The liquid mixture was diluted with ethyl acetate. The organic layer was washed with a saturated saline solution and then dried over anhydrous sodium sulfate. The drying agent was separated by filtration and then the filtrate was concentrated under vacuum to obtain the title compound (1.61 g, 82%).

ESI-MS (m/z):297 [M+H]$^+$.

Example 9

5-((2-(4-((4-Hydroxypiperidin-1-yl)methyl)benzamide)pyridin-4-yl)oxy)-6-methoxy-N-methyl-1H-indole-1-carboxamide

[Chemical Formula 63]

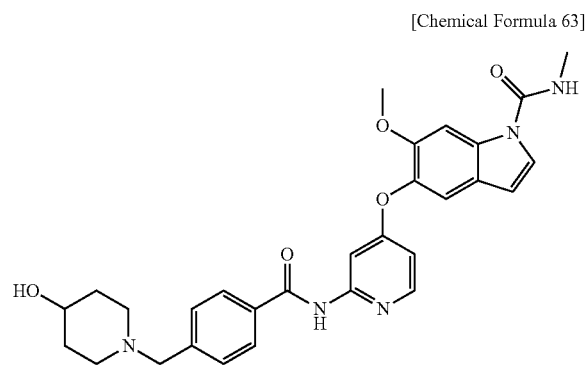 [SMILES: CNC(=O)n1ccc2cc(Oc3ccnc(NC(=O)c4ccc(CN5CCC(O)CC5)cc4)c3)c(OC)cc21]

Triethylamine (1.6 mL, 11.5 mmol) and commercially available 4-(chloromethyl)benzoyl chloride (1.37 g, 7.25 mmol) were added to a mixture of 5-((2-aminopyridin-4-yl)oxy)-6-methoxy-N-methyl-1H-indole-1-carboxamide described in Production Example 1-6 (905 mg, 2.90 mmol) and tetrahydrofuran (28 mL) under nitrogen atmosphere at 0° C. The mixture was stirred at room temperature for 100 minutes, then triethylamine (1.6 mL, 11.5 mmol) and 4-(chloromethyl)benzoyl chloride (0.90 g, 4.76 mmol) were added to the reaction mixture at 0° C., and then the resultant was stirred at room temperature for 1.5 hours. Water, tetrahydrofuran, and ethyl acetate were added to the reaction mixture for partition. The organic layer was washed with a saturated saline solution and then dried over anhydrous magnesium sulfate. The resultant was filtered with NH silica gel (ethyl acetate) and then concentrated under vacuum to obtain a crude product.

The crude product was dissolved in N,N-dimethylformamide (15 mL), commercially available 4-hydroxypiperidine (1.48 g, 14.6 mmol) was added under nitrogen atmosphere at room temperature, and the mixture was stirred for 16 hours. Water and ethyl acetate were added to the reaction mixture for partition and the aqueous layer was extracted with ethyl acetate. The combined organic layer was washed with water and a saturated saline solution, dried over anhydrous magnesium sulfate, and filtered. The solvent was evaporated, the resultant residue was dissolved in dichloromethane, and the resultant was purified with NH silica gel column chromatography (ethyl acetate:methanol=1:0-9:1-17:3-4:1). The target product was collected by filteration and washed with ethyl acetate to obtain the title compound (1.30 g, 84%).

$^1$H-NMR Spectrum (DMSO-d$_6$) δ (ppm): 1.32-1.44 (2H, m), 1.64-1.74 (2H, m), 1.97-2.09 (2H, m), 2.59-2.69 (2H, m), 2.86 (3H, d, J=4.2 Hz), 339-3.50 (3H, m), 3.76 (3H, s), 4.54 (1H, d, J=4.2 Hz), 6.63 (1H, d, J=3.7 Hz), 6.65 (1H, dd, J=5.7, 2.2 Hz), 7.37 (2H, d, J=8.1 Hz), 7.44 (1H, s), 7.66 (1H, d, J=2.4 Hz), 7.78 (1H, d, J=3.7 Hz), 7.92 (2H, d, J=8.2 Hz), 8.10 (1H, s), 8.15-8.22 (2H, m), 10.68 (1H, s).

Example 10

5-((2-(4-(((3S,4S)-3-Hydroxy-4-methoxypyrrolidin-1-yl)methyl)benzamide)pyridin-4-yl)oxy)-6-methoxy-N-methyl-1,4-indole-1-carboxamide

[Chemical Formula 64]

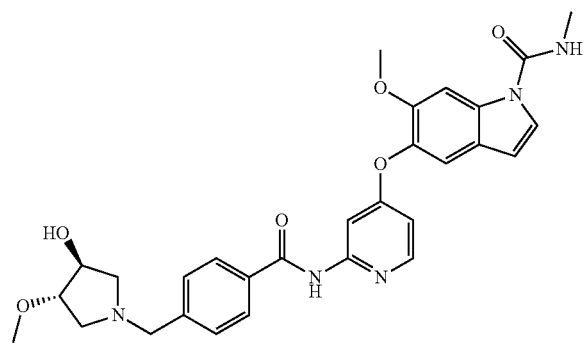

The crude product described in Example 9 (202 mg, 0.033 mmol) was dissolved in N,N-dimethylformamide (0.5 mL), then (3S,4S)-4-methoxypyrrolidin-3-ol (55.9 mg, 0.477 mmol) (described in EP 1375465) was added under nitrogen atmosphere at room temperature, and then the mixture was stirred for 200 minutes. Water and ethyl acetate were added to the reaction mixture for partition, and the organic layer was washed with a saturated saline solution and then dried over anhydrous sodium sulfate. The drying agent was filtered off, the solvent was evaporated, the resultant residue was dissolved in dichloromethane, and the resultant was purified with NH silica gel column chromatography (ethyl acetate: methanol=1:0-19:1-9:1). The residue was washed with diethyl ether to obtain the title compound (13.8 mg, 77%).

$^1$H-NMR. Spectrum (CDCl$_3$) δ (ppm): 2.32 (1H, dd, J=10.1, 4.2 Hz), 2.61-2.68 (1H, m), 2.70-2.77 (1H, m), 3.03-3.16 (4H, m), 3.36 (3H, s), 3.62-3.76 (4H, m), 3.87 (3H, s), 4.12-4.19 (1H, m), 5.42-5.51 (1H, m), 6.56 (1H, d, J=3.7 Hz), 6.59-6.62 (1H, m), 7.23 (1H, d, J=3.7 Hz), 7.32 (1H, s), 7.42 (2H, d, J=8.4 Hz), 7.81 (2H, d, J=8.1 Hz), 7.91 (1H, d, J=2.2 Hz), 8.03 (1H, s), 8.11 (1H, d, J=5.9 Hz), 8.48 (1H, brs).

Example 11

5-((2-(4-(2-(4-Ethylpiperazin-1-yl)ethyl)benzamide)pyridin-4-yl)oxy)-6-methoxy-N-methyl-1H-indole-1-carboxamide

[Chemical Formula 65]

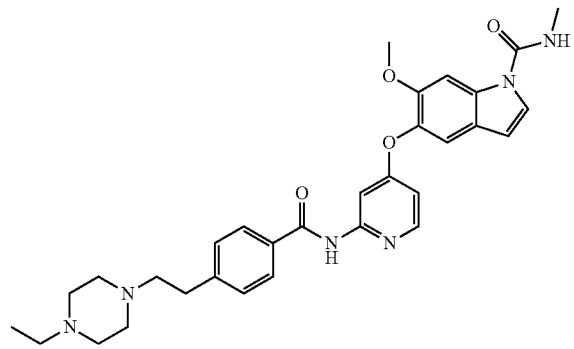

Thionyl chloride (0.116 mL, 1.60 mmol) was added to a mixture of commercially available 4-(2-chloroethyl)benzoic acid (88 mg, 0.479 mmol) and 1,2-dichloroethane (1.0 mL) under nitrogen atmosphere at room temperature, and the mixture was heated under reflux at 90° C. for 1.5 hours. The mixture was cooled to room temperature, then the solvent was evaporated, and the resultant was dissolved in tetrahydrofuran (1.0 mL), and thus an acid chloride solution was prepared. Triethylamine (0.443 mL, 3.20 mmol) was added to a mixture of 5-((2-aminopyridin-4-yl)oxy)-6-methoxy-N-methyl-1H-indole-1-carboxamide described in Production Example 1-6 (49.9 mg, 0.160 mmol) and N,N-dimethylformamide (0.5 mL) under nitrogen atmosphere at room temperature, and the mixture was cooled to 0° C. A previously prepared tetrahydrofuran solution of acid chloride was added at the same temperature, and the mixture was stirred at room temperature for 2.5 hours. Water and ethyl acetate were added to the reaction mixture for partition, then the organic layer was washed with a saturated saline solution and dried over anhydrous sodium sulfate. The solvent was evaporated, and the resultant residue was dissolved in dichloromethane, the resultant was purified with NH silica gel column chromatography (n-heptarie:ethyl acetate=3:1-0:1), and then the target fraction was concentrated under vacuum to obtain a crude product (48.9 mg).

The crude product (48.9 mg) was dissolved in N,N-dimethylformamide (0.25 mL), then commercially available N-ethylpiperazine (129 μL, 1.02 mmol) and N,N-diisopropylethylamine (26.6 μL, 0.153 mmol) were added under nitrogen atmosphere at morn temperature, and the mixture was heated and stirred at 60° C. for 16 hours. The mixture was cooled to mom temperature, then water and ethyl acetate were added to the reaction mixture for partition, and then the organic layer was washed with a saturated saline solution, dried over anhydrous sodium sulfate, and filtered. The solvent was evaporated, the resultant residue was dissolved in dichloromethane, and the resultant was purified with NH silica gel column chromatography (n-heptane:ethyl acetate=1:1-0:1-ethyl acetate:methanol=99:1-19:1). The mixture fraction was concentrated under vacuum and the residue was purified with NH silica gel TLC (ethyl acetate) to obtain the title compound (7.03 mg, 16%).

$^1$H-NMR Spectrum (CDCl$_3$) δ (ppm): 1.10 (3H, t, J=7.3 Hz), 2.44 (2H, q, J=7.0 Hz), 2.35-2.70 (10H, m), 2.81-2.90 (2H, m), 3.07 (3H, d, J=4.8 Hz), 3.86 (3H, s), 5.43-5.51 (1H, m), 6.56 (1H, d, J=3.7 Hz), 6.60 (1H, dd, J=5.9, 2.6 Hz), 7.23 (1H, d, J=3.7 Hz), 7.28-7.33 (3H, m), 7.78 (2H, d, J=8.4 Hz), 7.91 (1H, d, J=2.2 Hz), 8.03 (1H, s), 8.10 (1H, d, J=5.9 Hz), 8.46 (1H, brs).

Example 12

5-((2-(4-(2-(4-Hydroxypiperidin-1-yl)ethoxy)benzamide)pyridin-4-yl)oxy)-6-methoxy-N-methyl-1H-indole-1-carboxamide

[Chemical Formula 66]

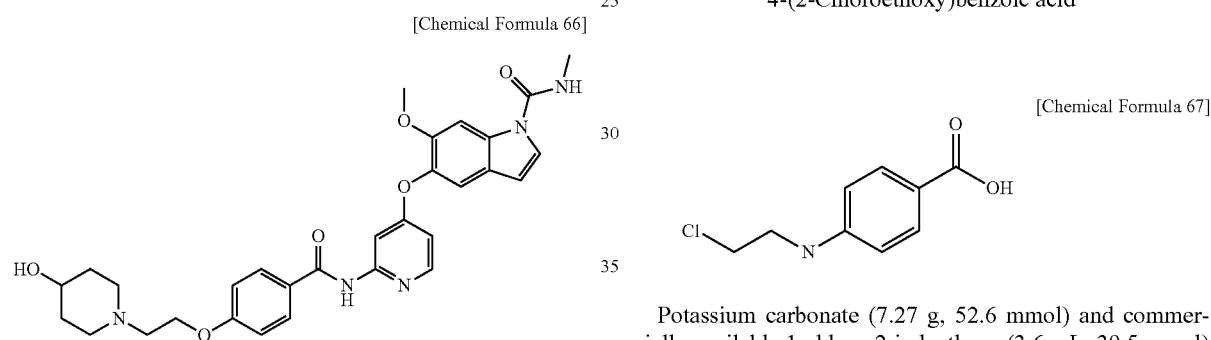

Oxalyl chloride (44 μL, 0.513 mmol) and a catalytic quantity of N,N-dimethylformamide were added to a mixture of 4-(2-chloroethoxy)benzoic acid described in Production Example 12-1 (51.2 mg, 0.255 mmol) and dichloromethane (2.0 mL) under nitrogen atmosphere at mom temperature, and the mixture was stirred for 45 minutes, Oxalyl chloride (44 μL, 0.513 mmol) was added to the reaction mixture at room temperature, and the mixture was stirred for 30 minutes. The solvent was evaporated and the resultant was dissolved in tetrahydrofuran (0.5 mL), and thus an acid chloride solution was prepared, Triethylamine (89 μL, 0.64 mmol) was added to a mixture of 5-((2-aminopyridin-4-yl)oxy)-6-methoxy-N-methyl-1H-indole-1-carboxamide described in Production Example 1-6 (40 mg, 0.128 mmol) and N,N-dimethylformamide (0.5 mL) under nitrogen atmosphere at room temperature. The previously prepared tetrahydrofuran solution of acid chloride was added at the same temperature, and the mixture was stirred at room temperature for 80 minutes. A saturated aqueous sodium bicarbonate solution and ethyl acetate were added to the reaction mixture for partition and the organic layer was dried over anhydrous sodium sulfate. The resultant was filtered with NH silica gel (ethyl acetate) and then concentrated under vacuum to obtain a crude product (80.6 mg).

The crude product (80.6 mg) was dissolved in N,N-dimethylformamide (0.7 mL), commercially available 4-hydroxypiperidine (93 mg, 0.919 mmol) was added under nitrogen atmosphere at room temperature, and the mixture was heated and stirred at 80° C. for 12 hours. The mixture was cooled to mom temperature, water and ethyl acetate were added to the reaction mixture for partition, and the aqueous layer was extracted with ethyl acetate once. The combined organic layer was washed with water and a saturated saline solution, then dried over anhydrous sodium sulfate, and then filtered. The solvent was evaporated and the resultant residue was purified with NH silica gel TLC (ethyl acetate:methanol=9:1). The resultant residue was purified with NH silica gel TLC (ethyl acetate) to obtain the title compound (10.8 mg, 30%).

$^1$H-NMR Spectrum (CDCl$_3$) δ (ppm): 1.55-1.67 (2H, m), 1.86-1.97 (2H, m), 2.31 (2H, t, J=9.5 Hz), 2.78-2.92 (4H, m), 3.06 (3H, d, J=4.4 Hz), 3.67-3.77 (1H, m), 3.86 (3H, s), 4.14 (2H, t, J=5.7 Hz), 5.50-5.59 (1H, m), 6.54 (1H, d, J=3.3 Hz), 6.60 (1H, dd, J=5.7, 2.4 Hz), 6.95 (2H, d, J=8.8 Hz), 7.22 (1H, d, J=3.7 Hz), 7.32 (1H, s), 7.81 (2H, d, J=8.8 Hz), 7.88 (1H, d, J=1.8 Hz), 8.03 (1H, s), 8.09 (1H, d, J=5.9 Hz), 8.47 (1H, brs).

The reagent 4-(2-chloroethoxy)benzoic acid was synthesized by the following method.

Production Example 12-1

4-(2-Chloroethoxy)benzoic acid

[Chemical Formula 67]

Potassium carbonate (7.27 g, 52.6 mmol) and commercially available 1-chloro-2-iodoethane (3.6 mL, 39.5 mmol) were added to a liquid mixture of commercially available methyl p-hydroxybenzoate (2.0 g, 13.1 mmol) and N,N-dimethylformamide (50 mL) under nitrogen atmosphere at room temperature, and the mixture was heated and stirred at 60° C. for 12 hours. The mixture was cooled to mom temperature and then a saturated aqueous ammonium chloride solution, water, and diethyl ether were added to the reaction mixture for partition. The organic layer was washed with water and a saturated saline solution, then dried over anhydrous magnesium sulfate, and then filtered and concentrated under vacuum. Tetrahydrofuran (25 mL), methanol (10 mL), and a 2 M sodium hydroxide solution (10 mL) were added to the residue at morn temperature, and the mixture was heated and stirred at 80° C. for 4 hours. The reaction mixture was cooled to 0° C., acidified with 5 M hydrochloric acid, and then the mixture was diluted with ethyl acetate for partition. The aqueous layer was extracted with ethyl acetate, the combined organic layer was washed with water and a saturated saline solution, then dried over anhydrous magnesium sulfate, and filtered. The solvent was evaporated, the precipitate was separated by filtration with a liquid mixture of ethyl acetate and tetrahydrofuran, the resultant was washed, and the filtrate was concentrated under vacuum. The residue was purified with silica gel column chromatography (n-heptane:ethyl acetate=3:1-2:1-1:1) and the target fraction was concentrated under vacuum to obtain the title compound (278 mg, 11%).

$^1$H-NMR Spectrum (DMSO-d$_6$) δ (ppm): 3.92-3.98 (2H, m), 4.26-4.35 (2H, m), 6.96-7.06 (2H, m), 7.82-7.91 (2H, m),12.68 (1H, bis).

Example 13

5-((2-(1-(1-Ethylpiperidin-4-yl)-1H-pyrazole-4-carboxamide)pyridin-4-yl)oxy)-6-methoxy-N-methyl-1H-indole-1-carboxamide

[Chemical Formula 68]

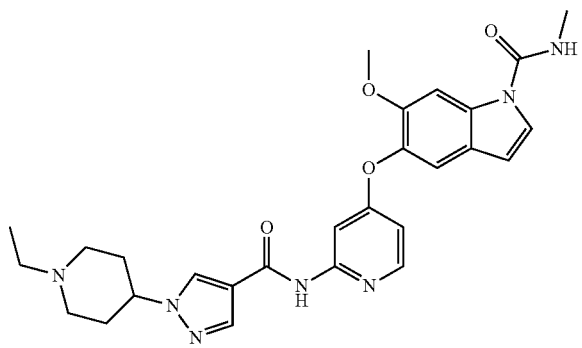

Acetaldehyde (8.9 mg, 0.202 mmol) and sodium triacetoxyborohydride (43.9 mg, 0.207 mmol) were added to a mixture of 6-methoxy-N-methyl-5-((2-(1-(piperidin-4-yl)-1H-pyrazole-4-carboxamide)pyridin-4-yl)oxy)-1H-indole-1-carboxamide described in Production Example 13-4 (20.3 mg, 0.041 mmol) and tetrahydrofuran (1.0 mL) at room temperature, and the mixture was stirred for 2.5 hours. A saturated aqueous sodium bicarbonate solution and ethyl acetate were added to the reaction mixture for partition. The organic layer was washed with a saturated saline solution, dried over anhydrous sodium sulfate, and filtered. The solvent was evaporated and the resultant residue was purified with NH silica gel TLC (ethyl acetate). The product was washed with diethyl ether to obtain the title compound (9.3 mg, 43%).

$^1$H-NMR Spectrum (CDCl$_3$) δ (ppm): 1.11 (3H, t, J=7.1 Hz), 1.94-2.24 (6H, m), 2.46 (2H, q, J=7.4 Hz), 3.03-3.11 (5H, m), 3.86 (3H, s), 4.09-4.19 (1H, m), 5.49-5.56 (1H, m), 6.54 (1H, d, J=2.9 Hz), 6.60 (1H, dd, J=5.9, 2.4 Hz), 7.22 (1H, d, J=3.7 Hz), 7.31 (1H, s), 7.81 (1H, d, J=2.0 Hz), 7.85 (1H, d, J=0.7 Hz), 7.96 (1H, s), 8.02 (1H, s), 8.08 (1H, d, J=5.9 Hz), 8.17 (1H, brs).

The starting material 6-methoxy-N-methyl-5-((2-(1-(piperidin-4-yl)-1H-pyrazole-4-carboxamide)pyridin-4-yl)oxy)-1H-indole-1-carboxamide was synthesized by the following method.

Production Example 13-1 tert-Butyl 4-((methylsulfonyl)oxy)piperidine-1-carboxylate

[Chemical Formula 69]

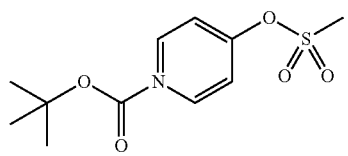

Commercially available methanesulfonyl chloride (6.35 mL, 82.0 mmol) and triethylamine (26.0 mL, 186 mmol) were added to a mixture of commercially available tert-butyl 4-hydroxy-1-piperidine carboxylate (15 g, 74.5 mmol) and tetrahydrofuran (200 mL) at 0° C., and the mixture was stirred for 30 minutes. Water and ethyl acetate were added to the reaction mixture for partition. The organic layer was dried and filtered by conventional methods. The solvent was evaporated, and the residue was collected by filteration and washed with n-heptane to obtain the title compound (19.8 g, 95%).

$^1$H-NMR Spectrum (CDCl$_3$) δ (ppm): 1.46 (9H, s), 1.72-1.88 (2H, m), 1.90-2.04 (2H, m), 3.03 (3H, s), 3.24-3.36 (2H, m), 3.64-3.77 (2H, m), 4.80-4.94 (1H, m).

Production Example 13-2 tert-Butyl 4-(4-(ethoxycarbonyl)-1H-pyrazol-1-yl)piperidine-1-carboxylate

[Chemical Formula 70]

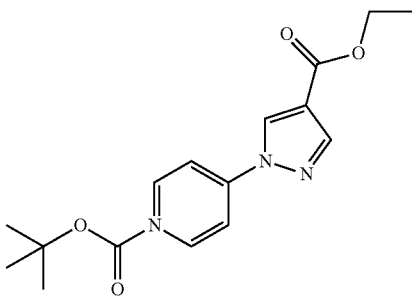

tert-Butyl 4-((methylsulfonyl)oxy)piperidine-1-carboxylate described in Production Example 13-1 (2.7 g, 9.67 mmol) and commercially available ethyl 4-pyrazole carboxylate (1.49 g, 10.6 mmol) were dissolved in N,N-dimethylformamide (30 mL), 50-72% oily sodium hydride (570 mg) was added at 0° C., and the mixture was heated and stirred at 60° C. for 11 hours. The reaction mixture was cooled to room temperature and water and ethyl acetate were added for partition. The organic layer was washed with water twice and then dried over anhydrous sodium sulfate and filtered. The solvent was evaporated, the resultant residue was dissolved in dichloromethane, the resultant was purified with silica gel column chromatography (n-heptane:ethyl acetate=4:1-1:1-1:3-0:1), and the target fraction was concentrated under vacuum to obtain the title compound (2.11 g, 68%).

$^1$H-NMR Spectrum (CDCl$_3$) δ (ppm): 1.34 (3H, t, J=7.1 Hz), 1.47 (9H, s), 1.82-1.96 (2H, m), 2.10-2.18 (2H, m), 2.82-2.96 (2H, m), 4.19-4.34 (3H, m), 4.29 (2H, q, J=7.1 Hz), 7.91 (1H, s), 7.92 (1H, s).

Production Example 13-3

1-(1-(tert-Butoxycarbonyl)piperidin-4-yl)-1H-pyrazole-4-carboxylic acid

[Chemical Formula 71]

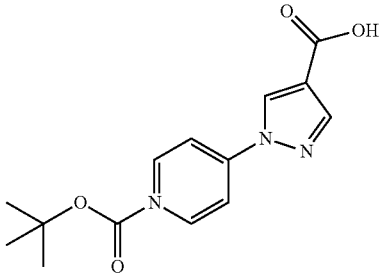

tert-Butyl 4-(4-(ethoxycarbonyl)-1H-pyrazol-1-yl)piperidine-1-carboxylate described in Production Example 13-2 (2.11 g, 6.53 mmol) was dissolved in methanol (60 mL), then potassium hydroxide (1.46 g, 26.1 mmol) dissolved in water (16 mL) was added, and then the mixture was stirred for 27 hours. The reaction mixture was concentrated under vacuum and diethyl ether was added for partition. Ethyl acetate was added to the aqueous layer for dilution, then a 5% aqueous potassium hydrogensulfate solution was added for acidification, and the mixture was extracted with ethyl acetate twice. The combined organic layer was dried over anhydrous magnesium sulfate and filtered. The solvent was evaporated to obtain the title compound (1.58 g, 82%).

$^1$H-NMR Spectrum (CDCl$_3$) δ (ppm): 1.48 (9H, s), 1.84-1.98 (2H, m), 2.11-2.20 (2H, m), 2.81-2.97 (2H, m), 4.18-4.36 (3H, m), 7.97 (1H, s), 7.98 (1H, s).

Production Example 13-4

6-Methoxy-N-methyl-5-((2-(1-(piperidin-4-yl)-1H-pyrazole-4-carboxamide)pyridin-4-yl)oxy)-1H-indole-1-carboxamide

[Chemical Formula 72]

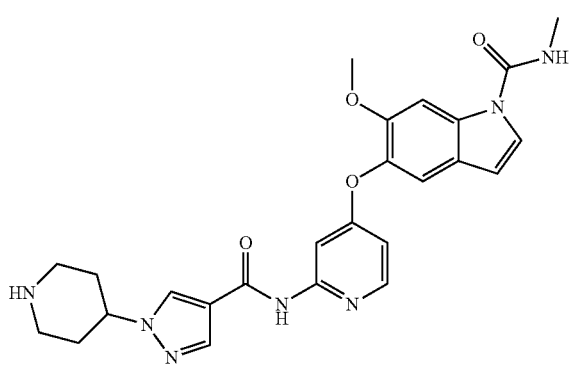

Benzotriazole (97 mg, 0.813 mmol) was dissolved in dichloromethane (4.0 mL), and thionyl chloride (59 μL, 0.813 mmol) was added at room temperature and the mixture was stirred for 5 minutes under nitrogen atmosphere. 1-(1-(tert-Butoxycarbonyl)piperidin-4-yl)-1H-pyrazole-4-carboxylic acid described in Production Example 13-3 (200 mg, 0.677 mmol) was added to the reaction mixture at room temperature, and the mixture was stirred for 25 minutes. The reaction mixture was filtered through a glass filter entirely covered with anhydrous sodium sulfate and then washed with dichloromethane, the filtrate was added to a mixture of 5-((2-aminopyridin-4-yl)oxy)-6-methoxy-N-methyl-1H-indole-1-carboxamide described in Production Example 1-6 (102 mg, 0.327 mmol), triethylamine (0.453 mL, 3.27 mmol), and 4-dimethylaminopyridine (3.99 mg, 0.033 mmol) in tetrahydrofuran (5.0 mL) at 0° C. The mixture was stirred at room temperature for 2 hours, then water and ethyl acetate were added to the reaction mixture for partition, then the organic layer was washed with a saturated saline solution and then dried over anhydrous sodium sulfate. The drying agent was filtered off and the filtrate was concentrated under vacuum. The residue was dissolved in tetrahydrofuran, an excessive quantity of 9.8 M methylamine methanol solution was added at room temperature, and the mixture was stirred for 4 hours. The reaction mixture was concentrated under vacuum and the residue was dissolved in dichloromethane, and the resultant was purified with NH silica gel column chromatography (n-heptane:ethyl acetate=−1:9-0:1). The target fraction was concentrated under vacuum to obtain a crude product (170 mg).

The crude product (170 mg) was dissolved in dichloromethane (1.8 mL) and trifluoroacetic acid (0.5 mL) was added at 0° C. The mixture was stirred at room temperature for 80 minutes, then was concentrated under vacuum, and the residue was dissolved in dichloromethane-triethylamine, then the resultant was purified with NH silica gel column chromatography (ethyl acetate:methanol=49:1-4:1), then the target fraction was concentrated under vacuum to obtain the title compound (812 mg, 51%).

$^1$H-NMR Spectrum (CDCl$_3$) δ (ppm): 1.78-1.91 (2H, m), 2.11-2.19 (2H, m), 2.75 (2H, td, J=12.3, 2.3 Hz), 3.05 (3H, d, J=4.6 Hz), 3.19-3.27 (2H, m), 3.85 (3H, s), 4.16426 (1H, m), 5.53-5.63 (1H, m), 6.53 (1H, d, J=3.5 Hz), 6.60 (1H, dd, J=5.8, 2.5 Hz), 7.22 (1H, d, J=3.8 Hz), 7.30 (1H, s), 7.81 (1H, d, J=2.4 Hz), 7.86 (1H, s), 7.96 (1H, s), 8.03 (1H, s), 8.08 (1H, d, J=5.9 Hz), 8.22 (1H, brs).

Example 14

5-((2-(4-((1-(2-Hydroxyethyl)piperidin-4-yl)oxy)benzamide)pyridin-4-yl)oxy)-6-methoxy-N-methyl-1H-indole-1-carboxamide

[Chemical Formula 73]

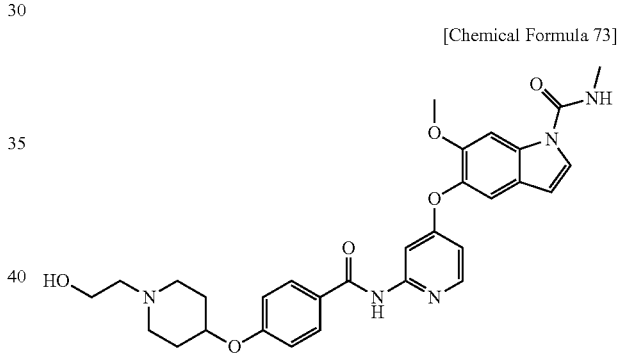

Benzotriazole (34.1 mg, 0.286 mmol) was dissolved in dichloromethane (1.5 mL), then thionyl chloride (20 μL, 0.274 mmol) was added under nitrogen atmosphere at room temperature, and then the mixture was stirred for 5 minutes. 4-((1-(tert-Butoxycarbonyl)piperidin-4-yl)oxy)benzoic acid described in Production Example 14-1 (79.3 mg, 0.247 mmol) was added to the reaction mixture at room temperature, and the mixture was stirred for 25 minutes. The reaction mixture was filtered through a glass filter entirely covered with anhydrous sodium sulfate and then washed with dichloromethane, then the filtrate was added to a mixture of 5-((2-aminopyridin-4-yl)oxy)-6-methoxy-N-methyl-1H-indole-1-carboxamide described in Production Example 1-6 (35.6 mg, 0.114 mmol), triethylamine (0.158 mL, 1.14 mmol), and 4-dimethylaminopyridine (1.39 mg, 0.011 mmol), in tetrahydrofuran (1.1 mL) at 0° C. The reaction mixture was stirred at room temperature for 1.5 hours, then water and ethyl acetate were added to the reaction mixture for partition, and then the organic layer was washed with a saturated saline solution and dried over anhydrous sodium sulfate. The drying agent was filtered off, the filtrate was concentrated under vacuum, the residue was dissolved in tetrahydrofuran, an excessive quantity of 9.8 M methylamine methanol solution was added at room temperature, and the mixture was stirred for 2 hours. The reaction mixture was concentrated under vacuum, the residue was dissolved in dichloromethane, and the resultant was purified with NH silica gel column chromatography (n-heptane:ethyl acetate=1:1-1:3-0:1). The target fraction was concentrated under vacuum to obtain a crude product A (41.1 mg).

The crude product A (41.1 mg) was dissolved in dichloromethane (0.6 mL) and trifluoroacetic acid (0.2 mL) was added at 0° C. The mixture was stirred at room temperature for 75 minutes and the resultant was concentrated under vacuum, the residue was dissolved in dichloromethane-triethylamine and then the resultant was purified with NH silica gel column chromatography (ethyl acetate:methanol=49:1-4:1), and then the target action was concentrated under vacuum to obtain a crude product B (34 mg).

Sodium triacetoxyborohydride (17.5 mg, 0.082 mmol) and commercially available 2-hydroxyacetaldehyde (4.95 mg, 0.082 mmol) were added to a mixture of the crude product B (8.5 mg, 0.016 mmol) and tetrahydrofuran (0.5 mL) at room temperature, and the mixture was stirred for 2 hours. A saturated aqueous sodium bicarbonate solution and ethyl acetate were added to the reaction mixture for partition. The organic layer was washed with a saturated saline solution, and then dried over anhydrous sodium sulfate and filtered. The solvent was evaporated and the resultant residue was purified with NH silica gel TLC (ethyl acetate). The residue was washed with diethyl ether to obtain the title compound (6.4 mg, 40%).

$^1$H-NMR Spectrum (CDCl$_3$) δ (ppm): 1.78-1.90 (2H, m), 1.95-2.06 (2H, m), 2.35-2.47 (2H, m), 2.57 (2H, t, J=5.6 Hz), 2.72-2.83 (2H, m), 3.07 (3H, d, J=4.4 Hz), 3.62 (2H, t, J=5.3 Hz), 3.86 (3H, s), 4.38-4.48 (1H, m), 5.45-5.54 (1H, m), 6.55 (1H, d, J=3.7 Hz), 6.59 (1H, dd, J=5.7, 2.4 Hz), 6.94 (2H, d, J=8.8 Hz), 7.23 (1H, d, J=3.7 Hz), 7.32 (1H, s), 7.81 (2H, d, J=8.8 Hz), 7.89 (1H, d, J=2.6 Hz), 8.03 (1H, s), 8.09 (1H, d, J=5.5 Hz), 8.45 (1H, brs).

The starting material 4-((1-(tert-butoxycarbonyl)piperidin-4-yl)oxy)benzoic acid was synthesized by the following method.

Production Example 14-1

4-((1-(tert-Butoxycarbonyl)piperidin-4-yl)oxy)benzoic acid

[Chemical Formula 74]

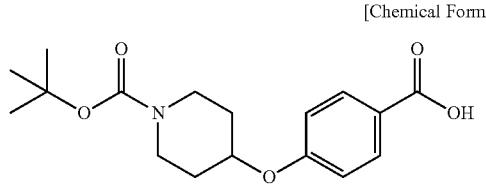

Diisopropyl azodicarboxylate (9.65 mL, 1.9 M, 18.3 mmol) was added to a mixture of commercially available benzyl 4-hydroxy benzoate (3 g, 13.1 mmol), commercially available tert-butyl 4-hydroxypiperidine-1-carboxylate (2.77 g, 13.8 mmol), triphenylphosphine (4.81 g, 18.3 mmol), and tetrahydrofuran (1501a) at 0° C., and the mixture was stirred at room temperature overnight. Water and ethyl acetate were added to the reaction mixture for partition. The organic layer was washed with a saturated aqueous sodium bicarbonate solution and then with a saturated saline solution, then dried over anhydrous magnesium sulfate and filtered. The solvent was evaporated, the resultant residue was purified with NH silica gel column chromatography (n-heptane:ethyl acetate=1:1), then the target fraction was concentrated under vacuum to obtain a crude product (3.8 g).

A part of the crude product (500 mg, 1.22 mmol) was dissolved in ethanol (5 mL), a 5 M sodium hydroxide solution (0.729 mL, 3.65 mmol) was added, and the mixture was heated and stirred at 50° C. for 7 hours. The reaction mixture was cooled to room temperature, and then 5 M hydrochloric acid and ethyl acetate were added for partition. The organic layer was dried and filtered by conventional methods. The solvent was evaporated and then the resultant was collected by filteration and washed with n-heptane to obtain the title compound (343 mg, 62%).

$^1$H-NMR Spectrum (CDCl$_3$) δ (ppm): 1.47 (9H, s), 1.65-1.84 (2H, m), 1.87-2.07 (2H, m), 3.30-3.51 (2H, m), 3.60-3.80 (2H, m), 4.50-4.66 (1H, m), 6.87-7.03 (2H, m), 7.98-8.14 (2H, m).

Example 15

6-Ethoxy-N-methyl-5-((2-(4-(piperidin-4-yl)benzamide)pyridin-4-yl)oxy)-1H-indole-1-carboxamide

[Chemical Formula 75]

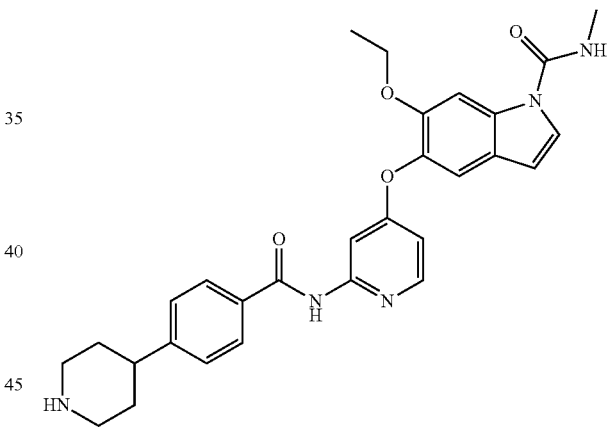

tert-Butyl 4-(4-((4-((6-ethoxy-1-(methylcarbamoyl)-1H-indol-5-yl)oxy)pyridin-2-yl) carbamoyl)phenyl)piperidine-1-carboxylate described in Production Example 15-8 (3.35 g, 5.46 mmol) was dissolved in dichloromethane (45 mL), and trifluoroacetic acid (15 mL) was added at 0° C. The mixture was stirred at room temperature for 110 minutes, then concentrated under vacuum, and the residue was dissolved in dichloromethanettiethylamine, then the resultant was purified with NH silica gel column chromatography (ethyl acetatenethanol=97:3-4:1) to obtain the title compound (2.41 g, 86%).

$^1$H-NMR Spectrum (CDCl$_3$) δ (ppm): 1.25 (3H, t, J=7.0 Hz), 1.50-1.70 (2H, m), 1.79-1.88 (2H, m), 2.63-2.80 (3H, m), 3.06 (3H, d, J=4.8 Hz), 3.16-3.24 (2H, m), 4.11 (2H, q, J=7.0 Hz), 5.46-5.54 (1H, m), 6.55 (1H, d, J=3.3 Hz), 6.60 (1H, dd, J=5.9, 2.6 Hz), 7.23 (1H, d, J=3.7 Hz), 7.29-7.34 (3H, m), 7.78-7.83 (2H, m), 7.92 (1H, d, J=2.2 Hz), 8.00 (1H, s), 8.08-8.11 (1H, m), 8.50 (1H, brs).

The starting material ten-butyl 4-(4-((4-((6-ethoxy-1-(methylcarbamoyl)-1H-indol-5-yl)oxy)pyridin-2-yl)carbamoyl)phenyl)piperidine-1-carboxylate was synthesized by the following method.

Production Example 15-1

4-Ethoxy-3-hydroxybenzaldehyde

[Chemical Formula 76]

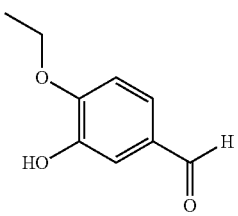

Commercially available 3,4-dihydroxy benzaldehyde (35.8 g, 259 mmol) and potassium carbonate (37.6 g, 272 mmol) were dissolved in N,N-dimethylformamide (150 mL), then commercially available iodoethane (22 mL, 275 mmol) was added under nitrogen atmosphere at 0° C., and then the mixture was stirred for 2 days. The solvent was evaporated under vacuum, the resultant was cooled to 0° C., and then 5 M hydrochloric acid, ethyl acetate, and water were added for partition. The aqueous layer was extracted with ethyl acetate, the combined organic layer was washed with water twice and then with a saturated saline solution, and the mixture was dried over anhydrous magnesium sulfate and then filtered. The solvent was evaporated, then dichloromethane was added, and then the precipitate was collected by filteration to obtain the title compound (25.8 g, 60%). The filtrate was purified with silica gel column chromatography (n-heptane: ethyl acetate=9:1-4:1-1:1). The target fraction was concentrated under vacuum, then diethyl ether and dichloromethane were added to the residue, and the precipitate was collected by filteration to obtain the title compound (3.45 g, 8.0%).

$^1$H-NMR Spectrum (CDCl$_3$) δ (ppm): 1.50 (31-1.1, J=7.1 Hz), 4.22 (2H, q, J=7.0 Hz), 5.75 (1H, s), 6.95 (1H, d, J=8.1 Hz), 7.39-7.45 (2H, m), 9.84 (1H, s).

Production Example 15-2

3-(Benzyloxy)-4-ethoxybenzaldehyde

[Chemical Formula 77]

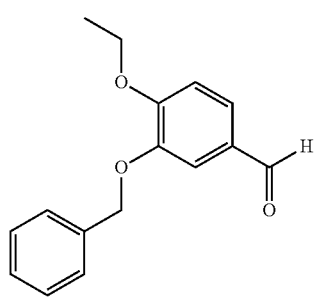

Potassium carbonate (19.8 g, 143 mmol) and benzyl chloride (16.5 mL, 143 mmol) were added to a suspension of 4-ethoxy-3-hydroxybenzaldehyde described in Production Example 15-1 (20 g, 120 mmol) in ethanol (200 mL) under nitrogen atmosphere at room temperature, and the mixture was heated and stirred at 90° C. for 2.5 hours. The mixture was cooled to 0° C., and 2 M hydrochloric acid, ethyl acetate, and water were added for partition. The organic layer was washed with a saturated saline solution, dried over anhydrous magnesium sulfate, and filtered. The solvent was evaporated and the resultant residue was purified with silica gel column chromatography (n-heptane:ethyl acetate=9:1-4:1-3:1). The target fraction was concentrated under vacuum to obtain the title compound (28.5 g, 92%).

$^1$H-NMR. Spectrum (CDCl$_3$) δ (ppm): 1.51 (3H, t, J=7.0 Hz), 4.20 (2H, q, J=7.0 Hz), 5.19 (2H, s), 6.98 (1H, d, J=8.8 Hz), 7.29-7.34 (1H, m), 7.35-7.41 (2H, m), 7.43-7.49 (4H, m), 9.81 (1H, s).

Production Example 15-3

(E)-2-(Benzyloxy)-1-ethoxy-4-(2-nitrovinyl)benzene

[Chemical Formula 78]

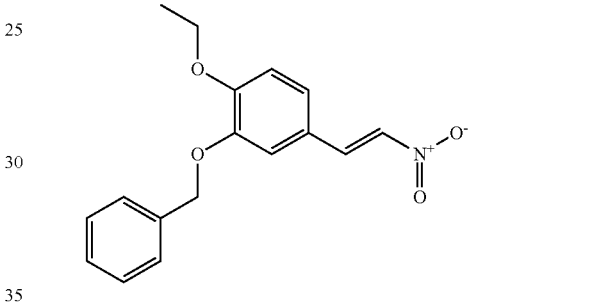

3-(Benzyloxy)-4-ethoxy benzaldehyde described in Production Example 15-2 (14.5 g, 56.4 mmol) was dissolved in acetic acid (45 mL), then ammonium acetate (5.22 g, 67.7 mmol) and nitromethane (7.5 mL, 138 mmol) were added under nitrogen atmosphere at room temperature, and the mixture was heated and stirred at 130° C. for 2.5 hours. The mixture was cooled to room temperature and the precipitate was collected by filteration and washed with ethanol to quantitatively obtain the title compound.

$^1$H-NMR Spectrum (CDCl$_3$) δ (ppm): 1.50 (3H, t, J=7.0 Hz), 4.17 (2H, q, J=7.2 Hz), 5.17 (2H, s), 6.92 (1H, d, J=8.4 Hz), 7.04 (1H, d, J=2.2 Hz), 7.16 (1H, dd, J=8.6, 2.0 Hz), 7.29-7.51 (6H, m), 7.90 (1H, d, J=13.5 Hz).

Production Example 15-4

6-Ethoxy-1H-indol-5-ol

[Chemical Formula 79]

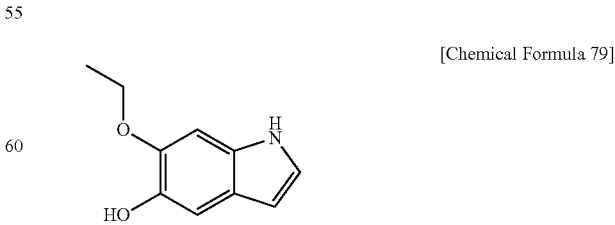

Fuming nitric acid (13 mL, 289 mmol) was slowly added to a mixture of (E)-2-(benzyloxy)-1-ethoxy-4-(2-nitrovinyl)benzene described in Production Example 15-3 (16.9 g, 56.6 mmol) and acetic acid (160 mL) at room temperature, and the mixture was stirred for 6 hours. The reaction mixture was poured onto ice, then the precipitate was collected by filteration and then washed with a liquid mixture of acetic acid and ethanol to obtain a crude product (19.5 g).

The crude product (19.5 g) was suspended in methanol (500 mL), then 10% palladium-carbon (water content, 50%) (6.85 g) was added, and the mixture was stirred under hydrogen atmosphere for 17 hours. The catalyst was filtered off with celite, and the resultant was washed with methanol. The filtrate was concentrated under vacuum and the resultant was dissolved in tetrahydrofuran and adsorbed by silica gel. The adsorbed silica gel was concentrated under vacuum and the resultant was purified with silica gel column chromatography (n-heptane:ethyl acetate=9:1-13:7). The target fraction was concentrated under vacuum, and the residue was collected by filteration and washed with diethyl ether to obtain the title compound (3.78 g, 38%).

$^1$H-NMR Spectrum (CDCl$_3$) δ (ppm): 1.48 (3H, t, J=6.9 Hz), 4.13 (2H, q, J=6.8 Hz), 5.50 (1H, s), 6.39-6.43 (1H, m), 6.87 (1H, s), 7.05-7.09 (1H, m), 7.13 (1H, s), 7.91 (1H, brs).

Production Example 15-5

N-(4-((6-Ethoxy-1H-indol-5-yl)oxy)pyridin-2-yl)acetamide

[Chemical Formula 80]

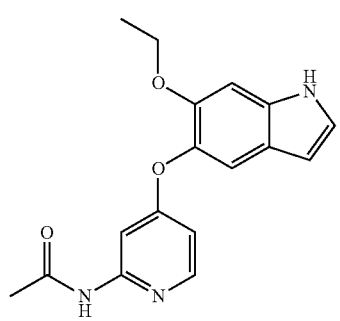

6-Ethoxy-1H-indol-5-ol described in Production Example 15-4 (7.0 g, 39.5 mmol) was dissolved in dimethylsulfoxide (40 mL) under nitrogen atmosphere, then N-(4-chloropyridin-2-yl)acetamide described in Production Example 1-5 (8.09 g, 47.4 mmol) and potassium tert-butoxide (4.88 g, 43.5 mmol) were added at room temperature, and the mixture was heated and stirred at 160° C. for 4 hours. The reaction liquid was cooled to room temperature and water and ethyl acetate were added for partition. The aqueous layer was extracted with ethyl acetate and the combined organic layer was washed with water twice and then with a saturated saline solution. The organic layer was dried over anhydrous magnesium sulfate and then filtered, and the filtrate was concentrated under vacuum. The residue was dissolved in dichloromethane, and the resultant was purified with silica gel column chromatography (n-heptane:ethyl acetate=3:1-2:1-3:2-1:3-1:4-0:1), and then the target fraction was concentrated under vacuum to obtain the title compound (7.16 g, 58%).

$^1$H-NMR Spectrum (CDCl$_3$) δ (ppm): 1.23 (3H, t, J=7.0 Hz), 2.14 (3H, s), 4.02 (2H, q, J=7.0 Hz), 6.46-6.49 (1H, m), 6.54 (1H, dd, J=5.9, 22 Hz), 7.01 (1H, s), 7.13-7.16 (1H, m), 7.35 (1H, s), 7.74 (1H, brs), 7.87 (1H, brs), 8.02 (1H, d, J=5.9 Hz), 8.10 (1H, brs).

Production Example 15-6

4-((6-Ethoxy-1H-indol-5-yl)oxy)pyridin-2-amine

[Chemical Formula 81]

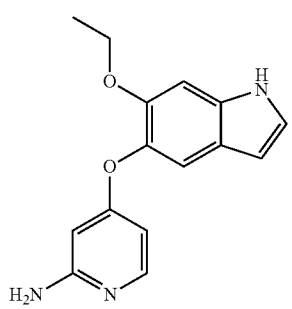

N-(4-((6-ethoxy-1H-indol-5-yl)oxy)pyridin-2-yl)acetamide described in Production Example 15-5 (7.16 g, 23.0 mmol) was dissolved in methanol (50 mL), a 2 M sodium hydroxide solution (50 mL) was added under nitrogen atmosphere at room temperature, and the mixture was heated and stirred at 75° C. for 2.5 hours. The reaction mixture was cooled to room temperature and then water and ethyl acetate were added for partition. The aqueous layer was extracted with ethyl acetate and the combined organic layer was washed with a saturated saline solution. The organic layer was dried over anhydrous magnesium sulfate, then the resultant was filtered and concentrated under vacuum. A liquid mixture of diethyl ether and ethyl acetate was added to the residue, and the mixture was collected by filteration and washed to obtain the title compound (5.35 g, 86%).

$^1$H-NMR Spectrum (CDCl$_3$) δ (ppm): 1.28 (3H, t, J=7.0 Hz), 4.02 (2H, q, J=7.0 Hz), 4.28 (2H, brs), 5.91 (1H, d, J=2.2 Hz), 6.29 (1H, dd, J=5.9, 2.2 Hz), 6.46-6.50 (1H, m), 7.00 (1H, s), 7.15-7.18 (1H, m), 7.33 (1H, s), 7.88 (1H, d, J=5.9 Hz), 8.13 (1H, brs).

Production Example 15-7

5-((2-Aminopyridin-4-yl)oxy)-6-ethoxy-N-methyl-1H-indole-1-carboxamide

[Chemical Formula 82]

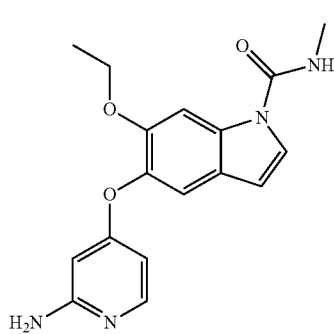

4-((6-Ethoxy-1H-indol-5-yl)oxy)pyridin-2-amine described in Production Example 15-6 (6.44 g, 23.9 mmol) was dissolved in N,N-dimethylformamide (80 mL), 50-72% oily sodium hydride (1.41 g) was added under nitrogen atmosphere at 0° C., and the mixture was stirred at mom temperature for 40 minutes. The mixture was cooled to 0° C. again, phenyl methylcarbamate described in Production Example 1-7 (5.78 g, 38.3 mmol) was added, and the mixture was stirred at room temperature for 3 hours. A saturated aqueous ammonium chloride solution, water, and ethyl acetate were added to the reaction mixture for partition. The aqueous layer was extracted with ethyl acetate and the combined organic layer was washed with water twice and then with a saturated saline solution. The organic layer was dried over anhydrous magnesium sulfate and then filtered, then the filtrate was concentrated under vacuum. A liquid mixture of diethyl ether and ethyl acetate was added to the residue, then the precipitate was collected by filtration and the resultant was washed with ethyl acetate again to obtain the title compound (4.24 g, 54%). The filtrate was purified with NH silica gel column chromatography (ethyl acetate:methanol=1:0-9:1), the target fraction was concentrated under vacuum, and then the residue was collected by filtration and washed with a liquid mixture of diethyl ether and ethyl acetate to obtain the title compound (1.58 g, 20%).

$^1$H-NMR. Spectrum (CDCl$_3$) δ (ppm): 1.29 (3H, t, J=7.0 Hz), 3.07 (3H, d, J=4.8 Hz), 4.09 (2H, q, J=7.0 Hz), 4.29 (2H, brs), 5.42-5.51 (1H, m), 5.90 (1H, d, J=22 Hz), 6.27 (1H, dd, J=6.2, 2.2 Hz), 6.55 (1H, dd, J=3.7, 0.7 Hz), 7.23 (1H, d, J=3.7 Hz), 7.27 (1H, s), 7.89 (1H, d, J=5.9 Hz), 7.98 (1H, s).

Production Example 15-8 tert-Butyl 4-(4-((4-((6-ethoxy-1-(methylcarbamoyl)-1H-indol-5-yl)oxy)pyridin-2-yl)carbamoyl)phenyl)piperidine-1-carboxylate

[Chemical Formula 83]

Benzotriazole (1.92 g, 16.1 mmol) was dissolved in dichloromethane (80 mL), thionyl chloride (1.15 mL, 15.8 mmol) was added under nitrogen atmosphere at morn temperature, and the mixture was stirred for 5 minutes. 4-(1-(tert-Butoxycarbonyl)piperidin-4-yl)benzoic acid described in Production Example 1-12 (4.1 g, 13.4 mmol) was added to the reaction mixture at room temperature, and the mixture was stirred for 25 minutes. The reaction mixture was filtered through a glass filter entirely covered with anhydrous sodium sulfate and then washed with dichloromethane, the filtrate was added to a mixture of 5-((2-aminopyridin-4-yl)oxy)-6-ethoxy-N-methyl-1H-indole-1-carboxamide described in Production Example 15-7 (2 g, 6.13 mmol), methylamine (8.5 mL, 61.3 mmol), and 4-dimethylaminopyridine (75 mg, 0.613 mmol) in tetrahydrofuran (40 mL) at 0° C. The mixture was stirred at room temperature for 14 hours, then water and ethyl acetate were added to the reaction mixture for partition. The organic layer was washed with a saturated saline solution, then the resultant was dried over anhydrous sodium sulfate and filtered. The filtrate was concentrated under vacuum, the residue was dissolved in tetrahydrofuran, an excessive quantity of 9.8 M methylamine methanol solution was added at room temperature, and the mixture was stirred for 5 hours. The reaction mixture was concentrated under vacuum, dichloromethane was added to the residue, and diethyl ether and ethyl acetate were further added, and then the product was collected by filtration and washed to obtain the title compound (3.08 g, 82%). The filtrate was concentrated under vacuum and the resultant was dissolved in dichloromethane and purified with NH silica gel column chromatography (n-heptane:ethyl acetate=1:1-1:9). The target fraction was concentrated under vacuum to obtain the title compound (273 mg, 7.3%).

$^1$H-NMR Spectrum (CDCl$_3$) δ (ppm): 1.25 (3H, t, J=7.0 Hz), 1.48 (9H, s), 1.50-1.70 (2H, m), 1.78-1.87 (2H, m), 2.64-2.87 (3H, m), 3.07 (3H, d, J=4.8 Hz), 4.11 (2H, q, J=7.0 Hz), 4.16-4.33 (2H, m), 5.45-5.52 (1H, m), 6.55 (1H, d, J=3.6 Hz), 6.60 (1H, dd, J=5.9, 2.3 Hz), 7.23 (1H, d, J=3.7 Hz), 7.28-7.33 (3H, m), 7.79-7.83 (2H, m), 7.92 (1H, d, J=2.2 Hz), 8.00 (1H, s), 8.09 (1H, d, J=5.9 Hz), 8.51 (1H, brs).

Example 16

6-Ethoxy-5-((2-(4-(1-ethylpiperidin-4-yl)benzamide)pyridin-4-yl)oxy)-N-methyl-1H-indole-1-carboxamide

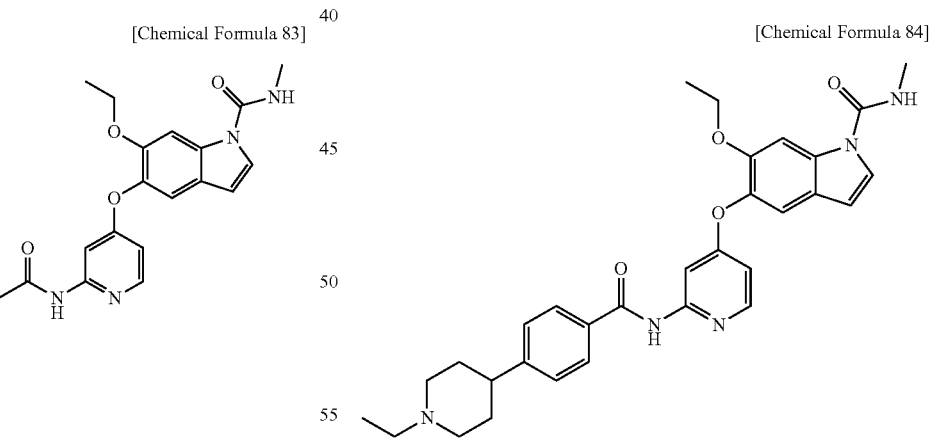

[Chemical Formula 84]

Sodium triacetoxyborohydride (1.36 g, 6.43 mmol) was added to a mixture of 6-ethoxy-N-methyl-5-((2-(4-(piperidin-4-yl)benzamide)pyridin-4-yl)oxy)-1H-indole-1-carboxamide described in Example 15 (2.2 g, 4.28 mmol) and tetrahydrofuran (33 mL) at room temperature, then a tetrahydrofuran solution (11 mL) of commercially available acetaldehyde (283 mg, 6.43 mmol) was added, and then the mixture was stirred at room temperature for 1.5 hours. Ethyl acetate and a saturated aqueous sodium bicarbonate solution were added to the reaction mixture for partition. The organic layer was washed with a saturated saline solution, and then dried over anhydrous sodium sulfate and filtered. The solvent was evaporated, and the residue thus obtained was combined with the residue obtained from the similar starting material 6-ethoxy-N-methyl-5-((2-(4-(piperidin-4-yl)benzamide) pyridin-4-yl)oxy)-1H-indole-1-carboxamide (200 mg, 0.389 mmol) by the similar method. Ethyl acetate was added to the combined residue and the product was collected by filteration to obtain the title compound (2.20 g, 87%).

$^1$H-NMR Spectrum (CDCl$_3$) δ (ppm): 1.15 (3H, t, J=7.2 Hz), 1.25 (3H, t, J=7.0 Hz), 1.82-1.92 (4H, m), 2.01-2.13 (2H, m), 2.43-2.62 (3H, m), 3.04 (3H, d, J=4.6 Hz), 3.08-3.17 (2H, m), 4.10 (2H, q, J=6.8 Hz), 5.55-5.62 (1H, m), 6.53 (1H, d, J=3.7 Hz), 6.60 (1H, dd, J=5.7, 2.2 Hz), 7.23 (1H, d, J=3.7 Hz), 7.30-7.35 (3H, m), 7.79 (2H, d, J=8.2 Hz), 7.91 (1H, d, J=2.2 Hz), 8.00 (1H, s), 8.09 (1H, d, J=5.7 Hz), 8.53 (1H, bis).

Example 17

6-Isopropoxy-N-methyl-5-((2-(4-(piperidin-4-yl) benzamide)pyridin-4-yl)oxy)-1H-indole-1-carboxamide

[Chemical Formula 85]

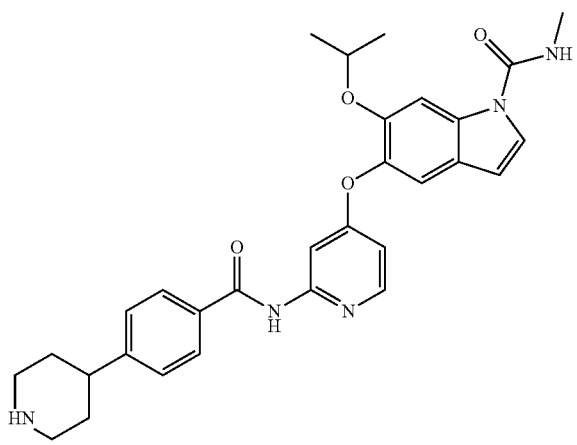

Benzotriazole (88.7 mg, 0.745 mmol) was dissolved in dichloromethane (4.0 mL), thionyl chloride (52 μL, 0.707 mmol) was added under nitrogen atmosphere at room temperature, and the mixture was stirred for 5 minutes. 4-(1-(tert-Butoxycarbonyl)piperidin-4-yl)benzoic acid described in Production Example 1-12 (180 mg, 0.589 mmol) was added to the reaction mixture at room temperature, and the mixture was stirred for 55 minutes. The reaction mixture was filtered through a glass filter entirely covered with anhydrous sodium sulfate and then washed with dichloromethane, the filtrate was added to a mixture of 5-((2-aminopyridin-4-yl)oxy)-6-isopropoxy-N-methyl-1H-indole-1-carboxamide described in Production Example 17-7 (77 mg, 0.226 mmol), triethylamine (0.314 mL, 2.26 mmol), and 4-dimethylaminopyridine (2.76 mg, 0.023 mmol) in tetrahydrofuran (2.0 mL), dichloromethane (5.0 mL), and N,N-dimethylformamide (0.2 mL) at 0° C. The mixture was stirred at room temperature for 140 minutes, and then water and ethyl acetate were added to the reaction mixture for partition. The organic layer was washed with water and a saturated saline solution, dried over anhydrous sodium sulfate, and filtered. The filtrate was concentrated under vacuum, the residue was dissolved in tetrahydrofuran, an excessive quantity of methylamine tetrahydrofuran solution was added at mom temperature, and the mixture was stirred for 30 minutes. The reaction mixture was concentrated under vacuum, the residue was dissolved in dichloromethane, and the resultant was purified with NH silica gel column chromatography (n-heptane:ethyl acetate=1:1-1:3-0:1), and the target fraction was concentrated under vacuum to obtain a crude product (111 mg).

The crude product (111 mg) was dissolved in dichloromethane (1.8 mL), and trifluoroacetic acid (0.65 mL) was added at 0° C. The mixture was stirred for 90 minutes at room temperature and then concentrated under vacuum, the residue was dissolved in dichloromethane-triethylamine, and then the resultant was purified with NH silica gel column chromatography (ethyl acetate:methanol=1:0-17:3-4:1) to obtain the title compound (85.4 mg, 92%).

$^1$H-NMR Spectrum (CDCl$_3$) δ (ppm): 1.22 (6H, d, J=6.0 Hz), 1.55-1.71 (2H, m), 1.79-1.88 (2H, m), 2.62-2.80 (3H, m), 3.05 (3H, d, J=4.8 Hz), 3.15-3.25 (2H, m), 4.52-4.64 (1H, m), 5.49-5.57 (1H, m), 6.54 (1H, d, J=3.7 Hz), 6.58 (1H, dd, J=5.7, 2.4 Hz), 7.24 (1H, d, J=3.8 Hz), 7.29-7.35 (3H, m), 7.80 (2H, d, J=8.2 Hz), 7.93 (1H, d, J=2.4 Hz), 8.01 (1H, s), 8.08 (1H, d, J=5.9 Hz), 8.51 (1H, brs).

The starting material 5-((2-aminopyridin-4-yl)oxy)-6-isopropoxy-N-methyl-1H-indole-1-carboxamide was synthesized by the following method.

Production Example 17-1

3-Hydroxy-4-isopropoxy benzaldehyde

[Chemical Formula 86]

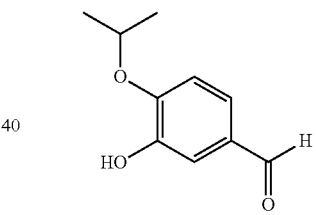

Commercially available 3,4-dihydroxybenzaldehyde (5 g, 36.2 mmol) and potassium carbonate (5.15 g, 37.3 mmol) were dissolved in N,N-dimethylformamide (20 mL), then 2-bromopropane (3.5 mL, 37.3 mmol) was added under nitrogen atmosphere at room temperature, and the mixture was heated and stirred at 40° C. for 2.5 hours. The reaction mixture was cooled to 0° C., and then 2 M hydrochloric acid, ethyl acetate, and water were added for partition. The aqueous layer was extracted with ethyl acetate, the combined organic layer was washed with water and a saturated saline solution, and the resultant was dried over anhydrous magnesium sulfate and then filtered. The solvent was evaporated, dichloromethane was added to the residue, the precipitate was separated by filtration, and the filtrate was concentrated under vacuum. The residue was purified with silica gel column chromatography (n-heptane:ethyl acetate=19:1-13:7) and then the target fraction was concentrated under vacuum to obtain the title compound (1.84 g, 28%).

$^1$H-NMR Spectrum (CDCl$_3$) δ (ppm): 1.42 (6H, d, J=5.9 Hz), 4.73 (1H, spt, J=6.1 Hz), 5.78 (1H, s), 6.95 (1H, d, J=8.1 Hz), 7.41 (1H, dd, J=8.2, 2.0 Hz), 7.44 (1H, d, J=1.8 Hz), 9.83 (1H, s).

Production Example 17-2

3-(Benzyloxy)-4-isopropoxybenzaldehyde

[Chemical Formula 87]

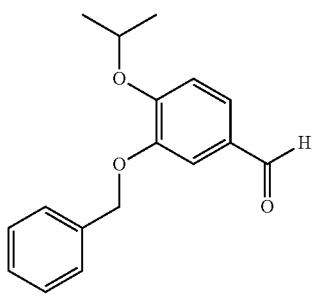

Potassium carbonate (1.83 g, 13.2 mmol) and benzyl chloride (1.55 mL, 13.5 mmol) were added to a suspension of 3-hydroxy-4-isopropoxybenzaldehyde described in Production Example 171 (1.84 g, 10.2 mmol) in ethanol (20 mL) under nitrogen atmosphere at room temperature, and the mixture was heated and stirred at 90° C. for 2 hours. The mixture was cooled to 0° C. and then 2 M hydrochloric acid, ethyl acetate, and water were added for partition. The organic layer was washed with a saturated saline solution, and the resultant was dried over anhydrous sodium sulfate, and then filtered. The solvent was evaporated, the resultant residue was dissolved in dichloromethane, and the resultant was purified with silica gel column chromatography (n-heptane:ethyl acetate=19:1-3:1). The target fraction was concentrated under vacuum to obtain the title compound (2.59 g, 94%).

$^1$H-NMR Spectrum (CDCl$_3$) δ (ppm): 1.42 (6H, d, J=6.0 Hz), 4.69 (1H, spt, J=6.1 Hz), 5.18 (2H, s), 7.00 (1H, d, J=8.1 Hz), 7.29-7.41 (3H, m), 7.43-7.48 (4H, m), 9.81 (1H, s).

Production Example 17-3

(E)-2-(Benzyloxy)-1-isopropoxy-4-(2-nitrovinyl)benzene

[Chemical Formula 88]

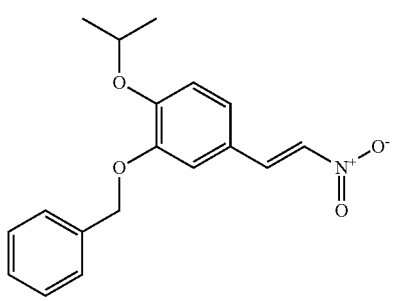

3-(Benzyloxy)-4-isopropoxybenzaldehyde described in Production Example 17-2 (2.59 g, 9.59 mmol) was dissolved in acetic acid (7.5 mL), then ammonium acetate (887 mg, 11.5 mmol) and nitromethane (1.25 mL, 23.1 mmol) were added under nitrogen atmosphere at room temperature, and the mixture was heated and stirred at 130° C. for 2 hours. The mixture was cooled to room temperature, and the precipitate was collected by filteration and washed with ethanol to obtain the title compound (2.20 g, 73%).

$^1$H-NMR Spectrum (CDCl$_3$) δ (ppm): 1.41 (6H, d, J=6.2 Hz), 4.55-4.71 (1H, m), 5.15 (2H, s), 6.94 (1H, d, J=8.4 Hz), 7.05 (1H, d, J=1.8 Hz), 7.15 (1H, dd, J=8.4, 1.8 Hz), 7.29-7.48 (6H, m), 7.90 (1H, d, J=13.5 Hz).

Production Example 17-4

6-Isopropoxy-1H-indol-5-ol

[Chemical Formula 89]

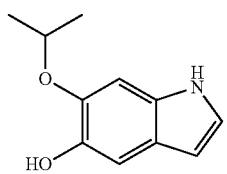

Fuming nitric acid (1.5 mL, 33.3 mmol) was slowly added to a mixture of (E)-2-(benzyloxy)-1-isopropoxy-4-(2-nitrovinyl)benzene described in Production Example 17-3 (2.20 g, 7.02 mmol) and acetic acid (20 mL) at mom temperature, and the mixture was stirred for 7.5 hours. The reaction mixture was poured onto ice, the precipitate was collected by filteration, and then the resultant was washed with a liquid mixture of acetic acid and ethanol to obtain a crude product (2.28 g).

The crude product (2.28 g) was suspended in methanol (60 mL), 10% palladium-carbon (water content, 50%) (677 mg) was added, and the mixture was stirred under hydrogen atmosphere for 14.5 hours. The catalyst was filtered off with celite, and the resultant was washed with methanol. The filtrate was concentrated under vacuum and purified with silica gel column chromatography (n-heptane:ethyl acetate=9:1-3:2). The target fraction was concentrated under vacuum to obtain the title compound (475 mg, 35%).

$^1$H-NMR Spectrum (CDCl$_3$) δ (ppm): 1.40 (6H, d, J=6.2 Hz), 4.57 (1H, spt, J=6.1 Hz), 5.55 (1H, s), 6.38-6.44 (1H, m), 6.90 (1H, s), 7.08 (1H, t, J=2.7 Hz), 7.13 (1H, s), 7.90 (1H, brs).

Production Example 17-5

N-(4-((6-Isopropoxy-1H-indol-5-yl)oxy)pyridin-2-yl)acetamide

[Chemical Formula 90]

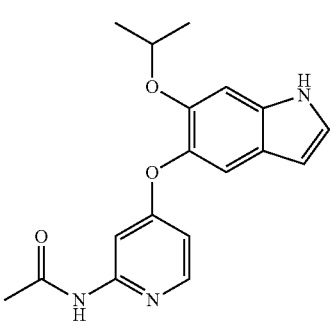

6-Isopropoxy-1H-indol-5-ol described in Production Example 17-4 (165 mg, 0.863 mmol) and N-(4-chloropyridin-2-yl)acetamide described in Production Example 1-5

(442 mg, 2.59 mmol) were dissolved in dimethylsulfoxide (2.0 mL) under nitrogen atmosphere, then potassium tert-butoxide (194 mg, 1.73 mmol) was added at room temperature, and the mixture was heated and stirred at 160° C. for 3 hours. The reaction liquid was cooled to room temperature and water and ethyl acetate were added for partition. The aqueous layer was extracted with ethyl acetate and the combined organic layer was washed with water and a saturated saline solution. The organic layer was dried over anhydrous magnesium sulfate and then filtered, then the filtrate was concentrated under vacuum. The residue was dissolved in dichloromethane, the resultant was purified with NH silica gel column chromatography (n-heptane:ethyl acetate=3:2-1:3), and then the target fraction was concentrated under vacuum to obtain the title compound (116 mg, 41%).

$^1$H-NMR Spectrum (CDCl$_3$) δ (ppm): 1.21 (6H, d, J=6.2 Hz), 2.14 (3H, s), 4.34-4.48 (1H, m), 6.45-6.53 (2H, m), 7.03 (1H, s), 7.16 (1H, t, J=2.7 Hz), 7.35 (1H, s), 7.77 (1H, brs), 7.85-8.05 (2H, m), 8.10 (1H, brs).

Production Example 17-6

4-((6-Isopropoxy-1H-indol-5-yl)oxy)pyridin-2-amine

[Chemical Formula 91]

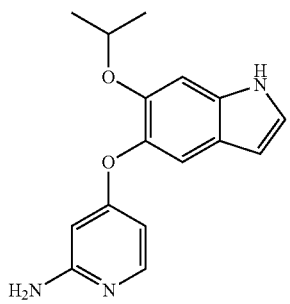

N-(4-((6-isopropoxy-1H-indol-5-yl)oxy)pyridin-2-yl)acetamide described in Production Example 17-5 (116 mg, 0.357 mmol) was dissolved in methanol (2.5 mL), 28% sodium methoxide (0.728 mL) was added under nitrogen atmosphere at room temperature, and the mixture was heated and stirred at 70° C. for 3 hours. The reaction mixture was cooled to room temperature and then water and ethyl acetate were added for partition. The organic layer was washed with a saturated saline solution and then dried over anhydrous sodium sulfate. The drying agent was filtered off and the resultant was concentrated under vacuum. The residue was dissolved in dichloromethane and the resultant was purified with silica gel column chromatography (n-heptane:ethyl acetate=3:7-0:1-ethyl acetate:methanol=99:1-9:1), then the target fraction was concentrated under vacuum to obtain the title compound (66.3 mg, 66%).

$^1$H-NMR Spectrum (CDCl$_3$) δ (ppm): 1.22 (6H, d, J=5.9 Hz), 4.28 (2H, brs), 4.36-4.47 (1H, m), 5.89 (1H, d, J=2.2 Hz), 6.29 (1H, dd, J=5.9, 2.2 Hz), 6.46-6.51 (1H, m), 7.04 (1H, s), 7.18 (1H, t, J=2.9 Hz), 7.34 (1H, s), 7.88 (1H, d, J=5.9 Hz), 8.12 (1H, brs).

Production Example 17-7

5-((2-Aminopyridin-4-yl)oxy)-6-isopropoxy-N-methyl-1H-indole-1-carboxamide

[Chemical Formula 92]

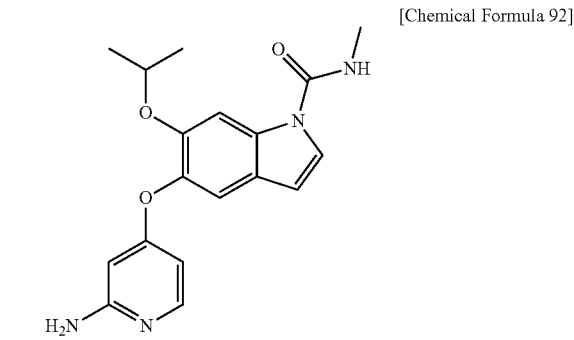 [SMILES: CNC(=O)n1ccc2cc(Oc3ccnc(N)c3)c(OC(C)C)cc21]

4-((6-Isopropoxy-1H-indol-5-yl)oxy)pyridin-2-amine described in Production Example 17-6 (65.6 mg, 0.232 mmol) was dissolved in N,N-dimethylformamide (1.5 mL), 50-72% oily sodium hydride (16.7 mg) was added under nitrogen atmosphere at 0° C., and the mixture was stirred at room temperature for 50 minutes. The mixture was cooled to 0° C. again, phenyl methylcarbamate described in Production Example 1-7 (69.2 mg, 0.458 mmol) was added, and the mixture was stirred at room temperature for 3 hours. A saturated aqueous ammonium chloride solution, water, and ethyl acetate were added to the reaction mixture for partition. The aqueous layer was extracted with ethyl acetate and the combined organic layer was washed with water and then with a saturated saline solution. The organic layer was dried over anhydrous magnesium sulfate and then filtered, then the filtrate was concentrated under vacuum. The residue was dissolved in dichloromethane and the resultant was purified with NH silica gel column chromatography (n-heptane:ethyl acetate=3:7-0:1-ethyl acetate:methanol=99:1-19:1), then the target fraction was concentrated under vacuum to obtain the title compound (77.0 mg, 98%).

$^1$H-NMR Spectrum (CDCl$_3$) δ (ppm): 1.24 (6H, d, J=6.0 Hz), 3.06 (3H, d, J=4.8 Hz), 4.32 (2H, brs), 4.56 (1H, spt, J=6.1 Hz), 5.50-5.61 (1H, m), 5.89 (1H, d, J=22 Hz), 6.27 (1H, dd, J=5.9, 2.2 Hz), 6.55 (1H, dd, J=3.6, 0.6 Hz), 7.24-7.28 (2H, m), 7.88 (1H, d, J=5.9 Hz), 8.00 (1H, s).

Example 18

(R)-5-((2-(4-(1-(2-Hydroxypropyl)piperidin-4-yl)benzamide)pyridin-4-yl)oxy)-6-isopropoxy-N-methyl-1H-indole-1-carboxamide

[Chemical Formula 93]

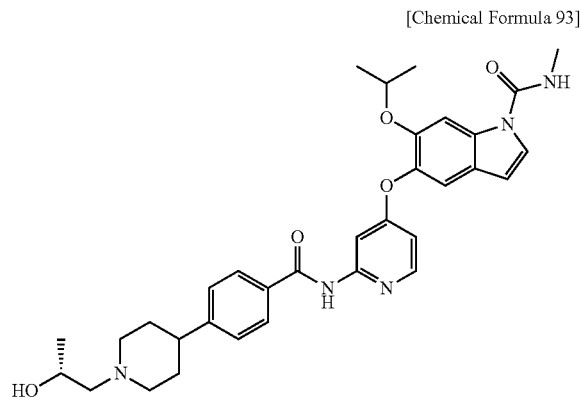 [SMILES: CNC(=O)n1ccc2cc(Oc3ccnc(NC(=O)c4ccc(C5CCN(C[C@@H](C)O)CC5)cc4)c3)c(OC(C)C)cc21]

Commercially available (R)-(+)-propylene oxide (20.5 mg, 0.353 mmol) was added to a mixture of 6-isopropoxy-N-methyl-5-((2-(4-(piperidin-4-yl)benzamide)pyridin-4-yl)oxy)-1H-indole-1-carboxamide described in Example 17 (12.7 mg, 0.024 mmol) and ethanol (0.5 rat), and the mixture was heated and stirred with a sealed tube at 80° C. for 3 hours and 40 minutes. The mixture was cooled to room temperature, then the reaction mixture was concentrated under vacuum, the resultant residue was dissolved in dichloromethane, and the resultant was purified with NH silica gel column chromatography (n-heptane:ethyl acetate=1:4-0:1-ethyl acetate:methanol=99:1-19:1). The target fraction was concentrated under vacuum, and the precipitate was collected by filteration and washed with diethyl ether to obtain the title compound (8.28 mg, 59%).

$^1$H-NMR Spectrum (CDCl$_3$) δ (ppm): 1.15 (3H, d, J=6.2 Hz), 1.22 (6H, d, J=6.2 Hz), 1.70-1.90 (3H, m), 2.00-2.09 (1H, m), 2.21-2.46 (3H, m), 2.53-2.64 (1H, m), 2.92 (1H, d, J=11.0 Hz), 3.07 (3H, d, J=4.8 Hz), 3.14 (1H, d, J=11.3 Hz), 3.80-3.91 (1H, m), 4.53-4.64 (1H, m), 5.44-5.52 (1H, m), 6.55 (1H, d, J=3.3 Hz), 6.58 (1H, dd, J=5.7, 2.4 Hz), 725 (1H, d, J=3.7 Hz), 7.30-7.36 (3H, m), 7.81 (2H, d, J=8.4 Hz), 7.93 (1H, d, J=2.2 Hz), 8.01 (1H, s), 8.09 (1H, d, J=5.9 Hz), 8.49 (1H, s).

Example 19

6-(Difluoromethoxy)-5-((2-(4-((4-hydroxypiperidin-1-yl)methyl)benzamide)pyridin-4-yl)oxy)-N-methyl-1H-indole-1-carboxamide

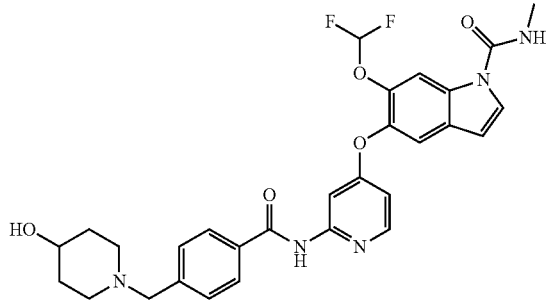

[Chemical Formula 94]

Triethylamine (17 μL, 0.123 mmol) and commercially available 4-(chloromethyl)benzoyl chloride (11.5 mg, 0.061 mmol) were added to a mixture of 5-((2-aminopyridin-4-yl)oxy)-6-(difluoromethoxy)-N-methyl-1H-indole-1-carboxamide described in Production Example 19-7 (4.3 mg, 0.012 mmol) and tetrahydrofuran (0.5 mL) under nitrogen atmosphere at room temperature. The mixture was stirred at room temperature for 2.5 hours and water and ethyl acetate were added to the reaction mixture for partition. The organic layer was washed with a saturated saline solution and then dried over anhydrous sodium sulfate and the resultant was filtered with NH silica gel (ethyl acetate) and concentrated under vacuum to obtain a crude product (6.18 mg).

The crude product (6.18 mg) was dissolved in N,N-dimethylformamide (0.5 mL), commercially available 4-hydroxypiperidine (17.7 mg, 0.175 mmol) was added under nitrogen atmosphere at room temperature, and the mixture was stirred for 14 hours. Water and ethyl acetate were added to the reaction mixture for partition, and the organic layer was washed with a saturated saline solution, dried over anhydrous sodium sulfate, and filtered. The solvent was evaporated and the resultant residue was purified with NH silica gel TLC (ethyl acetate) to obtain the title compound (6.0 mg, 86%).

$^1$H-NMR Spectrum (CDCl$_3$) δ (ppm): 1.50-1.66 (2H, m), 1.83-1.94 (2H, m), 2.16 (2H, t, J=9.7 Hz), 2.67-2.78 (2H, m), 3.08 (3H, d, J=4.4 Hz), 3.54 (2H, s), 3.62-3.77 (2H, m), 5.46-5.57 (1H, m), 6.53 (1H, t, J=73.9 Hz), 6.61 (1H, d, J=3.7 Hz), 6.64 (1H, dd, J=5.7, 2.4 Hz), 7.38-7.46 (4H, m), 7.80 (2H, d, J=8.1 Hz), 7.91 (1H, d, J=2.2 Hz), 8.15 (1H, d, J=5.9 Hz), 8.24 (1H, s), 8.53 (1H, brs).

The starting material 5-((2-aminopyridin-4-yl)oxy)-6-(difluoromethoxy)-N-methyl-1H-indole-1-carboxamide was synthesized by the following method.

Production Example 19-1

4-(Difluoromethoxy)-3-hydroxybenzaldehyde

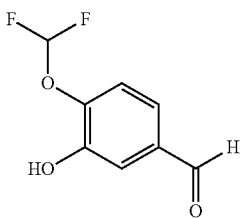

[Chemical Formula 95]

Commercially available 3,4-dihydroxybenzaldehyde (5 g, 36.2 mmol) and commercially available sodium chlorodifluoroacetate (5.57 g, 36.5 mmol) were dissolved in N,N-dimethylformamide (45 mL) and water (905 μL), and then sodium hydroxide (1.48 g, 37.0 mmol) was added at room temperature, and the mixture was heated and stirred at 120° C. for 2 hours. The solvent was evaporated under vacuum, the residue was cooled to 0° C., and 5 M hydrochloric acid and diethyl ether were added for partition. The organic layer was washed with water and a saturated saline solution, and then the solvent was evaporated. The residue was dissolved in dichloromethane and the resultant was purified with silica gel column chromatography (n-heptane:ethyl acetate 9:1-7:3), and then the target fraction was concentrated under vacuum to obtain the title compound (2.66 g, 39%).

$^1$H-NMR Spectrum (CDCl$_3$) δ (ppm): 5.69-5.74 (1H, m), 6.65 (1H, t, J=72.5 Hz), 7.23-7.31 (1H, m), 7.46 (1H, dd, J=8.4, 1.8 Hz), 7.54 (1H, d, J=1.8 Hz), 9.92 (1H, s).

Production Example 19-2

3-(Benzyloxy)-4-(difluoromethoxy)benzaldehyde

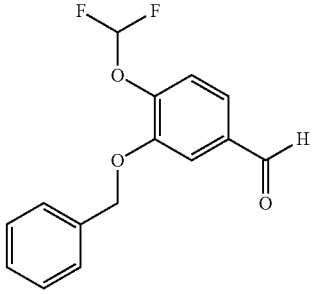

[Chemical Formula 96]

Potassium carbonate (3.91 g, 28.3 mmol) and benzyl bromide (2.5 mL, 21.1 mmol) were added to a solution of 4-(difluoromethoxy)-3-hydroxybenzaldehyde described in Production Example 19-1 (2.66 g, 14.2 mmol) in acetonitrile (50 mL) at room temperature, and the mixture was stirred at room temperature for 3 hours. The reaction mixture was filtered and then the solvent was evaporated. The resultant residue was purified with silica gel column chromatography (n-heptane:ethyl acetate=9:1-3:2). The target fraction was concentrated under vacuum and then the title compound was quantitatively obtained.

$^1$H-NMR Spectrum (CDCl$_3$) δ (ppm): 5.21 (2H, s), 6.68 (1H, t, J=74.3 Hz), 7.31-7.51 (7H, m), 7.57 (1H, d, J=1.8 Hz), 9.92 (1H, s).

Production Example 19-3

(E)-2-(Benzyloxy)-1-(difluoromethoxy)-4-(2-nitrovinyl)benzene

[Chemical Formula 97]

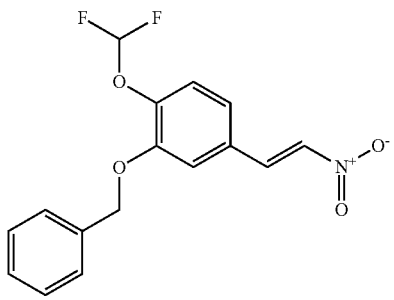

3-(Benzyloxy)-4-(difluoromethoxy)benzaldehyde described in Production Example 19-2 (3.94 g, 14.2 mmol) was dissolved in acetic acid (11 mL), then ammonium acetate (1.27 g, 16.4 mmol) and nitromethane (1.9 mL, 35.1 mmol) were added under nitrogen atmosphere at room temperature, and the mixture was heated and stirred at 130° C. for 2 hours. The mixture was cooled to room temperature and then heated and stirred at 130° C. again for 1 hour. The precipitate was collected by filtration and washed with a liquid mixture of acetic acid and ethanol to obtain the title compound (2.36 g, 52%). The filtrate was dissolved in dichloromethane and the resultant was purified with silica gel column chromatography (n-heptane:ethyl acetate=19:1-4:1), and then the target fraction was concentrated under vacuum. The precipitate was washed with ethanol to obtain the title compound (406 mg, 8.9%).

$^1$H-NMR Spectrum (CDCl$_3$) δ (ppm): 5.18 (2H, s), 6.65 (1H, t, J=74.3 Hz), 7.12-7.19 (2H, m), 7.21-7.29 (1H, m), 7.32-7.45 (5H, m), 7.48 (1H, d, J=13.9 Hz), 7.92 (1H, d, J=13.9 Hz).

Production Example 19-4

5-(Benzyloxy)-6-(difluoromethoxy)-1H-indole

[Chemical Formula 98]

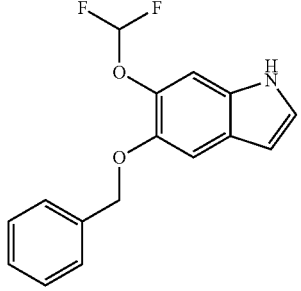

Fuming nitric acid (6.0 mL, 133 mmol) was slowly added to a mixture of (E)-2-(benzyloxy)-1-(difluoromethoxy)-4-(2-nitrovinyl)benzene described in Production Example 19-3 (2.77 g, 8.61 mmol) and acetic acid (36 mL) in an ice bath, and the mixture was stirred for 7.5 hours. A part of the reaction mixture was heated and stirred at 50° C. for 30 minutes, then at 70° C. for 40 minutes, and then at 75° C. for 165 minutes. A part of the reaction mixture was poured onto ice and the resultant was diluted with ethyl acetate for partition. The organic layer was washed with water and a saturated saline solution and dried over anhydrous magnesium sulfate, and then the solvent was evaporated. The residue was dissolved in dichloromethane and the resultant was purified with silica gel column chromatography (n-heptane:ethyl acetate=17:3-3:1), then the target fraction was concentrated under vacuum, and then the residue was collected by filtration and washed with diethyl ether to obtain a crude product A (23.6 mg). The remaining reaction mixture was heated and stirred at 65° C. for 3 hours, then the resultant was poured onto ice, and then the precipitate was collected by filtration and washed with a liquid mixture of acetic acid and ethanol to obtain a crude product B (603 mg). Ethyl acetate was added to the filtrate for partition. The organic layer was washed with water and a saturated saline solution, dried over anhydrous magnesium sulfate, and filtered, and then the solvent was evaporated. The residue was dissolved in dichloromethane and the resultant was purified with silica gel column chromatography (n-heptane:ethyl acetate=9:1-3:1), then the target fraction was concentrated under vacuum, diethyl ether was added to the residue, and the precipitate was collected by filtration to obtain a crude product C (73.3 mg).

The crude products A, B, and C (550 mg) were suspended in ethanol (5.5 mL), acetic acid (5.5 mL), and water (676 pt), then iron powder (419 mg, 7.51 mmol) was added under nitrogen atmosphere, and the mixture was heated and stirred at 70° C. for 1 hour. The reaction mixture was cooled to room temperature and ethyl acetate and an aqueous sodium disulfite solution were added for partition. The organic layer was washed with water and a saturated saline solution, dried over anhydrous magnesium sulfate, and filtered, and then the solvent was evaporated. The residue was dissolved in dichloromethane and the resultant was purified with NH silica gel column chromatography (n-heptane:ethyl acetate=9:1-3:2), and then the target fraction was concentrated under vacuum to obtain the title compound (245 mg, 13%).

$^1$H-NMR Spectrum (CDCl$_3$) δ (ppm): 5.15 (2H, s), 6.45-6.49 (1H, m), 6.58 (1H, t, J=76.0 Hz), 7.19-7.22 (1H, m), 7.23 (1H, s), 7.24-7.27 (1H, m), 7.29-7.43 (3H, m), 7.44-7.50 (2H, m), 8.12 (1H, brs).

Production Example 19-5

6-(Difluoromethoxy)-1H-indol-5-ol

[Chemical Formula 99]

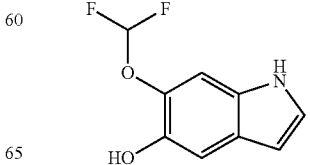

5-(Benzyloxy)-6-(difluoromethoxy)-1H-indole described in Production Example 19-4 (245 mg, 0.847 mmol) was dissolved in ethanol (8.0 mL), then 10% palladium-carbon (water content, 50%) (90 mg) was added at room temperature, and the mixture was stirred under hydrogen atmosphere for 75 minutes. The reaction mixture was diluted with ethyl acetate and the catalyst was filtered off with celite. The filtrate was concentrated under vacuum and then filtered with silica gel (ethyl acetate). The target fraction was concentrated under vacuum to quantitatively obtain the title compound.

$^1$H-NMR Spectrum (CDCl$_3$) δ (ppm): 5.15 (1H, s), 6.41-6.49 (1H, m), 6.53 (1H, t, J=74.1 Hz), 7.15-7.24 (3H, m), 8.06 (1H, brs).

Production Example 19-6

4-((6-(Difluoromethoxy)-1H-indol-5-yl)oxy)pyridin-2-amine

[Chemical Formula 100]

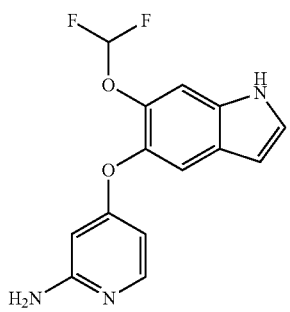

6-(Difluoromethoxy)-1H-indol-5-ol described in Production Example 19-5 (35.1 mg, 0.176 mmol), N-(4-chloropyridin-2-yl)acetamide described in Production Example 1-5 (89.0 mg, 0.522 mmol), and potassium tert-butoxide (44.0 mg, 0.392 mmol) were dissolved in dimethylsulfoxide (500 μL) under nitrogen atmosphere, and the mixture was heated and stirred at 160° C. for 80 minutes. The reaction liquid was cooled to room temperature and water and ethyl acetate were added for partition. The organic layer was washed with a saturated saline solution, dried over anhydrous sodium sulfate, and then filtered, and then the filtrate was concentrated under vacuum. The residue was dissolved in dichloromethane and the resultant was purified with NH silica gel column chromatography (n-heptane:ethyl acetate=1:1-0:1-ethyl acetate:methanol=99:1-9:1), then the target fraction was concentrated under vacuum to obtain a crude product (12.5 mg).

The crude product (12.5 mg) was dissolved in methanol (500 μL), 28% sodium methoxide (39 μL, 0.382 mmol) was added under nitrogen atmosphere at room temperature, and the mixture was heated and stirred at 65° C. for 1 hour. The mixture was cooled to room temperature, 28% sodium methoxide (39 μL, 0.382 mmol) was added, and the mixture was heated and stirred at 65° C. for 2.5 hours. Water and ethyl acetate were added to the reaction mixture for partition. The organic layer was washed with a saturated saline solution and then dried over anhydrous sodium sulfate. The drying agent was filtered of and the resultant was concentrated under vacuum. The residue was dissolved in dichloromethane and the resultant was purified with NH silica gel column chromatography (n-heptane:ethyl acetate=1:1-0:1-ethyl acetate: methanol=97:3-9:1), and then the target fraction was concentrated under vacuum to obtain the title compound (4.4 mg, 8.6%).

$^1$H-NMR Spectrum (CDCl$_3$) δ (ppm): 4.48 (2H, brs), 5.91 (1H, d, J=1.8 Hz), 6.28 (1H, dd, J=5.9, 1.8 Hz), 6.45 (1H, t, J=74.5 Hz), 6.52-6.58 (1H, m), 7.30 (1H, t, J=2.9 Hz), 7.36 (1H, s), 7.41 (1H, s), 7.90 (1H, d, J=5.9 Hz), 8.35 (1H, brs).

Production Example 19-7

5-((2-Aminopyridin-4-yl)oxy)-6-(difluoromethoxy)-N-methyl-1H-indole-1-carboxamide

[Chemical Formula 101]

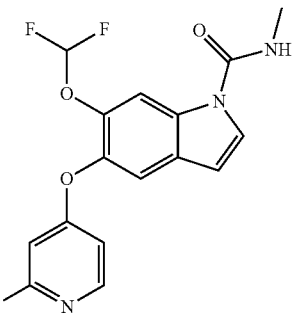

4-((6-(Difluoromethoxy)-1H-indol-5-yl)oxy)pyridin-2-amine described in Production Example 19-6 (4.4 mg, 0.015 mmol) was dissolved in N,N-dimethylformamide (500 μL), then 50-72% oily sodium hydride (4.1 mg) was added under nitrogen atmosphere at 0° C., and the mixture was stirred at room temperature for 30 minutes. The mixture was cooled to 0° C. again and phenyl methylcarbamate described in Production Example 1-7 (16.4 mg, 0.108 mmol) was added, and the mixture was stirred at room temperature for 50 minutes. Water and ethyl acetate were added to the reaction mixture for partition. The organic layer was washed with a saturated saline solution, then dried over anhydrous sodium sulfate and filtered, and then the filtrate was concentrated under vacuum. The residue was dissolved in dichloromethane and the resultant was purified with NH silica gel column chromatography (n-heptane:ethyl acetate=1:1-0:1-ethyl acetate:methanol=99:1-9:1), and then the target fraction was concentrated under vacuum to obtain the title compound (4.3 mg, 82%).

$^1$H-NMR Spectrum (CDCl$_3$) δ (ppm): 3.08 (3H, d, J=4.8 Hz), 4.44 (2H, brs), 5.49 (1H, brs), 5.91 (1H, d, J=1.8 Hz), 6.26 (1H, dd, J=6.2, 2.2 Hz), 6.50 (1H, t, J=74.0 Hz), 6.61 (1H, d, J=3.7 Hz), 7.35 (1H, s), 7.41 (1H, d, J=3.7 Hz), 7.92 (1H, d, J=5.9 Hz), 8.23 (1H, s).

Example 20

6-(2-Methoxyethoxy)-N-methyl-5-((2-(4-(piperidin-4-yl)benzamide)pyridin-4-yl)oxy)-1H-indole-1-carboxamide

[Chemical Formula 102]

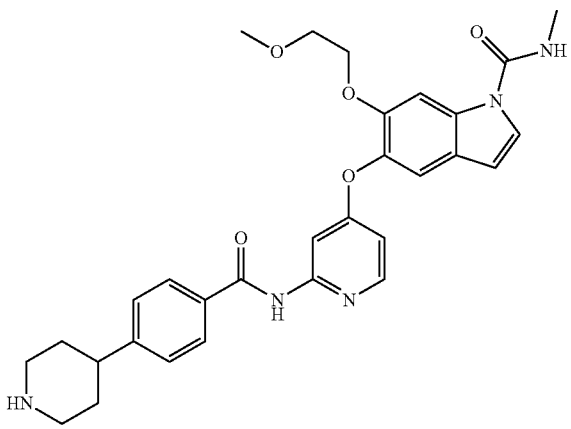

Benzotriazole (609 mg, 5.11 mmol) was dissolved in dichloromethane (25 mL), thionyl chloride (373 μL, 5.11 mmol) was added under nitrogen atmosphere at room temperature, and the mixture was stirred for 5 minutes. 4-(1-(tert-Butoxycarbonyl)piperidin-4-yl)benzoic acid described in Production Example 1-12 (1.3 g, 4.26 mmol) was added to the reaction mixture at room temperature, and the mixture was stirred for 30 minutes. The reaction mixture was filtered through a glass filter entirely covered with anhydrous sodium sulfate and the resultant was washed with dichloromethane, the filtrate was added to a mixture of 5-((2-aminopyridin-4-yl)oxy)-6-(2-methoxyethoxy)-N-methyl-1H-indole-1-carboxamide described in Production Example 20-7 (0.95 g, 2.67 mmol), triethylamine (1.86 mL, 13.3 mmol), and 4-dimethylaminopyridine (16 mg, 0.133 mmol) in N,N-dimethylformamide (3 mL) and dichloromethane (20 mL) at 0° C. over 5 minutes, and the mixture was rinsed with dichloromethane (10 mL) and then stirred at the same temperature for 5 minutes. The mixture was stirred at mom temperature for 2 hours, then a 40% aqueous methylamine solution (2.3 mL, 26.7 mmol) was added, and then the mixture was stirred at room temperature for 1.5 hours. A saturated aqueous sodium bicarbonate solution was added to the reaction mixture for partition and the aqueous layer was extracted with ethyl acetate three times. The combined organic layer was dried over anhydrous sodium sulfate. The drying agent was filtered off, then the filtrate was concentrated under vacuum and the resultant was purified with silica gel column chromatography (n-heptane:ethyl acetate=1:1-0:1-ethyl acetate:methanol=49:1-23:2) to obtain a crude product (1.11 g).

The crude product (1.11 g) was dissolved in dichloromethane (50 mL) and trifluoroacetic acid (5.0 mL) was added at room temperature. The mixture was stirred at room temperature for 30 minutes, then the resultant was concentrated under vacuum, and then the residue was dissolved in dichloromethane and triethylamine and the resultant was concentrated under vacuum. The residue was purified with NH silica gel column chromatography (ethyl acetate:methanol=1:0-22:3) to obtain the title compound (829 mg, 57%).

$^1$H-NMR Spectrum (500 MHz, CDCl$_3$) δ (ppm): 1.59-1.69 (2H, m), 1.83 (2H, d, J=14.1 Hz), 2.68 (1H, tt, J=12.0, 3.6 Hz), 2.75 (2H, td, J=12.2, 2.4 Hz), 3.04 (3H, d, J=4.9 Hz), 3.17-3.23 (2H, m), 3.26 (3H, s), 355-3.61 (2H, m), 4.15-4.21 (2H, m), 5.57-5.65 (1H, m), 6.53 (1H, d, J=3.4 Hz), 6.62 (1H, dd, J=5.8, 2.4 Hz), 7.25 (1H, d, J=3.9 Hz), 7.30-7.34 (3H, m), 7.77-7.82 (2H, m), 7.91 (1H, d, J=2.4 Hz), 8.02 (1H, s), 8.10 (1H, d, J=5.9 Hz), 8.50 (1H, brs).

The starting material 5-((2-aminopyridin-4-yl)oxy)-6-(2-methoxyethoxy)-N-methyl-1H-indole-1-carboxamide was synthesized by the following method.

Production Example 20-1

3-Hydroxy-4-(2-methoxyethoxy)benzaldehyde

[Chemical Formula 103]

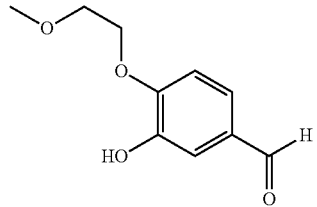

Commercially available 3,4-dihydroxybenzaldehyde (39.3 g, 285 mmol) and sodium carbonate (45.2 g, 427 mmol) were dissolved in N,N-dimethylformamide (400 mL), then commercially available 2-bromoethyl methyl ether (26.7 mL, 285 mmol) was added under nitrogen atmosphere at room temperature, and the mixture was stirred for 5 days. The mixture was cooled to 0° C. and then 2 M hydrochloric acid, ethyl acetate, and water were added for partition. The aqueous layer was extracted with ethyl acetate, then the combined organic layer was washed with a saturated saline solution and dried over anhydrous magnesium sulfate, and then filtered. The solvent was evaporated, dichloromethane was added, the precipitate was separated by filtration, and then the resultant filtrate was purified with silica gel column chromatography (n-heptane:ethyl acetate=17:3-1:1). The target fraction was concentrated under vacuum to obtain the title compound (12.9 g, 23%).

$^1$H-NMR Spectrum (CDCl$_3$) δ (ppm): 3.47 (3H, s), 3.76-3.80 (2H, m), 4.25-4.29 (2H, m), 6.40 (1H, brs), 7.01 (1H, J=8.4 Hz), 7.41 (1H, dd, J=8.2, 2.0 Hz), 7.45 (1H, d, J=1.8 Hz), 9.85 (1H, s).

Production Example 20-2

3-(Benzyloxy)-4-(2-methoxyethoxy)benzaldehyde

[Chemical Formula 104]

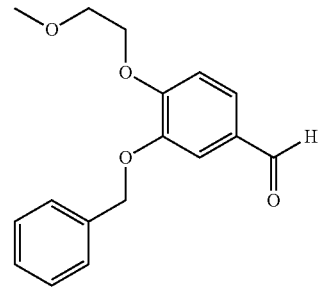

Potassium carbonate (11.8 g, 85.7 mmol) and benzyl chloride (10 mL, 86.9 mmol) were added to a liquid mixture of 3-hydroxy-4-(2-methoxyethoxy)benzaldehyde described in Production Example 20-1 (12.9 g, 65.9 mmol) in ethanol (130 mL) under nitrogen atmosphere at room temperature, and the mixture was heated under reflux at 90° C. for 2 hours. The mixture was cooled to 0° C. and then 2 M hydrochloric acid, ethyl acetate, and water were added for partition. The organic layer was washed with a saturated saline solution, dried over anhydrous magnesium sulfate, and then filtered. The solvent was evaporated and the resultant residue was purified with silica gel column chromatography (n-heptane:ethyl acetate=9:1-1:1). The target fraction was concentrated under vacuum to obtain the title compound (17.6 g, 93%).

$^1$H-NMR Spectrum (CDCl$_3$) δ (ppm): 3.46 (3H, s), 3.79-3.85 (2H, m), 4.24-4.30 (2H, m), 5.18 (2H, s), 7.03 (1H, d, J=8.1 Hz), 7.29-7.35 (1H, m), 7.35-7.41 (2H, m), 7.43-7.50 (4H, m), 9.82 (1H, s).

Production Example 20-3

(E)-2-(Benzyloxy)-1-(2-methoxyethoxy)-4-(2-nitrovinyl)benzene

[Chemical Formula 105]

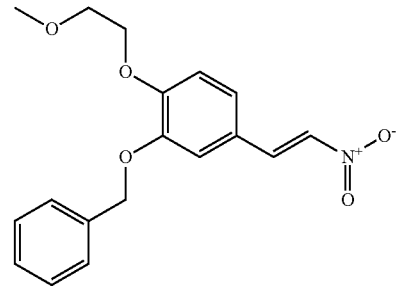

3-(Benzyloxy)-4-(2-methoxyethoxy)benzaldehyde described in Production Example 20-2 (17.6 g, 61.5 mmol) was dissolved in acetic acid (49.3 mL), then ammonium acetate (5.69 g, 73.8 mmol) and nitromethane (8.32 mL, 154 mmol) were added under nitrogen atmosphere at room temperature, and the mixture was heated under reflux at 130° C. for 2 hours. The mixture was cooled to room temperature and then the precipitate was collected by filteration and washed with ethanol to quantitatively obtain the title compound.

$^1$H-NMR Spectrum (CDCl$_3$) δ (ppm): 3.46 (3H, s), 3.78-3.84 (2H, m), 4.21-427 (2H, m), 5.16 (2H, s), 6.97 (1H, d, J=8.4 Hz), 7.06 (1H, d, J=1.8 Hz), 7.16 (1H, dd, J=8.4, 2.2 Hz), 7.30-7.48 (6H, m), 7.91 (1H, d, J=13.5 Hz).

Production Example 20-4

6-(2-Methoxyethoxy)-1H-indol-5-ol

[Chemical Formula 106]

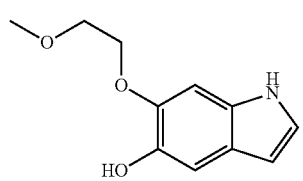

69% Nitric acid (15 mL, 233 mmol) was added to a mixture of (E)-2-(benzyloxy)-1-(2-methoxyethoxy)-4-(2-nitrovinyl) benzene described in Production Example 20-3 (20.2 g, 61.5 mmol) and acetic acid (120 mL) at 25° C., and the mixture was stirred at room temperature for 6 hours. The reaction mixture was poured onto ice, and the precipitate was collected by filteration and then washed with water to obtain a crude product (23.0 g).

The crude product (23.0 g) was suspended in methanol (500 mL), then 10% palladium-carbon (water content, 50%) (8 g) was added at room temperature, and the mixture was stirred under hydrogen atmosphere for 6 how. The catalyst was filtered off with celite, the filtrate was concentrated under vacuum, and the resultant was purified with silica gel column chromatography (n-heptane:ethyl acetate=2:1-1:1). The target fraction was concentrated under vacuum to obtain the title compound (3.94 g, 31%).

$^1$H-NMR Spectrum (CDCl$_3$) δ (ppm): 3.48 (3H, s), 3.69-3.78 (2H, m), 4.16-4.23 (2H, m), 6.24 (1H, s), 6.41 (1H, ddd, J=3.1, 2.1, 0.8 Hz), 6.97 (1H, s), 7.10 (1H, dd, J=3.2, 2.5 Hz), 7.15 (1H, s), 7.94 (1H, brs).

Production Example 20-5

N-(4-((6-(2-Methoxyethoxy)-1H-indol-5-yl)oxy) pyridin-2-yl)acetamide

[Chemical Formula 107]

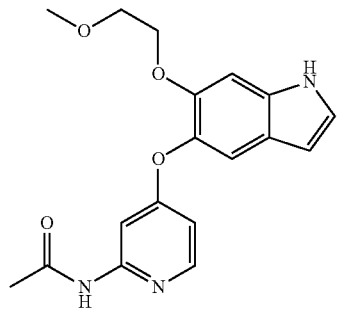

6-(2-Methoxyethoxy)-1H-indol-5-ol described in Production Example 20-4 (3.94 g, 19.0 mmol) and N-(4-chloropyridin-2-yl)acetamide described in Production Example 1-5 (3.25 g, 19.0 mmol) were dissolved in dimethylsulfoxide (25 mL), then 97% potassium tert-butoxide (2.20 g, 19.0 mmol) was added at room temperature, and the mixture was heated and stirred at 150° C. for 13 hours. Water and ethyl acetate were added to the reaction liquid at mom temperature for partition. The aqueous layer was extracted with ethyl acetate three times and the combined organic layer was washed with water. The organic layer was dried over anhydrous sodium sulfate. The drying agent was filtered off and the filtrate was concentrated under vacuum, and then the resultant was purified with NH silica gel column chromatography (n-heptane: ethyl acetate=2:3-0:1-ethyl acetate:methanol=49:1-9:1). The target fraction was concentrated under vacuum to obtain the title compound (3.45 g, 53%).

$^1$H-NMR Spectrum (500 MHz, CDCl$_3$) δ (ppm): 2.13 (3H, s), 327 (3H, s), 3.54-3.58 (2H, m), 4.07-4.11 (2H, m), 6.46-6.50 (1H, m), 6.54 (1H, dd, J=5.8, 1.9 Hz), 7.05 (1H, s), 7.14-7.17 (1H, m), 7.36 (1H, s), 7.75 (1H, brs), 8.02 (1H, d, 5.8 Hz), 8.10 (1H, brs), 8.19 (1H, brs).

Production Example 20-6

4-((6-(2-Methoxyethoxy)-1H-indol-5-yl)oxy)pyridin-2-amine

[Chemical Formula 108]

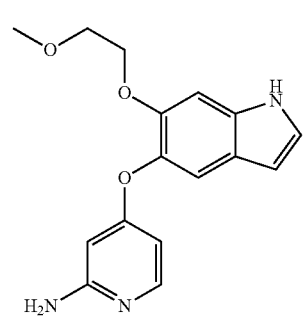

N-(4-((6-(2-methoxyethoxy)-1H-indol-5-yl)oxy)pyridin-2-yl)acetamide described in Production Example 20-5 (3.45 g, 10.1 mmol) was dissolved in methanol (50 mL), a 2 M sodium hydroxide solution (50 mL) was added at room temperature, and the mixture was heated and stirred at 70° C. for 3 hours. Water and ethyl acetate were added to the reaction mixture for partition. The aqueous layer was extracted with ethyl acetate three times and the combined organic layer was dried over anhydrous sodium sulfate. The drying agent was filtered off and the filtrate was concentrated under vacuum and the resultant was purified with NH silica gel column chromatography (n-heptane:ethyl acetate=3:7-0:1-ethyl acetate:methanol=49:1-24:1). The target fraction and the mixture fraction were concentrated under vacuum separately from each other, the mixture fraction was purified again with silica gel column chromatography (ethyl acetate:methanol=1:0-9:1), and then the resultant was combined with the above-described target fraction to obtain the title compound (2.60 g, 86%).

$^1$H-NMR Spectrum (500 MHz, CDCl$_3$) δ (ppm): 3.31 (3H, s), 3.58-3.63 (2H, m), 4.08-4.11 (2H, m), 4.28 (2H, brs), 5.90 (1H, d, J=2.4 Hz), 6.29 (1H, dd, J=6.1, 2.2 Hz), 6.44-6.52 (1H, m), 7.06 (1H, s), 7.15-7.20 (1H, m), 7.34 (1H, s), 7.88 (1H, d, J=5.8 Hz), 8.22 (1H, brs).

Production Example 20-7

5-((2-Aminopyridin-4-yl)oxy)-6-(2-methoxyethoxy)-N-methyl-1H-indole-1-carboxamide

[Chemical Formula 109]

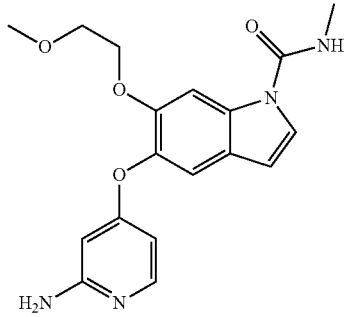

4-((6-(2-Methoxyethoxy)-1H-indol-5-yl)oxy)pyridin-2-amine described in Production Example 20-6 (2.60 g, 8.67 mmol) was dissolved in N,N-dimethylformamide (50 mL), then 50-72% oily sodium hydride (499 mg) was added under nitrogen atmosphere at room temperature. Phenyl methylcarbamate described in Production Example 1-7 (1.97 g, 13.0 mmol) was added, and the mixture was stirred at room temperature for 1 hour. The reaction mixture was cooled to 0° C. and ethyl acetate and water were added for partition. The aqueous layer was extracted with ethyl acetate twice, sodium chloride was added to the aqueous layer, and the resultant was extracted with ethyl acetate three times. The combined organic layer was dried over anhydrous sodium sulfate. The drying agent was filtered off and the filtrate was concentrated under vacuum, and then the resultant was purified with NH silica gel column chromatography (n-heptane:ethyl acetate=1:4-0:1-ethyl acetate:methanol=49:1-24:1). The target fraction was concentrated under vacuum, and ethyl acetate was added and the precipitate was collected by filteration and washed to obtain the title compound (2.23 g, 72%).
$^1$H-NMR Spectrum (500 MHz, CDCl$_3$) δ (ppm): 3.06 (3H, d, J=4.9 Hz), 3.29 (3H, s), 3.59-3.63 (2H, m), 4.14-4.17 (2H, m), 4.30 (2H, brs), 5.52-5.59 (1H, m), 5.89 (1H, d, J=2.4 Hz), 6.27 (1H, dd, J=5.8, 1.9 Hz), 6.55 (1H, d, J=3.9 Hz), 7.27-7.29 (2H, m), 7.89 (1H, d, J=5.9 Hz), 7.99 (1H, s).

Example 21

6-(2-Methoxyethoxy)-N-methyl-5-((2-(4-(1-methylpiperidin-4-yl)benzamide)pyridin-4-yl)oxy)-1H-indole-1-carboxamide

[Chemical Formula 110]

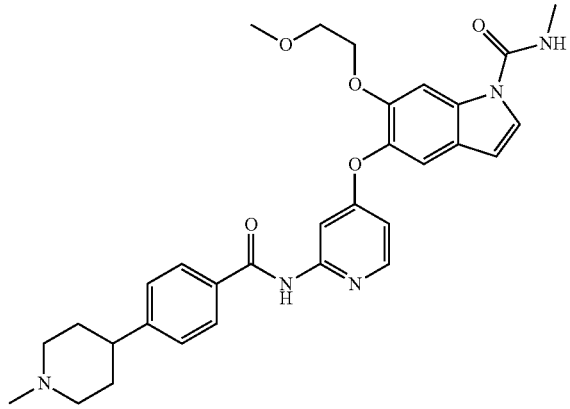

A 35% aqueous formaldehyde solution (186 μL, 2.36 mmol) and sodium triacetoxyborohydride (200 mg, 0.946 mmol) were added to a mixture of 6-(2-methoxyethoxy)-N-methyl-5-((2-(4-(piperidin-4-yl)benzamide)pyridin-4-yl) oxy)-1H-indole-1-carboxamide described in Example 20 (257 mg, 0.473 mmol) and tetrahydrofuran (30 mL) at room temperature, and the mixture was stirred at room temperature for 3 minutes. Acetic acid (54 μL, 0.946 mmol) was added to the reaction mixture, and the mixture was stirred at room temperature for 3 hours. A saturated aqueous sodium bicarbonate solution and ethyl acetate were added to the reaction mixture for partition. The aqueous layer was extracted with ethyl acetate three times, and the combined organic layer was dried over anhydrous sodium sulfate and filtered. The solvent was evaporated and the resultant residue was purified with NH silica gel column chromatography (ethyl acetate:methanol=1:0-23:2). The target fraction was concentrated under vacuum to quantitatively obtain the title compound.
$^1$H-NMR Spectrum (500 MHz, CDCl$_3$) δ (ppm): 1.75-1.88 (4H, m), 2.02-2.11 (2H, m), 2.33 (3H, s), 2.49-2.59 (1H, m), 2.99 (2H, d, J=11.2 Hz), 3.05 (3H, d, J=4.9 Hz), 3.26 (3H, s), 3.56-3.60 (2H, m), 4.15-4.21 (2H, m), 5.52-5.58 (1H, m), 6.54 (1H, d, J=3.9 Hz), 6.61 (1H, dd, J=5.8, 2.4 Hz), 7.25-7.27 (1H, m), 7.30-7.34 (3H, m), 7.79 (2H, d, J=8.3 Hz), 7.91 (1H, d, J=2.4 Hz), 8.01 (1H, s), 8.09 (1H, d, J=5.8 Hz), 8.48 (1H, brs).

Example 22

5-((2-(4-(1-(2-Hydroxyethyl)piperidin-4-yl)benzamide)pyridin-4-yl)oxy)-6-(2-methoxyethoxy)-N-methyl-1H-indole-1-carboxamide

[Chemical Formula 111]

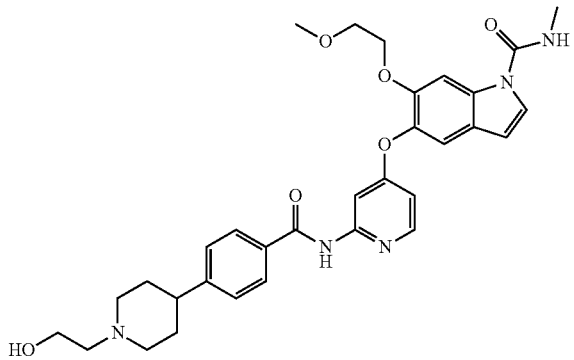

Sodium triacetoxyborohydride (286 mg, 1.35 mmol) and commercially available 2-hydroxyacetaldehyde (86.1 mg, 1.43 mmol) were added to a mixture of 6-(2-methoxyethoxy)-N-methyl-5-((2-(4-(piperidin-4-yl)benzamide)pyridin-4-yl) oxy)-1H-indole-1-carboxamide described in Example 20 (250 mg, 0.46 mmol) and tetrahydrofuran (10 mL) at room temperature, and the mixture was stirred at room temperature for 3 hours and 45 minutes. A saturated aqueous sodium bicarbonate solution and ethyl acetate were added to the reaction mixture for partition. The aqueous layer was extracted with ethyl acetate, and the combined organic layer was washed with a saturated saline solution, then dried over anhydrous sodium sulfate, and then filtered. The solvent was evaporated and the resultant residue was purified with NH silica gel column chromatography (ethyl acetate:methanol=1:0-97:3-9:1). The target fraction was concentrated under vacuum, then the precipitate was collected by filtration and washed with a liquid mixture of diethyl ether and n-hexane to obtain the title compound (236 mg, 87%).

$^1$H-NMR Spectrum (CDCl$_3$) δ (ppm): 1.70-1.92 (4H, m), 2.14-2.25 (2H, m), 2.53-2.64 (3H, m), 3.01-3.08 (5H, m), 3.26 (3H, s), 3.56-3.60 (2H, m), 3.63 (2H, t, J=5.4 Hz), 4.15-4.20 (2H, m), 5.50-5.59 (1H, m), 6.54 (1H, d, J=3.7 Hz), 6.61 (1H, dd, J=5.7, 2.4 Hz), 7.24-7.28 (1H, m), 7.30-7.35 (3H, m), 7.80 (2H, d, J=8.4 Hz), 7.91 (1H, d, J=2.2 Hz), 8.01 (1H, s), 8.09 (1H, d, 5.9 Hz), 8.50 (1H, brs).

Example 23

5-((2-(4-(1-Isopropylpiperidin-4-yl)benzamide)pyridin-4-yl)oxy)-6-(2-methoxyethoxy)-N-methyl-1H-indole-1-carboxamide

[Chemical Formula 112]

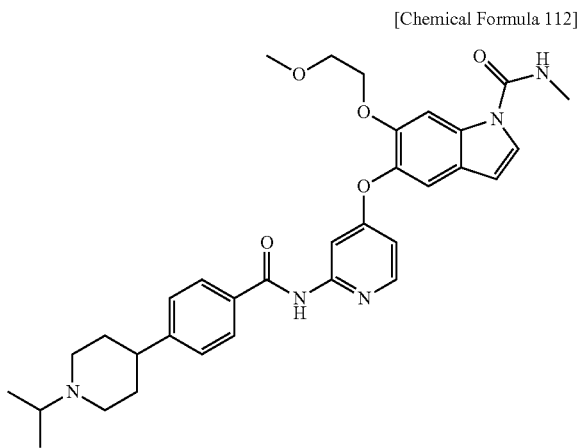 [SMILES: CNC(=O)n1ccc2cc(Oc3ccnc(NC(=O)c4ccc(C5CCN(C(C)C)CC5)cc4)c3)c(OCCOC)cc21]

Acetone (54 μL, 0.736 mmol), sodium triacetoxyborohydride (62.4 mg, 0.294 mmol), and acetic acid (17 μL, 0.294 mmol) were added to a solution of 6-(2-methoxyethoxy)-N-methyl-5-((2-(4-(piperidin-4-yl)benzamide)pyridin-4-yl)oxy)-1H-indole-1-carboxamide described in Example 20 (20 mg, 0.037 mmol) in tetrahydrofuran (3 mL) at room temperature. The reaction liquid was stilted at the same temperature overnight. A saturated aqueous sodium bicarbonate solution and ethyl acetate were added to the reaction liquid at room temperature for partition. The organic layer was washed with a saturated saline solution and then dried over anhydrous sodium sulfate. The drying agent was separated by filtration and then the resultant was concentrated under vacuum. The residue was purified with NH silica gel column chromatography (ethyl acetate) to obtain the title compound (6.6 mg, 31%).

$^1$H-NMR Spectrum (DMSO-d$_6$) δ (ppm): 0.99 (6H, d, J=6.6 Hz), 1.54-1.68 (2H, m), 1.70-1.81 (2H, m), 2.16-2.26 (2H, m), 2.44-2.57 (1H, m), 2.66-2.76 (1H, m), 2.82-2.91 (5H, m), 3.12 (3H, s), 3.45-3.52 (2H, m), 4.05-4.13 (2H, m), 6.63 (1H, d, J=3.7 Hz), 6.67 (1H, dd, J=5.7, 2.4 Hz), 7.33 (2H, d, J=8.4 Hz), 7.45 (1H, s), 7.69 (1H, d, J=2.6 Hz), 7.78 (1H, d, J=4.0 Hz), 7.89 (2H, d, J=8.4 Hz), 8.08 (1H, s), 8.14-8.21 (2H, m), 10.64 (1H, s).

Example 24

6-(2-Ethoxyethoxy)-N-methyl-5-((2-(4-(piperidin-4-yl)benzamide) pyridin-4-yl)oxy)-1H-indole-1-carboxamide

[Chemical Formula 113]

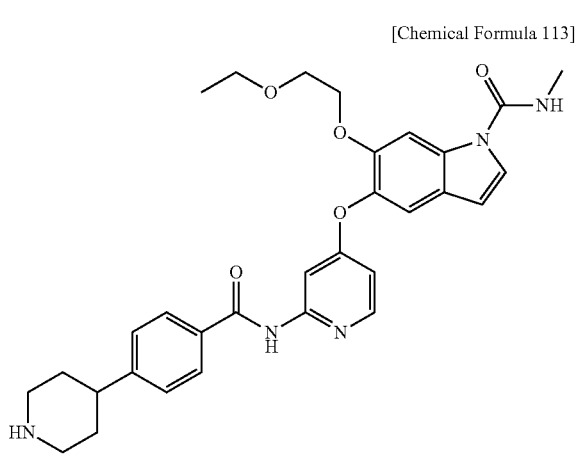 [SMILES: CCOCCOc1cc2c(ccn2C(=O)NC)cc1Oc1ccnc(NC(=O)c2ccc(C3CCNCC3)cc2)c1]

Trifluoroacetic acid (1.79 mL, 23.2 mmol) was added to a solution of tert-butyl 4-(4-((4-((6-(2-ethoxyethoxy)-1-(methylcarbamoyl)-1H-indol-5-yl)oxy)pyridin-2-yl)carbamoyl)phenyl)piperidine-1-carboxylate described in Production Example 24-9 (382 mg, 0.581 mmol) in dichloromethane (10 mL) at room temperature. The reaction liquid was stirred at the same temperature for 1 hour. The reaction liquid was concentrated under vacuum, and trifluoroacetic acid was removed. The residue was diluted with dichloromethane and then triethylamine was added to neutralize the trifluoroacetic acid. The solution was concentrated under vacuum and then the residue was purified with NH silica gel column chromatography (ethyl acetate:methanol=49:1-17:3) to obtain the title compound (276 mg, 85%).

$^1$H-NMR Spectrum (DMSO-d$_6$) δ (ppm): 0.94 (3H, t, J=7.0 Hz), 1.44-1.57 (2H, m), 1.63-1.72 (2H, m), 2.47-2.69 (3H, m), 2.85 (3H, d, J=4.4 Hz), 2.97-3.05 (2H, m), 3.29 (2H, q, J=7.0 Hz), 3.47-3.58 (2H, m), 4.04-4.13 (2H, m), 6.57-6.73 (2H, m), 7.31 (2H, d, J=8.1 Hz), 7.45 (1H, s), 7.70 (1H, d, J=2.2 Hz), 7.78 (1H, d, J=3.7 Hz), 7.90 (2H, d, J=8.8 Hz), 8.08 (1H, s), 8.13-8.24 (2H, m), 10.64 (1H, s).

The starting material tert-butyl 4-(4-((4-((6-(2-ethoxyethoxy)-1-(methylcarbamoyl)-1H-indol-5-yl)oxy)pyridin-2-yl)carbamoyl)phenyl)piperidine-1-carboxylate was synthesized by the following method.

Production Example 24-1

4-(2-Ethoxyethoxy)-3-hydroxybenzaldehyde

[Chemical Formula 114]

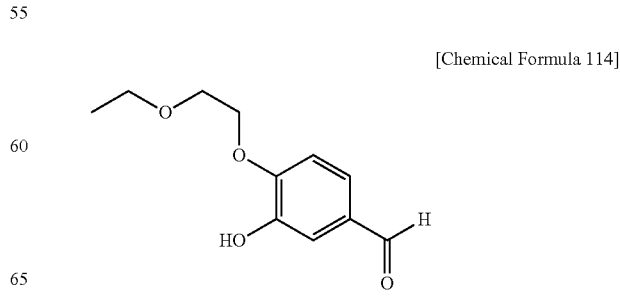

Commercially available 2-bromoethyl ethyl ether (33.8 g, 221 mmol) was added to a solution of commercially available 3,4-dihydroxybenzaldehyde (30.5 g, 221 mmol) and sodium carbonate (35.1 g, 331 mmol) in NP-dimethylformamide (310 mL) under nitrogen atmosphere at mom temperature. The liquid mixture was stirred at room temperature for 5 days. The reaction liquid was cooled to 0° C. and diluted with 2 M hydrochloric acid, ethyl acetate, and water. The aqueous layer was extracted with ethyl acetate. The combined organic layer was washed serially with water and a saturated saline solution and then dried over anhydrous magnesium sulfate. The drying agent was separated by filtration and then the filtrate was concentrated under vacuum. The insoluble matters were separated by filtration with dichloromethane and the raw material was removed. The filtrate was purified with silica gel column chromatography (n-heptane:ethyl acetate=17:3-1:1) to obtain the title compound (13.2 g, 28%).

$^1$H-NMR Spectrum (CDCl$_3$) δ (ppm): 1.27 (3H, t, J=7.0 Hz), 3.63 (2H, q, J=7.0 Hz), 3.80-3.85 (2H, m), 4.24-4.30 (2H, m), 6.65 (1H, s), 7.02 (1H, d, J=8.4 Hz), 7.38-7.42 (1H, m), 7.45 (1H, d, J=2.2 Hz), 9.85 (1H, s).

Production Example 24-2

3-(Benzyloxy)-4-(2-ethoxyethoxy)benzaldehyde

[Chemical Formula 115]

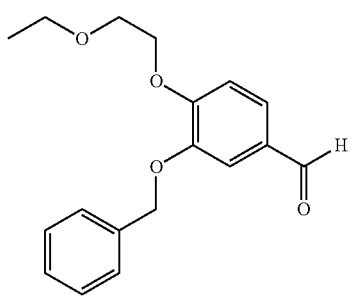

Potassium carbonate (11.3 g, 81.5 mmol) and benzyl chloride (9.5 mL, 82.6 mmol) were added to a solution of 4-(2-ethoxyethoxy)-3-hydroxybenzaldehyde described in Production Example 24-1 (13.2 g, 62.7 mmol) in ethanol (130 mL) under nitrogen atmosphere at room temperature. The liquid mixture was stirred under a thermal condition of 90° C. for 2 hours. The reaction liquid was cooled to 0° C. and then diluted with 2 M hydrochloric acid, ethyl acetate, and water. The organic layer was washed with a saturated saline solution and then dried over anhydrous magnesium sulfate. The drying agent was separated by filtration and the filtrate was concentrated under vacuum. The resultant residue was dissolved in dichloromethane and the resultant was purified with silica gel column chromatography (n-heptane:ethyl acetate=9:1-1:1) to obtain the title compound (13.5 g, 72%).

$^1$H-NMR Spectrum (CDCl$_3$) δ (ppm): 1.22 (3H, t, J=7.0 Hz), 3.63 (2H, q, J=7.0 Hz), 3.82-3.90 (2H, m), 4.23-4.30 (2H, m), 5.18 (2H, s), 7.03 (1H, d, J=7.7 Hz), 7.28-7.34 (1H, m), 7.35-7.42 (2H, m), 7.43-7.50 (4H, m), 9.82 (1H, s).

Production Example 24-3

(E)-2-(Benzyloxy)-1-(2-ethoxyethoxy)-4-(2-nitrovinyl)benzene

[Chemical Formula 116]

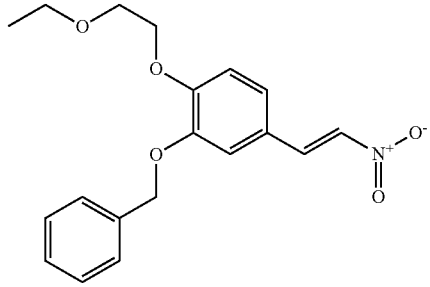

Ammonium acetate (4.16 g, 53.9 mmol) and nitromethane (6.1 mL, 113 mmol) were added to a solution of 3-(benzyloxy)-4-(2-ethoxyethoxy)benzaldehyde described in Production Example 24-2 (13.5 g, 45.0 mmol) in acetic acid (36 mL) under nitrogen atmosphere at room temperature. The liquid mixture was heated and stirred under reflux at 130° C. for 2 hours. The reaction liquid was allowed to stand to cool to room temperature. The precipitate was collected by filteration and washed with ethanol to quantitatively obtain the title compound.

$^1$H-NMR Spectrum (CDCl$_3$) δ (ppm): 1.22 (3H, t, J=7.1 Hz), 3.62 (2H, q, J=7.0 Hz), 3.82-3.88 (2H, m), 4.21-4.26 (2H, m), 5.16 (2H, s), 6.97 (1H, d, J=8.3 Hz), 7.06 (1H, d, J=2.2 Hz), 7.16 (1H, dd, J=8.3, 2.1 Hz), 7.29-7.50 (6H, m), 7.91 (1H, d, J=13.6 Hz).

Production Example 24-4

(E)-1-(Benzyloxy)-2-(2-ethoxyethoxy)-4-nitro-5-(2-nitrovinyl)benzene

[Chemical Formula 117]

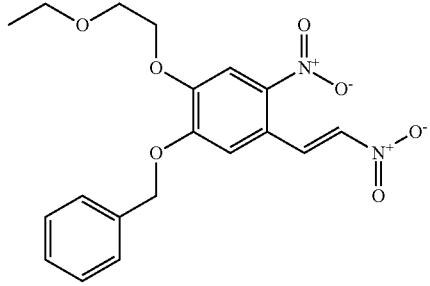

69% Nitric acid (11 mL, 171 mmol) was added to a solution of (E)-2-(benzyloxy)-1-(2-ethoxyethoxy)-4-(2-nitrovinyl)benzene described in Production Example 24-3 (15.4 g, 44.9 mmol) and acetic acid (100 mL) at 25° C., and the mixture was stirred for 6 hours. The reaction liquid was poured onto ice. The suspension was subjected to suction filtration and the product was washed with water to quantitatively obtain the title compound.

$^1$H-NMR Spectrum (CDCl$_3$) δ (ppm): 1.23 (3H, t, J=7.0 Hz), 3.62 (2H, q, J=6.9 Hz), 3.84-3.90 (2H, m), 4.29-4.34 (2H, m), 5.27 (2H, s), 6.93 (1H, s), 7.23 (1H, d, J=13.6 Hz), 7.35-7.50 (5H, m), 7.84 (1H, s), 8.57 (1H, d, J=13.5 Hz).

Production Example 24-5

6-(2-Ethoxyethoxy)-1H-indol-5-ol

[Chemical Formula 118]

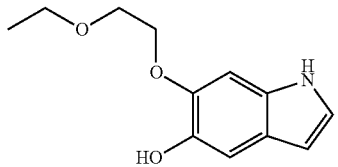

10% Palladium-carbon (water content, 50%) (6 g) was added to a solution of (E)-1-(benzyloxy)-2-(2-ethoxyethoxy)-4-nitro-5-(2-nitrovinyl)benzene described in Production Example 24-4 (17.5 g, 44.9 mmol) in methanol (180 mL) at room temperature. The reaction liquid was stirred under hydrogen atmosphere at room temperature. After 6 hours, the catalyst was filtered off with celite. The filtrate was concentrated under vacuum and then the residue was purified with silica gel column chromatography (n-heptane:ethyl acetate=2:1-1:1) to obtain the title compound (3.28 g, 33%).

$^1$H-NMR Spectrum (CDCl$_3$) δ (ppm): 1.29 (3H, t, J=7.0 Hz), 3.63 (2H, q, r=7.0 Hz), 3.73-3.80 (2H, m), 4.16-4.24 (2H, m), 6.41 (1H, td, J=2.1, 1.1 Hz), 6.46 (1H, s), 6.99 (1H, s), 7.10 (1H, dd, J=3.1, 2.4 Hz), 7.15 (1H, s), 7.93 (1H, bis).

Production Example 24-6

N-(4-((6-(2-Ethoxyethoxy)-1H-indol-5-yl)oxy)pyridin-2-yl)acetamide

[Chemical Formula 119]

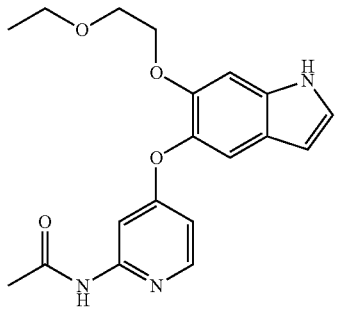

Dimethylsulfoxide (20 mL) was added to a mixture of 6-(2-ethoxyethoxy)-1H-indol-5-ol described in Production Example 24-5 (3.28 g, 14.8 mmol), N-(4-chloropyridin-2-yl)acetamide described in Production Example 1-5 (2.78 g, 16.3 mmol), and potassium tert-butoxide (1.83 g, 16.3 mmol) under nitrogen atmosphere at room temperature. The liquid mixture was stirred at 150° C. overnight. The reaction liquid was allowed to stand to cool to room temperature and then diluted with water and ethyl acetate. The organic layer was washed with a saturated saline solution and dried over anhydrous sodium sulfate, and then the drying agent was separated by filtration. The filtrate was concentrated under vacuum. The residue was purified with silica gel column chromatography (n-heptane:ethyl acetate=1:1-0:1-ethyl acetate:methanol=99:1-19:1) to obtain the title compound (2.5 g, 48%).

$^1$H-NMR Spectrum (CDCl$_3$) δ (ppm): 1.09 (3H, t, J=7.0 Hz), 2.14 (3H, s), 3.41 (2H, q, J=7.0 Hz), 3.56-3.66 (2H, m), 4.05-4.13 (2H, m), 6.44-6.50 (1H, m), 6.53 (1H, dd, J=5.9, 2.6 Hz), 7.05 (1H, d, J=0.7 Hz), 7.16 (1H, dd, J=3.3, 2.6 Hz), 7.36 (1H, s), 7.75 (1H, brs), 8.01 (1H, d, J=5.9 Hz), 8.11 (1H, brs), 8.19 (1H, brs).

Production Example 24-7

4-((6-(2-Ethoxyethoxy)-1H-indol-5-yl)oxy)pyridin-2-amine

[Chemical Formula 120]

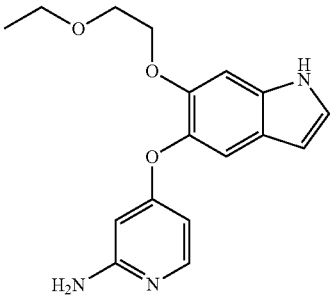

A 2 M sodium hydroxide solution (20 mL) was added to a solution of N-(4-((6-(2-ethoxyethoxy)-1H-indol-5-yl)oxy)pyridin-2-yl)acetamide described in Production Example 24-6 (2.5 g, 7.04 mmol) in methanol (20 mL) under nitrogen atmosphere at room temperature, and the mixture was heated and stirred under reflux at 75° C. for 2 hours. The reaction liquid was allowed to stand to cool to room temperature and then diluted with ethyl acetate and water. The organic layer was washed with a saturated saline solution and then dried over anhydrous sodium sulfate. The drying agent was separated by filtration and then the filtrate was concentrated under vacuum. The resultant residue was purified with silica gel column chromatography (n-heptane:ethyl acetate=1:9-0:1-ethyl acetate:methanol=49:1-24:1) to obtain the title compound (1.92 g, 87%).

$^1$H-NMR Spectrum (CDCl$_3$) δ (ppm): 1.12 (3H, t, J=7.0 Hz), 3.45 (2H, q, J=7.2 Hz), 3.60-3.72 (2H, m), 4.03-4.13 (2H, m), 4.29 (2H, s), 5.89 (1H, d, J=1.8 Hz), 6.29 (1H, dd, J—6.2, 2.2 Hz), 6.44-6.54 (1H, m), 7.05 (1H, s), 7.18 (1H, dd, J=3.1, 2.4 Hz), 7.34 (1H, s), 7.88 (1H, d, J=5.9 Hz), 8.25 (1H, brs).

Production Example 24-8

5-((2-Aminopyridin-4-yl)oxy)-6-(2-ethoxyethoxy)-N-methyl-1H-indole-1-carboxamide

[Chemical Formula 121]

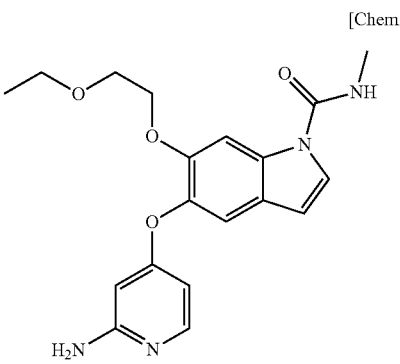

50-72% Oily sodium hydride (265 mg) was added to a solution of 4-((6-(2-ethoxyethoxy)-1H-indol-5-yl)oxy)pyridin-2-amine described in Production Example 24-7 (1.92 g, 6.13 mmol) in N,N-dimethylformamide (20 mL) under nitrogen atmosphere at 0° C. The reaction liquid was stirred at the same temperature for 10 minutes. Phenyl methylcarbamate described in Production Example 1-7 (1.20 g, 7.97 mmol) was added to the reaction liquid, and then the mixture was warmed to mom temperature and stirred for 1 hour. Water and ethyl acetate were added to the reaction liquid. The organic layer was washed serially with water and a saturated saline solution and then dried over anhydrous sodium sulfate. The drying agent was separated by filtration and then the filtrate was concentrated under vacuum. The residue was purified with NH silica gel column chromatography (the solution: n-heptane:ethyl acetate=9:1-0:1) to obtain the title compound (1.97 g, 87%).

$^1$H-NMR Spectrum (DMSO-d$_6$) δ (ppm): 1.01 (3H, t, J=7.0 Hz), 2.84 (3H, d, J=4.4 Hz), 3.37 (2H, q, J=7.1 Hz), 3.54-3.59 (2H, m), 4.02-4.10 (2H, m), 5.69 (1H, d, J=2.2 Hz), 5.77 (2H, s), 6.09 (1H, dd, J=5.9, 2.2 Hz), 6.60 (1H, d, J=3.3 Hz), 7.35 (1H, s), 7.71-7.77 (2H, m), 8.04 (1H, s), 8.09-8.17 (1H, m).

Production Example 24-9 tert-Butyl 4-(4-((4-((6-(2-ethoxyethoxy)-1-(methyl-carbamoyl)-1H-indol-5-yl)oxy)pyridin-2-yl)carbamoyl)phenyl)piperidine-1-carboxylate

[Chemical Formula 122]

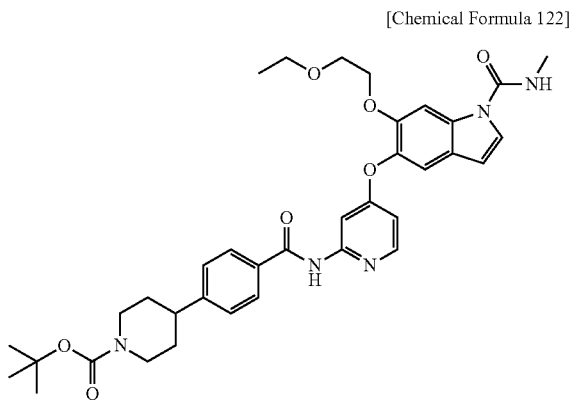 [SMILES: CCOCCOc1cc2c(ccn2C(=O)NC)cc1Oc1ccnc(NC(=O)c2ccc(C3CCN(C(=O)OC(C)(C)C)CC3)cc2)c1]

Thionyl chloride (370 μL, 5.06 mmol) was added to a solution of benzotriazole (603 mg, 5.06 mmol) in dichloromethane (20 mL) under nitrogen atmosphere at room temperature. The mixture was stirred at room temperature for 5 minutes, then 4-(1-(tert-butoxycarbonyl)piperidin-4-yl)benzoic acid described in Production Example 1-12 (1.03 g, 3.38 mmol) was added, and the mixture was stirred for 1 hour. The reaction liquid was filtered through anhydrous sodium sulfate on the glass filter, and the resultant was washed with dichloromethane. Triethylamine (1.87 mL, 13.5 mmol), 4-dimethylaminopyridine (16.5 mg, 0.135 mmol), and a solution of 5-((2-aminopyridin-4-yl)oxy)-6-(2-ethoxyethoxy)-N-methyl-1H-indole-1-carboxamide described in Production Example 24-8 (500 mg, 1.35 mmol) in tetrahydrofuran (5 mL) were serially added to the resultant filtrate under nitrogen atmosphere at 0° C., and the mixture was stirred at room temperature for 4 hours. An excessive quantity of methylamine was added to the reaction liquid and then the resultant was diluted with ethyl acetate and water for partition. The organic layer was washed with a saturated saline solution and then dried over anhydrous sodium sulfate, and the drying agent was separated by filtration. The filtrate was concentrated under vacuum. The resultant residue was purified with NH silica gel column chromatography (n-heptane:ethyl acetate=2:3-0:1) to obtain the title compound (383 mg, 43%).

$^1$H-NMR Spectrum (DMSO-d$_6$) δ (ppm): 0.94 (3H, t, J=7.1 Hz), 1.42 (9H, s), 1.43-1.60 (2H, m), 1.69-1.84 (2H, m), 2.75 (3H, brs), 2.85 (3H, d, J=4.4 Hz), 3.29 (2H, q, J=7.0 Hz), 3.47-3.58 (2H, m), 3.98416 (4H, m), 6.56-6.71 (2H, m), 7.34 (2H, d, J=8.4 Hz), 7.45 (1H, s), 7.70 (1H, d, J=2.6 Hz), 7.78 (1H, d, J=3.7 Hz), 7.90 (2H, d, J=8.4 Hz), 8.08 (1H, s), 8.12-8.24 (2H, m), 10.66 (1H, s).

Example 25

6-(2-Ethoxyethoxy)-5-((2-(4-(1-(2-hydroxyethyl)piperidin-4-yl)benzamide)pyridin-4-yl)oxy)-N-methyl-1H-indole-1-carboxamide

[Chemical Formula 123]

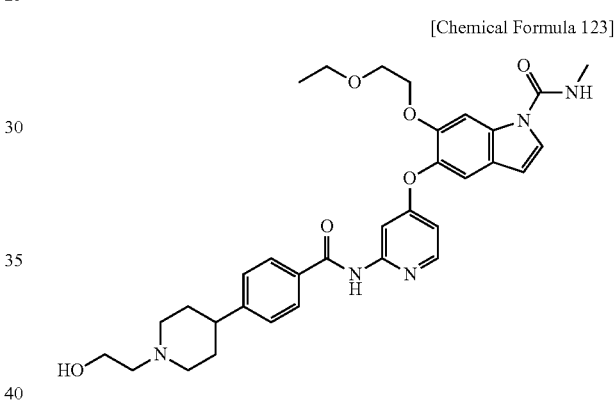

Commercially available 2-hydroxyacetaldehyde (48.5 mg, 0.807 mmol), sodium triacetoxyborohydride (91 mg, 0.43 mmol), and acetic acid (25 μL, 0.43 mmol) were added to a suspension of 6-(2-ethoxyethoxy)-N-methyl-5-((2-(4-(piperidin-4-yl)benzamide) pyridin-4-yl)oxy)-1H-indole-1-carboxamide described in Example 24 (30 mg, 0.054 mmol) in tetrahydrofuran (3 mL) at room temperature. The reaction liquid was stirred at room temperature for 2 hours. A saturated aqueous sodium bicarbonate solution was added to the reaction liquid at room temperature, and the mixture was diluted with ethyl acetate. The organic layer was washed with a saturated saline solution, dried over anhydrous sodium sulfate, and the solvent was concentrated under vacuum. The resultant residue was purified with NH silica gel column chromatography (ethyl acetate) to obtain the title compound (20.1 mg, 62%).

$^1$H-NMR Spectrum (CDCl$_3$) δ (ppm): 1.07 (3H, t, J=7.0 Hz), 1.67-1.99 (4H, m), 2.20 (2H, td, J=11.7, 2.6 Hz), 2.53-2.66 (3H, m), 2.98-3.11 (5H, m), 3.40 (2H, q, J=7.0 Hz), 3.59-3.69 (4H, m), 4.16-4.20 (2H, m), 5.02 (1H, s), 5.69-5.80 (1H, m), 6.51 (1H, d, J=3.7 Hz), 6.62 (1H, dd, J=5.7, 2.4 Hz), 7.25 (1H, d, J=3.7 Hz), 7.28-7.36 (3H, m), 7.76-7.83 (2H, m), 7.91 (1H, d, J=2.6 Hz), 8.02 (1H, s), 8.09 (1H, d, J=5.9 Hz), 8.62 (1H, s).

Example 26

6-(2-Ethoxyethoxy)-5-((2-(4-(1-ethylazetidin-3-yl)benzamide) pyridin-4-yl)oxy)-N-methyl-1H-indole-1-carboxamide

[Chemical Formula 124]

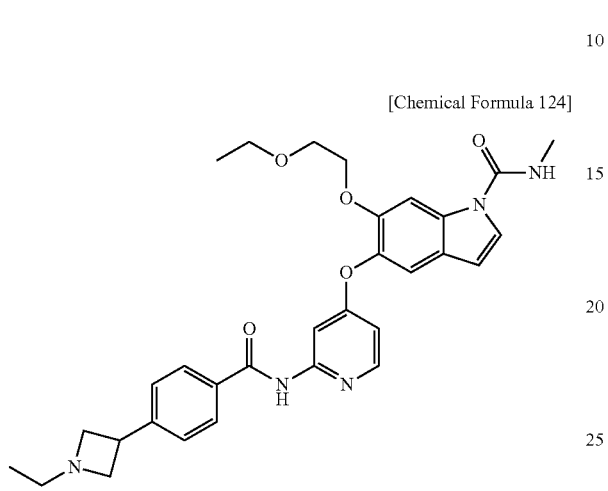

Sodium triacetoxyborohydride (172 mg, 0.812 mmol) and acetaldehyde (51.2 mg, 1.16 mmol) were added to a mixture of 5-((2-(4-(azetidin-3-yl)benzamide)pyridin-4-yl)oxy)-6-(2-ethoxyethoxy)-N-methyl-1H-indole-1-carboxamide described in Production Example 26-6 (215 mg, 0.406 mmol) and tetrahydrofuran (4.0 mL) at room temperature, and the mixture was stirred at room temperature for 1.5 hours. A saturated aqueous sodium bicarbonate solution and ethyl acetate were added to the reaction mixture for partition. The organic layer was washed with a saturated saline solution, then dried over anhydrous sodium sulfate, and filtered. The solvent was evaporated, the resultant residue was dissolved in dichloromethane, and the resultant was purified with NH silica gel column chromatography (n-heptane:ethyl acetate=2:3-0:1-ethyl acetate:methanol=99:1-19:1). The target fraction was concentrated under vacuum, then the residue was collected by filteration and washed with diethyl ether to obtain the title compound (180 mg, 79%).

$^1$H-NMR Spectrum (CDCl$_3$) δ (ppm): 1.00 (3H, t, J=7.1 Hz), 1.07 (3H, t, J=7.0 Hz), 2.51 (2H, q, J=7.1 Hz), 3.06 (3H, d, J=4.8 Hz), 3.09-3.16 (2H, m), 3.40 (2H, q, J=7.1 Hz), 3.60-3.65 (2H, m), 3.71-3.80 (3H, m), 4.15-4.20 (2H, m), 5.47-5.57 (1H, m), 6.54 (1H, d, J=3.7 Hz), 6.61 (1H, dd, J=5.7, 2.4 Hz), 7.24-7.27 (1H, m), 7.34 (1H, s), 7.36-7.40 (2H, m), 7.77-7.83 (2H, m), 7.91 (1H, d, J=2.2 Hz), 8.01 (1H, s), 8.10 (1H, d, J=5.9 Hz), 8.47 (1H, brs).

The starting material 5-((2-(4-(azetidin-3-yl)benzamide)pyridin-4-yl)oxy)-6-(2-ethoxyethoxy)-N-methyl-1H-indole-1-carboxamide was synthesized by the following method.

Production Example 26-1 tert-Butyl 3-(4-((4-((6-(2-ethoxyethoxy)-1-(methylcarbamoyl)-1H-indol-5-yl)oxy)pyridin-2-yl)carbamoyl)phenyl)azetidine-1-carboxylate

[Chemical Formula 125]

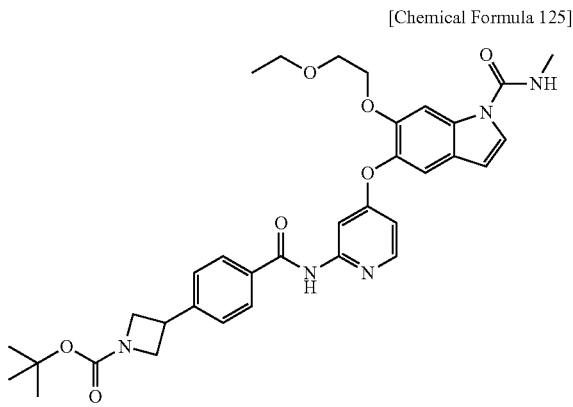 [SMILES: CCOCCOc1cc2c(ccn2C(=O)NC)cc1Oc1ccnc(NC(=O)c2ccc(C3CN(C(=O)OC(C)(C)C)C3)cc2)c1]

Benzotriazole (335 mg, 2.81 mmol) was dissolved in dichloromethane (20 mL), and thionyl chloride (200 μL, 2.74 mmol) was added under nitrogen atmosphere at room temperature, and the mixture was stirred for 5 minutes. 4-(1-(tert-Butoxycarbonyl) azetidin-3-yl)benzoic acid described in Production Example 26-5 (650 mg, 2.34 mmol) was added to the reaction mixture at room temperature, and the mixture was stirred for 25 minutes. The reaction mixture was filtered through a glass filter entirely covered with anhydrous sodium sulfate and then the resultant was washed with dichloromethane, and then the filtrate was added to a mixture of 5-((2-aminopyridin-4-yl)oxy)-6-(2-ethoxyethoxy)-N-methyl-1H-indole-1-carboxamide described in Production Example 24-8 (300 mg, 0.810 mmol), triethylamine (1.3 mL, 9.38 mmol), and 4-dimethylaminopyridine (9.9 mg, 0.081 mmol) in tetrahydrofuran (16 mL) at 0° C. The mixture was stirred at room temperature for 3 hours, then water and ethyl acetate were added to the reaction mixture for partition, and the organic layer was washed with a saturated saline solution and then dried over anhydrous magnesium sulfate. The drying agent was filtered off, then the filtrate was concentrated under vacuum, the residue was dissolved in tetrahydrofuran, an excessive quantity of 9.8 M methylamine methanol solution was added at room temperature, and the mixture was stirred for 75 minutes. The reaction mixture was concentrated under vacuum, the residue was dissolved in dichloromethane, and the resultant was purified with NH silica gel column chromatography (n-heptane:ethyl acetate=1:1-1:3-0:1-ethyl acetate: methanol=9:1). The mixture fraction was concentrated under vacuum, the residue was dissolved in dichloromethane, and the resultant was purified with NH silica gel column chromatography (n-heptane:ethyl acetate=2:3-1:3-0:1-ethyl acetate: methanol=9:1). The target fraction was concentrated under vacuum to obtain the title compound (279 mg, 76%).

$^1$H-NMR Spectrum (CDCl$_3$) δ (ppm): 1.07 (3H, t, J=7.0 Hz), 1.47 (9H, s), 2.81 (3H, d, J=4.8 Hz), 3.40 (2H, q, J=6.8 Hz), 3.60-3.65 (2H, m), 3.73-3.83 (1H, m), 3.93-4.01 (2H, m), 4.15420 (2H, m), 4.35 (2H, t, J=8.6 Hz), 5.44-5.54 (1H, m), 6.56 (1H, d, J=3.7 Hz), 6.61 (1H, dd, J=5.9, 1.8 Hz), 7.23-7.29 (1H, m), 7.34 (1H, s), 7.42 (2H, d, J=8.4 Hz), 7.85 (2H, d, J=8.4 Hz), 7.91 (1H, d, J=2.2 Hz), 8.01 (1H, s), 8.09 (1H, d, J=5.9 Hz), 8.55 (1H, brs).

Production Example 26-2 tert-Butyl 3-((methylsulfonyl)oxy)azetidine-1-carboxylate

[Chemical Formula 126]

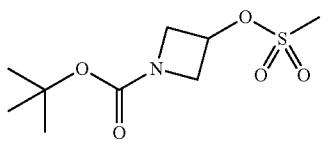

Methanesulfonyl chloride (2.57 mL, 33.3 mmol) and triethylamine (11.6 mL, 83.1 mmol) were added to a solution of commercially available N—BOC-3-hydroxy azetidine (4.8 g, 27.7 mmol) in tetrahydrofuran (100 mL) under nitrogen atmosphere at room temperature. The reaction liquid was stirred at room temperature for 2 hours. A saturated aqueous sodium bicarbonate solution was added to the reaction liquid at room temperature, and the mixture was diluted with ethyl acetate. The organic layer was washed with a saturated saline solution and then dried over anhydrous sodium sulfate. The drying agent was separated by filtration and then the filtrate was concentrated under vacuum. The residue was purified with silica gel column chromatography (n-heptane:ethyl acetate=9:1-1:1) to quantitatively obtain the title compound.

$^1$H-NMR Spectrum (CDCl$_3$) δ (ppm): 1.45 (9H, s), 3.07 (3H, s), 4.03-4.18 (2H, m), 4.22-4.36 (2H, m), 5.12-5.27 (1H, m).

Production Example 26-3 tert-Butyl 3-iodoazetidine-1-carboxylate

[Chemical Formula 127]

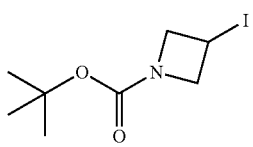

Potassium iodide (51.0 g, 307 mind) was added to a solution of tert-butyl 3-((methylsulfonyl)oxy)azetidine-1-carboxylate described in Production Example 26-2 (7.72 g, 30.7 mmol) in dimethylsulfoxide (80 mL) under nitrogen atmosphere at room temperature, and the mixture was stirred at 140° C. for 2 hours. The reaction liquid was diluted with diethyl ether and water. The aqueous layer was extracted with diethyl ether. The combined organic layer was washed serially with an aqueous sodium pyrosulfite solution and a saturated saline solution and then dried over anhydrous sodium sulfate. The drying agent was separated by filtration and then the resultant was concentrated under vacuum. The residue was purified with silica gel column chromatography (n-heptane:ethyl acetate 9:1-1:1) to obtain the title compound (5.91 g, 68%).

$^1$H-NMR Spectrum (CDCl$_3$) δ (ppm): 1.44 (9H, s), 4.25-4.33 (2H, m), 4.42-4.51 (1H, m), 4.61-4.69 (2H, m).

Production Example 26-4 tert-Butyl 3-(4-(ethoxycarbonyl)phenyl)azetidine-1-carboxylate

[Chemical Formula 128]

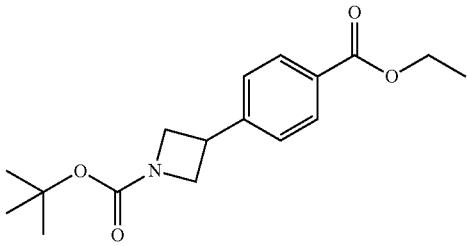

1,2-Dibromoethane (0.286 mL, 3.32 mmol) was added to a suspension of zinc powder (2.12 g, 32.4 mmol) in tetrahydrofuran (10 mL) under nitrogen atmosphere at room temperature. The liquid mixture was stirred at 65° C. for 10 minutes. The reaction liquid was allowed to stand to cool to room temperature, then chlorotrimethylsilane (0.400 mL, 3.13 mmol) was added, and the mixture was stirred at room temperature for 30 minutes. A solution of tert-butyl 3-iodoazetidine-1-carboxylate described in Production Example 26-3 (5.91 g, 20.9 mmol) in tetrahydrofuran (10 mL) was added to the reaction liquid over 5 minutes, and the mixture was stirred at room temperature for 40 minutes (a solution A). A solution of iris(dibenzylideneacetone)dipalladium(0) (382 mg, 0.418 mmol) and tri-2-furylphosphine (402 mg, 1.73 mmol) in tetrahydrofuran (10 mL) was stirred under nitrogen atmosphere at room temperature for 15 minutes, and then the previously prepared solution A was added at room temperature. Subsequently, a solution of ethyl 4-iodobenzoate (6.92 g, 25.1 mmol) in tetrahydrofuran (18.5 mL) was added under nitrogen atmosphere at room temperature. The reaction liquid was stirred at 65° C. overnight. The reaction liquid was allowed to stand to cool to room temperature, then was filtered with celite, and the resultant was washed with ethyl acetate. The filtrate was washed serially with a saturated aqueous sodium bicarbonate solution and a saturated saline solution and then dried over anhydrous sodium sulfate. The drying agent was separated by filtration and then the filtrate was concentrated under vacuum. The residue was dissolved in dichloromethane, then the resultant was purified with silica gel column chromatography (n-heptane:ethyl acetate=9:1-4:1) to obtain the title compound (4.35 g, 68%).

$^1$H-NMR Spectrum (CDCl$_3$) δ (ppm): 1.40 (3H, t, J=8.0 Hz), 1.47 (9H, s), 3.71-3.84 (1H, m), 3.95-4.02 (2H, m), 4.32-4.44 (4H, m), 7.34-7.42 (2H, m), 7.98-8.07 (2H, m).

Production Example 26-5

4-(1-(tert-Butoxycarbonyl)azetidin-3-yl)benzoic acid

[Chemical Formula 129]

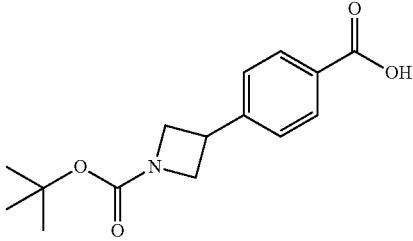

A 2 M sodium hydroxide solution (28.5 mL, 57.0 mmol) was added to a solution of tert-butyl 3-(4-(ethoxycarbonyl)phenyl)azetidine-1-carboxylate described in Production Example 26-4 (4.35 g, 14.2 mmol) in tetrahydrofuran (32 mL) and methanol (7 mL) at 25° C. The reaction liquid was stirred at 60° C. for 1 hour. 2 M hydrochloric acid (28.5 mL) was added to the reaction liquid, and the mixture was diluted with ethyl acetate. The organic layer was washed with a saturated saline solution and then dried over anhydrous sodium sulfate. The drying agent was separated by filtration and then the filtrate was concentrated under vacuum. The residue was purified with silica gel column chromatography (n-heptane:ethyl acetate=9:1-1:1) to obtain the title compound (3.4 g, 86%).

$^1$H-NMR Spectrum (CDCl$_3$) δ (ppm): 1.48 (9H, s), 3.71-3.88 (1H, m), 3.96-4.04 (2H, m), 4.37 (2H, t, J=8.6 Hz), 7.42 (2H, d, J=8.4 Hz), 8.09 (2H, d, J=8.3 Hz).

Production Example 26-6

5-((2-(4-(Azetidin-3-yl)benzamide)pyridin-4-yl)oxy)-6-(2-ethoxyethoxy)-N-methyl-1H-indole-1-carboxamide

[Chemical Formula 130]

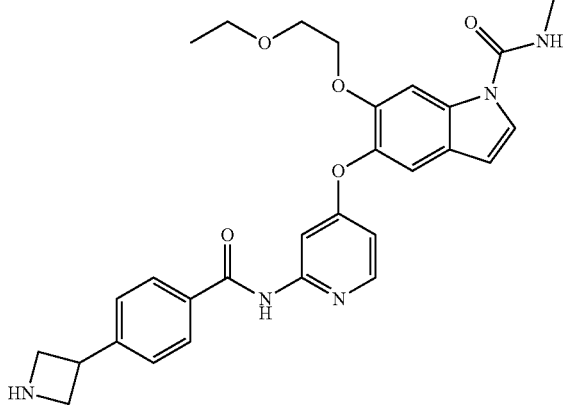

tert-Butyl 3-(4-((4-((6-(2-ethoxyethoxy)-1-(methylcarbamoyl)-1H-indol-5-yl)oxy)pyridin-2-yl)carbamoyl)phenyl)azetidine-1-carboxylate described in Production Example 26-1 (279 mg, 0.443 mmol) was dissolved in dichloromethane (8.0 mL), and trifluoroacetic acid (1.6 mL) was added at 0° C. The mixture was stirred at room temperature for 40 minutes and then concentrated under vacuum, the residue was dissolved in dichloromethane and triethylamine, and the resultant was purified with NH silica gel column chromatography (ethyl acetate:methanol=97:3-4:1) to obtain the title compound (215 mg, 92%).

$^1$H-NMR Spectrum (CDCl$_3$) δ (ppm): 1.07 (3H, t, J=7.0 Hz), 3.05 (3H, d, J=4.8 Hz), 3.40 (2H, q, J=7.0 Hz), 3.61-3.65 (2H, m), 3.81 (2H, t, J=7.0 Hz), 3.93-4.09 (3H, m), 4.15-4.20 (2H, m), 5.51-5.63 (1H, m), 6.53 (1H, d, J=3.7 Hz), 6.61 (1H, dd, J=5.9, 2.2 Hz), 7.24-7.28 (1H, m), 7.33 (11i, s), 7.40 (2H, d, J=8.1 Hz), 7.82 (2H, d, J=8.1 Hz), 7.91 (1H, d, J=2.2 Hz), 8.01 (1H, s), 8.09 (1H, d, J=5.5 Hz), 8.52 (1H, brs).

Example 27

6-(2-Ethoxyethoxy)-5-((2-(4-(1-(2-hydroxyethyl)azetidin-3-yl)benzamide)pyridin-4-yl)oxy)-N-methyl-1H-indole-1-carboxamide

[Chemical Formula 131]

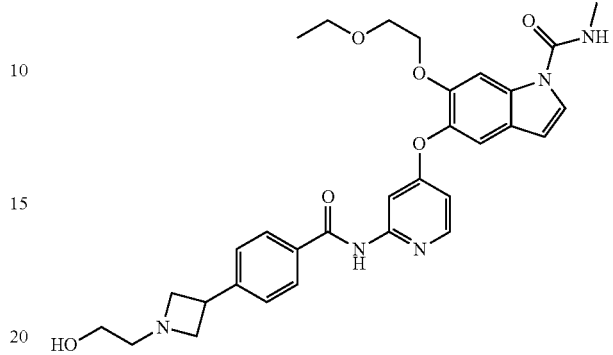

Commercially available 2-hydroxyacetaldehyde (45.9 mg, 0.765 mmol), sodium triacetoxyborohydride (86 mg, 0.408 mmol), and acetic acid (23 μL, 0.408 mmol) were added to a solution of 5-((2-(4-(azetidin-3-yl)benzamide)pyridin-4-yl)oxy)-6-(2-ethoxyethoxy)-N-methyl-1H-indole-1-carboxamide described in Production Example 26-6 (27 mg, 0.051 mmol) in tetrahydrofuran (2 mL) at room temperature, and the mixture was stirred at the same temperature for 2 hours. A saturated aqueous sodium bicarbonate solution was added to the reaction liquid at room temperature, and the mixture was diluted with ethyl acetate. The organic layer was washed with a saturated saline solution and then dried over anhydrous sodium sulfate. The drying agent was separated by filtration and the filtrate was concentrated under vacuum. The residue was purified with NH silica gel column chromatography (ethyl acetate) to obtain the title compound (20.0 mg, 68%).

$^1$H-NMR Spectrum (CDCl$_3$) δ (ppm): 1.08 (3H, t, J=7.0 Hz), 2.68-2.76 (2H, m), 3.06 (3H, d, J=4.81-1z), 3.27-3.34 (2H, m), 3.40 (2H, q, J=7.0 Hz), 3.55-3.67 (4H, m), 3.71-3.94 (3H, m), 4.15-4.22 (2H, m), 5.53-5.65 (1H, m), 6.55 (1H, d, J=3.7 Hz), 6.62 (1H, dd, J=5.9, 2.2 Hz), 7.23-7.29 (1H, m), 7.34 (1H, s), 7.38 (2H, d, J=8.4 Hz), 7.83 (2H, d, J=8.1 Hz), 7.91 (1H, d, J=2.6 Hz), 8.01 (1H, s), 8.09 (1H, d, J=5.9 Hz), 8.63 (1H, his).

Example 28

6-(2-Ethoxyethoxy)-5-((2-(6-(1-ethylpiperidin-4-yl)nicotinamide) pyridin-4-yl)oxy)-N-methyl-1H-indole-1-carboxamide

[Chemical Formula 132]

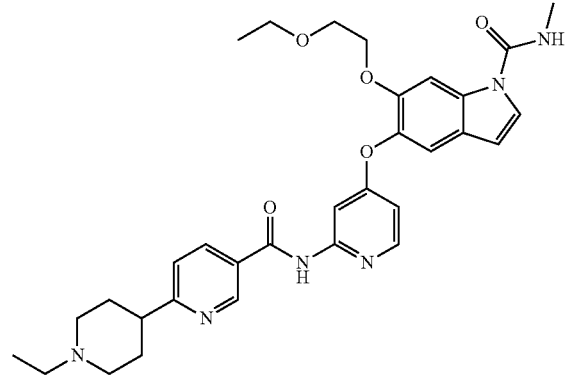

Acetaldehyde (38 μL, 0.671 mmol), acetic acid (20 μL, 0.358 mmol), and sodium triacetoxyborohydride (76 mg, 0.358 mmol) were added to a solution of 6-(2-ethoxyethoxy)-N-methyl-5-((2-(6-(piperidin-4-yl)nicotinamide)pyridin-4-yl)oxy)-1H-indole-1-carboxamide described in Production Example 28-5 (25 mg, 0.045 mmol) in tetrahydrofuran (3 mL) at room temperature, and the mixture was stirred for 1 hour. A saturated aqueous sodium bicarbonate solution was added to the reaction liquid at room temperature, and the mixture was diluted with ethyl acetate. The organic layer was washed with a saturated saline solution and then dried over anhydrous sodium sulfate. The drying agent was separated by filtration and then the filtrate was concentrated under vacuum. The residue was purified with NH silica gel column chromatography (ethyl acetate) to obtain the title compound (13.6 mg, 52%).

$^1$H-NMR Spectrum (CDCl$_3$) δ (ppm): 1.07 (3H, t, J=7.0 Hz), 1.13 (3H, t, J=7.1 Hz), 1.78-1.93 (2H, m), 1.94-2.15 (4H, m), 2.46 (2H, q, J=7.3 Hz), 2.74-2.86 m), 3.00-3.17 (5H, m), 3.40 (2H, q, J=7.1 Hz), 3.63 (2H, t, J=4.8 Hz), 4.18 (2H, t, J=4.8 Hz), 5.45-5.57 (1H, m), 6.56 (1H, d, J=3.3 Hz), 6.61 (1H, dd, J=5.9, 1.5 Hz), 7.20-7.39 (3H, m), 7.84-7.92 (1H, m), 8.02 (1H, s), 8.05-8.15 (2H, m), 8.49 (1H, s), 8.93-9.07 (1H, m).

The starting material 6-(2-ethoxyethoxy)-N-methyl-5-((2-(6-(piperidin-4-yl)nicotinamide)pyridin-4-yl)oxy)-1H-indole-1-carboxamide was synthesized by the following method.

Production Example 28-1

1'-tert-Butyl 5-methyl 5',6'-dihydro-[2,4'-bipyridine]-1',5(2'H)-dicarboxylate

[Chemical Formula 133]

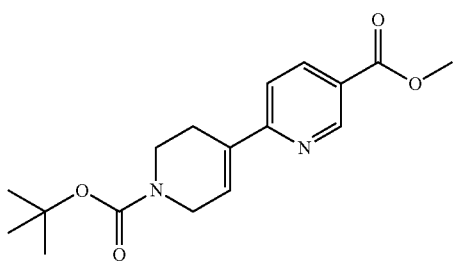

N,N-dimethylformamide (100 mL) was added to commercially available 1-N—BOC-4-(4,4,5,5-tetramethyl-[1,3,2]dioxaborolan-2-yl)-3,6-dihydro-2H-pyridine (4.68 g, 15.1 mmol), commercially available methyl 6-chloronicotinate (2.81 g, 16.4 mmol), 1,1'-bis(diphenylphosphino)ferrocenedichloropalladium(II) (1.17 g, 1.60 mmol), and potassium carbonate (7.02 g, 50.8 mmol). The reaction liquid was stirred under nitrogen atmosphere at 100° C. for 2 hours. The reaction liquid was allowed to stand to cool to room temperature and then diluted with ethyl acetate and water. The aqueous layer was extracted with ethyl acetate. The combined organic layer was washed serially with a dilute aqueous ammonia solution and a saturated saline solution, and then dried over anhydrous sodium sulfate. The drying agent was separated by filtration and then the filtrate was concentrated under vacuum. The residue was purified with silica gel column chromatography (n-heptane:ethyl acetate=9:1-1:1) to obtain the title compound (1.07 g, 22%).

$^1$H-NMR Spectrum (CDCl$_3$) δ (ppm): 1.49 (9H, s), 2.59-2.73 (2H, m), 3.66 (2H, t, J=5.5 Hz), 3.95 (3H, s), 4.17 (2H, d, J=2.9 Hz), 6.79 (1H, dt, J=3.4, 1.8 Hz), 7.44 (1H, d, J=8.4 Hz), 8.25 (1H, dd, J=8.4, 2.2 Hz), 9.15 (1H, dd, J=2.2, 0.7 Hz).

Production Example 28-2

Methyl 6-(1-(tart-butoxycarbonyl)piperidin-4-yl)nicotinate

[Chemical Formula 134]

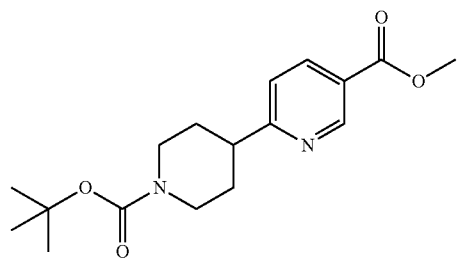

10% Palladium-carbon (water content, 50%) (213 mg) was added to a solution of 1'-tert-butyl 5-methyl 5',6'-dihydro-[2,4'-bipyridine]-1',5(2'H)-dicarboxylate described in Production Example 28-1 (1.06 g, 3.33 mmol) in ethanol (71 mL) and tetrahydrofuran (12 mL), and the mixture was stirred under hydrogen atmosphere at mom temperature for 2 hours. The mixture was filtered, then the filtrate was concentrated under vacuum, and the residue was purified with NH silica gel column chromatography (n-heptane:ethyl acetate=9:1-1:1) to quantitatively obtain the title compound.

$^1$H-NMR Spectrum (CDCl$_3$) δ (ppm): 1.48 (9H, s), 1.73 (2H, qd, J=12.6, 4.4 Hz), 1.88-1.97 (2H, m), 2.76-2.98 (3H, m), 3.94 (3H, s), 4.27 (2H, brs), 7.22-7.26 (1H, m), 8.23 (1H, dd, J=8.4, 2.2 Hz), 9.09-9.18 (1H, m).

Production Example 28-3

6-(1-(tert-Butoxycarbonyl)piperidin-4-yl)nicotinic acid

[Chemical Formula 135]

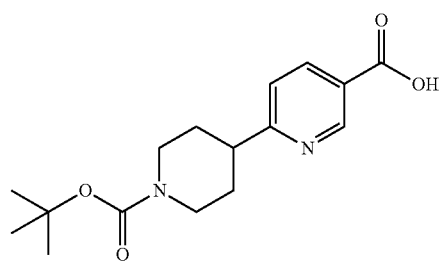

A 2 M sodium hydroxide solution (20 mL) was added to a solution of methyl 6-(1-(tert-butoxycarbonyl)piperidin-4-yl)nicotinate described in Production Example 28-2 (1.07 g, 3.32 mmol) in ethanol (5 mL), and the mixture was stirred for 1 hour. 2 M hydrochloric acid was added to the reaction liquid at 0° C. The aqueous layer was extracted with ethyl acetate.

The combined organic layer was washed with a saturated saline solution and then dried over anhydrous sodium sulfate. The drying agent was separated by filtration and then the filtrate was concentrated under vacuum to obtain the title compound (534 mg, 52%).

$^1$H-NMR Spectrum (DMSO-$d_6$) δ (ppm): 1.42 (9H, s), 1.58 (2H, qd, J=12.6, 4.4 Hz), 1.77-1.89 (2H, m), 2.67-3.04 (3H, m), 3.95-4.17 (2H, m), 7.40 (1H, d, J=7.7 Hz), 8.16 (1H, dd, J=8.1, 2.2 Hz), 8.97 (1H, dd, J=2.2, 0.7 Hz).

Production Example 28-4 tert-Butyl 4-(5-((4-((6-(2-ethoxyethoxy)-1-(methyl-carbamoyl)-1H-indol-5-yl)oxy)pyridin-2-yl)carbamoyl)pyridin-2-yl)piperidine-1-carboxylate

[Chemical Formula 136]

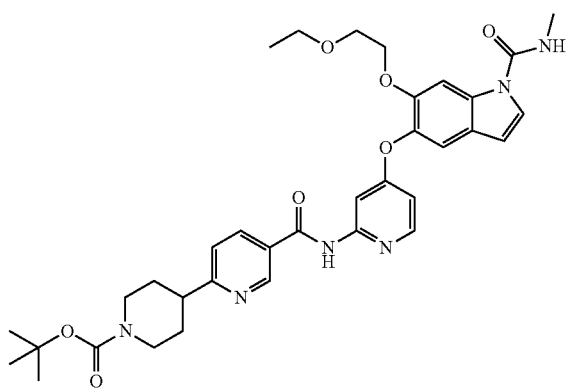

Oxalyl chloride (74 µL, 0.864 mmol) and one drop of N,N-dimethylformamide were added to a solution of 6-(1-(tert-butoxycarbonyl)piperidin-4-yl)nicotinic acid described in Production Example 28-3 (80 mg, 0.216 mmol) in dichloromethane (2 mL) at 0° C., and the mixture was stirred for 30 minutes. The reaction liquid was concentrated under vacuum. The residue was dissolved in tetrahydrofuran (2 mL), then triethylamine (301 µL, 2.16 mmol) and 5-((2-aminopyridin-4-yl)oxy)-6-(2-ethoxyethoxy)-N-methyl-1H-indole-1-carboxamide described in Production Example 24-8 (80 mg, 0.216 mmol) were added, and the mixture was stiffed for 5 hours. An excessive quantity of methylamine was added to the reaction liquid, and then the mixture was diluted with water and ethyl acetate for partition. The organic layer was washed with a saturated saline solution and then dried over anhydrous sodium sulfate. The drying agent was separated by filtration and then the filtrate was concentrated under vacuum. The residue was purified with NH silica gel column chromatography (n-heptane:ethyl acetate=1:1) to obtain the title compound (80 mg, 56%).

$^1$H-NMR Spectrum (CDCl$_3$) δ (ppm): 1.04 (3H, t, J=7.0 Hz), 1.45 (9H, s), 1.68 (2H, qd, J=12.6, 4.4 Hz), 1.83-1.93 (2H, m), 2.69-2.92 (3H, m), 2.96 (3H, d, J=4.8 Hz), 3.37 (2H, q, J=7.0 Hz), 3.56-3.63 (2H, m), 4.11-4.15 (2H, m), 4.21 (2H, brs), 6.10-6.20 (1H, m), 6.44 (1H, d, J=3.7 Hz), 6.58 (1H, dd, J=5.7, 2.4 Hz), 7.21 (1H, d, J=7.7 Hz), 7.24-7.31 (2H, m), 7.86 (1H, d, J=2.2 Hz), 7.95 (1H, d, J=5.9 Hz), 8.02 (1H, s), 8.07 (1H, dd, J=8.2, 2.4 Hz), 8.96-9.02 (1H, m), 9.20 (1H, brs).

Production Example 28-5

6-(2-Ethoxyethoxy)-N-methyl-5-((2-(6-(piperidin-4-yl) nicotinamide)pyridin-4-yl)oxy)-1H-indole-1-carboxamide

[Chemical Formula 137]

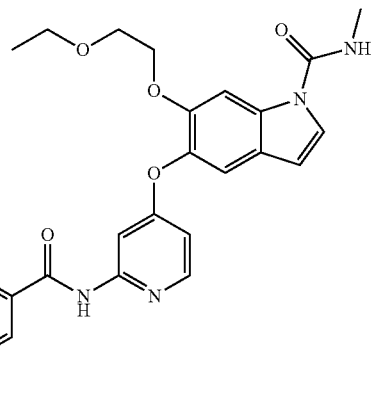

Trifluoroacetic acid (374 µL, 4.86 mmol) was added to a solution of tert-butyl 4-(5-((4-((6-(2-ethoxyethoxy)-1-(methylcarbamoyl)-1H-indol-5-yl)oxy)pyridin-2-yl)carbamoyl)pyridin-2-yl)piperidine-1-carboxylate described in Production Example 28-4 (80 mg, 0.121 mmol) in dichloromethane (3 mL) at room temperature, and the mixture was stirred for 1.5 hours. The reaction liquid was concentrated under vacuum. The residue was dissolved in dichloromethane and then triethylamine was added to neutralize the trifluoroacetic acid. The solution was concentrated under vacuum and then the residue was purified with NH silica gel column chromatography (ethyl acetate:methanol=49:1-17:3) to obtain the title compound (51.3 mg, 76%).

$^1$H-NMR Spectrum (CDCl$_3$) δ (ppm): 1.07 (3H, t, J=7.1 Hz), 1.72 (2H, qd, J=12.4, 4.0 Hz), 1.87-1.97 (2H, m), 2.76 (2H, td, J=12.3, 2.6 Hz), 2.84-2.95 (1H, m), 2.99 (3H, d, J=4.4 Hz), 3.16-3.28 (2H, m), 3.40 (2H, q, J=7.1 Hz), 3.59-3.68 (2H, m), 4.14-4.20 (2H, m), 6.04-6.17 (1H, m), 6.48 (1H, d, J=3.7 Hz), 6.62 (1H, dd, J=5.7, 2.4 Hz), 7.23-7.29 (2H, m), 7.31 (1H, s), 7.88 (1H, d, J=2.2 Hz), 7.98-8.05 (2H, m), 8.10 (1H, dd, J=8.2, 2.4 Hz), 9.02 (1H, dd, J=2.6, 0.7 Hz).

Example 29

(S)-6-(2-Ethoxyethoxy)-5-((2-(4-((2-hydroxymethyl) pyrrolidin-1-yl)methyl)benzamide)pyridin-4-yl) oxy)-N-methyl-1H-indole-1-carboxamide

[Chemical Formula 138]

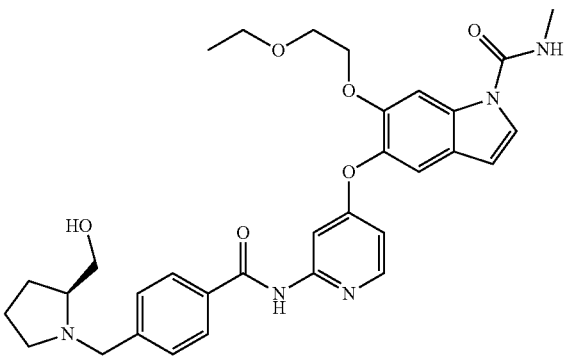

Commercially available L-prolinol (31.3 mg, 0.309 mmol) was added to a mixture of 5-((2-(4-(chloromethyl)-N-(4-(chloromethyl)benzoyl)benzamide)pyridin-4-yl)oxy)-6-(2-ethoxyethoxy)-N-methyl-1H-indole-1-carboxamide described in Production Example 29-1 (19.6 mg, 0.029 mmol) and N,N-dimethylformamide (500 μL) at room temperature, and the mixture was stirred under nitrogen atmosphere for 17.5 hours. Water and ethyl acetate were added to the reaction mixture for partition. The organic layer was washed with a saturated saline solution, and then dried over anhydrous sodium sulfate and filtered. The solvent was evaporated, the resultant residue was purified with NH silica gel TLC (ethyl acetate), and the product was collected by filteration and washed with diethyl ether to obtain the title compound (13.3 mg, 78%).

$^1$H-NMR Spectrum (CDCl$_3$) δ (ppm): 1.08 (3H, t, J=7.1 Hz), 1.65-1.99 (5H, m), 2.23-2.32 (1H, m), 2.71-2.79 (1H, m), 2.92-2.99 (1H, m), 3.06 (3H, d, J=4.8 Hz), 3.37-3.48 (4H, m), 3.61-3.69 (3H, m), 4.03 (1H, d, J=13.5 Hz), 4.16-4.20 (2H, m), 5.48-5.56 (1H, m), 6.55 (1H, d, J=3.7 Hz), 6.61 (1H, dd, J=5.9, 2.6 Hz), 7.24-7.28 (1H, m), 7.34 (1H, s), 7.41 (2H, d, J=8.4 Hz), 7.79-7.84 (2H, m), 7.91 (1H, d, J=2.2 Hz), 8.01 (1H, s), 8.10 (1H, d, J=5.5 Hz), 8.50 (1H, brs).

The starting material 5-((2-(4-(chloromethyl)-N-(4-(chloromethyl)benzoyl)benzamide)pyridin-4-yl)oxy)-6-(2-ethoxyethoxy)-N-methyl-1H-indole-1-carboxamide was synthesized by the following method.

Production Example 29-1

5-((2-(4-(Chloromethyl)-N-(4-(chloromethyl)benzoyl)benzamide)pyridin-4-yl)oxy)-6-(2-ethoxyethoxy)-N-methyl-1H-indole-1-carboxamide

[Chemical Formula 139]

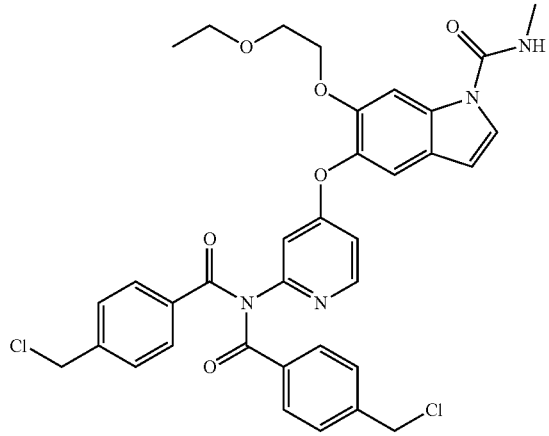

Triethylamine (300 μL, 2.16 mmol) and commercially available 4-(chloromethyl)benzoyl chloride (221 mg, 1.17 mmol) were added to a mixture of 5-((2-aminopyridin-4-yl)oxy)-6-(2-ethoxyethoxy)-N-methyl-1H-indole-1-carboxamide described in Production Example 24-8 (107 mg, 0.289 mmol) and tetrahydrofuran (8.0 mL) under nitrogen atmosphere at 0° C. The mixture was stirred at room temperature for 1 hour and then water and ethyl acetate were added to the reaction mixture for partition. The organic layer was washed with a saturated saline solution, then dried over anhydrous sodium sulfate, and then filtered with NH silica gel. The filtrate was concentrated under vacuum to quantitatively obtain the title compound.

$^1$H-NMR Spectrum (CDCl$_3$) δ (ppm): 1.11 (3H, t, J=7.0 Hz), 3.06 (3H, d, J=4.8 Hz), 3.43 (2H, q, J=7.0 Hz), 3.56-3.60 (2H, m), 4.08-4.12 (2H, m), 4.56 (4H, s), 5.41-5.49 (1H, m), 6.55 (1H, d, J=3.7 Hz), 6.67 (1H, d, J=2.2 Hz), 6.71 (1H, dd, J=5.9, 2.2 Hz), 7.24 (1H, s), 7.25-7.28 (1H, m), 7.34-7.39 (4H, m), 7.69-7.75 (4H, m), 798 (1H, s), 8.17 (1H, d, J=5.9 Hz).

Example 30

5-((2-(4-(((3S,5R)-3,5-Dimethylpiperazin-1-yl)methyl)benzamide) pyridin-4-yl)oxy)-6-(2-ethoxyethoxy)-N-methyl-1H-indole-1-carboxamide

[Chemical Formula 140]

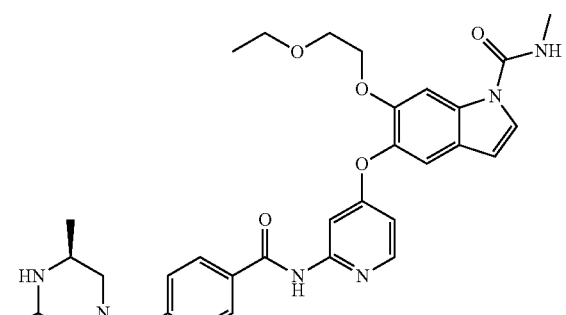

Commercially available cis-2,6-dimethylpiperazine (32.5 mg, 0.285 mmol) was added to a mixture of 5-((2-(4-(chloromethyl)-N-(4-(chloromethyl)benzoyl)benzamide)pyridin-4-yl)oxy)-6-(2-ethoxyethoxy)-N-methyl-1H-indole-1-carboxamide described in Production Example 29-1 (21.1 mg, 0.031 mmol) and N,N-dimethylformamide (500 μL) at room temperature, and the mixture was stirred under nitrogen atmosphere for 13 hours and 20 minutes. Water and ethyl acetate were added to the reaction mixture for partition. The organic layer was washed with a saturated saline solution, and then dried over anhydrous sodium sulfate and filtered. The solvent was evaporated and the resultant residue was purified with NH silica gel TLC (ethyl acetate), then the product was collected by filtration and washed with diethyl ether to obtain the title compound (14.4 mg, 77%).

$^1$H-NMR Spectrum (CDCl$_3$) δ (ppm): 1.02 (6H, d, J=6.2 Hz), 1.07 (3H, t, J=7.0 Hz), 1.63 (2H, t, J=10.6 Hz), 2.69-2.76 (2H, m), 2.89-2.99 (2H, m), 3.07 (3H, d, J=4.8 Hz), 3.40 (2H, q, J=7.0 Hz), 3.52 (2H, s), 3.61-3.65 (2H, m), 4.16-4.20 (2H, m), 5.45-5.52 (1H, m), 6.55 (1H, d, J=3.7 Hz), 6.60 (1H, dd, J=5.9, 2.2 Hz), 7.25-7.27 (1H, m), 7.34 (1H, s), 7.43 (2H, d, J=8.1 Hz), 7.79-7.83 (2H, m), 7.92 (1H, d, J=2.2 Hz), 8.01 (1H, s), 8.10 (1H, d, J=5.9 Hz), 8.47 (1H, brs).

Example 31

(R)-6-(2-Ethoxyethoxy)-5-((2-(5-((3-hydroxypyrrolidin-1-yl)methyl)thiophene-2-carboxamide)pyridin-4-yl)oxy-N-methyl-1H-indole-1-carboxamide

[Chemical Formula 141]

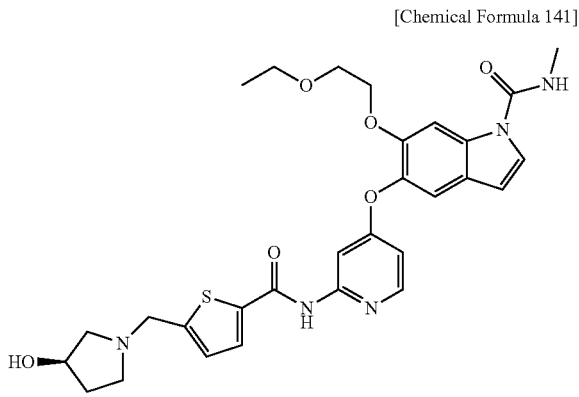 [SMILES: CCOCCOc1cc2c(ccn2C(=O)NC)cc1Oc1ccnc(NC(=O)c2ccc(CN3CC[C@@H](O)C3)s2)c1]

Thionyl chloride (2.8 mL, 38.4 mmol) and N,N-dimethylformamide (5.87 µL, 0.076 mmol) were added to 5-(hydroxymethyl)thiophene-2-carboxylic acid described in Production Example 31-1 (120 mg, 0.759 mmol), and the mixture was heated and stirred at 90° C. for 2 hours. The reaction mixture was evaporated under vacuum to obtain a crude product A (148 mg).

Triethylamine (191 µL, 1.38 mmol) and a tetrahydrofuran solution (1.0 mL) of a part of the crude product A (74.0 mg, 0.379 mmol) were added to a mixture of 5-((2-aminopyridin-4-yl)oxy)-6-(2-ethoxyethoxy)-N-methyl-1H-indole-1-carboxamide described in Production Example 24-8 (51.1 mg, 0.138 mmol) and tetrahydrofuran (1.4 mL) under nitrogen atmosphere at 0° C. The mixture was stirred at room temperature for 170 minutes and then water and ethyl acetate were added to the reaction mixture for partition. The organic layer was washed with a saturated saline solution, then dried over anhydrous sodium sulfate and filtered with NH silica gel, and then the resultant was concentrated under vacuum to obtain a crude product B (86.7 mg).

A part of the crude product B (17.3 mg) was dissolved in N,N-dimethylformamide (1.0 mL), commercially available (R)-3-hydroxy pyrrolidine (24.4 mg, 0.28 mmol) was added under nitrogen atmosphere at room temperature, and the mixture was stirred for 17 hours. Water and ethyl acetate were added to the reaction mixture for partition, and the organic layer was washed with a saturated saline solution, dried over anhydrous sodium sulfate, and filtered. The solvent was evaporated and the resultant residue was purified with NH silica gel TLC (ethyl acetate), then the product was collected by filtration and washed with n-hexane to obtain the title compound (9.0 mg, 56%).

$^1$H-NMR Spectrum (CDCl$_3$) δ (ppm): 1.07 (3H, t, J=6.8 Hz), 1.71-1.81 (1H, m), 2.13-2.24 (1H, m), 2.34-2.43 (1H, m), 2.57-2.64 (1H, m), 2.69-2.76 (1H, m), 2.87-2.97 (1H, m), 3.06 (3H, d, J=4.8 Hz), 3.39 (2H, q, J=7.3 Hz), 3.59-3.64 (2H, m), 3.84 (2H, s), 4.14419 (2H, m), 4.31-4.37 (1H, m), 5.48-5.55 (1H, m), 6.54 (1H, d, J=3.7 Hz), 6.61 (1H, dd, J=5.9, 2.4 Hz), 6.91 (1H, d, J=3.5 Hz), 7.24-7.28 (1H, m), 7.32 (1H, s), 7.47 (1H, d, J=3.9 Hz), 7.78-7.82 (1H, m), 7.99 (1H, s), 8.08 (1H, d, J=5.7 Hz), 8.34 (1H, brs).

Production Example 31-1

5-(Hydroxymethyl)thiophene-2-carboxylic acid

[Chemical Formula 142]

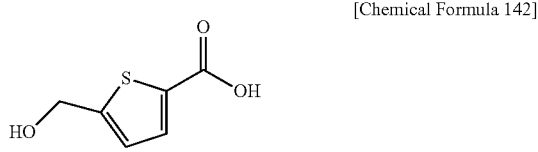

Sodium borohydride (218 mg, 5.76 mmol) was added to a solution of commercially available 5-formyl-2-thiophenecarboxylic acid (599 mg, 3.84 mmol) in methanol (19 mL), and the mixture was stiffed under nitrogen atmosphere at room temperature for 4 hours and 30 minutes. Acetone was added to the reaction mixture, and the mixture was concentrated under vacuum. 2 M hydrochloric acid and ethyl acetate were added to the residue for partition, and the aqueous layer was extracted with ethyl acetate. The combined organic layer was washed with water, dried over anhydrous sodium sulfate, and filtered. The filtrate was concentrated under vacuum and the precipitate was washed with diethyl ether and n-hexane to obtain the title compound (529 mg, 87%).

$^1$H-NMR Spectrum (DMSO-d$_6$) δ (ppm): 4.61-4.74 (2H, m), 5.65-72 (1H, m), 6.97-7.7.03 (1H, m), 7.55-7.62 (1H, m), 12.92 (1H, brs).

Example 32

6-(3-Methoxypropoxy)-N-methyl-5-((2-(4-(1-methylazetidin-3-yl)benzamide)pyridin-4-yl)oxy)-1H-indole-1-carboxamide

[Chemical Formula 143]

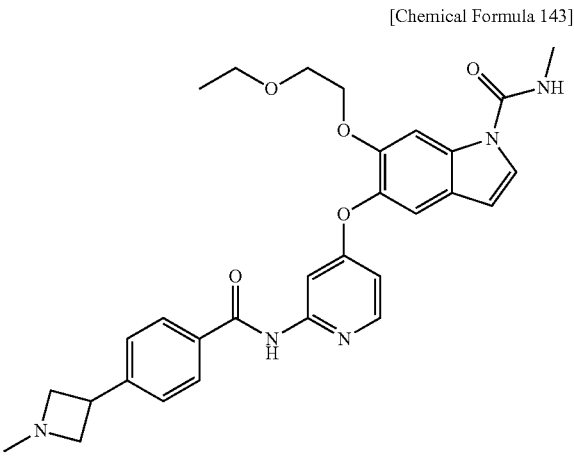

Formaldehyde (12 µL, 0.425 mmol), acetic acid (13 µL, 0.227 mmol), and sodium triacetoxyborohydride (48.0 mg, 0.227 mmol) were added to a solution of 5-((2-(4-(azetidin-3-yl)benzamide)pyridin-4-yl)oxy)-6-(3-methoxypropoxy)-N-methyl-1H-indole-1-carboxamide described in Production Example 3240 (15 mg, 0.028 mmol) in tetrahydrofuran (2 mL) at room temperature. The reaction liquid was stirred at mom temperature for 1 hour. A saturated aqueous sodium bicarbonate solution and ethyl acetate were added to the reaction liquid at room temperature. The organic layer was washed with a saturated saline solution and then dried over anhydrous sodium sulfate. The drying agent was separated by filtration and the filtrate was concentrated under vacuum. The residue was purified with NH silica gel column chromatography (ethyl acetate) to obtain the title compound (8.8 mg, 57%).

$^1$H-NMR Spectrum (DMSO-$d_6$) δ (ppm): 1.76 (2H, t, J=6.4 Hz), 2.25 (3H, s), 2.85 (3H, d, J=4.4 Hz), 3.02-3.13 (7H, m), 3.54-3.65 (3H, m), 3.99 (2H, t, J=6.2 Hz), 6.64 (1H, d, J=3.3 Hz), 6.69 (1H, dd, J=5.9, 2.6 Hz), 7.42 (2H, d, J=8.4 Hz), 7.46 (1H, s), 7.69 (1H, d, J=2.6 Hz), 7.77 (1H, d, J=3.7 Hz), 7.92 (2H, d, J=8.4 Hz), 8.06 (1H, s), 8.14-8.19 (1H, m), 8.21 (1H, d, J=5.9 Hz), 10.70 (1H, s).

The starting material 5-((2-(4-(azetidin-3-yl)benzamide) pyridin-4-yl)oxy)-6-(3-methoxypropoxy)-N-methyl-1H-indole-1-carboxamide was synthesized by the following method.

Production Example 32-1

3-Hydroxy-4-(3-methoxypropoxy)benzaldehyde

[Chemical Formula 144]

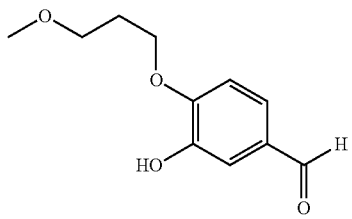

Commercially available 1-bromo-3-methoxypropane (24.0 g, 157 mmol) was added to a solution of commercially available 3,4-dihydroxybenzaldehyde (21.7 g, 157 mmol) and sodium carbonate (25.0 g, 236 mmol) in N,N-dimethylformamide (50 mL) under nitrogen atmosphere at room temperature. The reaction liquid was stirred at room temperature for 3 days and 4 hours. 2 M hydrochloric acid, ethyl acetate, and water were added to the reaction liquid at 0° C. The aqueous layer was extracted with ethyl acetate. The combined organic layer was washed serially with water and a saturated saline solution and then dried over anhydrous sodium sulfate. The drying agent was separated by filtration and the filtrate was concentrated under vacuum. The insoluble matters were separated by filtration with dichloromethane and the filtrate was concentrated under vacuum. The residue was purified with silica gel column chromatography (n-heptane:ethyl acetate=17:3-1:1) to obtain the title compound (17.2 g, 52%).

$^1$H-NMR Spectrum (CDCl$_3$) δ (ppm): 2.07-2.18 (2H, m), 3.38 (3H, s), 3.59 (2H, t, J=5.9 Hz), 4.26 (2H, t, J=6.2 Hz), 6.21 (1H, s), 7.00 (1H, d, J=8.1 Hz), 7.35-7.48 (2H, m), 9.85 (1H, s).

Production Example 32-2

3-(Benzyloxy)-4-(3-methoxypropoxy)benzaldehyde

[Chemical Formula 145]

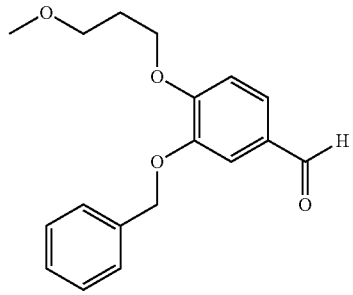

Potassium carbonate (14.7 g, 106 mmol) and benzyl chloride (12.2 mL, 106 mmol) were added to a solution of 3-hydroxy-4-(3-methoxypropoxy)benzaldehyde described in Production Example 32-1 (17.2 g, 81.7 mmol) in ethanol (200 mL) under nitrogen atmosphere at room temperature, and the mixture was stirred under a thermal condition of 90° C. for 2 hours. The reaction liquid was cooled to 0° C., and the mixture was diluted with 2 M hydrochloric acid, ethyl acetate, and water. The organic layer was washed with a saturated saline solution and then dried over anhydrous magnesium sulfate. The drying agent was separated by filtration and then the filtrate was concentrated under vacuum. The residue was purified with silica gel column chromatography (n-heptane: ethyl acetate=4:1-3:7) to obtain the title compound (19.8 g, 81%).

$^1$H-NMR Spectrum (CDCl$_3$) δ (ppm): 2.10-2.20 (2H, m), 3.35 (3H, d, J=0.7 Hz), 3.59 (2H, t, J=6.0 Hz), 4.21 (2H, t, J=6.4 Hz), 5.18 (2H, s), 6.95-7.09 (1H, m), 7.28-7.50 (7H, m), 9.76-9.87 (1H, m).

Production Example 32-3

(E)-2-(Benzyloxy)-1-(3-methoxypropoxy)-4-(2-nitrovinyl)benzene

[Chemical Formula 146]

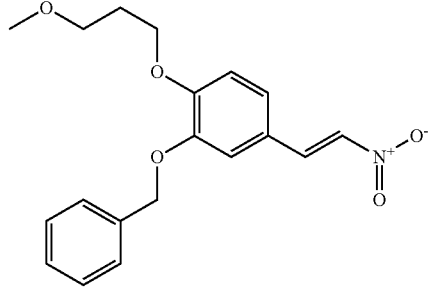

Ammonium acetate (6.10 g, 79.1 mmol) and nitromethane (8.93 mL, 165 mmol) were added to a solution of 3-(benzyloxy)-4-(3-methoxypropoxy)benzaldehyde described in Production Example 32-2 (19.8 g, 65.9 mmol) in acetic acid (52.8 mL) under nitrogen atmosphere at room temperature. The liquid mixture was stirred under a thermal condition of 130° C. for 2 hours. The reaction liquid was allowed to stand to cool to room temperature, then the precipitate was collected by filteration and washed with ethanol to quantitatively obtain the title compound.

¹H-NMR Spectrum (CDCl₃) δ (ppm): 2.07-2.17 (2H, m), 3.35 (3H, s), 3.59 (2H, t, J=6.0 Hz), 4.19 (2H, t, J=6.4 Hz), 5.16 (2H, s), 6.96 (1H, d, J=8.4 Hz), 7.05 (1H, d, J=1.8 Hz), 7.16 (1H, dd, J=8.4, 1.8 Hz), 7.29-7.47 (6H, m), 7.91 (1H, d, J=13.5 Hz).

Production Example 32-4

(E)-1-(Benzyloxy)-2-(3-methoxypropoxy)-4-nitro-5-(2-nitrovinyl)benzene

[Chemical Formula 147]

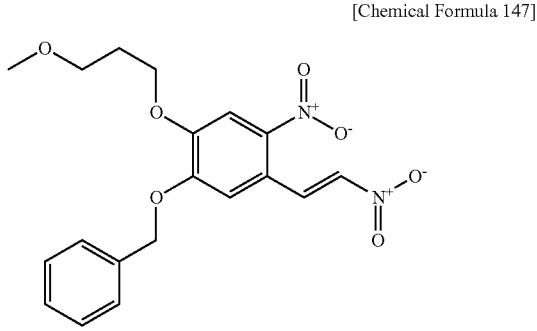 [SMILES: COCCCOc1cc([N+](=O)[O-])c(/C=C/[N+](=O)[O-])cc1OCc1ccccc1]

69% Nitric acid (16 mL, 249 mmol) was added to a liquid mixture of (E)-2-(benzyloxy)-1-(3-methoxypropoxy)-4-(2-nitrovinyl)benzene described in Production Example 32-3 (22.6 g, 65.9 mmol) in acetic acid (150 mL) at room temperature. The liquid mixture was stirred at mom temperature for 6 hours. The reaction liquid was transferred into an ice bath, then the precipitate was collected by filtration and washed with water to quantitatively obtain the title compound.

¹H-NMR Spectrum (CDCl₃) δ (ppm): 2.10-2.13 (2H, m), 3.36 (3H, s), 3.59 (2H, t, J=5.9 Hz), 4.25 (2H, t, J=6.4 Hz), 5.27 (2H, s), 6.93 (1H, s), 7.24 (1H, d, J=13.6 Hz), 7.34-7.46 (5H, m), 7.78 (1H, s), 8.52-8.62 (1H, m).

Production Example 32-5

6-(3-Methoxypropoxy)-1H-indol-5-ol

[Chemical Formula 148]

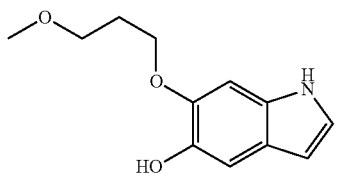

10% Palladium-carbon (water content, 50%) (8 g) was added to a solution of (E)-1-(benzyloxy)-2-(3-methoxypropoxy)-4-nitro-5-(2-nitrovinyl)benzene described in Production Example 32-4 (19.6 g, 50.5 mmol) in methanol (300 mL) at room temperature. The liquid mixture was stirred under hydrogen atmosphere at room temperature for 6 hours. The reaction liquid was filtered through celite and then the filtrate was concentrated under vacuum. The residue was purified with silica gel column chromatography (n-heptane:ethyl acetate=2:1-1:1) to obtain the title compound (3.81 g, 34%).

¹H-NMR Spectrum (CDCl₃) δ (ppm): 2.05-2.13 (2H, m), 3.40 (3H, s), 3.61 (2H, t, J=6.0 Hz), 4.16 (2H, t, J=6.0 Hz), 5.97-6.05 (1H, m), 6.36-6.46 (1H, m), 6.92 (1H, s), 7.08 (1H, t, J=2.8 Hz), 7.14 (1H, s), 7.26 (1H, s), 7.82-8.06 (1H, m).

Production Example 32-6

N-(4-((6-(3-Methoxypropoxy)-1H-indol-5-yl)oxy)pyridin-2-yl)acetamide

[Chemical Formula 149]

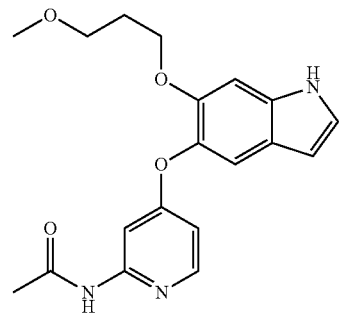

Dimethylsulfoxide (25 mL) was added to a mixture of 6-(3-methoxypropoxy)-1H-indol-5-ol described in Production Example 32-5 (3.81 g, 17.2 mmol), N-(4-chloropyridin-2-yl)acetamide described in Production Example 1-5 (3.23 g, 18.9 mmol), and potassium tert-butoxide (2.12 g, 18.9 mmol) under nitrogen atmosphere at room temperature. The liquid mixture was stirred at 150° C. for 14 hours. The reaction liquid was cooled to room temperature, and then ethyl acetate and water were added. The organic layer was washed with a saturated saline solution and then dried over anhydrous sodium sulfate. The drying agent was separated by filtration and then the filtrate was concentrated under vacuum. The residue was purified with silica gel column chromatography (n-heptane:ethyl acetate=1:1-0:1-ethyl acetate:methanol=49:1) to obtain the title compound (2.83 g, 46%).

¹H-NMR Spectrum (CDCl₃) δ (ppm): 1.85-1.91 (2H, m), 2.13 (3H, s), 3.20 (3H, s), 3.24 (2H, t, J=6.2 Hz), 4.02 (2H, t, J=6.2 Hz), 6.44-6.49 (1H, m), 6.51-6.56 (1H, m), 6.95-7.02 (1H, m), 7.10-7.18 (1H, m), 7.31-7.38 (1H, m), 7.71-7.82 (1H, m), 7.97-8.06 (1H, m), 8.20-8.30 (1H, m), 8.36-8.52 (1H, m).

Production Example 32-7

4-((6-(3-Methoxypropoxy)-1H-indol-5-yl)oxy)pyridin-2-amine

[Chemical Formula 150]

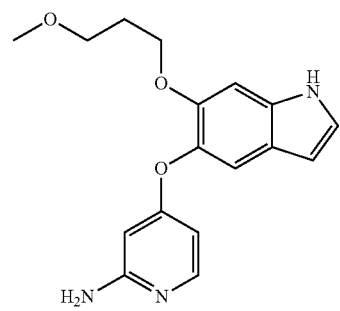

A 2 M sodium hydroxide solution (30 mL) was added to a solution of N-(4-((6-(3-methoxypropoxy)-1H-indol-5-yl)oxy)pyridin-2-yl)acetamide described in Production Example 32-6 (2.8 g, 7.88 mmol) in methanol (30 mL) under nitrogen atmosphere at room temperature. The liquid mixture was stirred under reflux under a thermal condition of 75° C. for 2 hours. The reaction liquid was allowed to stand to cool to room temperature, and then ethyl acetate and water were added. The organic layer was washed with a saturated saline solution and then dried over anhydrous sodium sulfate. The drying agent was separated by filtration and then the filtrate was concentrated under vacuum. The residue was purified with silica gel column chromatography (n-heptane:ethyl acetate=1:9-0:1-ethyl acetate:methanol=49:1) to obtain the title compound (2.24 g, 91%).

$^1$H-NMR Spectrum (CDCl$_3$) δ (ppm): 1.75-1.92 (2H, m), 3.23 (3H, s), 3.28 (2H, t, J=6.0 Hz), 4.03 (2H, t, J=6.0 Hz), 4.30 (2H, s), 5.89 (1H, d, J=2.2 Hz), 6.29 (1H, dd, J=5.9, 2.2 Hz), 6.46-6.53 (1H, m), 7.01 (1H, s), 7.16 (1H, dd, J=3.3, 2.6 Hz), 7.35 (1H, s), 7.88 (1H, d, J=5.9 Hz), 8.14-8.26 (1H, m).

Production Example 32-8

5-((2-Aminopyridin-4-yl)oxy)-6-(3-methoxypropoxy)-N-methyl-1H-indole-1-carboxamide

[Chemical Formula 151]

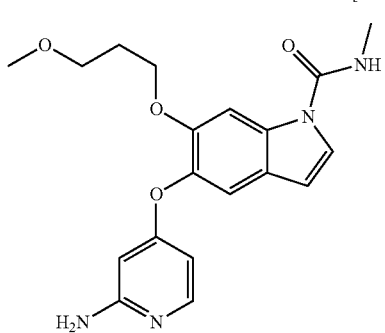

50-72% Oily sodium hydride (308 mg) was added to a solution of 4-((6-(3-methoxypropoxy)-1H-indol-5-yl)oxy)pyridin-2-amine described in Production Example 32-7 (2.23 g, 7.12 mmol) in N,N-dimethylformamide (30 mL) under nitrogen atmosphere at 0° C. The reaction liquid was stirred for 10 minutes, then phenyl methylcarbamate described in Production Example 1-7 (1.40 g, 9.25 mmol) was added, and the resultant was further stirred at the same temperature for 30 minutes. Water and ethyl acetate were added to the reaction liquid. The organic layer was washed serially with water and a saturated saline solution and then dried over anhydrous sodium sulfate. The drying agent was separated by filtration and then the filtrate was concentrated under vacuum. The residue was purified with NH silica gel column chromatography (n-heptane:ethyl acetate=9:1-0:1) to obtain the title compound (2.44 g, 93%).

$^1$H-NMR Spectrum (DMSO-d$_6$) δ (ppm): 1.73-1.86 (2H, m), 2.81-2.87 (3H, m), 3.12 (3H, d, J=1.8 Hz), 3.16-3.24 (2H, m), 3.98 (2H, t, J=5.7 Hz), 5.62-5.71 (1H, m), 5.78 (2H, s), 6.06-6.15 (1H, m), 6.61 (11f, dd, J=3.5, 1.7 Hz), 7.36 (1H, d, J=1.8 Hz), 7.71-7.78 (2H, m), 7.98-8.04 (1H, m), 8.10-8.22 (1H, m).

Production Example 32-9 tert-Butyl 3-(4-((4-((6-(3-methoxypropoxy)-1-(methylcarbamoyl)-1H-indol-5-yl)oxy)pyridin-2-yl)carbamoyl)phenyl)azetidine-1-carboxylate

[Chemical Formula 152]

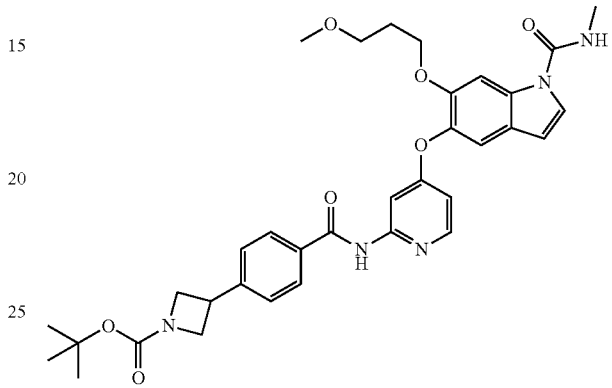

Thionyl chloride (118 μL, 1.62 mmol) was added to a solution of benzotriazole (193 mg, 1.62 mmol) in dichloromethane (5 mL) under nitrogen atmosphere at room temperature, and the mixture was stirred for 5 minutes. 4-(1-(tert-Butoxycarbonyl)azetidin-3-yl)benzoic acid described in Production Example 26-5 (300 mg, 1.08 mmol) was added to the reaction liquid, and the mixture was further stirred for 1 hour. The reaction liquid was filtered through anhydrous sodium sulfate on the glass filter, and the resultant was washed with dichloromethane. A solution of triethylamine (748 μL, 5.40 mmol), 4-dimethylaminopyridine (6.60 mg, 0.054 mmol), and 5-((2-aminopyridin-4-yl)oxy)-6-(3-methoxypropoxy)-N-methyl-1H-indole-1-carboxamide described in Production Example 32-8 (200 mg, 0.54 mmol) in tetrahydrofuran (10 mL) was added to the resultant dichloromethane solution under nitrogen atmosphere at 0° C., and the mixture was stirred for 4 hours and 20 minutes. The reaction liquid was diluted with ethyl acetate and water. The organic layer was washed with a saturated saline solution and then dried over anhydrous sodium sulfate. The drying agent was separated by filtration and then the filtrate was concentrated under vacuum. Tetrahydrofuran and an excessive quantity of methylamine tetrahydrofuran solution were added to the residue, and the mixture was stirred at room temperature. The liquid mixture was concentrated under vacuum. The residue was purified with silica gel column chromatography (n-heptane:ethyl acetate=2:3-0:1) to obtain the title compound (146 mg, 43%).

$^1$H-NMR Spectrum (CDCl$_3$) δ (ppm): 1.43-1.51 (9H, m), 1.80-1.95 (2H, m), 2.95 (3H, d, J=4.8 Hz), 3.17 (3H, s), 3.20-327 (2H, m), 3.69-3.82 (1H, m), 3.95 (2H, dd, J=8.6, 6.0 Hz), 4.05-4.17 (2H, m), 4.33 (2H, t, J=8.6 Hz), 6.13-6.25 (1H, m), 6.44 (1H, d, J=3.7 Hz), 6.63 (1H, dd, J=5.7, 2.4 Hz), 6.97 (1H, s), 7.24 (2H, d, J=3.7 Hz), 7.38 (2H, d, J=8.4 Hz), 7.83 (2H, d, J=8.4 Hz), 7.88 (1H, d, J=2.6 Hz), 8.01-8.09 (2H, m), 8.79-9.00 (1H, m).

Production Example 32-10

5-((2-(4-(Azetidin-3-yl)benzamide)pyridin-4-yl)oxy)-6-(3-methoxypropoxy)-N-methyl-1H-indole-1-carboxamide

[Chemical Formula 153]

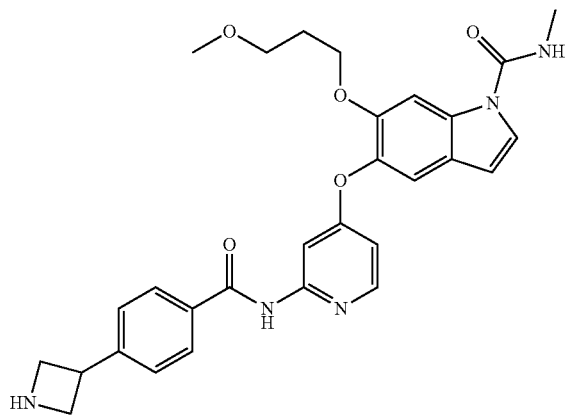

Trifluoroacetic acid (713 μL, 9.25 mmol) was added to a solution of tert-butyl 3-(4-((4-((6-(3-methoxypropoxy)-1-(methylcarbamoyl)-1H-indol-5-yl)oxy)pyridin-2-yl)carbamoyl)phenyl)azetidine-1-carboxylate described in Production Example 32-9 (146 mg, 0.231 mmol) in dichloromethane (5 mL) at room temperature. The reaction liquid was stirred for 1.5 hours, and then the resultant was concentrated under vacuum. The residue was dissolved in dichloromethane and triethylamine to neutralize the trifluoroacetic acid, and then the resultant was concentrated under vacuum. The residue was purified with NH silica gel column chromatography (ethyl acetate:methanol=49:1-17:3) to obtain the title compound (96.2 mg, 79%).

$^1$H-NMR Spectrum (CDCl$_3$) δ (ppm): 1.82-1.95 (2H, m), 3.06 (3H, d, J=4.8 Hz), 3.19 (3H, s), 3.24 (2H, t, J=6.4 Hz), 3.79-4.00 (5H, m), 4.11 (2H, t, J=6.0 Hz), 5.56-5.64 (1H, m), 6.55 (1H, d, J=3.7 Hz), 6.61 (1H, dd, J=5.9, 2.2 Hz), 7.21-7.29 (1H, m), 7.34 (1H, s), 7.41 (2H, d, J=8.4 Hz), 7.84 (2H, d, J=8.4 Hz), 7.92 (1H, d, J=2.2 Hz), 8.00 (1H, s), 8.10 (1H, d, J=5.9 Hz), 8.56-8.68 (1H, m).

Example 33

5-((2-(4-(1-Ethylpiperidin-4-yl)benzamide)pyridin-4-yl)oxy)-6-(3-fluoropropoxy)-N-methyl-1H-indole-1-carboxamide

[Chemical Formula 154]

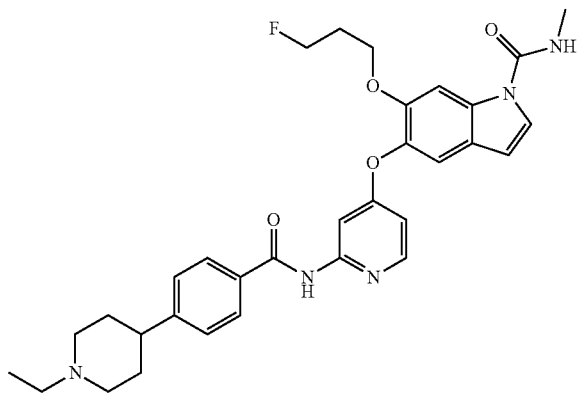

Benzotriazole (37.8 mg, 0.317 mmol) was dissolved in dichloromethane (2.0 mL), thionyl chloride (24 μL, 0.322 mmol) was added under nitrogen atmosphere at room temperature, and the mixture was stirred for 5 minutes. 4-(1-(tert-Butoxycarbonyl) piperidin-4-yl)benzoic acid described in Production Example 1-12 (82 mg, 0.269 mmol) was added to the reaction mixture at morn temperature, and the mixture was stirred for 20 minutes. The reaction mixture was filtered through a glass filter entirely covered with anhydrous sodium sulfate and then washed with dichloromethane, the filtrate was added to a mixture of 5-((2-aminopyridin-4-yl)oxy)-6-(3-fluoropropoxy)-N-methyl-1H-indole-1-carboxamide described in Production Example 33-6 (34.4 mg, 0.096 mmol), triethylamine (133 pt, 0.960 mmol), and 4-dimethylaminopyridine (1.17 mg, 0.0096 mmol) in tetrahydrofuran (1.5 mL) at 0° C., and the mixture was stirred at room temperature for 320 minutes. Water and ethyl acetate were added to the reaction mixture for partition, then the organic layer was washed with a saturated saline solution and dried over anhydrous sodium sulfate. The resultant was purified with NH silica gel column chromatography, then the filtrate was concentrated under vacuum. The residue was dissolved in tetrahydrofuran, an excessive quantity of 9.8 M methylamine methanol solution was added at room temperature, and the mixture was stirred for 50 minutes. The reaction mixture was concentrated under vacuum, the residue was dissolved in dichloromethane, and the resultant was purified with NH silica gel column chromatography (n-heptane:ethyl acetate=1:1-3:7-0:1). The target fraction was concentrated under vacuum to obtain a crude product A (46.3 mg).

The crude product A (46.3 mg) was dissolved in dichloromethane (1.25 mL), and trifluoroacetic acid (250 μL) was added at 0° C. The mixture was stirred at room temperature for 20 minutes and then concentrated under vacuum, then the residue was dissolved in dichloromethane-triethylamine, and the resultant was purified with NH silica gel column chromatography (ethyl acetate:methanol=97:3-4:1). The target fraction was concentrated under vacuum to obtain a crude product B (35.8 mg).

Sodium triacetoxyborohydride (10.4 mg, 0.049 mmol) and acetaldehyde (2.17 mg, 0.049 mmol) were added to a mixture of a part of crude product B (9.0 mg, 0.016 mmol) and tetrahydrofuran (500 μL) at room temperature, and the mixture was stirred at room temperature for 140 minutes. A saturated aqueous sodium bicarbonate solution and ethyl acetate were added to the reaction mixture for partition. The organic layer was washed with a saturated saline solution, and then dried over anhydrous sodium sulfate and filtered. The solvent was evaporated and the resultant residue was purified with NH silica gel TLC (ethyl acetate). The resultant solid was washed with diethyl ether to obtain the title compound (6.7 mg, 49%).

$^1$H-NMR Spectrum (CDCl$_3$) δ (ppm): 1.14 (3H, t, J=7.1 Hz), 1.76-1.91 (4H, m), 1.93-2.12 (4H, m), 2.41-2.64 (3H, m), 3.03-3.17 (5H, m), 4.16 (2H, t, J=6.0 Hz), 4.24 (1H, t, J=5.9 Hz), 4.36 (1H, t, J=5.7 Hz), 5.46-5.57 (1H, m), 6.55 (1H, d, J=3.3 Hz), 6.58 (1H, dd, J—5.9, 2.2 Hz), 7.24 (1H, d, J=3.7 Hz), 7.31-7.36 (3H, m), 7.80 (2H, d, J=8.1 Hz), 7.90 (1H, d, J=2.2 Hz), 8.02 (1H, s), 8.10 (1H, d, J=5.9 Hz), 8.49 (1H, brs).

The starting material 5-((2-aminopyridin-4-yl)oxy)-6-(3-fluoropropoxy)-N-methyl-1H-indole-1-carboxamide was synthesized by the following method.

Production Example 33-1

4-(3-Fluoropropoxy)-3-hydroxybenzaldehyde

[Chemical Formula 155]

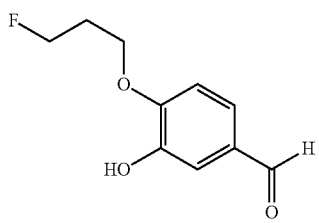

Commercially available 3,4-dihydroxybenzaldehyde (6.5 g, 47.1 mmol) and potassium carbonate (6.83 g, 49.4 mmol) were suspended in N,N-dimethylformamide (30 mL), then 3-fluoropropyl 4-methylbenzenesulfonate described in Production Example 5-1 (11.3 g, 48.4 mmol) was added under nitrogen atmosphere at loom temperature, and the mixture was stirred for 37 hours. The mixture was cooled to 0° C. and then 2 M hydrochloric acid, ethyl acetate, and water were added for partition. The organic layer was washed with water and a saturated saline solution, dried over anhydrous magnesium sulfate, and then filtered. The solvent was evaporated and the resultant residue was purified with silica gel column chromatography (n-heptane:ethyl acetate=4:1-2:1-1:1). The target fraction was concentrated under vacuum to obtain the title compound (4.62 g, 50%).

$^1$H-NMR Spectrum (CDCl$_3$) δ (ppm): 2.23 (1H, quin, J=5.9 Hz), 2.30 (1H, quin, J=5.8 Hz), 4.31 (2H, t, J=6.2 Hz), 4.60 (1H, t, J=5.6 Hz), 4.72 (1H, t, J=5.6 Hz), 5.70 (1H, s), 6.99 (1H, d, J=8.2 Hz), 7.41-7.47 (2H, m), 9.85 (1H, s).

Production Example 33-2

3-(Benzyloxy)-4-(3-fluoropropoxy)benzaldehyde

[Chemical Formula 156]

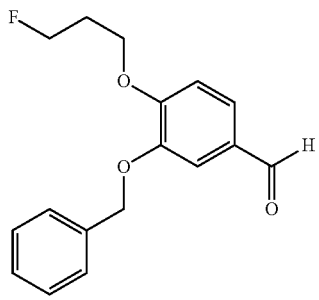

Potassium carbonate (3.87 g, 28.0 mmol) and benzyl chloride (3.2 mL, 27.8 mmol) were added to a suspension of 4-(3-fluoropropoxy)-3-hydroxybenzaldehyde described in Production Example 33-1 (4.62 g, 23.3 mmol) in ethanol (46 mL) under nitrogen atmosphere at mom temperature, and the mixture was stirred at 90° C. for 1.5 hours. The reaction mixture was cooled to 0° C., then 2 M hydrochloric acid, ethyl acetate, and water were added for partition. The organic layer was washed with a saturated saline solution, dried over anhydrous magnesium sulfate, and then filtered. The solvent was evaporated and the resultant residue was purified with silica gel column chromatography (n-heptane:ethyl acetate=9:1-3:2-1:1). The target fraction was concentrated under vacuum to obtain the title compound (6.14 g, 91%).

$^1$H-NMR Spectrum (CDCl$_3$) δ (ppm): 222 (1H, quin, J=5.9 Hz), 2.29 (1H, quin, J=5.9 Hz), 4.25 (2H, t, J=6.2 Hz), 4.62 (1H, t, J=5.7 Hz), 4.74 (1H, t, J=5.7 Hz), 5.18 (2H, s), 7.02 (1H, d, J=8.1 Hz), 7.29-7.50 (7H, m), 9.83 (1H, s).

Production Example 33-3

(E)-2-(Benzyloxy)-1-(3-fluoropropoxy)-4-(2-nitrovinyl)benzene

[Chemical Formula 157]

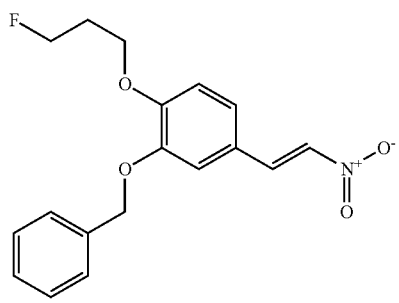

3-(Benzyloxy)-4-(3-fluoropropoxy)benzaldehyde described in Production Example 33-2 (6.14 g, 21.3 mmol) was dissolved in acetic acid (17.0 mL), then ammonium acetate (1.97 g, 25.6 mmol) and nitromethane (2.8 mL, 51.7 mmol) were added under nitrogen atmosphere at room temperature, and the mixture was heated and stirred at 130° C. for 2 hours. The mixture was cooled to mom temperature, then the precipitate was collected by filteration and washed with a small quantity of ethanol to quantitatively obtain the title compound.

$^1$H-NMR Spectrum (CDCl$_3$) δ (ppm): 2.21 (1H, quin, J=6.0 Hz), 2.28 (1H, quin, J=5.9 Hz), 4.22 (2H, J=6.0 Hz), 4.62 (1H, t, J=5.7 Hz), 4.73 (1H, t, J=5.7 Hz), 5.15 (2H, s), 6.95 (1H, d, J=8.4 Hz), 7.06 (1H, d, J=1.8 Hz), 7.17 (1H, dd, J=8.2, 2.0 Hz), 7.29-7.49 (6H, m), 7.91 (1H, d, J=13.5 Hz).

Production Example 33-4

6-(3-Fluoropropoxy)-1H-indol-5-ol

[Chemical Formula 158]

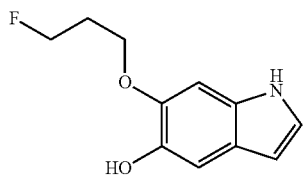

Fuming nitric acid (4.80 mL, 107 mmol) was added to a mixture of (E)-2-(benzyloxy)-1-(3-fluoropropoxy)-4-(2-nitrovinyl)benzene described in Production Example 33-3 (7.06 g, 21.3 mmol) and acetic acid (61 mL) in an ice bath, and the mixture was stirred at mom temperature for 2.5 hours. The reaction mixture was poured onto ice, the precipitate was collected by filteration, and then the resultant was washed with a liquid mixture of a small quantity of acetic acid and ethanol to obtain a crude product (8.02 g).

The crude product (8.02 g) was suspended in methanol (150 mL), then 10% palladium-carbon (water content, 50%) (2.27 g) was added, and the mixture was stirred under hydrogen atmosphere for 6 hours. The inside of the reaction system was substituted with nitrogen, then the mixture was diluted with methanol. The catalyst was filtered off with celite, then the filtrate was concentrated under vacuum, and the resultant was purified with silica gel column chromatography (n-heptane:ethyl acetate=9:1-1:1). The target fraction was concentrated under vacuum to obtain the title compound (1.47 g, 33%).

$^1$H-NMR Spectrum (CDCl$_3$) δ (ppm): 2.22 (1H, quin, J=5.9 Hz), 2.29 (1H, quin, J=5.9 Hz), 4.23 (2H, t, J=6.0 Hz), 4.62 (1H, t, J=5.7 Hz), 4.74 (1H, t, J=5.7 Hz), 5.42 (1H, s), 6.42 (1H, ddd, J=3.1, 2.2, 0.9 Hz), 6.91 (1H, s), 7.09 (1H, dd, J=3.1, 2.4 Hz), 7.15 (1H, s), 7.94 (1H, brs).

Production Example 33-5

4-((6-(3-Fluoropropoxy)-1H-indol-5-yl)oxy)pyridin-2-amine

[Chemical Formula 159]

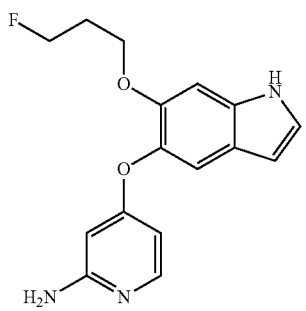

6-(3-Fluoropropoxy)-1H-indol-5-ol described in Production Example 33-4 (1.47 g, 7.04 mmol), N-(4-chloropyridin-2-yl)acetamide described in Production Example 1-5 (1.32 g, 7.74 mmol), and potassium tert-butoxide (864 mg, 7.70 mmol) were dissolved in dimethylsulfoxide (7.0 mL), and the mixture was heated and stirred under nitrogen atmosphere at 160° C. for 4.5 hours. The reaction liquid was cooled to room temperature, and then water and ethyl acetate were added for partition. The aqueous layer was extracted with ethyl acetate again, then the combined organic layer was washed with water and a saturated saline solution and then dried over anhydrous magnesium sulfate. The drying agent was filtered off, the filtrate was concentrated under vacuum, and the resultant was purified with NH silica gel column chromatography (n-heptane:ethyl acetate=4:1-1:1-0:1-ethyl acetate:methanol=99:1-9:1). The target fraction was concentrated under vacuum to obtain a crude product (177 mg).

The resultant crude product (177 mg) was dissolved in methanol (2.5 mL), a 2 M sodium hydroxide solution (2.5 mL) was added under nitrogen atmosphere at room temperature, and the mixture was heated and stirred at 70° C. for 2 hours. The reaction mixture was cooled to room temperature and then water and ethyl acetate were added for partition. The organic layer was washed with a saturated saline solution and dried over anhydrous sodium sulfate. The drying agent was filtered off, then the filtrate was concentrated under vacuum, and the resultant was purified with silica gel column chromatography (n-heptane:ethyl acetate=2:3-1:4-0:1-ethyl acetate:methanol=19:1). The target fraction was concentrated under vacuum to obtain the title compound (49.4 mg, 23%).

$^1$H-NMR Spectrum (CDCl$_3$) δ (ppm): 1.95-2.11 (2H, m), 4.07 (2H, t, J=5.9 Hz), 4.28-4.47 (4H, m), 5.88 (1H, d, J=22 Hz), 6.28 (1H, dd, J=5.9, 2.2 Hz), 6.48-6.52 (1H, m), 7.02 (1H, s), 7.16-7.20 (1H, m), 7.35 (1H, s), 7.88 (1H, d, J=5.9 Hz), 8.25 (1H, brs).

Production Example 33-6

5-((2-Aminopyridin-4-yl)oxy)-6-(3-fluoropropoxy)-N-methyl-1H-indole-1-carboxamide

[Chemical Formula 160]

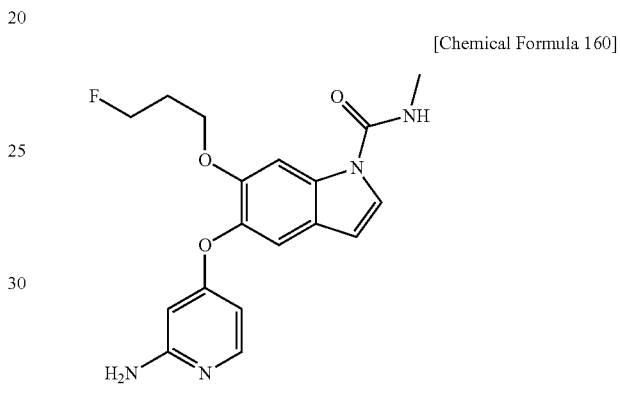

4-((6-(3-Fluoropropoxy)-1H-indol-5-yl)oxy)pyridin-2-amine described in Production Example 33-5 (49.4 mg, 0.164 mmol) was dissolved in N,N-dimethylformamide (1.6 mL), 50-72% oily sodium hydride (14.9 mg) was added under nitrogen atmosphere at 0° C., and the mixture was stirred at room temperature for 15 minutes. The mixture was cooled to 0° C. again, phenyl methylcarbamate described in Production Example 1-7 (62.0 mg, 0.41 mmol) was added, and the mixture was stirred at room temperature for 3.5 hours. A saturated aqueous ammonium chloride solution, water, and ethyl acetate were added to the reaction mixture for partition. The organic layer was washed with a saturated saline solution and then dried over anhydrous sodium sulfate. The drying agent was filtered off, the filtrate was concentrated under vacuum, and the resultant was purified with NH silica gel column chromatography (n-heptane:ethyl acetate=1:4-0:1-ethyl acetate:methanol=99:1-9:1). The target fraction was concentrated under vacuum to obtain the title compound (34.4 mg, 59%).

$^1$H-NMR Spectrum (CDCl$_3$) δ (ppm): 1.95-2.11 (2H, m), 3.07 (3H, dd, J=4.7, 1.2), 4.12-4.17 (2H, m), 4.29 (1H, t, J=5.8 Hz), 4.38-4.52 (3H, m), 5.50 (1H, brs), 5.87 (1H, d, 2.0 Hz), 6.26 (1H, dd, J=6.0, 2.1 Hz), 6.56 (1H, d, J=3.7 Hz), 7.23-7.27 (1H, m), 7.29 (1H, s), 7.87 (1H, d, J=6.0 Hz), 8.00 (1H, s).

According to Examples 1 to 33, the example compounds illustrated in Tables 1 and 2 were synthesized from 5-((2-aminopyridin-4-yl)oxy)-6-methoxy-N-methyl-1H-indole-1-carboxamide described in Production Example 1-6.

TABLE 1
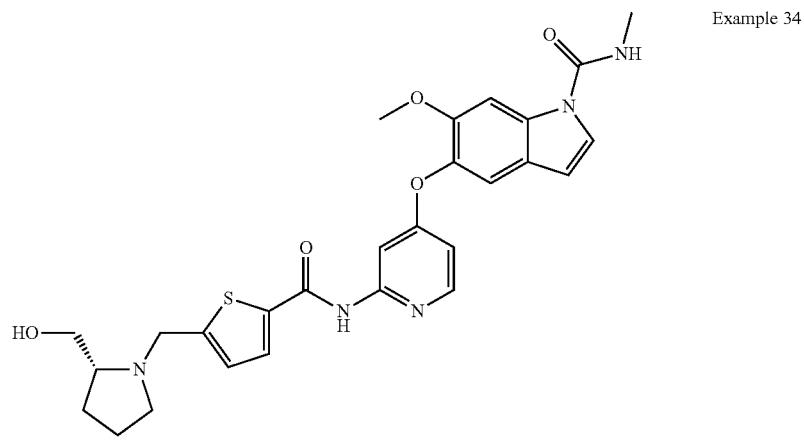
Example 34
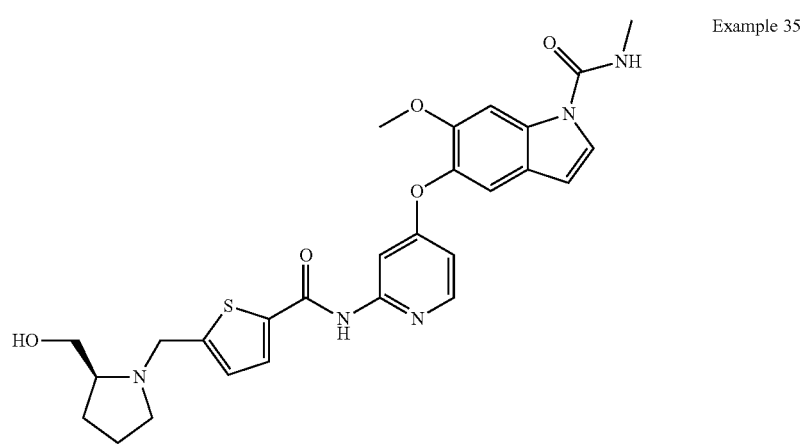
Example 35
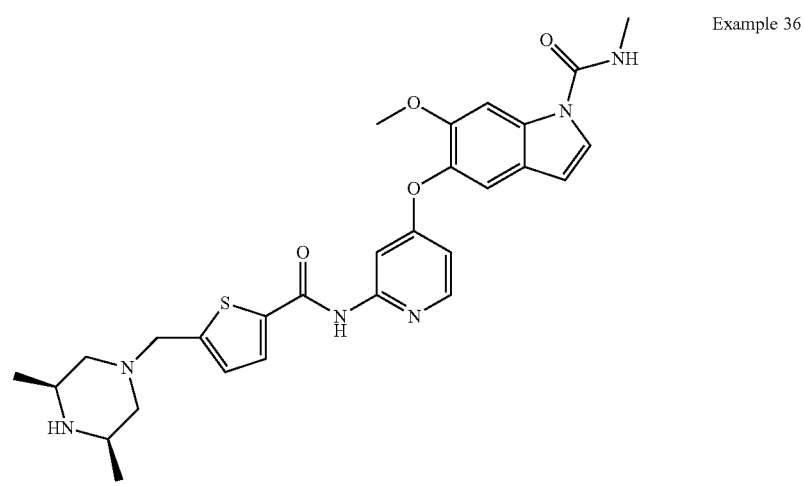
Example 36

TABLE 1-continued
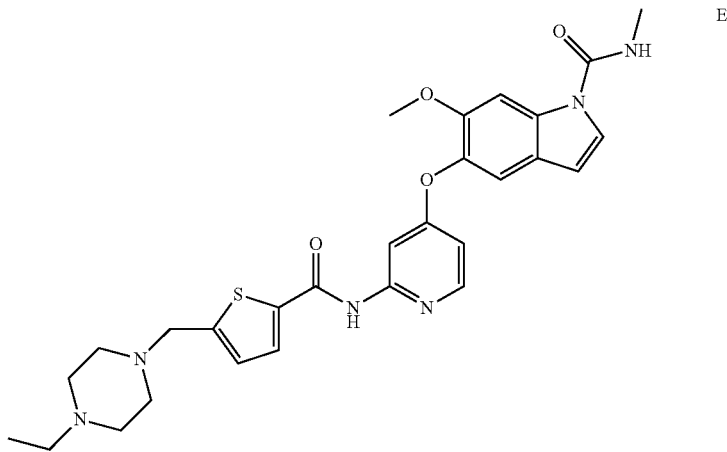
Example 37
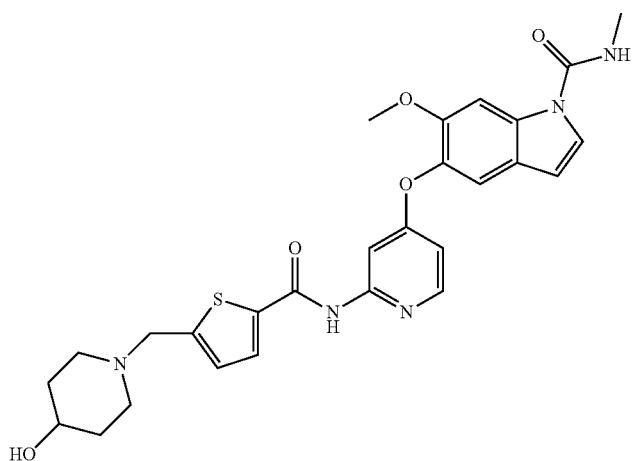 [SMILES: CNC(=O)n1ccc2cc(Oc3ccnc(NC(=O)c4ccc(CN5CCC(O)CC5)s4)c3)c(OC)cc21]
Example 38
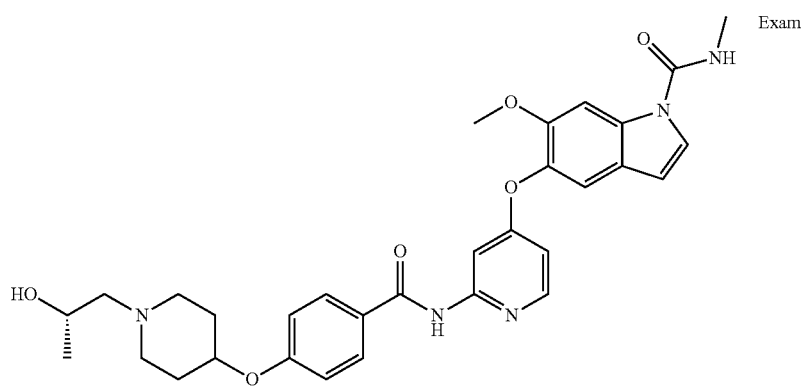
Example 42

TABLE 1-continued
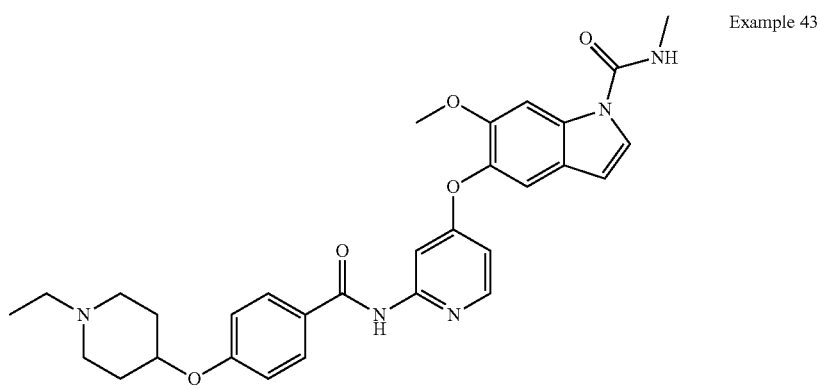
Example 43
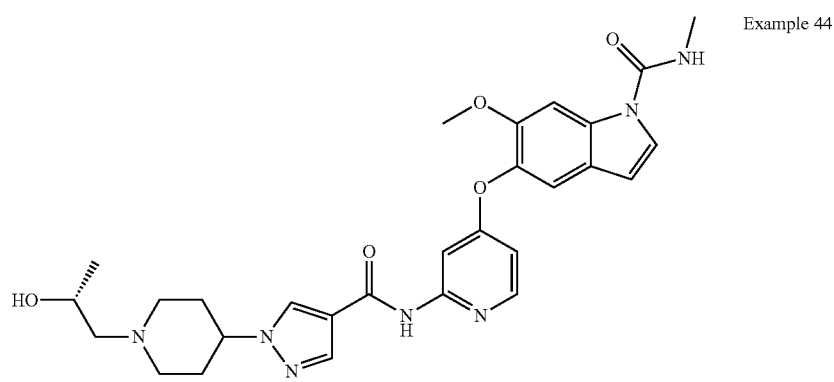
Example 44
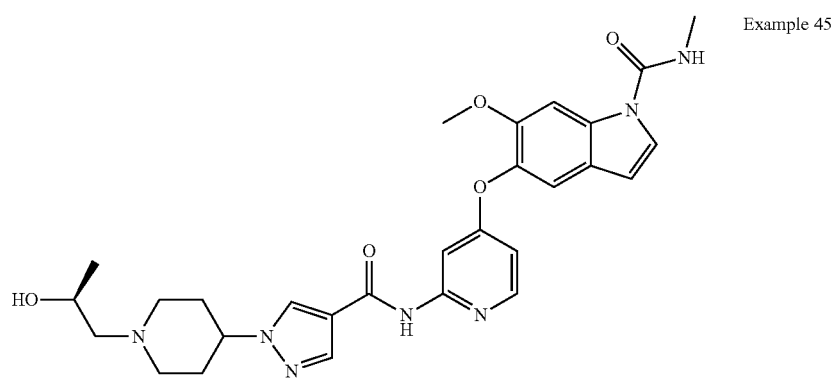
Example 45
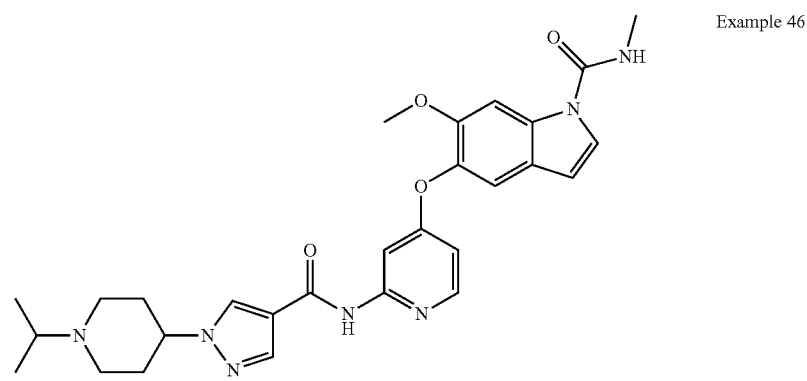
Example 46

TABLE 1-continued
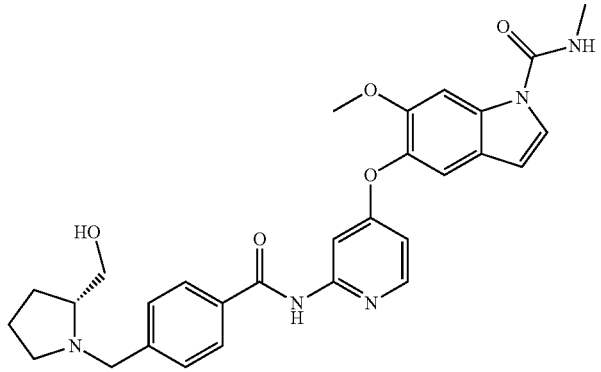 [SMILES: CNC(=O)n1ccc2cc(Oc3ccnc(NC(=O)c4ccc(CN5CCC[C@@H]5CO)cc4)c3)c(OC)cc21]
Example 50
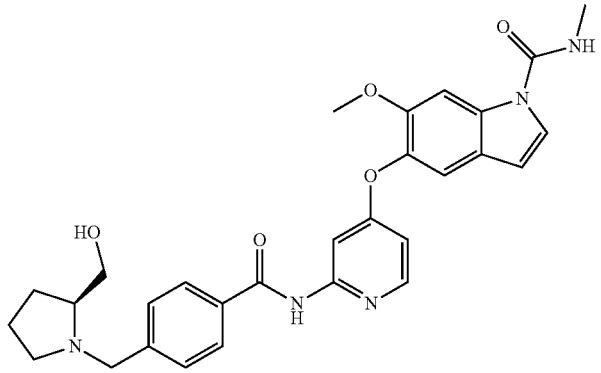 [SMILES: CNC(=O)n1ccc2cc(Oc3ccnc(NC(=O)c4ccc(CN5CCC[C@H]5CO)cc4)c3)c(OC)cc21]
Example 51
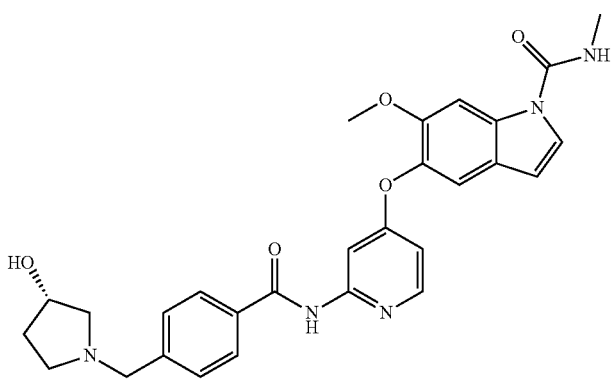 [SMILES: CNC(=O)n1ccc2cc(Oc3ccnc(NC(=O)c4ccc(CN5CC[C@H](O)C5)cc4)c3)c(OC)cc21]
Example 52
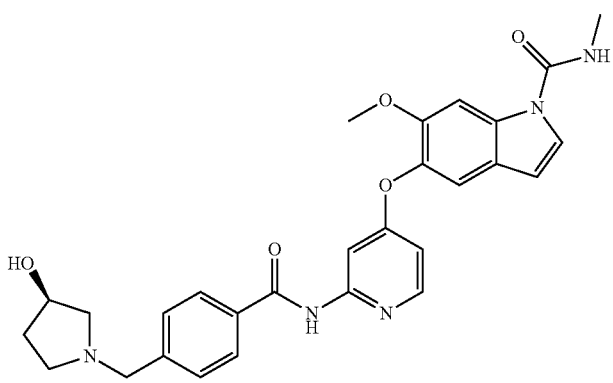 [SMILES: CNC(=O)n1ccc2cc(Oc3ccnc(NC(=O)c4ccc(CN5CC[C@@H](O)C5)cc4)c3)c(OC)cc21]
Example 53

TABLE 1-continued
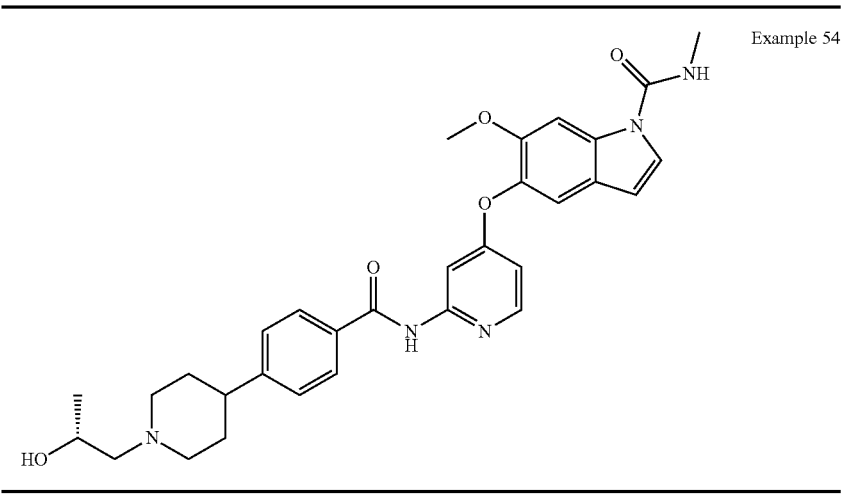
Example 54
TABLE 2
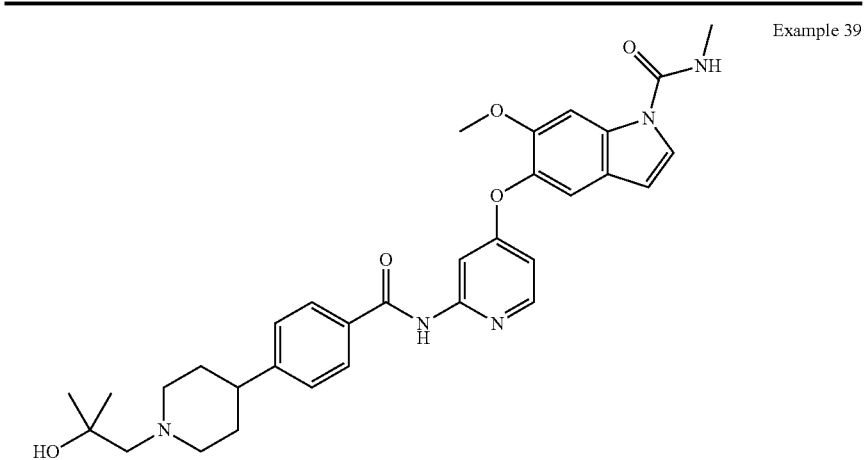
Example 39
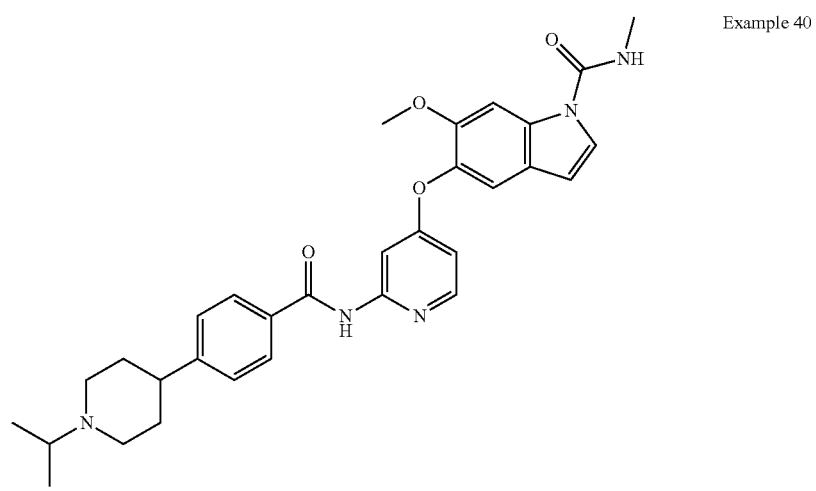
Example 40

TABLE 2-continued
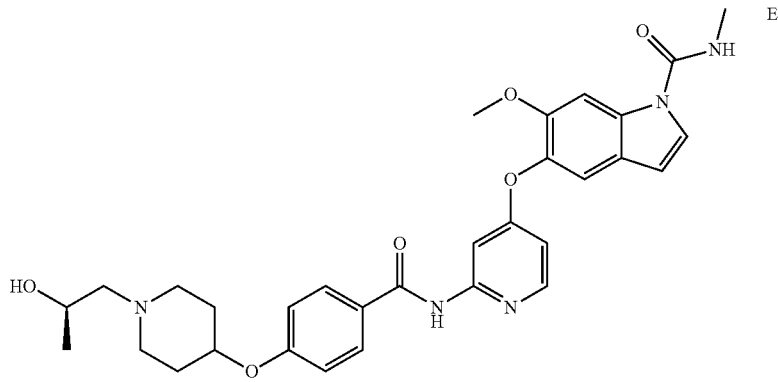
Example 41
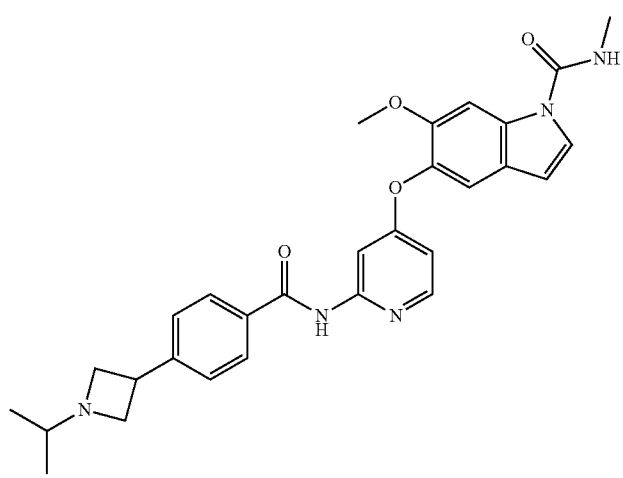 [SMILES: CNC(=O)n1ccc2cc(Oc3ccnc(NC(=O)c4ccc(C5CN(C(C)C)C5)cc4)c3)c(OC)cc21]
Example 47
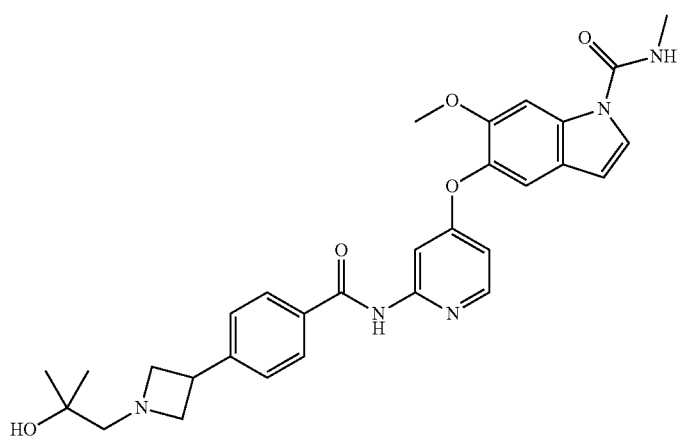 [SMILES: CNC(=O)n1ccc2cc(Oc3ccnc(NC(=O)c4ccc(C5CN(CC(C)(C)O)C5)cc4)c3)c(OC)cc21]
Example 48

TABLE 2-continued
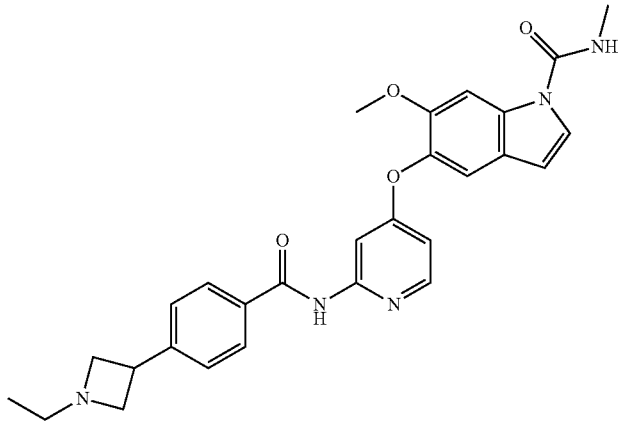 [SMILES: CCN1CC(c2ccc(C(=O)Nc3cc(Oc4cc5ccn(C(=O)NC)c5cc4OC)ccn3)cc2)C1]
Example 49
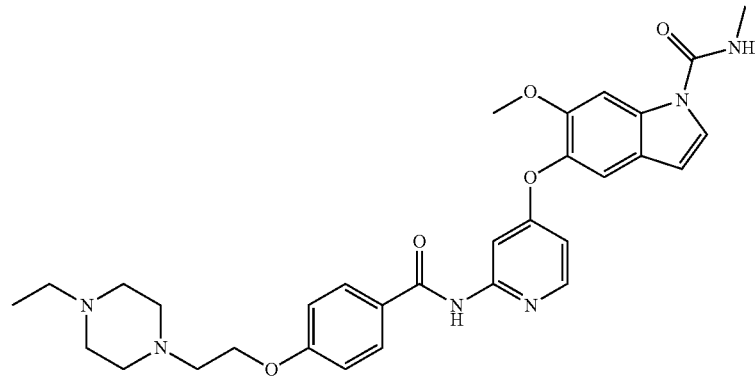 [SMILES: CCN1CCN(CCOc2ccc(C(=O)Nc3cc(Oc4cc5ccn(C(=O)NC)c5cc4OC)ccn3)cc2)CC1]
Example 55
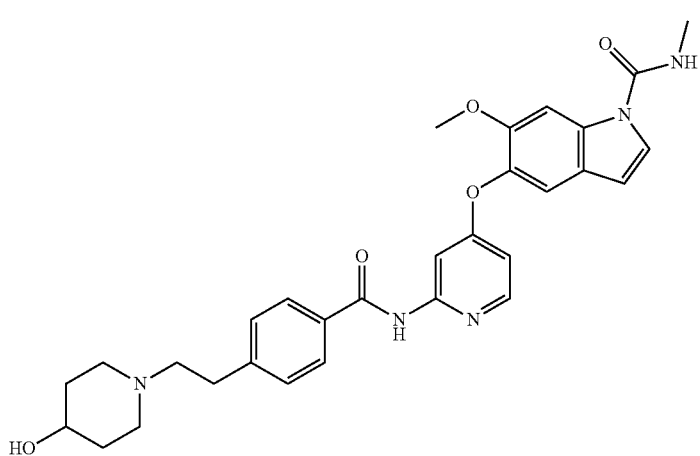 [SMILES: CNC(=O)n1ccc2cc(Oc3ccnc(NC(=O)c4ccc(CCN5CCC(O)CC5)cc4)c3)c(OC)cc21]
Example 56

TABLE 2-continued
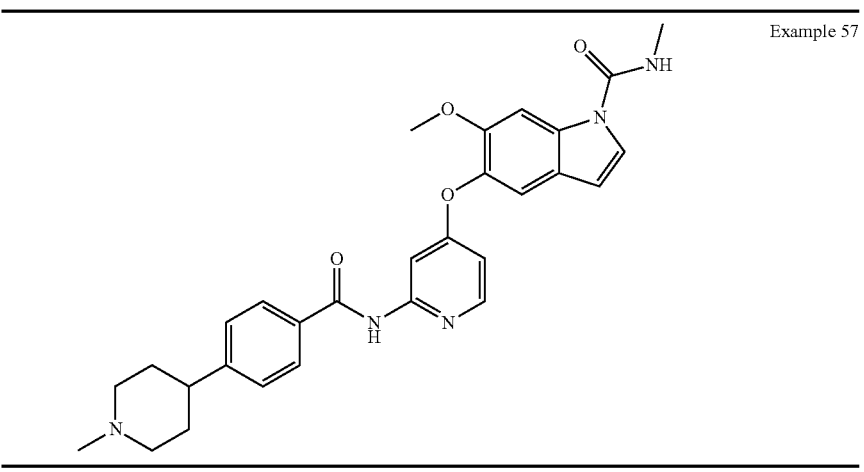
Example 57
According to Examples 1 to 33, the example compounds illustrated in Table 3 were synthesized from 5-((2-aminopyridin-4-yl)oxy)-6-ethoxy-N-methyl-1H-indole-1-carboxamide described in Production Example 15-7.
TABLE 3
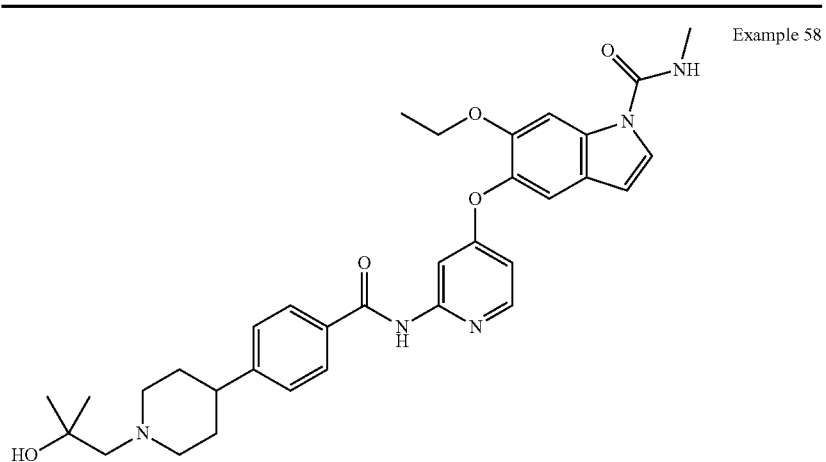
Example 58
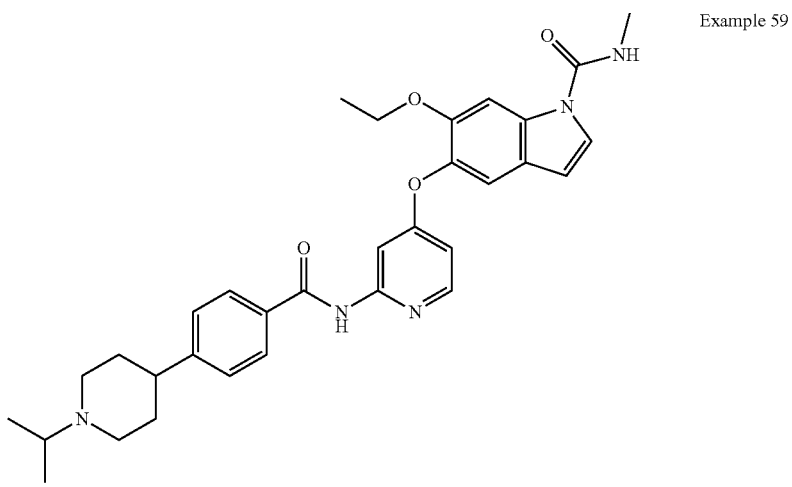
Example 59

TABLE 3-continued
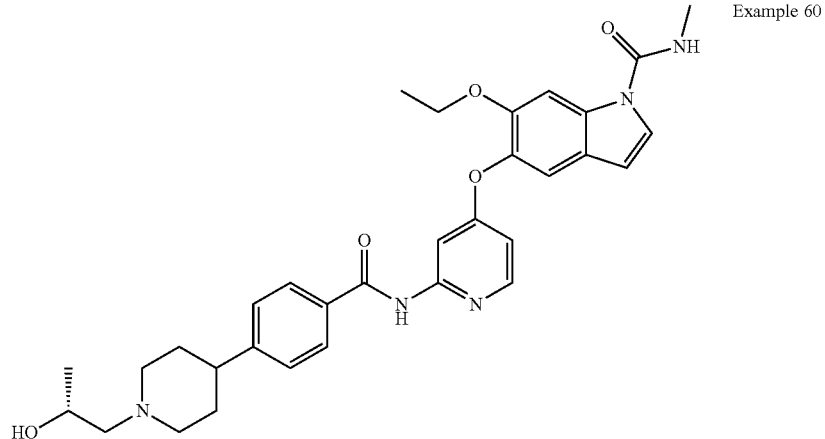
Example 60
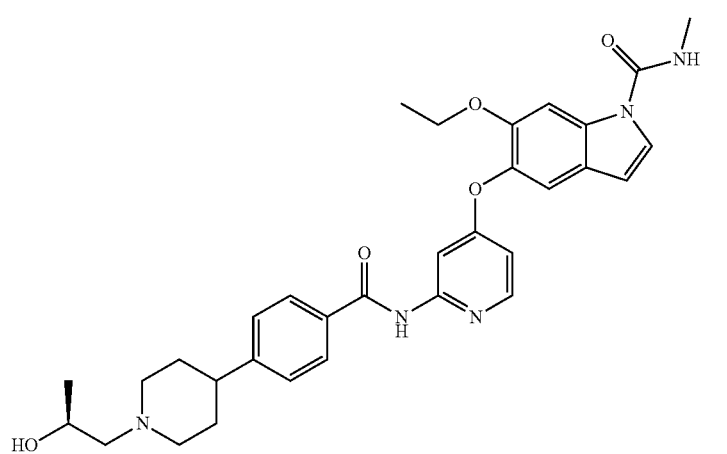 [SMILES: CCOc1cc2c(ccn2C(=O)NC)cc1Oc1ccnc(NC(=O)c2ccc(C3CCN(C[C@H](C)O)CC3)cc2)c1]
Example 61
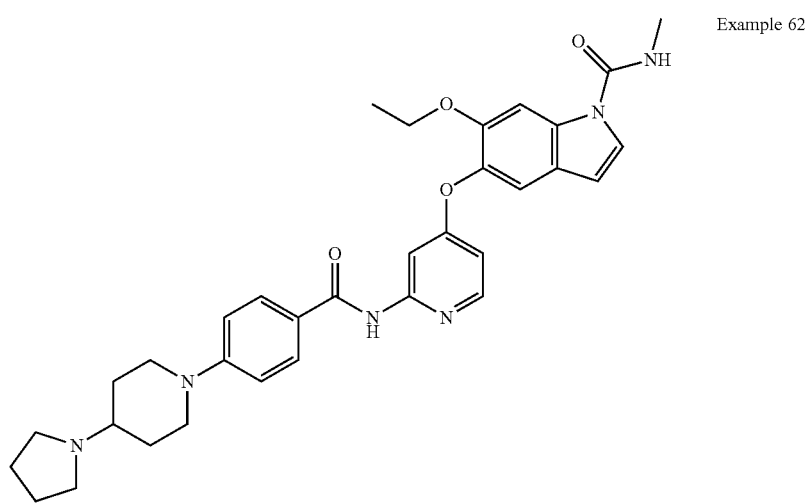
Example 62

TABLE 3-continued
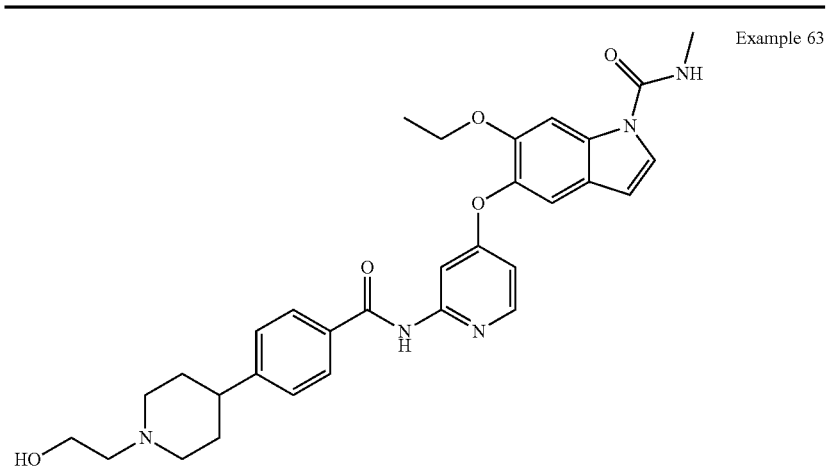
Example 63
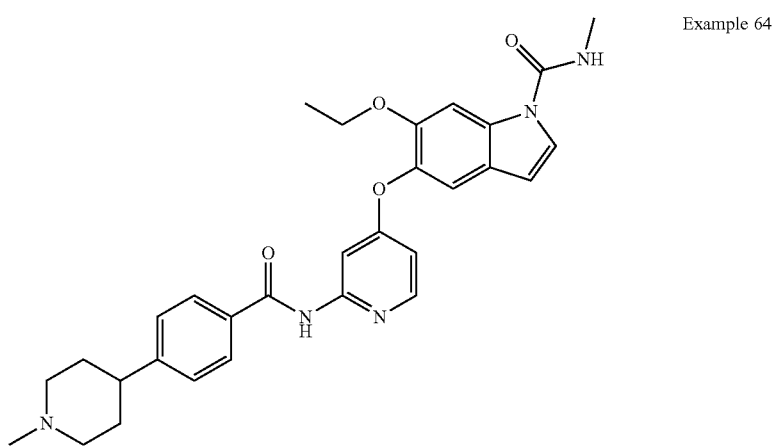
Example 64
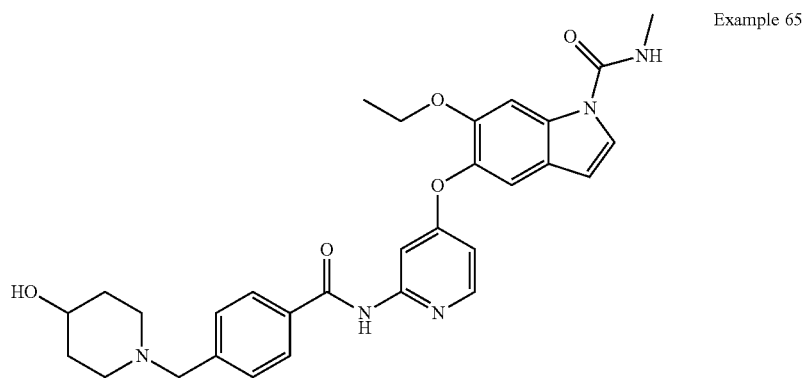
Example 65

According to Examples 1 to 33, the example compounds illustrated in Table 4 were synthesized from 5-((2-aminopyridin-4-yl)oxy)-6-isopropoxy-N-methyl-1H-indole-1-carboxamide described in Production Example 17-7.
TABLE 4
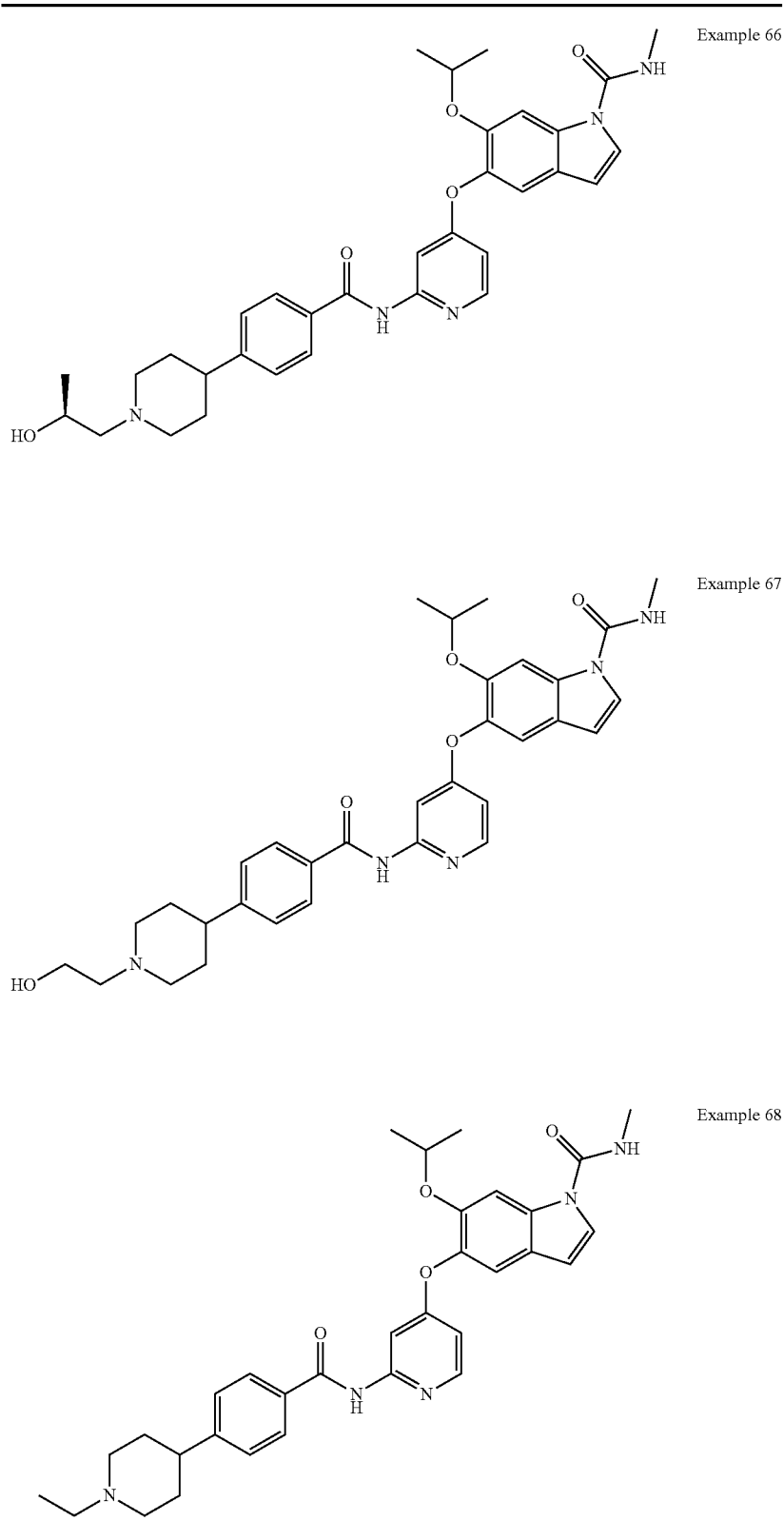

TABLE 4-continued
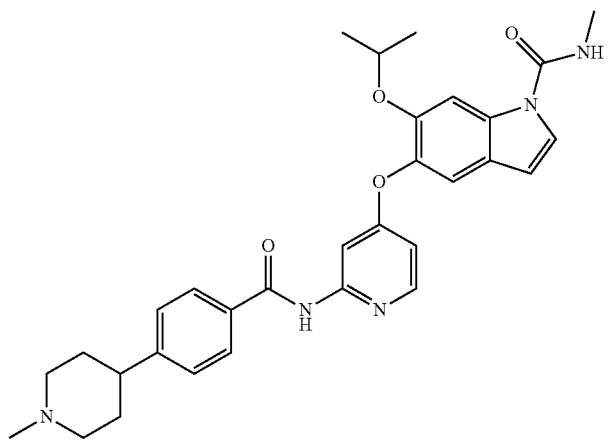
Example 69
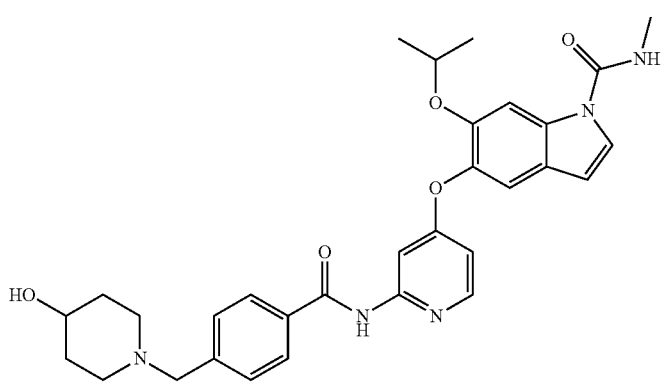 [SMILES: CNC(=O)n1ccc2cc(Oc3ccnc(NC(=O)c4ccc(CN5CCC(O)CC5)cc4)c3)c(OC(C)C)cc21]
Example 70
According to Examples 1 to 33, the example compounds illustrated in Table 5 were synthesized from 5-((2-aminopyridin-4-yl)oxy)-6-(3-fluoropropoxy)-N-methyl-1H-indole-1-carboxamide described in Production Example 33-6.
TABLE 5
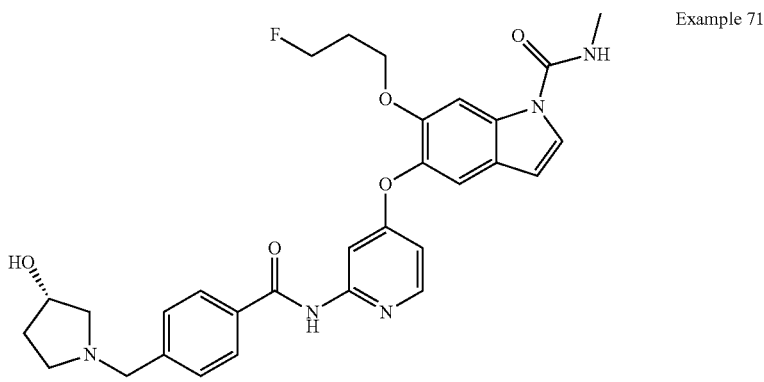
Example 71

TABLE 5-continued
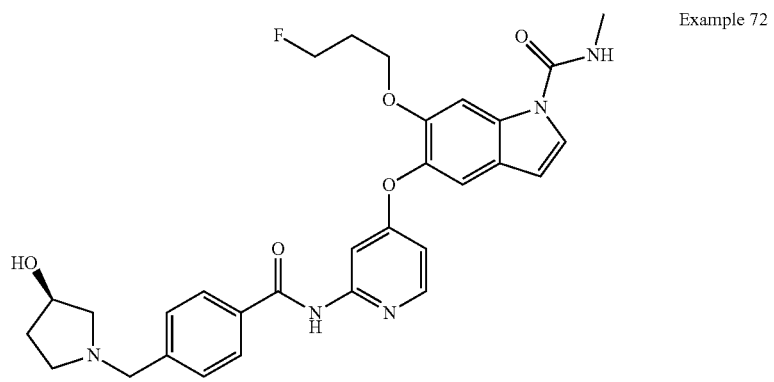
Example 72
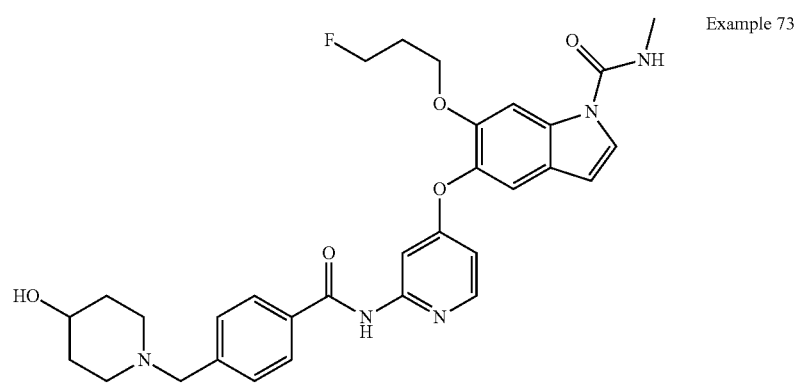
Example 73
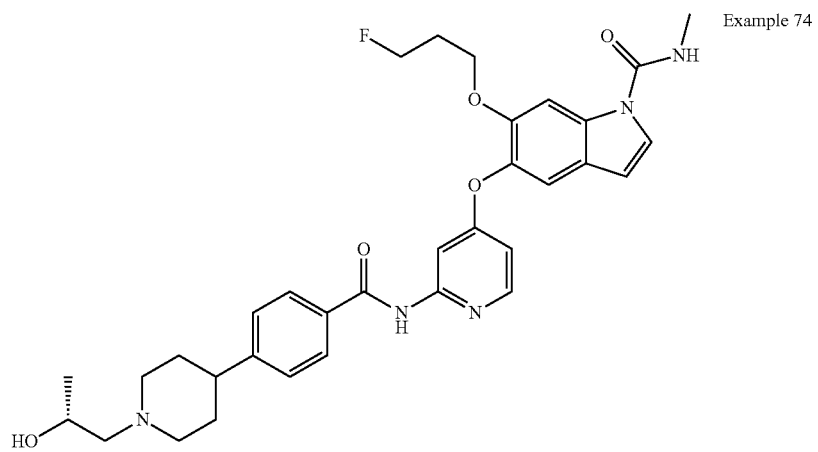
Example 74
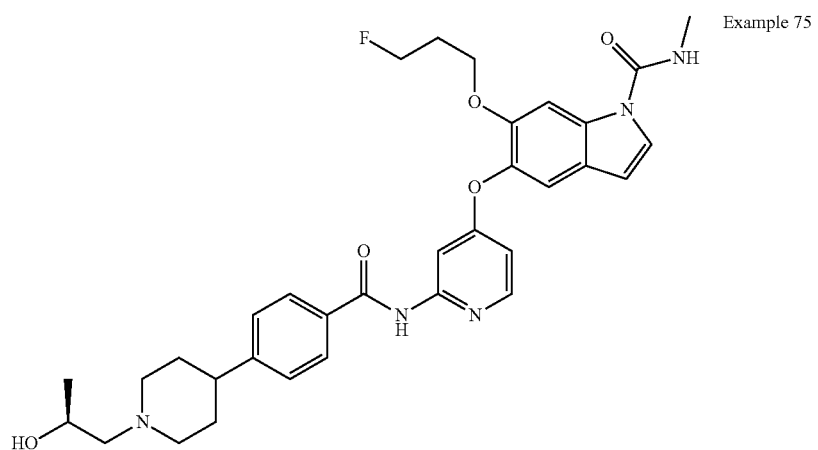
Example 75

TABLE 5-continued
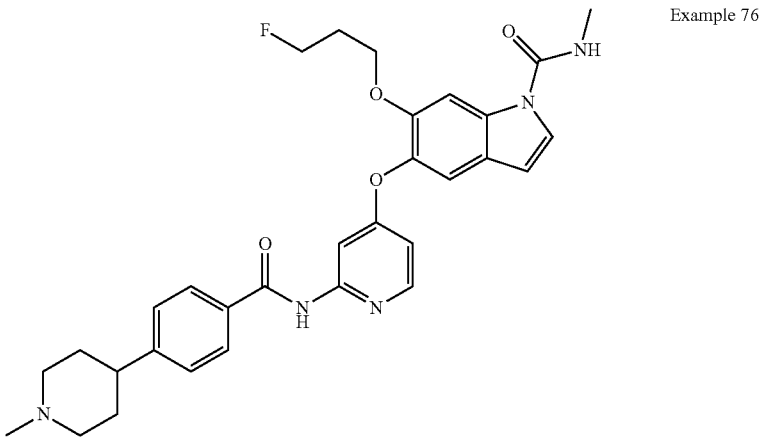
Example 76
According to Examples 1 to 33, the example compounds illustrated in Table 6 were synthesized from 5-((2-aminopyridin-4-yl)oxy)-6-(2-methoxyethoxy)-N-methyl-1H-indole-1-carboxamide described in Production Example 20-7.
TABLE 6
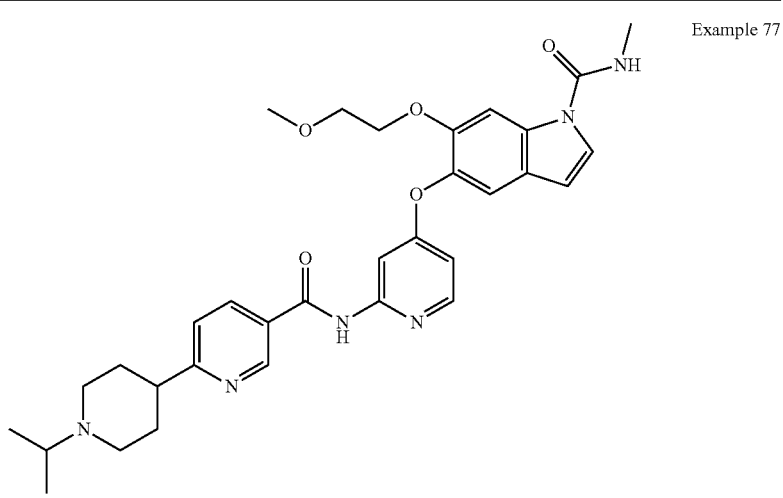
Example 77
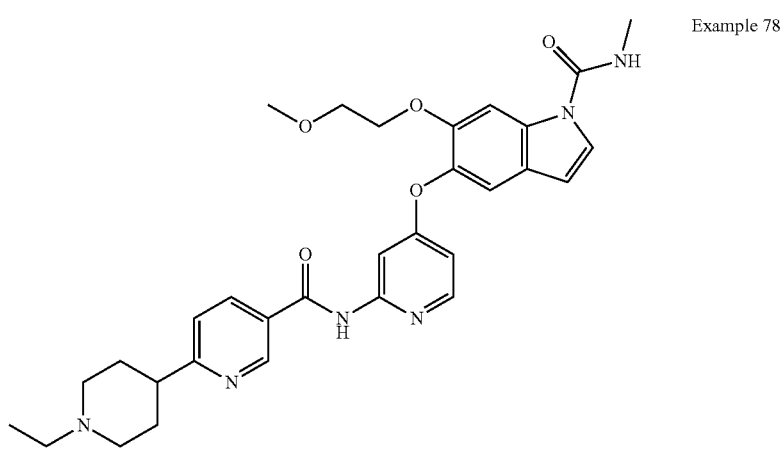
Example 78

TABLE 6-continued
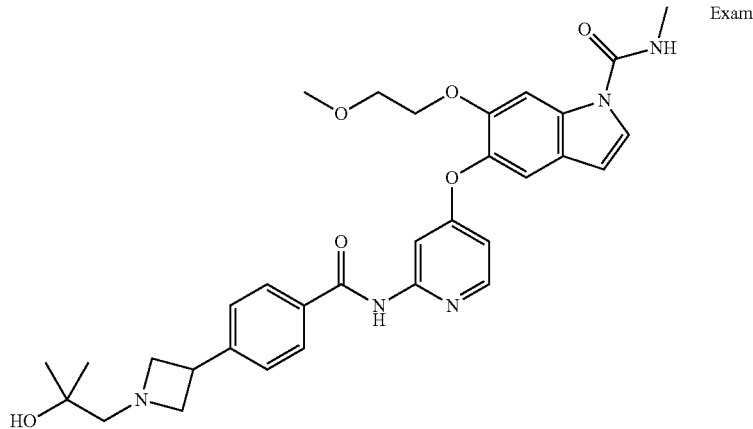
Example 79
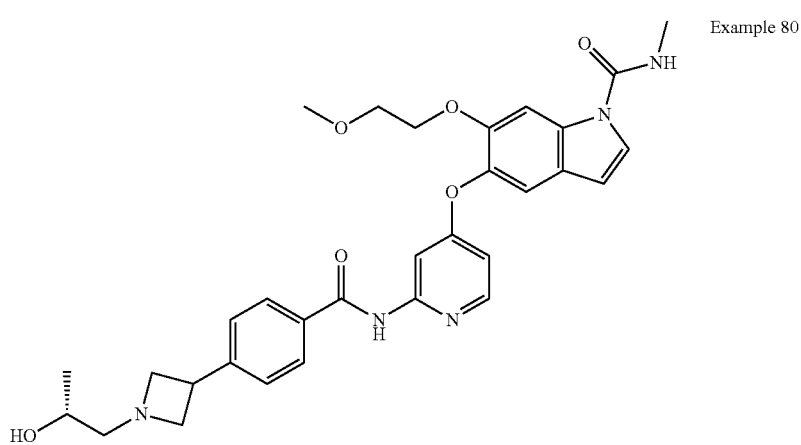
Example 80
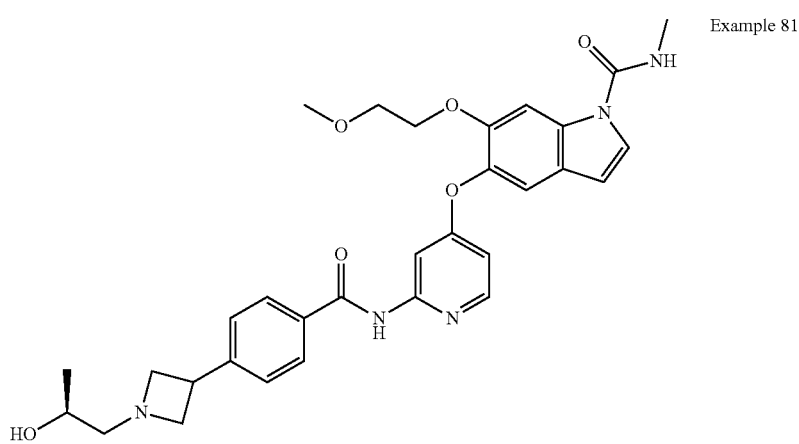
Example 81

TABLE 6-continued
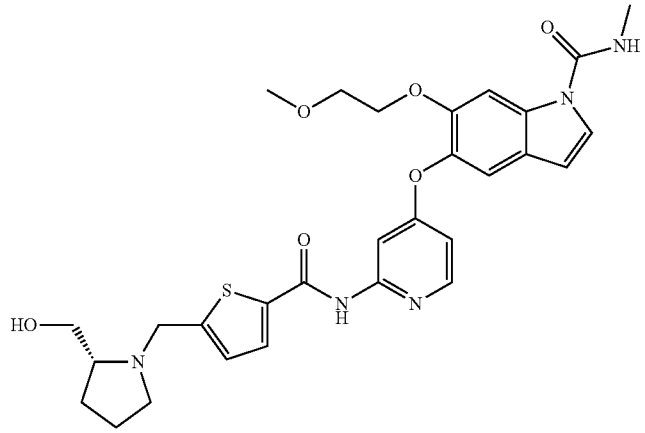 [SMILES: CNC(=O)n1ccc2cc(Oc3ccnc(NC(=O)c4ccc(CN5CCC[C@@H]5CO)s4)c3)c(OCCOC)cc21]
Example 82
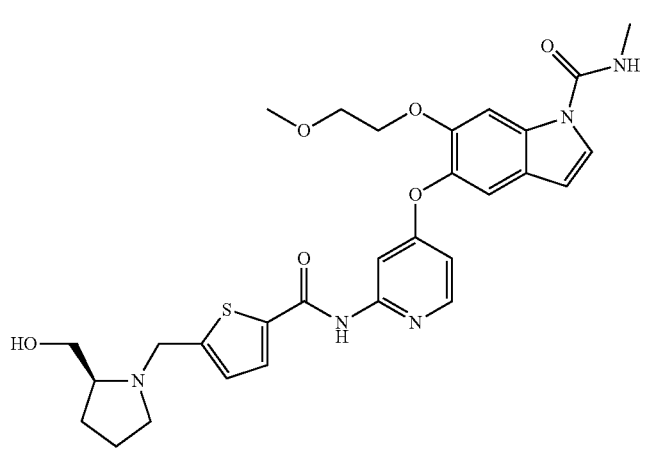 [SMILES: CNC(=O)n1ccc2cc(Oc3ccnc(NC(=O)c4ccc(CN5CCC[C@H]5CO)s4)c3)c(OCCOC)cc21]
Example 83
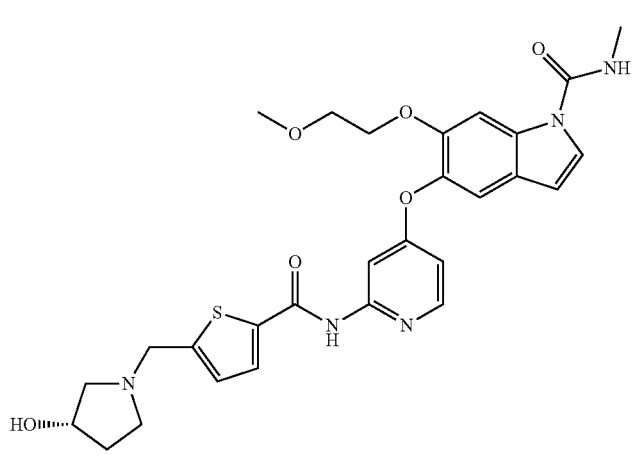 [SMILES: CNC(=O)n1ccc2cc(Oc3ccnc(NC(=O)c4ccc(CN5CC[C@H](O)C5)s4)c3)c(OCCOC)cc21]
Example 84

TABLE 6-continued
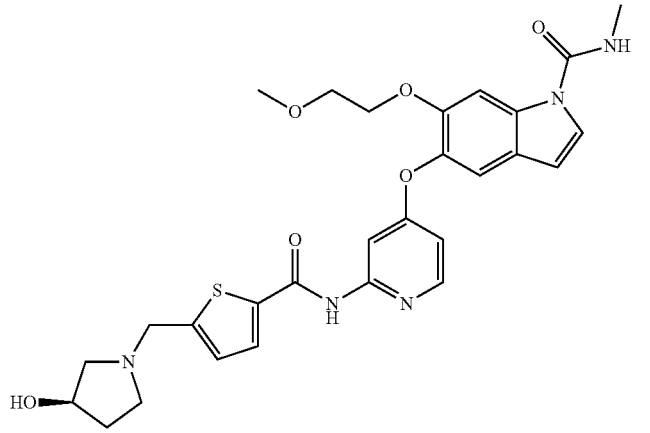 [SMILES: CNC(=O)n1ccc2cc(Oc3ccnc(NC(=O)c4ccc(CN5CC[C@@H](O)C5)s4)c3)c(OCCOC)cc21]
Example 85
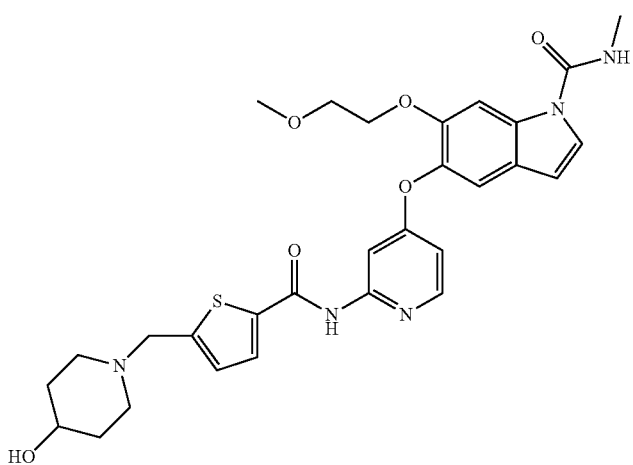 [SMILES: CNC(=O)n1ccc2cc(Oc3ccnc(NC(=O)c4ccc(CN5CCC(O)CC5)s4)c3)c(OCCOC)cc21]
Example 86
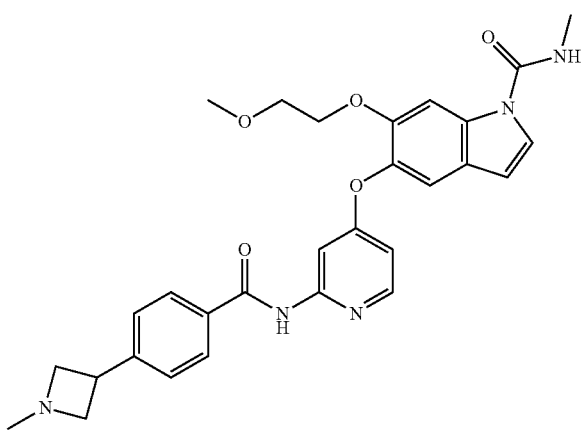
Example 87

TABLE 6-continued
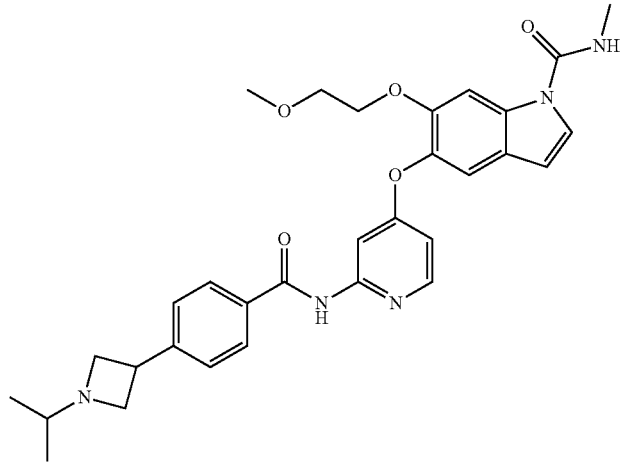 [SMILES: CNC(=O)n1ccc2cc(Oc3ccnc(NC(=O)c4ccc(C5CN(C(C)C)C5)cc4)c3)c(OCCOC)cc21]
Example 88
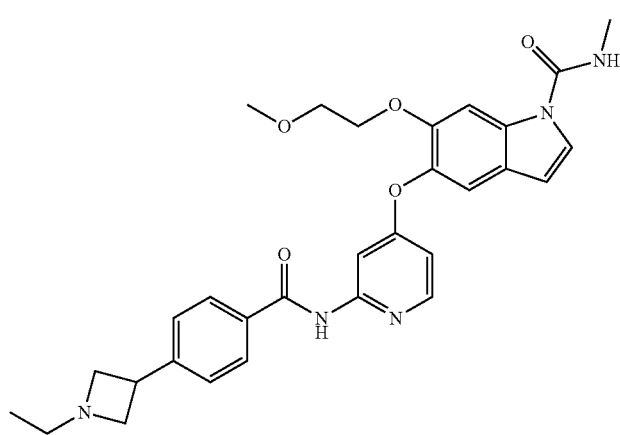 [SMILES: CCN1CC(c2ccc(C(=O)Nc3cc(Oc4cc5ccn(C(=O)NC)c5cc4OCCOC)ccn3)cc2)C1]
Example 89
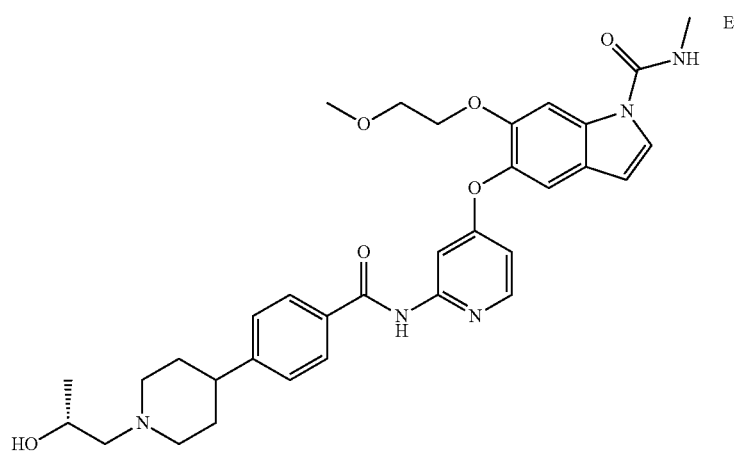
Example 90

TABLE 6-continued
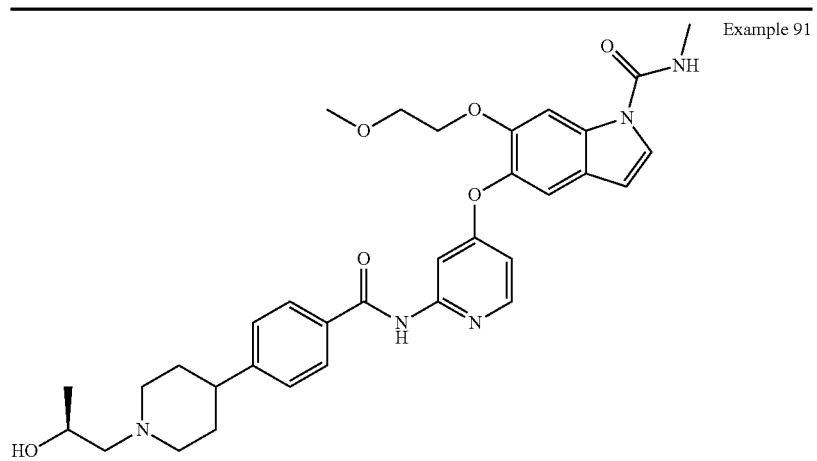
Example 91
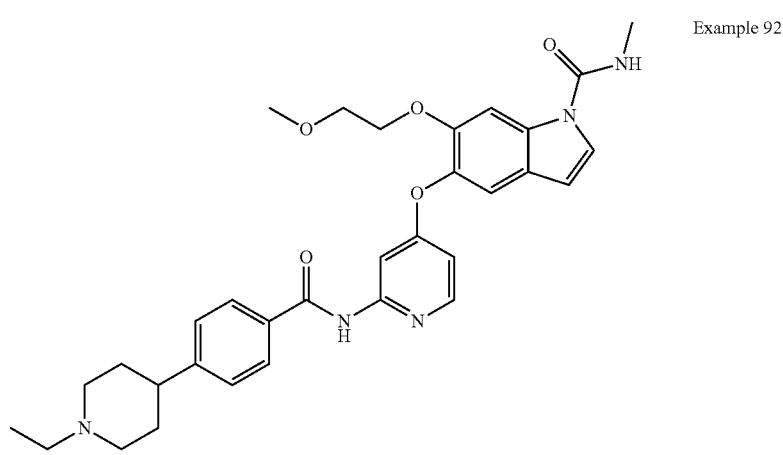
Example 92
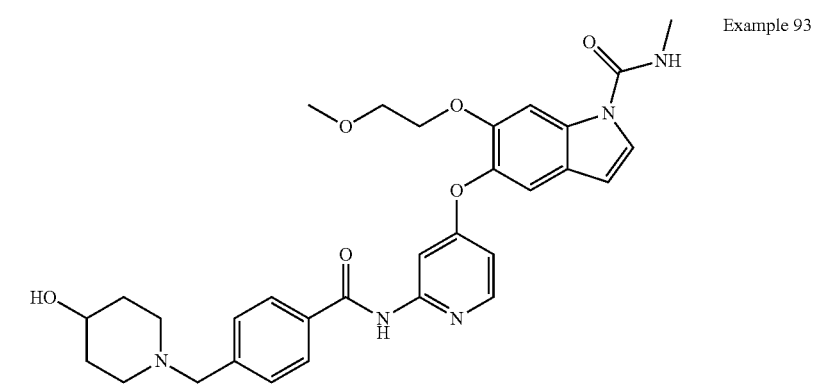
Example 93
According to Examples 1 to 33, the example compounds illustrated in Tables 7 and 8 were synthesized from 5-((2-aminopyridin-4-yl)oxy)-6-(2-ethoxyethoxy)-N-methyl-1,1-indole-1-carboxamide described in Production Example 24-8.

TABLE 7
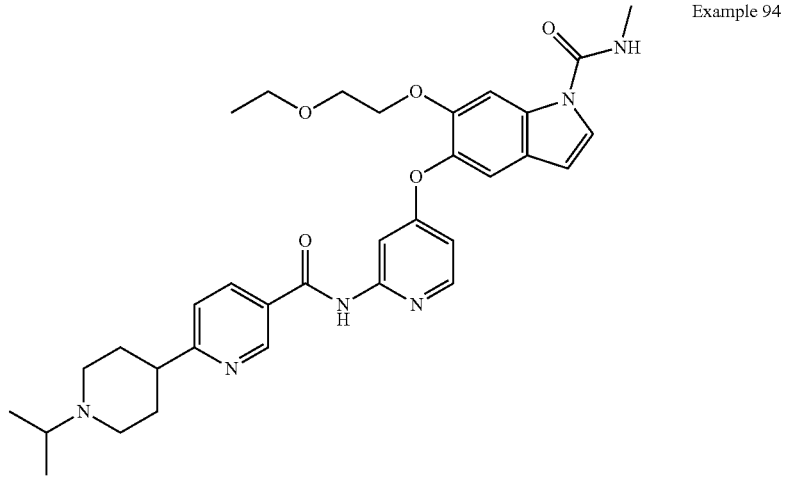
Example 94
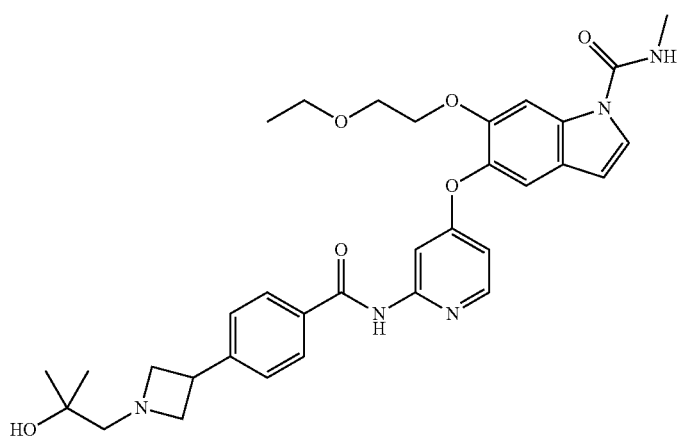 [SMILES: CCOCCOc1cc2c(ccn2C(=O)NC)cc1Oc1ccnc(NC(=O)c2ccc(C3CN(CC(C)(C)O)C3)cc2)c1]
Example 95
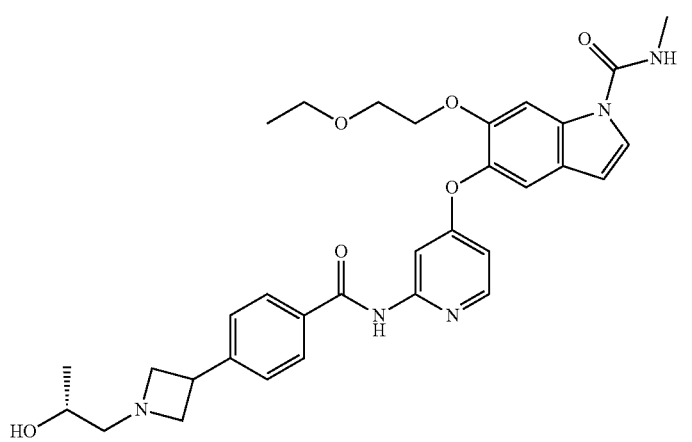 [SMILES: CCOCCOc1cc2c(ccn2C(=O)NC)cc1Oc1ccnc(NC(=O)c2ccc(C3CN(C[C@@H](C)O)C3)cc2)c1]
Example 96

TABLE 7-continued

Example 97

Example 102

Example 103

TABLE 7-continued

Example 104

Example 105

Example 110

TABLE 7-continued
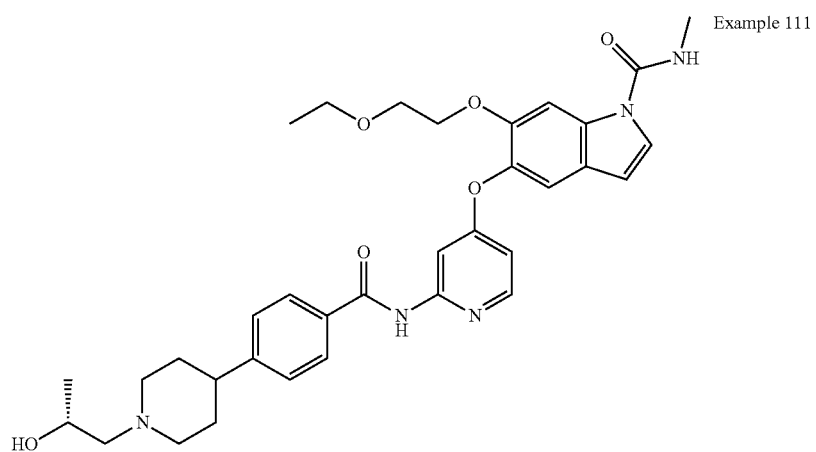
Example 111
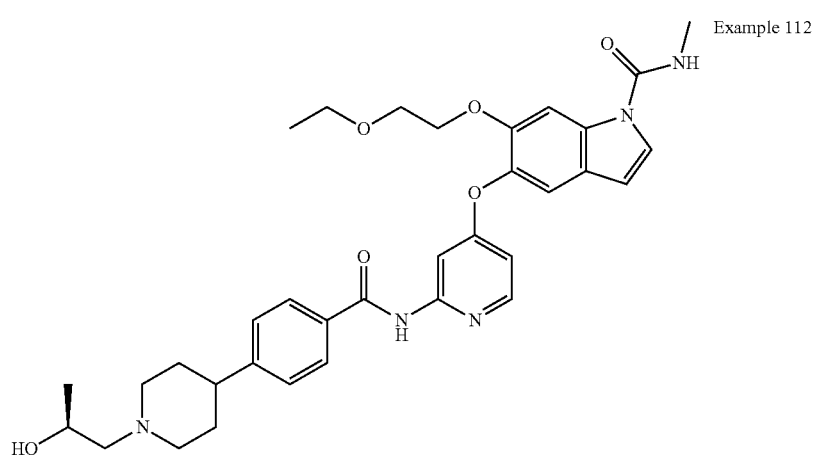
Example 112
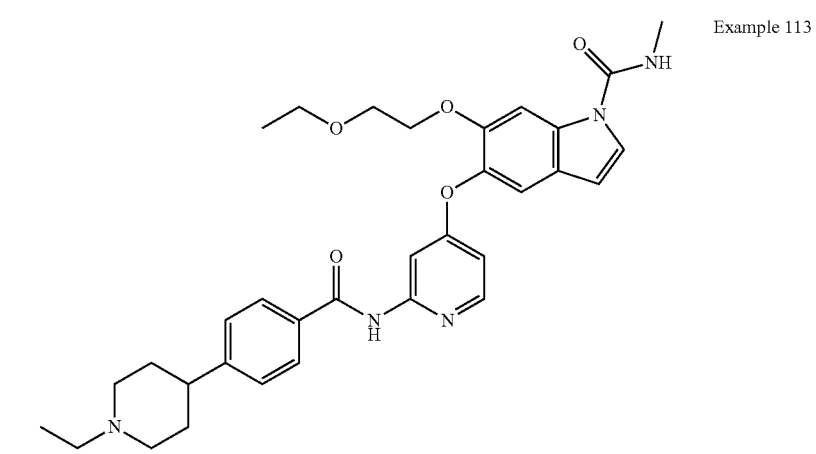
Example 113

TABLE 8
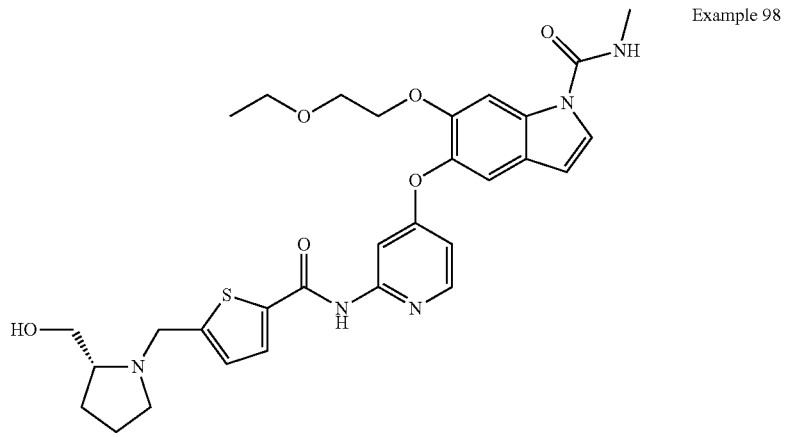
Example 98
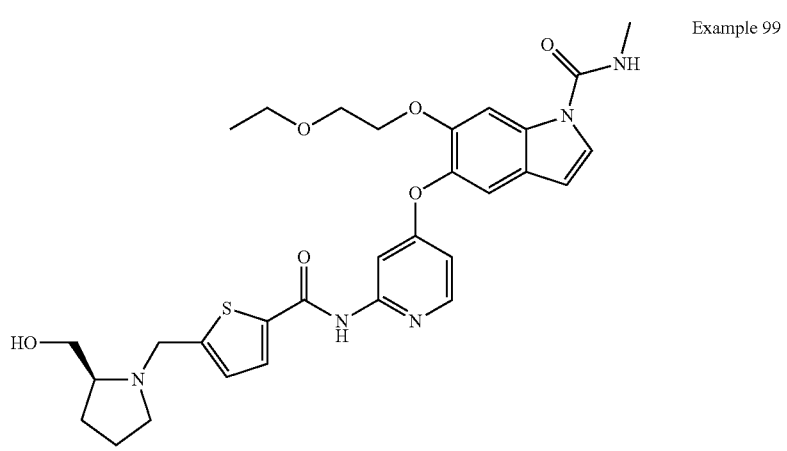
Example 99
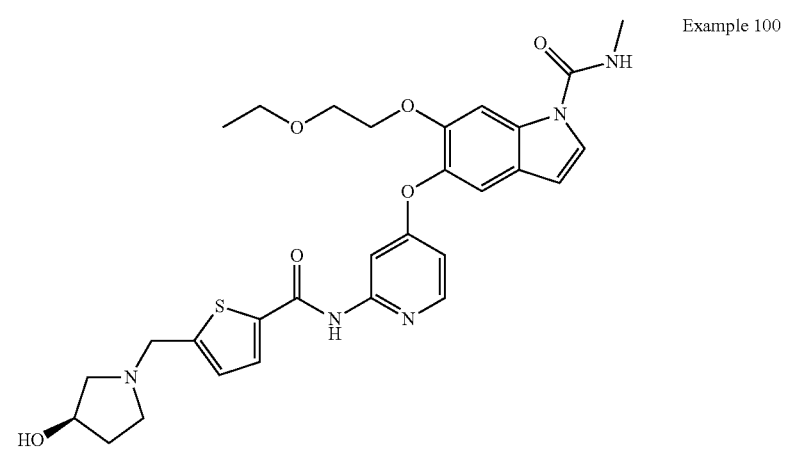
Example 100

TABLE 8-continued
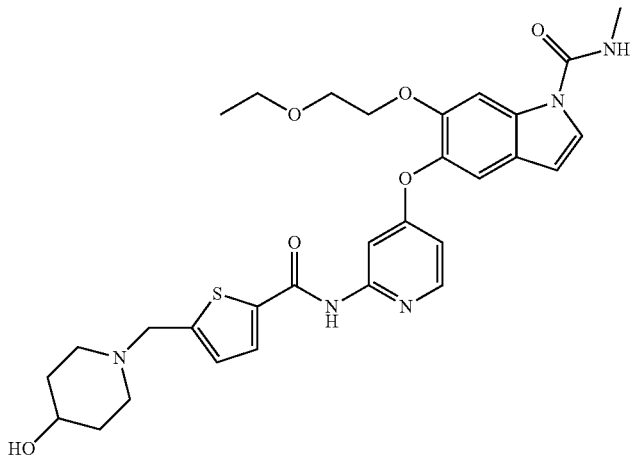 [SMILES: CCOCCOc1cc2c(ccn2C(=O)NC)cc1Oc1ccnc(NC(=O)c2ccc(CN3CCC(O)CC3)s2)c1]
Example 101
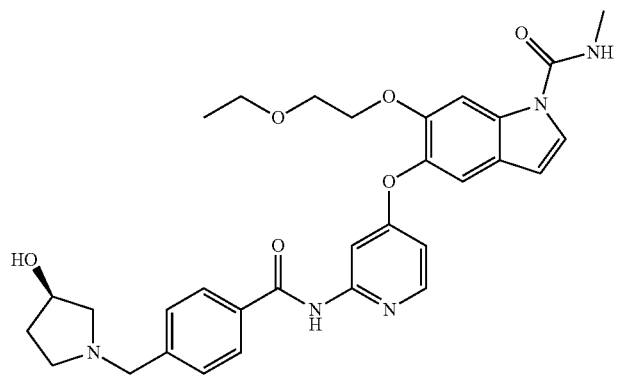 [SMILES: CCOCCOc1cc2c(ccn2C(=O)NC)cc1Oc1ccnc(NC(=O)c2ccc(CN3CC[C@@H](O)C3)cc2)c1]
Example 106
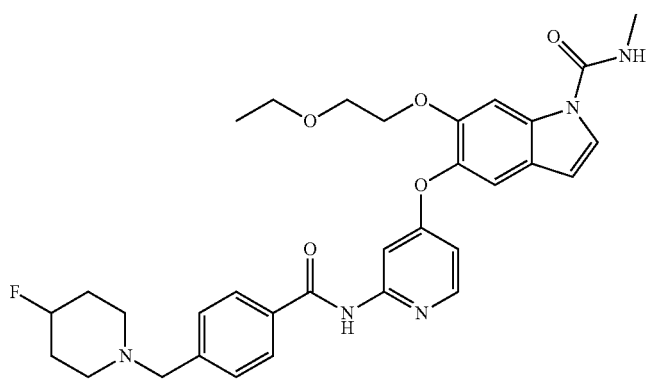 [SMILES: CCOCCOc1cc2c(ccn2C(=O)NC)cc1Oc1ccnc(NC(=O)c2ccc(CN3CCC(F)CC3)cc2)c1]
Example 107
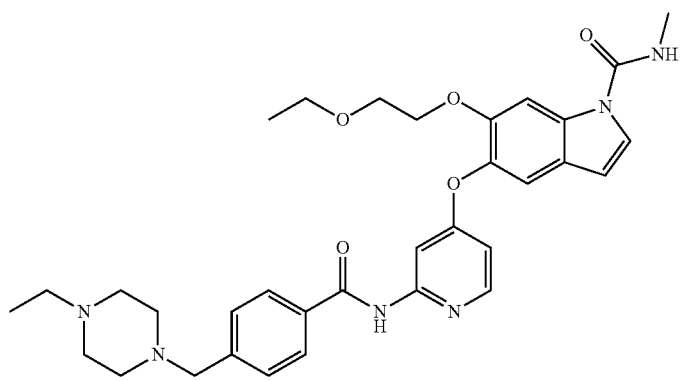 [SMILES: CCOCCOc1cc2c(ccn2C(=O)NC)cc1Oc1ccnc(NC(=O)c2ccc(CN3CCN(CC)CC3)cc2)c1]
Example 108

TABLE 8-continued
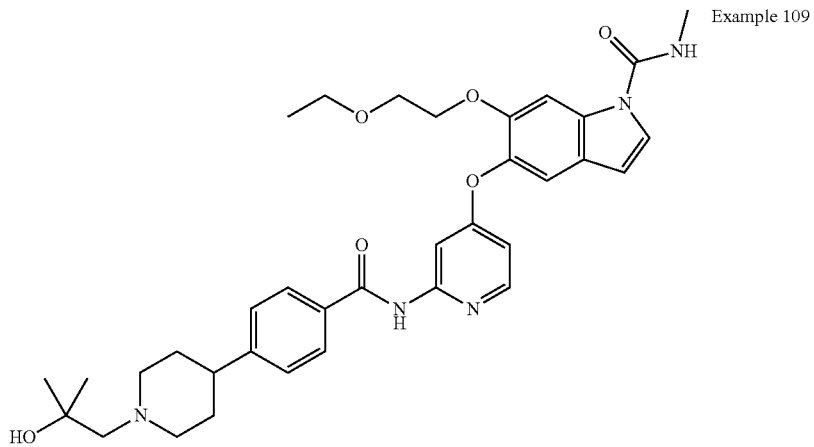
Example 109
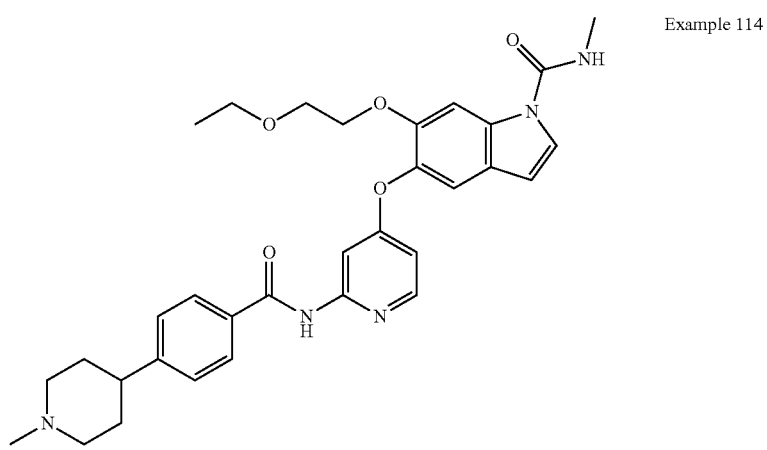
Example 114
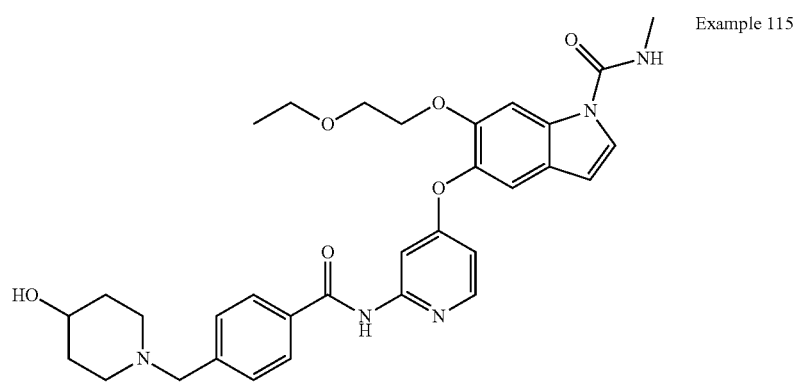
Example 115
According to Examples 1 to 33, the example compounds illustrated in Table 9 were synthesized from 5-((2-aminopyridin-4-yl)oxy)-6-(3-methoxypropoxy)-N-methyl-1H-indole-1-carboxamide described in Production Example 32-8.

TABLE 9
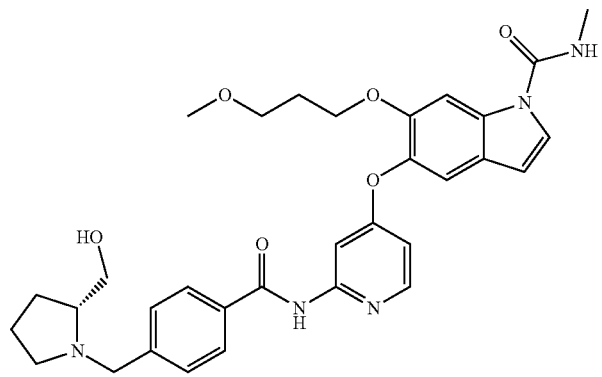 [SMILES: CNC(=O)n1ccc2cc(Oc3ccnc(NC(=O)c4ccc(CN5CCC[C@@H]5CO)cc4)c3)c(OCCCOC)cc21]
Example 116
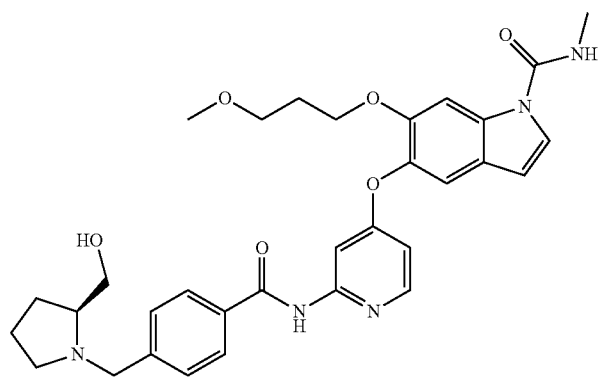 [SMILES: CNC(=O)n1ccc2cc(Oc3ccnc(NC(=O)c4ccc(CN5CCC[C@H]5CO)cc4)c3)c(OCCCOC)cc21]
Example 117
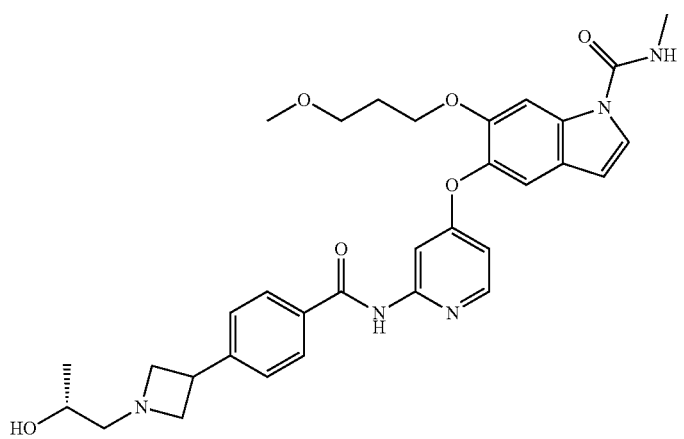 [SMILES: CNC(=O)n1ccc2cc(Oc3ccnc(NC(=O)c4ccc(C5CN(C[C@@H](C)O)C5)cc4)c3)c(OCCCOC)cc21]
Example 118
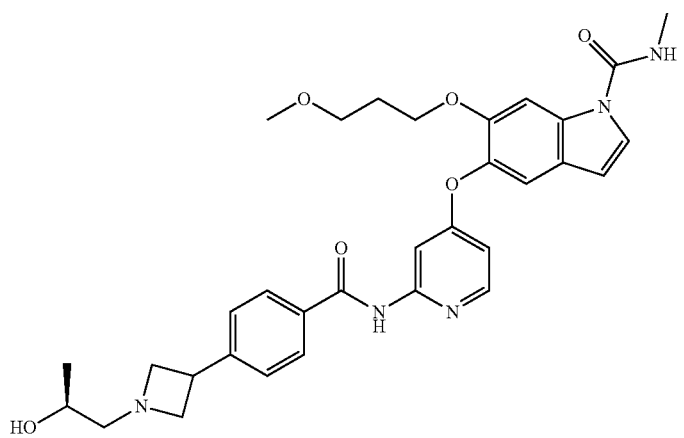 [SMILES: CNC(=O)n1ccc2cc(Oc3ccnc(NC(=O)c4ccc(C5CN(C[C@H](C)O)C5)cc4)c3)c(OCCCOC)cc21]
Example 119

TABLE 9-continued
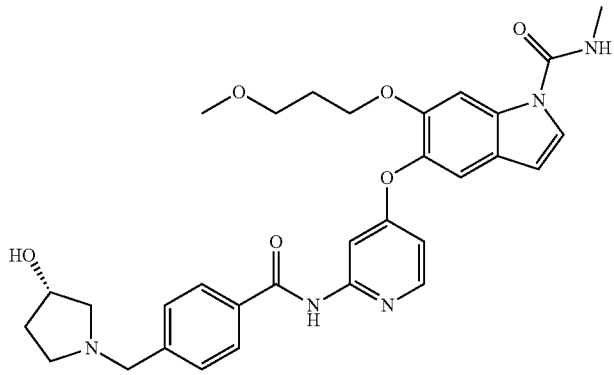 [SMILES: CNC(=O)n1ccc2cc(Oc3ccnc(NC(=O)c4ccc(CN5CC[C@H](O)C5)cc4)c3)c(OCCCOC)cc21]
Example 120
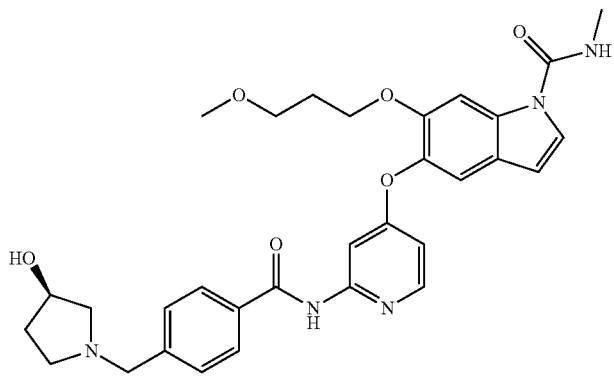 [SMILES: CNC(=O)n1ccc2cc(Oc3ccnc(NC(=O)c4ccc(CN5CC[C@@H](O)C5)cc4)c3)c(OCCCOC)cc21]
Example 121
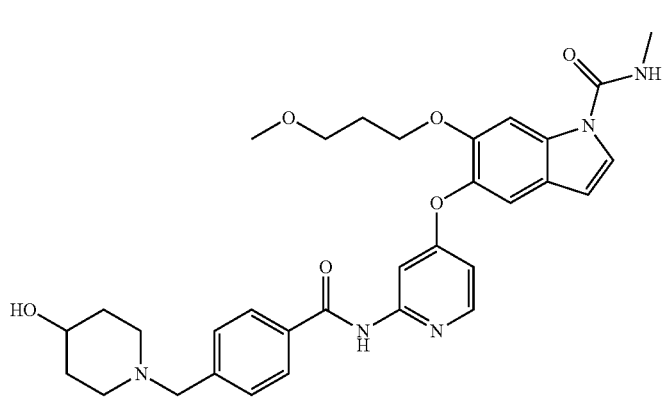 [SMILES: CNC(=O)n1ccc2cc(Oc3ccnc(NC(=O)c4ccc(CN5CCC(O)CC5)cc4)c3)c(OCCCOC)cc21]
Example 122
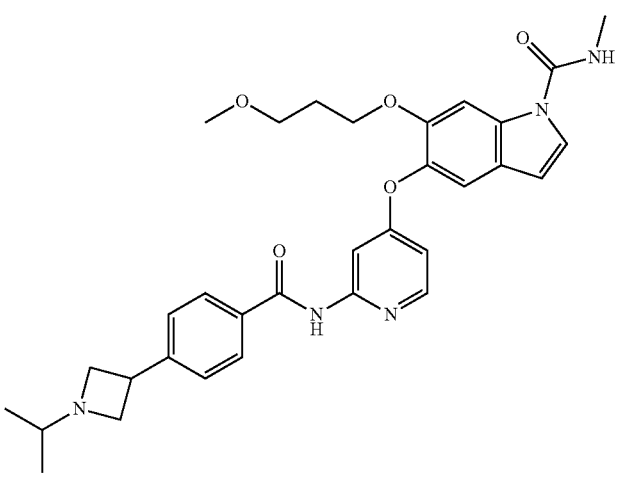 [SMILES: CNC(=O)n1ccc2cc(Oc3ccnc(NC(=O)c4ccc(C5CN(C(C)C)C5)cc4)c3)c(OCCCOC)cc21]
Example 123

TABLE 9-continued
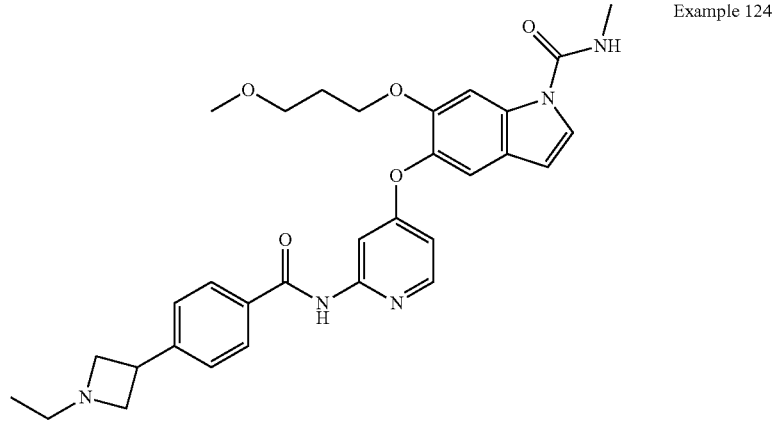
Example 124
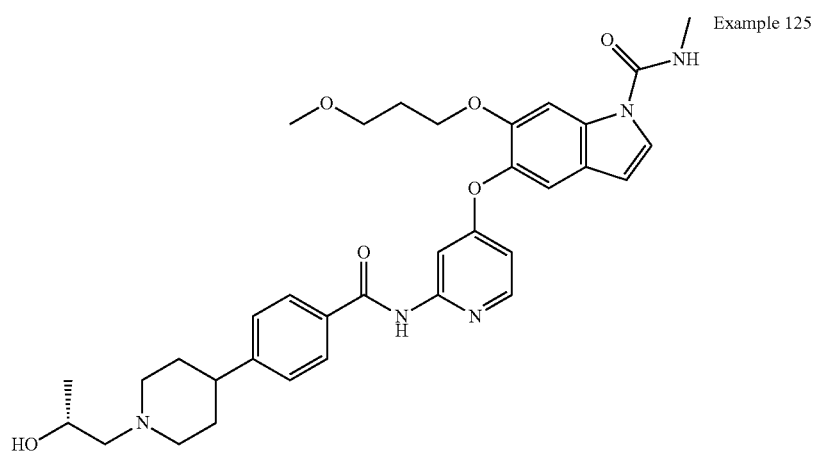
Example 125
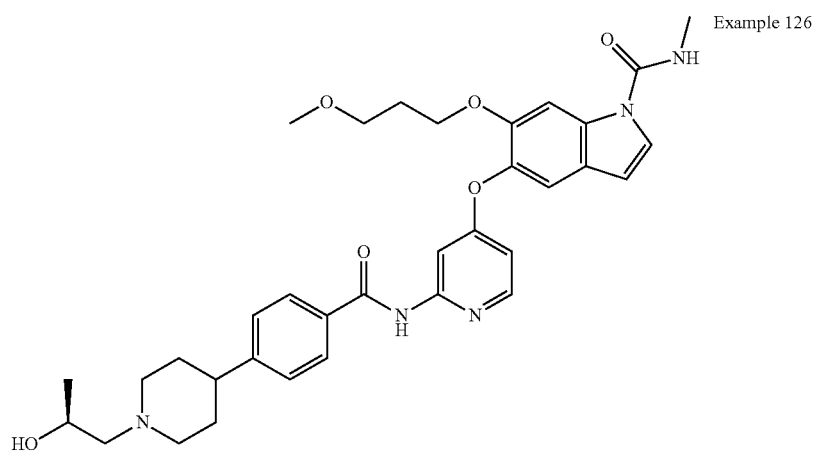
Example 126

TABLE 9-continued
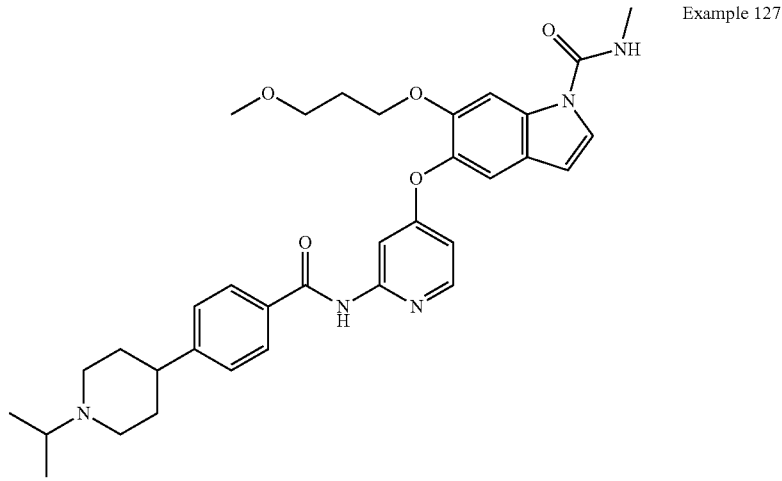
Example 127
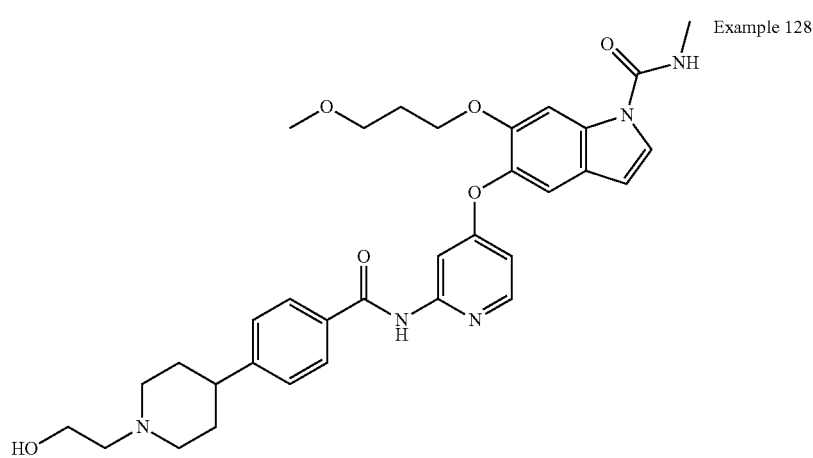
Example 128
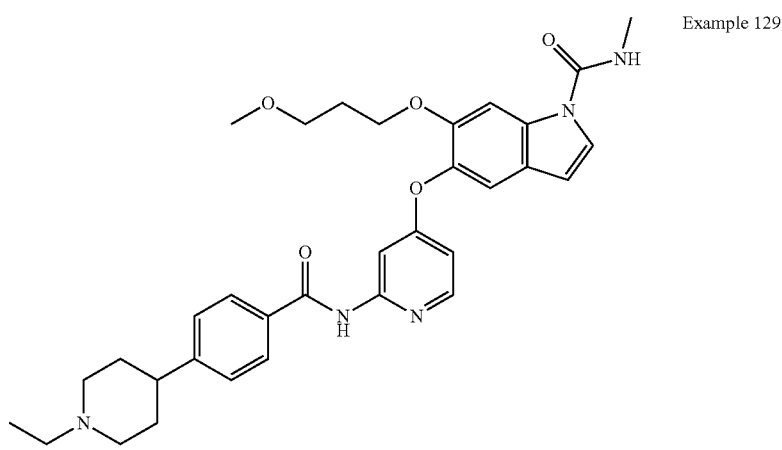
Example 129

TABLE 9-continued

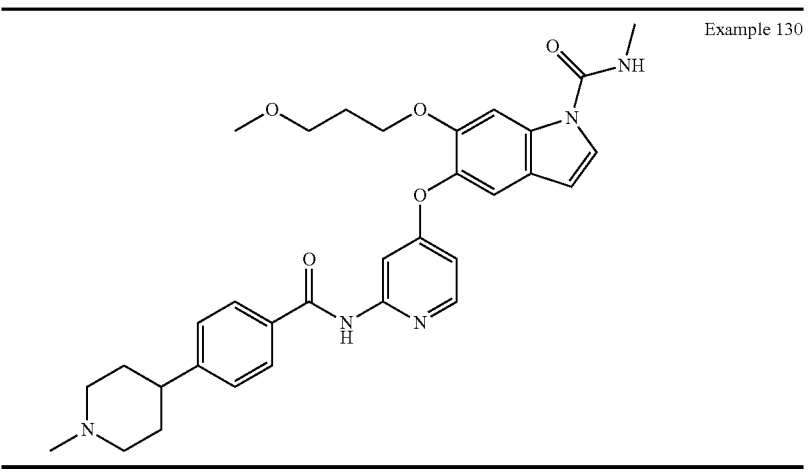

Example 130

The mass spectra (ESI-MS (m/z)) of the compounds of Examples 34 to 130 are illustrated in Table 10.

TABLE 10

| Example No. | ESI-MS (m/z) |
|---|---|
| Example 34 | 536[M + H]+ |
| Example 35 | 536[M + H]+ |
| Example 36 | 549[M + H]+ |
| Example 37 | 549[M + H]+ |
| Example 38 | 536[[M + H]+ |
| Example 39 | 572[M + H]+ |
| Example 40 | 542[M + H]+ |
| Example 41 | 574[M + H]+ |
| Example 42 | 574[M + H]+ |
| Example 43 | 544[M + H]+ |
| Example 44 | 548[M + H]+ |
| Example 45 | 548[M + H]+ |
| Example 46 | 532[M + H]+ |
| Example 47 | 514[M + H]+ |
| Example 48 | 544[M + H]+ |
| Example 49 | 500[M + H]+ |
| Example 50 | 530[M + H]+ |
| Example 51 | 530[M + H]+ |
| Example 52 | 516[M + H]+ |
| Example 53 | 516[M + H]+ |
| Example 54 | 558[M + H]+ |
| Example 55 | 573[M + H]+ |
| Example 56 | 544[M + H]+ |
| Example 57 | 514[M + H]+ |
| Example 58 | 586[M + H]+ |
| Example 59 | 556[M + H]+ |
| Example 60 | 572[M + H]+ |
| Example 61 | 572[M + H]+ |
| Example 62 | 583[M + H]+ |
| Example 63 | 558[M + H]+ |
| Example 64 | 528[M + H]+ |
| Example 65 | 544[M + H]+ |
| Example 66 | 586[M + H]+ |
| Example 67 | 572[M + H]+ |
| Example 68 | 556[M + H]+ |
| Example 69 | 542[M + H]+ |
| Example 70 | 558[M + H]+ |
| Example 71 | 562[M + H]+ |
| Example 72 | 562[M + H]+ |
| Example 73 | 576[M + H]+ |
| Example 74 | 604[M + H]+ |
| Example 75 | 604[M + H]+ |
| Example 76 | 560[M + H]+ |
| Example 77 | 587[M + H]+ |
| Example 78 | 573[M + H]+ |
| Example 79 | 588[M + H]+ |
| Example 80 | 574[M + H]+ |
| Example 81 | 574[M + H]+ |
| Example 82 | 580[M + H]+ |
| Example 83 | 580[M + H]+ |
| Example 84 | 566[M + H]+ |
| Example 85 | 566[M + H]+ |
| Example 86 | 580[M + H]+ |
| Example 87 | 530[M + H]+ |
| Example 88 | 558[M + H]+ |
| Example 89 | 544[M + H]+ |
| Example 90 | 602[M + H]+ |
| Example 91 | 602[M + H]+ |
| Example 92 | 572[M + H]+ |
| Example 93 | 574[M + H]+ |
| Example 94 | 601[M + H]+ |
| Example 95 | 602[M + H]+ |
| Example 96 | 588[M + H]+ |
| Example 97 | 588[M + H]+ |
| Example 98 | 594[M + H]+ |
| Example 99 | 594[M + H]+ |
| Example 100 | 580[M + H]+ |
| Example 101 | 594[M + H]+ |
| Example 102 | 544[M + H]+ |
| Example 103 | 572[M + H]+ |
| Example 104 | 588[M + H]+ |
| Example 105 | 574[M + H]+ |
| Example 106 | 574[M + H]+ |
| Example 107 | 590[M + H]+ |
| Example 108 | 601[M + H]+ |
| Example 109 | 630[M + H]+ |
| Example 110 | 600[M + H]+ |
| Example 111 | 616[M + H]+ |
| Example 112 | 616[M + H]+ |
| Example 113 | 586[M + H]+ |
| Example 114 | 572[M + H]+ |
| Example 115 | 588[M + H]+ |
| Example 116 | 588[M + H]+ |
| Example 117 | 588[M + H]+ |
| Example 118 | 588[M + H]+ |
| Example 119 | 588[M + H]+ |
| Example 120 | 574[M + H]+ |
| Example 121 | 574[M + H]+ |
| Example 122 | 588[M + H]+ |
| Example 123 | 572[M + H]+ |
| Example 124 | 558[M + H]+ |
| Example 125 | 616[M + H]+ |
| Example 126 | 616[M + H]+ |
| Example 127 | 600[M + H]+ |
| Example 128 | 602[M + H]+ |
| Example 129 | 586[M + H]+ |
| Example 130 | 572[M + H]+ |

Pharmacological Test Examples

1. FGFR1 Kinase Assay

In this assay, the inhibitory activity of a test substance against the tyrosine kinase activity of FGFR1 protein is measured.

To each well of a flat bottom 96 well white plate (Sumitomo Bakelite Co., Ltd., MS-8496W), 10 μl of FGFR1 protein (Cama Biosciences, Inc., 08-133) solution diluted to 1 μg/mL with an assay buffer (20 mM HEPES NaOH, 0.01% Triton X-100, 2 mM DTT, and 5 mM $MgCl_2$), 10 μl, of an assay buffer solution containing CSK-tide substrate (Ana Spec Inc., 63843) in a final concentration of 1000 nM and ATP (Promega Corporation, V9102) in a final concentration of 58.3 μM, and 5 μl of a test substance diluted with the assay buffer were added, and the reaction was performed at room temperature for 1 hour (kinase reaction). For measuring kinase activity, ADP-Glo™ Kinase Assay (Promega Corporation, V9102) was used. After the reaction, 25 μL of ADP-Glo reagent was added to each well of the plate, and the reaction was performed at morn temperature for 40 minutes to stop the kinase reaction and to deplete the remaining ATP. The kinase detection reagent was further added, and the reaction was performed at room temperature for 40 minutes, so as to cause conversion from ADP to ATP, a luciferase/luciferin coupling reaction and a luminous reaction by ATP. To evaluate the enzyme activity, the amount of luminescence in each well was measured by Envision™ (PerkinElmer Co., Ltd.). The luminescence values of the wells containing the kinase protein without adding the test substance was defined as 100% and the luminescence value of the wells adding neither the test substance nor the kinase protein was defined as 0%. Then, a luminescence value ratio in the presence of the test substance was calculated. On the basis of this luminescence value ratio, the concentration of the test substance necessary for inhibiting the kinase activity by 50% (i.e., an $IC_{50}$ value) was calculated, and shown in Tables 11 and 12.

<Data of FGFR1 Cell-Free Kinase Inhibitory Activity>

TABLE 11

| Example No. | FGFR1 ($IC_{50}$ (nM)) | Example No. | FGFR1 ($IC_{50}$ (nM)) |
|---|---|---|---|
| Example 1 | 9.8 | Example 66 | 10.3 |
| Example 2 | 10.1 | Example 67 | 11.2 |
| Example 3 | 7.9 | Example 68 | 11.7 |
| Example 4 | 7.2 | Example 69 | 12.4 |
| Example 5 | 12.0 | Example 70 | 32.0 |
| Example 6 | 11.0 | Example 71 | 18.4 |
| Example 7 | 11.6 | Example 72 | 22.5 |
| Example 8 | 13.2 | Example 73 | 24.2 |
| Example 9 | 30.0 | Example 74 | 8.5 |
| Example 10 | 37.7 | Example 75 | 8.0 |
| Example 11 | 18.0 | Example 76 | 10.4 |
| Example 12 | 19.9 | Example 77 | 19.1 |
| Example 13 | 31.2 | Example 78 | 20.2 |
| Example 14 | 10.9 | Example 79 | 8.5 |
| Example 15 | 12.5 | Example 80 | 8.5 |
| Example 16 | 11.5 | Example 81 | 7.0 |
| Example 17 | 14.6 | Example 82 | 6.4 |
| Example 18 | 12.7 | Example 83 | 10.2 |
| Example 19 | 13.5 | Example 84 | 8.6 |
| Example 20 | 5.6 | Example 85 | 6.7 |
| Example 21 | 5.7 | Example 86 | 6.5 |
| Example 22 | 5.8 | Example 87 | 7.1 |
| Example 23 | 5.3 | Example 88 | 6.7 |
| Example 24 | 4.4 | Example 89 | 5.7 |
| Example 25 | 5.2 | Example 90 | 7.0 |
| Example 26 | 6.3 | Example 91 | 5.0 |
| Example 27 | 8.0 | Example 92 | 5.4 |
| Example 28 | 11.2 | Example 93 | 14.9 |
| Example 29 | 10.0 | Example 94 | 10.6 |
| Example 30 | 14.5 | Example 95 | 5.7 |
| Example 31 | 6.5 | Example 96 | 11.0 |
| Example 32 | 10.9 | Example 97 | 7.2 |
| Example 33 | 8.5 | Example 98 | 6.6 |

TABLE 12

| Example No. | FGFR1 ($IC_{50}$ nM)) | Example No. | FGFR1 ($IC_{50}$ (nM)) |
|---|---|---|---|
| Example 34 | 12.3 | Example 99 | 5.1 |
| Example 35 | 10.8 | Example 100 | 5.4 |
| Example 36 | 11.2 | Example 101 | 5.6 |
| Example 37 | 10.9 | Example 102 | 6.5 |
| Example 38 | 10.5 | Example 103 | 5.0 |
| Example 39 | 7.9 | Example 104 | 12.1 |
| Example 40 | 8.9 | Example 105 | 8.6 |
| Example 41 | 10.6 | Example 106 | 8.9 |
| Example 42 | 13.0 | Example 107 | 16.1 |
| Example 43 | 12.5 | Example 108 | 11.5 |
| Example 44 | 22.8 | Example 109 | 3.9 |
| Example 45 | 26.5 | Example 110 | 5.4 |
| Example 46 | 24.1 | Example 111 | 4.2 |
| Example 47 | 12.8 | Example 112 | 3.4 |
| Example 48 | 12.1 | Example 113 | 4.2 |
| Example 49 | 11.7 | Example 114 | 3.7 |
| Example 50 | 32.3 | Example 115 | 10.3 |
| Example 51 | 18.3 | Example 116 | 22.3 |
| Example 52 | 23.7 | Example 117 | 10.7 |
| Example 53 | 23.4 | Example 118 | 7.0 |
| Example 54 | 5.5 | Example 119 | 11.5 |
| Example 55 | 34.1 | Example 120 | 16.6 |
| Example 56 | 24.2 | Example 121 | 16.1 |
| Example 57 | 10.0 | Example 122 | 17.9 |
| Example 58 | 9.8 | Example 123 | 8.9 |
| Example 59 | 8.7 | Example 124 | 8.5 |
| Example 60 | 9.6 | Example 125 | 5.2 |
| Example 61 | 8.9 | Example 126 | 6.4 |
| Example 62 | 18.8 | Example 127 | 7.1 |
| Example 63 | 10.0 | Example 128 | 6.1 |
| Example 64 | 11.8 | Example 129 | 7.0 |
| Example 65 | 33.8 | Example 130 | 6.2 |

2. FGFR2 Kinase Assay

In this assay, the inhibitory activity of a test substance against the tyrosine kinase activity of FGFR2 protein is measured.

To each well of a flat bottom 96 well white plate (Sumitomo Bakelite Co., Ltd., MS-8496W), 10 μl of FGFR2 protein (Cama Biosciences, Inc., 08434) solution diluted to 1 μg/mL with an assay buffer (20 mM HEPES-NaOH, 0.01% Triton X-100, 2 mM DTT, and 5 mM $MgCl_2$), 10 μL of an assay buffer solution containing CSK-tide substrate (Ana Spec Inc., 63843) in a final concentration of 1000 nM and ATP (Promega Corporation, V9102) in a final concentration of 35 μM, and 5 μl of a test substance diluted with the assay buffer were added, and the reaction was performed at room temperature for 1 hour (kinase reaction). For measuring kinase activity, ADP-Glo™ Kinase Assay (Promega Corporation, V9102) was used. After the reaction, 25 μL of ADP-Glo reagent was added to each well of the plate, and the reaction was performed at room temperature for 40 minutes to stop the kinase reaction and to deplete the remaining ATP. The kinase detection reagent was further added, and the reaction was performed at room temperature for 40 minutes, so as to cause conversion from ADP to ATP, a luciferase/luciferin coupling reaction and a luminous reaction by ATP. To evaluate the enzyme activity, the amount of luminescence in each well was measured by Envision™ (PerkinElmer Co., Ltd.). The luminescence values of the wells containing the kinase protein without adding the test substance was defined as 100% and that the luminescence values of the wells adding neither the test substance nor the kinase protein was defined as 0%. Then, a luminescence value ratio in the presence of the test substance was calculated. On the basis of this luminescence value ratio, the concentration of the test substance necessary for inhibiting the kinase activity by 50% (i.e., an $IC_{50}$ value) was calculated, and shown in Table 13.

<Data of FGFR2 Cell-Free Kinase Inhibitory Activity>

TABLE 13

| Example No. | FGFR2 $IC_{50}$ (nM)) |
|---|---|
| Example 2 | 6.4 |
| Example 21 | 5.1 |
| Example 22 | 4.5 |

3. FGFR3 Kinase Assay

In this assay, the inhibitory activity of a test substance against the tyrosine kinase activity of FGFR3 protein is measured.

To each well of a flat bottom 96 well white plate (Sumitomo Bakelite Co., Ltd., MS-8496W), 10 μl of FGFR3 protein (Cama Biosciences, Inc., 08-135) solution diluted to 1 μg/mL with an assay buffer (20 mM HEPES NaOH, 0.01% Triton X-100, 2 mM DTT, and 5 mM $MgCl_2$), 10 μL of an assay buffer solution containing CSK-tide substrate (Ana Spec Inc., 63843) in a final concentration 011000 nM and ATP (Promega Corporation, V9102) in a final concentration of 16.7 μM, and 5 μl of a test substance diluted with the assay buffer were added, and the reaction was performed at room temperature for 2 hours (kinase reaction). For measuring kinase activity, ADP-Glo™ Kinase Assay (Promega Corporation, V9102) was used. After the reaction, 25 pt of ADP-Glo reagent was added to each well of the plate, and the reaction was performed at room temperature for 40 minutes to stop the kinase reaction and to deplete the remaining ATP. The kinase detection reagent was further added, and the reaction was performed at room temperature for 40 minutes, so as to cause conversion from ADP to ATP, a luciferase/luciferin coupling reaction and a luminous reaction by ATP. To evaluate the enzyme activity, the amount of luminescence in each well was measured by Envision™ (PerkinElmer Co., Ltd.). The luminescence values of the wells containing the kinase protein without adding the test substance was defined as 100% and the luminescence values of the wells adding neither the test substance nor the kinase protein was defined as 0%. Then, a luminescence value ratio in the presence of the test substance was calculated. On the basis of this luminescence value ratio, the concentration of the test substance necessary for inhibiting the kinase activity by 50% (i.e., an $IC_{50}$ value) was calculated, and shown in Table 14.

<Data of FGFR3 Cell-Free Kinase Inhibitory Activity>

TABLE 14

| Example No. | FGFR3 ($IC_{50}$ (nM)) |
|---|---|
| Example 2 | 7.9 |
| Example 21 | 6.0 |
| Example 22 | 5.4 |

4. FGFR4 Kinase Assay

In this assay, the inhibitory activity of a test substance against the tyrosine kinase activity of FGFR4 protein is measured.

To each well of a flat bottom 96 well white plate (Sumitomo Bakelite Co., Ltd., MS-8496W), 10 μl FGFR4 protein (Carna Biosciences, Inc., 08-136) solution diluted to 1 μg/mL with an assay buffer (20 mM HEPES-NaOH, 0.01% Triton X-100, 2 mM DTT, 5 mM $MgCl_2$ and 2 mM $MnCl_2$), 10 μL of an assay buffer solution containing CSK-tide substrate (Ana Spec Inc., 63843) in a final concentration of 1000 nM and ATP (Promega Corporation, V9102) in a final concentration of 75 μM, and 5 μl of a test substance diluted with the assay buffer were added and the reaction was performed at room temperature for 2 hours (kinase reaction). For measuring kinase activity, ADP-Glo™ Kinase Assay (Promega Corporation, V9102) was used, After the reaction, 25 μL of ADP-Glo reagent was added to each well of the plate, and the reaction was performed at room temperature for 40 minutes to stop the kinase reaction and to deplete the remaining ATP. The kinase detection reagent was further added, and the reaction was performed at room temperature for 40 minutes, so as to cause conversion from ADP to ATP, a luciferase/luciferin coupling reaction and a luminous reaction by ATP. To evaluate the enzyme activity the amount of luminescence in each well was measured by Envision™ (PerkinElmer Co., Ltd.). The luminescence value of the wells containing the kinase protein without adding the test substance was defined as 100% and the luminescence value of the wells adding neither the test substance nor the kinase protein was defined as 0%. Then, a luminescence value ratio in the presence of the test substance was calculated. On the basis of this luminescence value ratio, the concentration of the test substance necessary for inhibiting the kinase activity by 50% (i.e., an $IC_{50}$ value) was calculated, and shown in Table 15.

<Data of FGFR4 Cell-Free Kinase Inhibitory Activity>

TABLE 15

| Example No. | FGFR4 ($IC_{50}$ (nM)) |
|---|---|
| Example 2 | 651.1 |
| Example 21 | 683.3 |
| Example 22 | 644.5 |

5. SNU-16 Growth Inhibition Assay

In this assay, the growth inhibitory activity of a test substance in a human stomach cancer cell line harboring FGFR2 gene amplification is measured.

It has been reported that a human stomach cancer cell line SNU-16 (ATCC Number CRL-5974) harbors FGFR2 gene amplification (Cancer Res. 2008. 68: 2340-2348). SNU-16 cells were maintained in RPM-1640 (Wako Pure Chemical Industries, Ltd., 187-02021) medium containing 10% fetal bovine serum (FBS: Cell Culture Technologies, CC3008-504), and penicillin and streptomycin (Wako Pure Chemical Industries, Ltd., 168-23191) in a 5% $CO_2$ incubator (37° C.). To each well of a 96 well plate (Becton, Dickinson and Company, 35-3075), 150 μL of SNU-16 cell suspension adjusted to a concentration of $1 \times 10^4$ cells/mL with RPMI-1640 medium containing 10% FBS, and penicillin and streptomycin was added, and the cell was incubated overnight in a 5% $CO_2$ incubator (37° C.). On the next day, 50 μL of a test substance diluted with RPMI-1640 medium containing 10% FES, and penicillin and streptomycin was added to each well, and the resultant was incubated for 3 days in a 5% $CO_2$ incubator (37° C.). Then, 10 μL of Cell Counting Kit-8 (Dojindo Laboratories, CK04) was added to each well, and the resultant was incubated for 1 to 2 hours in a 5% $CO_2$ incubator (37° C.) to cause a color reaction. The absorbance value was measured with ENVISION™ (PerkinElmer Co., Ltd.) at 450 nm. Absorbance value of the wells containing cells without adding the test substance was defined as 100% and the absorbance value of the wells containing no cells was defined as 0%. Then, an absorbance ratio in the presence of the test substance was calculated. The concentration of the test substance necessary for inhibiting the cell growth by 50% (i.e., an $IC_{50}$ value) was calculated, and shown in Tables 16 and 17.

<Data of Evaluation of SNU-16 Growth Inhibitory Activity>

TABLE 16

| Example No. | SNU-16 ($IC_{50}$ (nM)) | Example No. | SNU-16 ($IC_{50}$ (nM)) |
| --- | --- | --- | --- |
| Example 1 | 7.5 | Example 66 | 16.1 |
| Example 2 | 6.2 | Example 67 | 17.6 |
| Example 3 | 7.7 | Example 68 | 20.0 |
| Example 4 | 6.9 | Example 69 | 17.5 |
| Example 5 | 13.4 | Example 70 | 22.4 |
| Example 6 | 9.1 | Example 71 | 17.0 |
| Example 7 | 9.6 | Example 72 | 17.1 |
| Example 8 | 15.4 | Example 73 | 17.4 |
| Example 9 | 24.0 | Example 74 | 8.4 |
| Example 10 | 28.7 | Example 75 | 7.3 |
| Example 11 | 14.5 | Example 76 | 7.5 |
| Example 12 | 13.0 | Example 77 | 9.6 |
| Example 13 | 10.9 | Example 78 | 6.2 |
| Example 14 | 9.5 | Example 79 | 4.6 |
| Example 15 | 9.7 | Example 80 | 3.8 |
| Example 16 | 12.2 | Example 81 | 3.8 |
| Example 17 | 17.7 | Example 82 | 6.2 |
| Example 18 | 13.9 | Example 83 | 10.2 |
| Example 19 | 14.1 | Example 84 | 6.2 |
| Example 20 | 7.5 | Example 85 | 6.9 |
| Example 21 | 4.2 | Example 86 | 6.2 |
| Example 22 | 3.0 | Example 87 | 3.9 |
| Example 23 | 6.5 | Example 88 | 6.9 |
| Example 24 | 6.2 | Example 89 | 6.5 |
| Example 25 | 3.8 | Example 90 | 6.1 |
| Example 26 | 5.6 | Example 91 | 5.3 |
| Example 27 | 6.2 | Example 92 | 5.8 |
| Example 28 | 7.3 | Example 93 | 17.6 |
| Example 29 | 8.8 | Example 94 | 7.9 |
| Example 30 | 14.5 | Example 95 | 5.1 |
| Example 31 | 4.7 | Example 96 | 6.4 |
| Example 32 | 6.8 | Example 97 | 3.6 |
| Example 33 | 8.1 | Example 98 | 6.3 |

TABLE 17

| Example No. | SNU-16 ($IC_{50}$ (nM)) | Example No. | SNU-16 ($IC_{50}$ (nM)) |
| --- | --- | --- | --- |
| Example 34 | 14.0 | Example 99 | 6.3 |
| Example 35 | 9.8 | Example 100 | 5.8 |
| Example 36 | 11.0 | Example 101 | 6.8 |
| Example 37 | 9.4 | Example 102 | 3.7 |
| Example 38 | 8.0 | Example 103 | 5.4 |
| Example 39 | 7.8 | Example 104 | 13.7 |
| Example 40 | 8.3 | Example 105 | 7.8 |
| Example 41 | 9.3 | Example 106 | 9.0 |
| Example 42 | 14.1 | Example 107 | 22.0 |
| Example 43 | 11.8 | Example 108 | 14.7 |
| Example 44 | 16.3 | Example 109 | 6.7 |
| Example 45 | 15.5 | Example 110 | 5.8 |
| Example 46 | 17.4 | Example 111 | 5.1 |
| Example 47 | 13.1 | Example 112 | 3.8 |
| Example 48 | 11.7 | Example 113 | 5.7 |
| Example 49 | 9.6 | Example 114 | 4.7 |
| Example 50 | 16.6 | Example 115 | 11.4 |
| Example 51 | 12.5 | Example 116 | 22.6 |

TABLE 17-continued

| Example No. | SNU-16 ($IC_{50}$ (nM)) | Example No. | SNU-16 ($IC_{50}$ (nM)) |
| --- | --- | --- | --- |
| Example 52 | 14.4 | Example 117 | 16.6 |
| Example 53 | 14.5 | Example 118 | 8.6 |
| Example 54 | 6.4 | Example 119 | 11.9 |
| Example 55 | 20.8 | Example 120 | 16.7 |
| Example 56 | 15.0 | Example 121 | 14.9 |
| Example 57 | 7.6 | Example 122 | 11.3 |
| Example 58 | 10.0 | Example 123 | 8.5 |
| Example 59 | 14.5 | Example 124 | 8.9 |
| Example 60 | 14.7 | Example 125 | 7.2 |
| Example 61 | 10.7 | Example 126 | 6.6 |
| Example 62 | 27.4 | Example 127 | 7.1 |
| Example 63 | 9.6 | Example 128 | 6.4 |
| Example 64 | 10.3 | Example 129 | 7.7 |
| Example 65 | 23.6 | Example 130 | 6.8 |

6. HUVEC Growth Inhibition Assay

In this assay, the inhibitory activity of a test substance against the growth of human vascular endothelial cells induced by VEGF is measured.

Normal human umbilical vein endothelial cells (HUVEC) were isolated according to a reported method (Shin Seikagaku Jikken Koza "Saibo Baiyo Gijutsu" (New Lectures on Biochemical Experiments "Cell Culture Techniques" (in Japanese), p. 197-202). The cells were cultured to be confluent with EGM-2 medium (LONZA Inc., CC-3162) in a 5% $CO_2$ incubator (37° C.).

To each well of a 96 well plate (Becton, Dickinson and Company, 35-3075), 100 of HUVEC cell suspension adjusted to a concentration of $1.5 \times 10^4$ cells/mL with EGM-2 medium containing 2% fetal bovine serum (FBS: Cell Culture Technologies, CC3008-504), was seeded, and the resultant was incubated overnight in a 5% $CO_2$ incubator (37° C.). On the next day, 50 µL of a test substance diluted with EGM-2 medium containing 2% FBS, and 50 µL of VEGF (R & D Systems, 293-VE-010) adjusted to a final concentration of 10 ng/mL in EGM-2 medium containing 2% FBS were added to each well respectively, and the resultant was incubated for 3 days in a 5% $CO_2$ incubator (37° C.). Then, 20 µL of Cell Counting Kit-8 (Dojindo Laboratories, CK04) was added to each well, and the resultant was incubated for 3 to 4 hours in a 5% $CO_2$ incubator (37° C.) to cause a color reaction. The absorbance value was measured with ENVISION™ (PerkinElmer Co., Ltd.) at 450 nm. The absorbance values of the wells without adding the test substance but with VEGF addition was defined as 100% and the absorbance values of the wells with neither the test substance nor VEGF addition was defined as 0%. Then, an absorbance ratio in the presence of the test substance was calculated. On the basis of the absorbance ratio, the concentration of the test substance necessary for inhibiting the HUVEC growth by 50% in the presence of VEGF (i.e., an $IC_{50}$ value) was calculated, and shown in Tables 18 and 19.

<Data of Evaluation of HUVEC Growth Inhibitory Activity>

TABLE 18

| Example No. | HUVEC ($IC_{50}$ (nM)) | Example No. | HUVEC ($IC_{50}$ (nM)) |
| --- | --- | --- | --- |
| Example 1 | 98.7 | Example 66 | 203.4 |
| Example 2 | 130.5 | Example 67 | 223.3 |
| Example 3 | 95.0 | Example 68 | 255.6 |
| Example 4 | 93.0 | Example 69 | 214.2 |
| Example 5 | 386.7 | Example 70 | 609.9 |
| Example 6 | 180.1 | Example 71 | 647.8 |

TABLE 18-continued

| Example No. | HUVEC (IC$_{50}$ (nM)) | Example No. | HUVEC (IC$_{50}$ (nM)) |
|---|---|---|---|
| Example 7 | 205.3 | Example 72 | 681.4 |
| Example 8 | 139.9 | Example 73 | 702.8 |
| Example 9 | 645.8 | Example 74 | 198.0 |
| Example 10 | 350.2 | Example 75 | 211.1 |
| Example 11 | 131.5 | Example 76 | 247.5 |
| Example 12 | 141.2 | Example 77 | 1029.4 |
| Example 13 | 396.5 | Example 78 | 835.4 |
| Example 14 | 169.0 | Example 79 | 88.5 |
| Example 15 | 168.3 | Example 80 | 181.5 |
| Example 16 | 165.3 | Example 81 | 126.2 |
| Example 17 | 292.8 | Example 82 | 263.7 |
| Example 18 | 179.7 | Example 83 | 309.5 |
| Example 19 | 151.1 | Example 84 | 255.3 |
| Example 20 | 459.3 | Example 85 | 235.3 |
| Example 21 | 225.0 | Example 86 | 250.3 |
| Example 22 | 189.5 | Example 87 | 259.4 |
| Example 23 | 300.4 | Example 88 | 357.8 |
| Example 24 | 237.2 | Example 89 | 416.2 |
| Example 25 | 191.0 | Example 90 | 203.1 |
| Example 26 | 258.1 | Example 91 | 191.1 |
| Example 27 | 217.8 | Example 92 | 182.2 |
| Example 28 | 663.7 | Example 93 | 886.9 |
| Example 29 | 600.1 | Example 94 | 606.8 |
| Example 30 | 565.5 | Example 95 | 116.4 |
| Example 31 | 186.3 | Example 96 | 179.2 |
| Example 32 | 203.3 | Example 97 | 158.7 |
| Example 33 | 273.6 | Example 98 | 228.3 |

TABLE 19

| Example No. | HUVEC (IC$_{50}$ (nM)) | Example No. | HUVEC (IC$_{50}$ (nM)) |
|---|---|---|---|
| Example 34 | 194.8 | Example 99 | 224.4 |
| Example 35 | 139.1 | Example 100 | 207.1 |
| Example 36 | 135.7 | Example 101 | 181.6 |
| Example 37 | 79.1 | Example 102 | 226.4 |
| Example 38 | 137.3 | Example 103 | 295.5 |
| Example 39 | 124.1 | Example 104 | 599.6 |
| Example 40 | 162.3 | Example 105 | 687.3 |
| Example 41 | 178.8 | Example 106 | 726.4 |
| Example 42 | 183.9 | Example 107 | 906.7 |
| Example 43 | 165.6 | Example 108 | 362.8 |
| Example 44 | 392.4 | Example 109 | 186.5 |
| Example 45 | 379.4 | Example 110 | 233.7 |
| Example 46 | 402.3 | Example 111 | 195.0 |
| Example 47 | 174.0 | Example 112 | 201.7 |
| Example 48 | 77.8 | Example 113 | 195.9 |
| Example 49 | 162.8 | Example 114 | 201.4 |
| Example 50 | 393.6 | Example 115 | 615.6 |
| Example 51 | 410.1 | Example 116 | 520.1 |
| Example 52 | 388.3 | Example 117 | 534.0 |
| Example 53 | 400.6 | Example 118 | 183.4 |
| Example 54 | 86.7 | Example 119 | 241.7 |
| Example 55 | 201.4 | Example 120 | 457.1 |
| Example 56 | 96.8 | Example 121 | 517.9 |
| Example 57 | 126.9 | Example 122 | 494.3 |
| Example 58 | 251.6 | Example 123 | 156.1 |
| Example 59 | 252.7 | Example 124 | 196.7 |
| Example 60 | 178.1 | Example 125 | 202.8 |
| Example 61 | 181.9 | Example 126 | 197.1 |
| Example 62 | 222.9 | Example 127 | 226.2 |
| Example 63 | 170.4 | Example 128 | 216.7 |
| Example 64 | 175.4 | Example 129 | 248.5 |
| Example 65 | 575.0 | Example 130 | 253.8 |

7. NCI-H1581 Growth Inhibition Assay

In this assay, the growth inhibitory activity of a test substance in a human lung cancer cell line harboring FGFR1 gene amplification is measured.

It has been reported that a human lung cancer cell line of NCI-H1581 (ATCC Number CRL-5878) harbors FGFR1 gene amplification (PLoS One, 2011; 6: e20351, Sci Transl Med 2010; 2: 62ra93). NCI-H1581 cells were maintained in RPME-1640 (Wako Pure Chemical Industries, Ltd., 187-02021) medium containing 10% FBS, and penicillin and streptomycin (Wako Pure Chemical Industries, Ltd., 168-23191) in a 5% $CO_2$ incubator (37° C.). To each well of a 96 well plate (Becton, Dickinson and Company, 35-3075), 150 µL of a NCI-H1581 cell suspension adjusted to a concentration of $1.3 \times 10^4$ cells/mL with RPM-1640 medium containing 10% FBS, and penicillin and streptomycin was added, and the cell was incubated overnight in a 5% $CO_2$ incubator (37° C.). On the next day, 50 µl of a test substance diluted with an RPMI-1640 medium containing 10% FBS, and penicillin and streptomycin was added to each well, and the resultant was cultured for 3 days in a 5% $CO_2$ incubator (37° C.). Then, 10 µL of Cell Counting Kit-8 (Dojindo Laboratories, CK04) was added to each well, and the resultant was incubated for 2 to 3 hours in a 5% $CO_2$ incubator (37° C.) to cause a color reaction. The absorbance value was measured with ENVISION™ (PerkinElmer Co., Ltd.) at 450 nm. The absorbance values of the wells containing cells without adding the test substance was defined as 100% and the absorbance values of the wells containing no cells was defined as 0%. Then, an absorbance ratio in the presence of the test substance was calculated. The concentration of each test substance necessary for inhibiting the cell growth by 50% (i.e., an IC$_{50}$ value) was calculated, and shown in Table 20.

<Data of Evaluation of NCI-H1581 Growth Inhibitory Activity>

TABLE 20

| Example No. | NCI-H1581 (IC$_{50}$ (nM)) |
|---|---|
| Example 2 | 8.5 |
| Example 3 | 7.6 |
| Example 4 | 9.4 |
| Example 9 | 18.1 |
| Example 16 | 18.4 |
| Example 21 | 4.5 |
| Example 22 | 4.4 |

8. Antitumor Effect in SNU-16 Subcutaneous Xenograft Model in Mice

Human stomach cancer cell line SNU-16, which had been cultured in an RPMI-1640 medium containing 10% FBS, and penicillin and streptomycin, were adjusted to a concentration of $1 \times 10^8$ cells/mL with Hanks' Balanced Salt Solution (GIBCO #24020) to prepare a cell suspension, and the suspension was mixed with MATRIGEL (BD Biosciences, Cat#354234) in a ratio of 1:1 to prepare a cell suspension in a concentration of $5 \times 10^7$ cells/ml. The cell suspension was inoculated in a volume of 100 ut into a subcutaneous part of a right flank of nude mice, 6 to 7 weeks of ages (BALB/cAielnu/nu, female, Clea Japan Inc.). Seven days after cell inoculation, the shortest diameter and the longest diameter of a tumor in each mouse were measured by using an electronic digital caliper (Digimatie™ caliper, Mitutoyo Corporation), so as to calculate the volume of the tumor in accordance with the following calculation formula:

Tumor volume(mm$^3$)Longest diameter(mm)×Shortest diameter(mm)×Shortest diameter(mm)/2

On the basis of the volumes of tumors obtained on the first day of administration, the nude mice were grouped such that averages of the tumor volumes were substantially equal among the groups. Each test substance was dissolved in DMSO, Tween 80 was added thereto to prepare a solution in a 10-fold concentration and the thus prepared solution was stored at the freezer before use. Immediately before the administration, the stock solution was diluted with a 5% glucose solution to obtain a final administration solution (in which a ratio in % among DMSO, Tween 80 and the 5% glucose solution was 3.5:6.5:90). Each evaluation sample was orally administered to test substance administration group at a volume of 0.4 mL per 20 g of body weight once a day continuously for 11 days, and in a control group, an administration solvent was orally administered under the same conditions. Incidentally, the experiment was conducted on groups each consisting of 5 mice.

With respect to each of the control group and test substance administration group, a ratio of the weight measured on the final day to the weight measured on the first day (relative body weight: RBW) was calculated. If a ratio of the RBW of the test substance administration group/the RBW of the control group is 0.9 or mom, the corresponding test substance administration group was defined as a well-tolerated. In the test substance administration group thus defined as well-tolerated, a ratio of the tumor volume of the test substance-dosing group to the tumor volume of the control group obtained on the last day (TIC) (%) was calculated, and shown in Table 21.

<Data of Evaluation of Antitumor Effect in SNU-16 Subcutaneous Xenograft Model in Mice>

TABLE 21

| Example No. | Dose (mg/kg) | T/C (%) |
|---|---|---|
| Example 2 | 6.25 | 51 |
|  | 12.5 | 28 |
|  | 25 | 18 |
| Example 3 | 6.25 | 45 |
|  | 12.5 | 27 |
|  | 25 | 19 |
| Example 4 | 6.25 | 40 |
|  | 12.5 | 27 |
|  | 25 | 15 |
| Example 9 | 25 | 55 |
|  | 50 | 39 |
|  | 100 | 30 |
| Example 16 | 6.25 | 39 |
|  | 12.5 | 21 |
|  | 25 | 15 |
| Example 21 | 6.25 | 49 |
|  | 12.5 | 26 |
|  | 25 | 16 |
|  | 50 | 7 |
| Example 22 | 6.25 | 49 |
|  | 12.5 | 26 |
|  | 25 | 17 |
|  | 50 | 18 |
| Example 25 | 6.25 | 31 |
|  | 12.5 | 23 |
|  | 25 | 14 |
|  | 50 | 12 |
| Example 26 | 6.25 | 45 |
|  | 12.5 | 36 |
|  | 25 | 22 |
|  | 50 | 27 |

9. Antitumor Effect NCI-H1581 Subcutaneous Xenograft Model in Mice

Human lung cancer cell line NCI-H1581, which had been cultured in RPMI-1640 medium containing 10% FBS, and penicillin and streptomycin, were adjusted to a concentration of $1 \times 10^8$ cells/mL with Hanks' Balanced Salt Solution (GIBCO #24020) to prepare a cell suspension, and the suspension was mixed with MATRIGEL in a ratio of 1:1 to prepare a cell suspension in a concentration of $5 \times 10^7$ cells/mL. The cell suspension was inoculated in a volume of 100 μL into a subcutaneous part of a right flank of each of nude mice, 6 to 7 weeks of ages (BALB/cAJcl-nu/nu, female, Clea Japan Inc.). Ten to 11 days after the cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formula:

Tumor volume(mm³)=Longest diameter(mm)×Shortest diameter(mm)×Shortest diameter(mm)/2

On the basis of the volumes of tumors obtained on the first day of administration, the nude mice were grouped such that averages of the tumor volumes were substantially equal among the groups. Each test substance was dissolved in DMSO, Tween 80 was added thereto to prepare a solution in a 10-fold concentration and the thus prepared solution was stored at the freezer before use. Immediately before the administration, the stock solution was diluted with a 5% glucose solution to obtain a final administration solution (in which a ratio in % among DMSO, Tween 80 and the 5% glucose solution was 3.5:6.5:90). Each evaluation sample was orally administered to test substance administration group at a volume of 0.4 mL per 20 g of body weight once a day continuously for 11 days, and in a control group, an administration solvent was orally administered under the same conditions. Incidentally, the experiment was conducted on groups each consisting of 5 mice.

With respect to each of the control group and test substance administration group, a ratio of the weight measured on the final day to the weight measured on the first day (relative body weight: RBW) was calculated. If a ratio of the RBW of the test substance administration group/the RBW of the control group is 0.9 or more, the corresponding test substance administration group was defined as a well-tolerated. In the test substance administration group thus defined as well-tolerated, a ratio of the tumor volume of the test substance-dosing group to the tumor volume of the control group obtained on the last day (TIC) (%) was calculated, and shown in Table 22.

<Data of Evaluation of Antitumor Effect in NCI-H1581 Subcutaneous Xenograft Model in Mice>

TABLE 22

| Example No. | Dose (mg/kg) | T/C (%) |
|---|---|---|
| Example 2 | 6.25 | 36 |
|  | 12.5 | 19 |
|  | 25 | 11 |
| Example 16 | 6.25 | 50 |
|  | 12.5 | 25 |
|  | 25 | 15 |
| Example 21 | 6.25 | 36 |
|  | 12.5 | 18 |
|  | 25 | 10 |
|  | 50 | 6 |
| Example 22 | 6.25 | 46 |
|  | 12.5 | 21 |
|  | 25 | 13 |
|  | 50 | 8 |

10. AN3CA Growth Inhibition Assay

In this assay, the growth inhibitory activity of a test substance in a human endometrial cancer cell line expressing N549K mutant-type FGFR2 is measured, It has been reported that a human endometrial cancer cell line of AN3CA (ATCC Number HIB-111) expresses N549K mutant-type FGFR2 (Prot Natl Acad Sci USA. 2008.105: 8713-8717). AN3CA cells were maintained in RPM-1640 (Wako Pure Chemical Industries, Ltd., 187-02021) medium containing 10% FBS, and penicillin and streptomycin (Wako Pure Chemical Industries, Ltd., 168-23191) in a 5% $CO_2$ incubator (37° C.). To each well of a 96 well plate (Becton, Dickinson and Company, 35-3075), 150 µL of an AN3CA cell suspension adjusted to a concentration of $1.3 \times 10^4$ cells/mL with RPM-1640 medium containing 10% FBS, and penicillin and streptomycin was added, and the cell was incubated overnight in a 5% $CO_2$ incubator (37° C.). On the next day, 50 µl of a test substance diluted with an RPM-1640 medium containing 10% FBS, and penicillin and streptomycin was added to each well, and the resultant was cultured for 3 days in a 5% $CO_2$ incubator (37° C.). Then, 10 µL of Cell Counting Kit-8 (Dojindo Laboratories, CK04) was added to each well, and the resultant was incubated for 1 to 2 hours in a 5% $CO_2$ incubator (37° C.) to cause a color reaction. The absorbance value was measured with ENVISION™ (PerkinElmer Co., Ltd.) at 450 nm. The absorbance values of the wells containing cells without adding the test substance was defined as 100% and the absorbance values of the wells containing no cells was defined as 0%. Then, an absorbance ratio in the presence of the test substance was calculated. The concentration of each test substance necessary for inhibiting the cell growth by 50% (i.e., an $IC_{50}$ value) was calculated, and shown in Table 23.

<Data of Evaluation of AN3CA Growth Inhibitory Activity>

TABLE 23

| Example No. | AN3CA ($IC_{50}$ (nM)) |
|---|---|
| Example 2 | 25.1 |
| Example 21 | 24.6 |
| Example 22 | 11.0 |

11. MFE296 Growth Inhibition Assay

In this assay, the growth inhibitory activity of a test substance in a human endometrial cancer cell line expressing N549K mutant-type FGFR2 is measured.

It has been reported that a human endometrial cancer cell line of MFE296 (DSMZ Number ACC-419) expresses N549K mutant-type FGFR2 (Proc Natl Acad Sci USA. 2008.105:8713-8717). MFE296 cells were maintained in RPM-1640 (Wako Pure Chemical Industries, Ltd., 187.-02021) medium containing 10% FBS, and penicillin and streptomycin (Wako Pure Chemical Industries, Ltd., 168-23191) in a 5% $CO_2$ incubator (37° C.). To each well of a 96 well plate (Becton, Dickinson and Company, 35-3075), 150 µL of a MFE296 cell suspension adjusted to a concentration of $1.3 \times 10^4$ cells/mL with RPMI-1640 medium containing 10% FBS, and penicillin and streptomycin was added, and the cell was incubated overnight in a 5% $CO_2$ incubator (37° C.). On the next day, 50 µl of a test substance diluted with an RPMI-1640 medium containing 10% FBS, and penicillin and streptomycin was added to each well, and the resultant was cultured for 3 days in a 5% $CO_2$ incubator (37° C.). Then, 10 µL of Cell Counting Kit-8 (Dojindo Laboratories, CK04) was added to each well, and the resultant was incubated for 1 to 2 hours in a 5% $CO_2$ incubator (37° C.) to cause a color reaction. The absorbance value was measured with ENVISION™ (PerkinElmer Co., Ltd.) at 450 nm. The absorbance values of the wells containing cells without adding the test substance was defined as 100% and the absorbance values of the wells containing no cells was defined as 0%. Then, an absorbance ratio in the presence of the test substance was calculated. The concentration of each test substance necessary for inhibiting the cell growth by 50% (i.e., an $IC_{50}$ value) was calculated, and shown in Table 24.

Data of Evaluation of MFE296 Growth Inhibitory Activity>

TABLE 24

| Example No. | MFE296 ($IC_{50}$ (nM)) |
|---|---|
| Example 2 | 10.4 |
| Example 21 | 8.8 |
| Example 22 | 12.2 |

12. MFE280 Growth Inhibition Assay

In this assay, the growth inhibitory activity of a test substance in a human endometrial cancer cell line expressing 5252 mutant-type FGFR2 is measured.

It has been reported that a human endometrial cancer cell line of MFE280 (DSMZ Number ACC-410) expresses S252 mutant-type FGFR2 (Prot Natl Acad Sci USA. 2008.105: 8713-8717). MFE280 cells were maintained in RPMI-1640 (Wako Pure Chemical Industries, Ltd., 187-02021) medium containing 10% FBS, and penicillin and streptomycin (Wako Pure Chemical Industries, Ltd., 168-23191) in a 5% $CO_2$ incubator (37° C.). To each well of a 96 well plate (Becton, Dickinson and Company, 35-3075), 150 µL of a MFE280 cell suspension adjusted to a concentration of $1.3 \times 10^4$ cells/mL with RPMI-1640 medium containing 10% FBS, and penicillin and streptomycin was added, and the cell was incubated overnight in a 5% $CO_2$ incubator (37° C.). On the next day, 50 µl of a test substance diluted with an RPMI-1640 medium containing 10% FBS, and penicillin and streptomycin was added to each well, and the resultant was cultured for 3 days in a 5% $CO_2$ incubator (37° C.). Then, 10 µL of Cell Counting Kit-8 (Dojindo Laboratories, CK04) was added to each well, and the resultant was incubated for 1 to 2 hours in a 5% $CO_2$ incubator (37° C.) to cause a color reaction. The absorbance value was measured with ENVISION™ (PerkinElmer Co., Ltd.) at 450 nm. The absorbance values of the wells containing cells without adding the test substance was defined as 100% and the absorbance values of the wells containing no cells was defined as 0%. Then, an absorbance ratio in the presence of the test substance was calculated. The concentration of each test substance necessary for inhibiting the cell growth by 50% (i.e., an $IC_{50}$ value) was calculated, and shown in Table 25.

<Data of Evaluation of MFE280 Growth Inhibitory Activity>

TABLE 25

| Example No. | MFE280 ($IC_{50}$ (nM)) |
|---|---|
| Example 2 | 44.1 |
| Example 21 | 27.6 |
| Example 22 | 17.1 |

13. Antitumor Effect in AN3CA Subcutaneous Xenograft Model in Mice

Human endometrial cancer cell line AN3CA (ATCC Number HTB-111), which had been cultured in an RPM-1640 medium containing 10% FBS, and penicillin and streptomycin, were adjusted to a concentration of $1 \times 10^8$ cells/mL with Hanks' Balanced Salt Solution (GIBCO #24020) to prepare a cell suspension, and the suspension was mixed with MATRIGEL (BD Biosciences, Cat#354234) in a ratio of 1:1 to prepare a cell suspension in a concentration of $5 \times 10^7$ cells/ml. The cell suspension was inoculated in a volume of 100 into a subcutaneous part of a right flank of nude mice, 7 weeks of age (BALB/cAJcl-nu/nu, female, Clea Japan Inc.). Eleven days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formula:

Tumor volume(mm³)=Longest diameter(mm)×Shortest diameter(mm)×Shortest diameter(mm)/2

On the basis of the volumes of tumors obtained on the first day of administration, the nude mice were grouped such that averages of the tumor volumes were substantially equal among the groups. Each test substance was dissolved in DMSO, Tween 80 was added thereto to prepare a solution in a 10-fold concentration and the thus prepared solution was stored at the freezer before use. Immediately before the administration, the stock solution was diluted with a 5% glucose solution to obtain a final administration solution (in which a ratio in % among DMSO, Tween 80 and the 5% glucose solution was 3.5:6.5:90). Each evaluation sample was orally administered to test substance administration group at a volume of 0.4 mL per 20 g of body weight once a day continuously for 14 days, and in a control group, an administration solvent was orally administered under the same conditions. Incidentally, the experiment was conducted on groups each consisting of 5 mice.

With respect to each of the control group and test substance administration group, a ratio of the weight measured on the final day to the weight measured on the first day (relative body weight: RBW) was calculated. If a ratio of the RBW of the test substance administration group/the RBW of the control group is 0.9 or more, the corresponding test substance administration group was defined as a well-tolerated. In the test substance administration group thus defined as well-tolerated, a ratio of the tumor volume of the test substance-dosing group to the tumor volume of the control group obtained on the last day (T/C) (%) was calculated, and shown in Table 26.

<Data of Evaluation of Antitumor Effect in AN3CA Subcutaneous Xenograft Model in Mice>

TABLE 26

| Example No. | Dose (mg/kg) | T/C (%) |
|---|---|---|
| Example 22 | 6.25 | 29 |
| | 12.5 | 11 |
| | 25 | 4 |
| | 50 | 2 |

14. Antitumor Effect in MFE296 Subcutaneous Xenograft Model in Mice

Human endometrial cancer cell line MFE296 (DSMZ Number ACC-419), which had been cultured in an RPMI-1640 medium containing 10% FBS, and penicillin and streptomycin, were adjusted to a concentration of 1×10⁸ cells/mL with Hanks' Balanced Salt Solution (GIBCO #24020) to prepare a cell suspension, and the suspension was mixed with MATRIGEL (BD Biosciences, Cat#354234) in a ratio of 1:1 to prepare a cell suspension in a concentration of 5×10⁷ cells/ml. The suspension was inoculated in a volume of 100 μL into a subcutaneous part of a right flank of nude mice, 7 weeks of age (BALB/cAJcl-nu/nu, female, Clea Japan Inc.). Twelve days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formula:

Tumor volume(mm³)=Longest diameter(mm)×Shortest diameter(mm)×Shortest diameter(mm)/2

On the basis of the volumes of tumors obtained on the first day of administration, the nude mice were grouped such that averages of the tumor volumes were substantially equal among the groups. Each test substance was dissolved in DMSO, Tween 80 was added thereto to prepare a solution in a 10-fold concentration and the thus prepared solution was stored at the freezer before use. Immediately before the administration, the stock solution was diluted with a 5% glucose solution to obtain a final administration solution (in which a ratio in % among DMSO, Tween 80 and the 5% glucose solution was 3.5:6.5:90). Each evaluation sample was orally administered to test substance administration group at a volume of 0.4 mL per 20 g of body weight once a day continuously for 14 days, and in a control group, an administration solvent was orally administered under the same conditions. Incidentally, the experiment was conducted on groups each consisting of 5 mice.

With respect to each of the control group and test substance administration group, a ratio of the weight measured on the final day to the weight measured on the first day (relative body weight: RBW) was calculated. If a ratio of the RBW of the test substance administration group/the RBW of the control group is 0.9 or more, the corresponding test substance administration group was defined as a well-tolerated. In the test substance administration group thus defined as well-tolerated, a ratio of the tumor volume of the test substance-dosing group to the tumor volume of the control group obtained on the last day (T/C) (%) was calculated, and shown in Table 27.

<Data of Evaluation of Antitumor Effect in MFE296 Subcutaneous Xenograft Model in Mice>

TABLE 27

| Example No. | Dose (mg/kg) | T/C (%) |
|---|---|---|
| Example 22 | 6.25 | 91 |
| | 12.5 | 85 |
| | 25 | 60 |
| | 50 | 54 |

15. Antitumor Effect in MFE280 Subcutaneous Xenograft Model in Mice

Human endometrial cancer cell line MFE280 (DSMZ Number ACC-410), which had been cultured in an RPMI-1640 medium containing 10% FBS, and penicillin and streptomycin, were adjusted to a concentration of 4.7×10⁷ cells/mL with Hanks' Balanced Salt Solution (GIBCO 1124020) to prepare a cell suspension, and the suspension was mixed with MATRIGEL (BD Biosciences, Cat#354234) in a ratio of 1:1 to prepare a cell suspension in a concentration of 2.4×10⁷ cells/ml. The cell suspension was inoculated in a volume of 100 μL into a subcutaneous part of a right flank of nude mice, 7 weeks of age (BALB/cAJcl-nu/nu, female, Clea Japan Inc.). Thirty five days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formula:

Tumor volume(mm³)=Longest diameter(mm)×Shortest diameter(mm)×Shortest diameter(mm)/2

On the basis of the volumes of tumors obtained on the fast day of administration, the nude mice were grouped such that averages of the tumor volumes were substantially equal among the groups. Each test substance was dissolved in DMSO, Tween 80 was added thereto to prepare a solution in a 10-fold concentration and the thus prepared solution was stored at the freezer before use. Immediately before the administration, the stock solution was diluted with a 5% glucose solution to obtain a final administration solution (in which a ratio in % among DMSO, Tween 80 and the 5% glucose solution was 3.5:6.5:90). Each evaluation sample was orally administered to test substance administration group at a volume of 0.4 mL per 20 g of body weight once a day continuously for 14 days, and in a control group, an administration solvent was orally administered under the same conditions. Incidentally, the experiment was conducted on groups each consisting of 5 mice.

With respect to each of the control group and test substance administration group, a ratio of the weight measured on the final day to the weight measured on the first day (relative body weight: RBW) was calculated. If a ratio of the RBW of the test substance administration group/the RBW of the control group is 0.9 or more, the corresponding test substance administration group was defined as a well-tolerated. In the test substance administration group thus defined as well-tolerated, a ratio of the tumor volume of the test substance-dosing group to the tumor volume of the control group obtained on the last day (TIC) (%) was calculated, and shown in Table 28.

<Data of Evaluation of Antitumor Effect in MFE280 Subcutaneous Xenograft Model in Mice>

TABLE 28

| Example No. | Dose (mg/kg) | T/C (%) |
| --- | --- | --- |
| Example 22 | 6.25 | 72 |
| | 12.5 | 57 |
| | 25 | 31 |
| | 50 | 11 |

16. RT112/84 Growth Inhibition Assay

In this assay, the growth inhibitory activity of a test substance in a human bladder cancer cell line expressing FGFR3-TACC3 fusion protein is measured. RT112/84 cells (ECACC Number EC85061106-F0) were maintained in RPMI-1640 (Wako Pure Chemical Industries, Ltd., 187-02021) medium containing 10% PBS, and penicillin and streptomycin (Wako Pure Chemical Industries, Ltd., 168-23191) in a 5% $CO_2$ incubator (37° C.). To each well of a 96 well plate (Becton, Dickinson and Company, 35-3075), 150 μL of a RE112/84 cell suspension adjusted to a concentration of $1.3 \times 10^4$ cells/mL with RPM-1640 medium containing 10% FBS, and penicillin and streptomycin was added, and the cell was incubated overnight in a 5% $CO_2$ incubator (37° C.). On the next day, 50 μl of a test substance diluted with an RPM-1640 medium containing 10% FBS, and penicillin and streptomycin was added to each well, and the resultant was cultured for 3 days in a 5% $CO_2$ incubator (37° C.). Then, 10 μl, of Cell Counting Kit-8 (Dojindo Laboratories, CK04) was added to each well, and the resultant was incubated for 1 to 2 hours in a 5% $CO_2$ incubator (37° C.) to cause a color reaction. The absorbance value was measured with ENVISION™ (PerkinElmer Co., Ltd.) at 450 nm. The absorbance values of the wells containing cells without adding the test substance was defined as 100% and the absorbance values of the wells containing no cells was defined as 0%. Then, an absorbance ratio in the presence of the test substance was calculated. The concentration of each test substance necessary for inhibiting the cell growth by 50% (i.e., an $IC_{50}$ value) was calculated, and shown in Table 29.

<Data of Evaluation of RT112/84 Growth Inhibitory Activity>

TABLE 29

| Example No. | RT112/84 ($IC_{50}$ (nM)) |
| --- | --- |
| Example 2 | 42.3 |
| Example 21 | 19.4 |
| Example 22 | 19.0 |

17. SW780 Growth Inhibition Assay

In this assay, the growth inhibitory activity of a test substance in a human bladder cancer cell line expressing FGFR3-BAIAP2L1 fusion protein is measured.

It has been repotted that a human bladder cancer cell line of SW780 (ATCC Number CRL-2169) expresses FGFR3-BAIAP2L1 fusion protein (Hum Mol Genet, 2013.22:795-803). SW780 cells (ECACC Number EC85061106-F0) were maintained in RPMI-1640 (Wako Pure Chemical Industries, Ltd., 187-02021) medium containing 10% FBS, and penicillin and streptomycin (Wako Pure Chemical Industries, Ltd., 168-23191) in a 5% $CO_2$ incubator (37° C.). To each well of a 96 well plate (Becton, Dickinson and Company, 35-3075), 150 μL of a SW780 cell suspension adjusted to a concentration of $2.6 \times 10^4$ cells/mL with RPMI-1640 medium containing 1% FBS, and penicillin and streptomycin was added, and the cell was incubated overnight in a 5% $CO_2$ incubator (37° C.). On the next day, 50 μl of a test substance diluted with an RPM-1640 medium containing 1% FBS, and penicillin and streptomycin was added to each well, and the resultant was cultured for 3 days in a 5% $CO_2$ incubator (37° C.). Then, 10 μL of Cell Counting Kit-8 (Dojindo Laboratories, CK04) was added to each well, and the resultant was incubated for 1 to 2 hours in a 5% $CO_2$ incubator (37° C.) to cause a color reaction. The absorbance value was measured with ENVISION (1 M) (PerkinElmer Co., Ltd.) at 450 nm. The absorbance values of the wells containing cells without adding the test substance was defined as 100% and the absorbance values of the wells containing no cells was defined as 0%. Then, an absorbance ratio in the presence of the test substance was calculated. The concentration of each test substance necessary for inhibiting the cell growth by 50% (i.e., an $IC_{50}$ value) was calculated, and shown in Table 30.

<Data of Evaluation of SW780 Growth Inhibitory Activity>

TABLE 30

| Example No. | SW780 ($IC_{50}$ (nM)) |
| --- | --- |
| Example 22 | 20.3 |

18. RT4 Growth Inhibition Assay

In this assay, the growth inhibitory activity of a test substance in a human bladder cancer cell line expressing FGFR3-TACC3 fusion protein is measured.

It has been reported that a human bladder cancer cell line of RT4 (ATCC Number HTB-2) expresses FGFR3-TACC3 fusion protein (Hum Mol. Genet.2013.22:795-803). RT4 cells were maintained in RPMI-1640 (Wako Pure Chemical Industries, Ltd., 187-02021) medium containing 10% FBS, and penicillin and streptomycin (Wako Pure Chemical Industries, Ltd., 168-23191) in a 5% $CO_2$ incubator (37° C.). To each well of a 96 well plate (Becton, Dickinson and Company, 35-3075), 150 μL of a RT4 cell suspension adjusted to a concentration of 2.6×10⁴ cells/mL with RPMI-1640 medium containing 10% FBS, and penicillin and streptomycin was added, and the cell was incubated overnight in a 5% $CO_2$ incubator (37° C.). On the next day, 50 μl of a test substance diluted with an RPM-1640 medium containing 10% PBS, and penicillin and streptomycin was added to each well, and the resultant was cultured for 3 days in a 5% $CO_2$ incubator (37° C.). Then, 10 μL of Cell Counting Kit-8 (Dojindo Laboratories, CK04) was added to each well, and the resultant was incubated for 1 to 2 hours in a 5% $CO_2$ incubator (37° C.) to cause a color reaction. The absorbance value was measured with ENVISION™ (PerkinElmer Co., Ltd.) at 450 nm. The absorbance values of the wells containing cells without adding the test substance was defined as 100% and the absorbance values of the wells containing no cells was defined as 0%. Then, an absorbance ratio in the presence of the test substance was calculated. The concentration of each test substance necessary for inhibiting the cell growth by 50% (i.e., an $IC_{50}$ value) was calculated, and shown in Table 31.

<Data of Evaluation of RT4 Growth Inhibitory Activity>

TABLE 31

| Example No. | RT4 ($IC_{50}$ (nM)) |
|---|---|
| Example 22 | 16.4 |

19. Antitumor Effect in RT112/84 Subcutaneous Xenograft Model in Mice

Human endometrial cancer cell line RT112/84 (ECACC Number EC85061106-F0), which had been cultured in an RPMI-1640 medium containing 10% PBS, and penicillin and streptomycin, were adjusted to a concentration of 1×10⁸ cells/mL with Hanks' Balanced Salt Solution (GIBCO 1424020) to prepare a cell suspension, and the suspension was mixed with MATRIGEL (BD Biosciences, Cat/354234) in a ratio of 1:1 to prepare a cell suspension in a concentration of 5×10⁷ cells/ml. The cell suspension was inoculated in a volume of 100 μL into a subcutaneous part of a right flank of nude mice, 7 weeks of age (BALB/cAJcl-nu/nu, female, Clea Japan Inc.). Ten days after cell inoculation, the shortest diameter and the longest diameter of a tumor in each mouse were measured by using an electronic digital caliper (Digimatic™ caliper, Mitutoyo Corporation), so as to calculate the volume of the tumor in accordance with the following calculation formula:

Tumor volume(mm³)=Longest diameter(mm)×Shortest diameter(mm)×Shortest diameter(mm)/2

On the basis of the volumes of tumors obtained on the first day of administration, the nude mice were grouped such that averages of the tumor volumes were substantially equal among the groups. Each test substance was dissolved in DMSO, Tween 80 was added thereto to prepare a solution in a 10-fold concentration and the thus prepared solution was stored at the freezer before use. Immediately before the administration, the stock solution was diluted with a 5% glucose solution to obtain a final administration solution (in which a ratio in % among DMSO, Tween 80 and the 5% glucose solution was 3.5:65:90). Each evaluation sample was orally administered to test substance administration group at a volume of 0.4 mL per 20 g of body weight once a day continuously for 14 days, and in a control group, an administration solvent was orally administered under the same conditions. Incidentally, the experiment was conducted on groups each consisting of 5 mice.

With respect to each of the control group and test substance administration group, a ratio of the weight measured on the final day to the weight measured on the first day (relative body weight: RBW) was calculated. If a ratio of the RBW of the test substance administration group/the RBW of the control group is 0.9 or more, the corresponding test substance administration group was defined as a well-tolerated. In the test substance administration group thus defined as well-tolerated, a ratio of the tumor volume of the test substance-dosing group to the tumor volume of the control group obtained on the last day (TIC) (%) was calculated, and shown in Table 32.

<Data of Evaluation of Antitumor Effect in RT112/84 Subcutaneous Xenograft Model in Mice>

TABLE 32

| Example No. | Dose (mg/kg) | T/C (%) |
|---|---|---|
| Example 22 | 25 | 62 |
|  | 50 | 33 |

What is claimed is:

1. A compound represented by the following formula (I) or a pharmaceutically acceptable salt thereof:

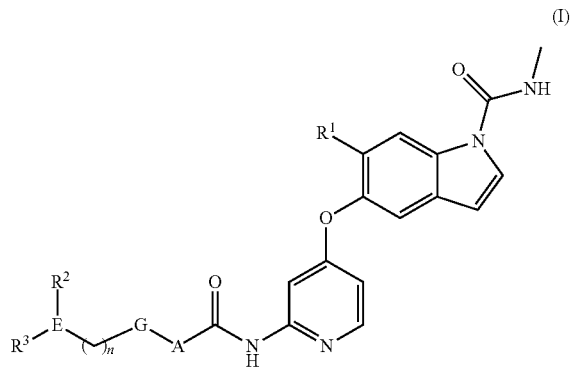

(I)

wherein
n represents 0;
A represents a $C_{6-10}$ arylene group;
G represents a single bond;
E represents a $C_{3-5}$ nitrogen-containing non-aromatic heterocycle;
R¹ represents a $C_{1-6}$ alkoxy group optionally substituted by 1 to 3 halogen atoms, or a $C_{1-6}$ alkoxy $C_{1-6}$ alkoxy group optionally substituted by 1 to 3 halogen atoms;
R² represents a hydrogen atom, a halogen atom, a hydroxyl group, a $C_{1-6}$ alkyl group optionally substituted by 1 to 3 halogen atoms, a hydroxy $C_{1-6}$ alkyl group optionally substituted by 1 to 3 halogen atoms, or a $C_{3-5}$ nitrogen-containing non-aromatic heterocyclic group; and
R³ represents a hydrogen atom, a $C_{1-6}$ alkyl group optionally substituted by 1 to 3 halogen atoms, or a $C_{1-6}$ alkoxy group optionally substituted by 1 to 3 halogen atoms, with the proviso that when E represents an azetidine ring and R² or R³ is present on a nitrogen atom on the azetidine ring, the R² or R³ does not represent a hydrogen atom.

2. The compound or the pharmaceutically acceptable salt thereof according to claim 1, wherein
A represents a phenylene group; and
E represents an azetidine ring, a pyrrolidine ring, a piperidine ring or a piperazine ring.

3. The compound or the pharmaceutically acceptable salt thereof according to claim 1, wherein
A represents a phenylene group; and
E represents an azetidine ring or a piperidine ring.

4. The compound or the pharmaceutically acceptable salt thereof according to claim 1, wherein
A represents a phenylene group; and
E represents a piperidine ring.

5. The compound or the pharmaceutically acceptable salt thereof according to claim 1, wherein
$R^1$ represents a $C_{1-6}$ alkoxy group or a $C_{1-6}$ alkoxy $C_{1-6}$ alkoxy group;
$R^2$ represents a hydrogen atom, a hydroxyl group, a $C_{1-6}$ alkyl group or a hydroxy $C_{1-6}$ alkyl group; and
$R^3$ represents a hydrogen atom.

6. The compound or the pharmaceutically acceptable salt thereof according to claim 1, wherein $R^1$ represents a $C_{1-6}$ alkoxy $C_{1-6}$ alkoxy group.

7. The compound or the pharmaceutically acceptable salt thereof according to claim 1, represented by the following formula (II):

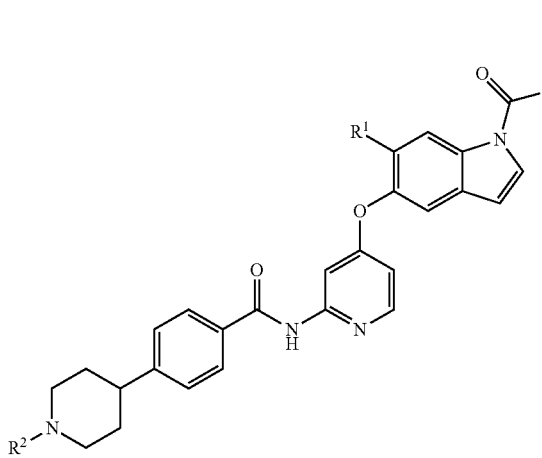

(II)

wherein
$R^1$ represents a $C_{1-6}$ alkoxy $C_{1-6}$ alkoxy group; and
$R^2$ represents a hydrogen atom, a $C_{1-6}$ alkyl group or a hydroxy $C_{2-6}$ alkyl group.

8. The compound or the pharmaceutically acceptable salt thereof according to claim 1, represented by the following formula (III):

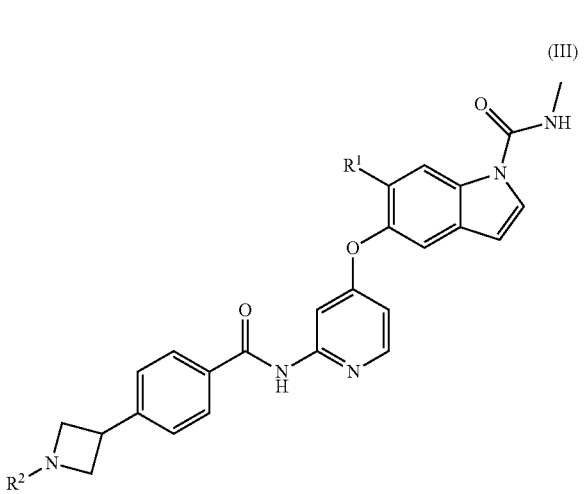

(III)

wherein
$R^1$ represents a $C_{1-6}$ alkoxy $C_{1-6}$ alkoxy group; and
$R^2$ represents a $C_{1-6}$ alkyl group or a hydroxy $C_{2-6}$ alkyl group.

9. 5-((2-(4-(1-Ethylpiperidin-4-yl)benzamide)pyridin-4-yl)oxy)-6-methoxy-N-methyl-1H-indole-1-carboxamide represented by the following structural formula, or a pharmaceutically acceptable salt thereof:

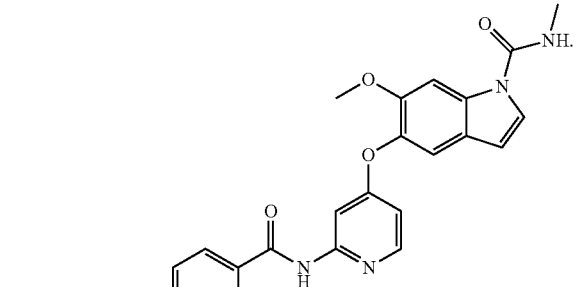

10. 6-(2-Methoxyethoxy)-N-methyl-5-(2-(4-(1-methylpiperidin-4-yl)benzamide)pyridin-4-yl)oxy)-1H-indole-1-carboxamide represented by the following structural formula, or a pharmaceutically acceptable salt thereof:

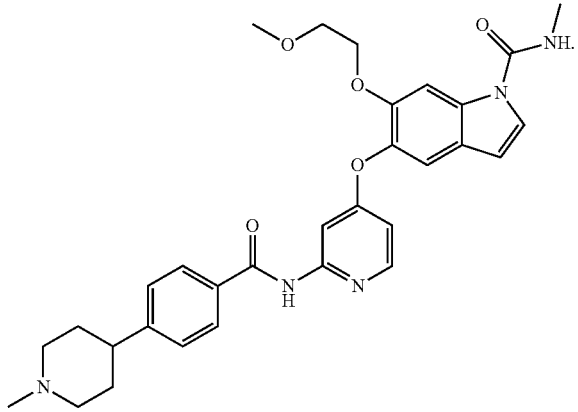

11. 5-((2-(4-(1-(2-Hydroxyethyl)piperidin-4-yl)benzamide)pyridin-4-yl)oxy)-6-(2-methoxyethoxy)-N-methyl-1H-indole-1-carboxamide represented by the following structural formula, or a pharmaceutically acceptable salt thereof:

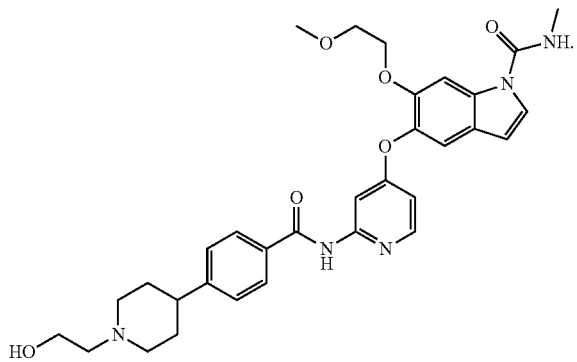 [SMILES: CNC(=O)n1ccc2cc(Oc3ccnc(NC(=O)c4ccc(C5CCN(CCO)CC5)cc4)c3)c(OCCOC)cc21]

12. The compound or the pharmaceutically acceptable salt thereof according to claim 1, wherein the compound is 6-(2-Ethoxyethoxy)-5-((2-(4-(1-(2-hydroxyethyl)piperidin-4-yl)benzamide)pyridin-4-yl)oxy)-N-methyl-1H-indole-1-carboxamide represented by the following structural formula:

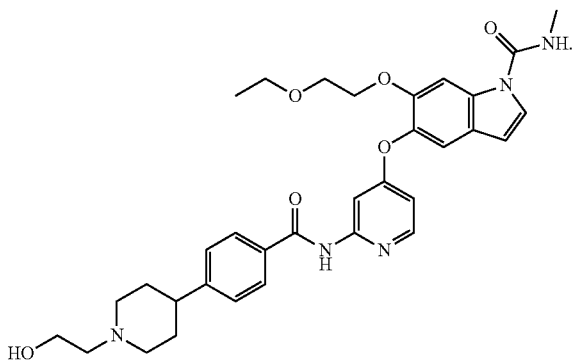 [SMILES: CCOCCOc1cc2c(ccn2C(=O)NC)cc1Oc1ccnc(NC(=O)c2ccc(C3CCN(CCO)CC3)cc2)c1]

13. The compound or the pharmaceutically acceptable salt thereof according to claim 1, wherein the compound is 6-(2-Ethoxyethoxy)-5-((2-(4-(1-ethylazetidin-3-yl)benzamide)pyridin-4-yl)oxy)-N-methyl-1H-indole-1-carboxamide represented by the following structural formula:

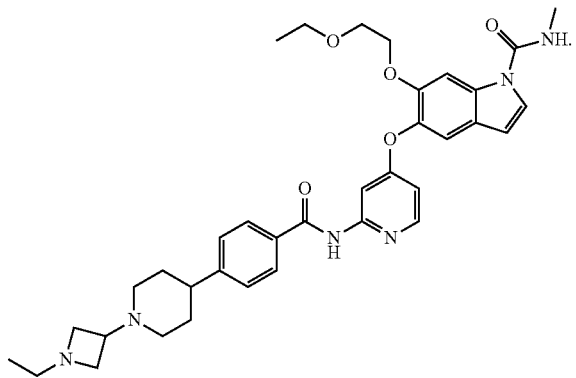 [SMILES: CCOCCOc1cc2c(ccn2C(=O)NC)cc1Oc1ccnc(NC(=O)c2ccc(C3CCN(C4CN(CC)C4)CC3)cc2)c1]

14. A pharmaceutical composition comprising a compound or the pharmaceutically acceptable salt thereof according to claim 1.

15. A pharmaceutical composition comprising the compound or the pharmaceutically acceptable salt thereof according to claim 9.

16. A pharmaceutical composition comprising the compound or the pharmaceutically acceptable salt thereof according to claim 10.

17. A pharmaceutical composition comprising the compound or the pharmaceutically acceptable salt thereof according to claim 11.

18. A pharmaceutical composition comprising the compound or the pharmaceutically acceptable salt thereof according to claim 12.

19. A pharmaceutical composition comprising the compound or the pharmaceutically acceptable salt thereof according to claim 13.

20. A method for treating or non-small-cell lung carcinoma in a subject in need thereof comprising administrating to the subject a pharmacologically effective dose of the compound or the pharmaceutically acceptable salt thereof according to claim 1.

21. A method for treating or non-small-cell lung carcinoma in a subject in need thereof comprising administrating to the subject a pharmacologically effective dose of the compound or the pharmaceutically acceptable salt thereof according to claim 9.

22. A method for treating or non-small-cell lung carcinoma in a subject in need thereof comprising administrating to the subject a pharmacologically effective dose of the compound or the pharmaceutically acceptable salt thereof according to claim 10.

23. A method for treating or non-small-cell lung carcinoma in a subject in need thereof comprising administrating to the subject a pharmacologically effective dose of the compound or the pharmaceutically acceptable salt thereof according to claim 11.

24. A method for treating non-small-cell lung carcinoma in a subject in need thereof comprising administrating to the subject a pharmacologically effective dose of the compound or the pharmaceutically acceptable salt thereof according to claim 12.

25. A method for treating non-small-cell lung carcinoma in a subject in need thereof comprising administrating to the subject a pharmacologically effective dose of the compound or the pharmaceutically acceptable salt thereof according to claim 13.

* * * * *

UNITED STATES PATENT AND TRADEMARK OFFICE
CERTIFICATE OF CORRECTION

PATENT NO. : 8,933,099 B2  
APPLICATION NO. : 14/183864  
DATED : January 13, 2015  
INVENTOR(S) : Setsuo Funasaka et al.

Page 1 of 2

It is certified that error appears in the above-identified patent and that said Letters Patent is hereby corrected as shown below:

In the Claims

Column 218, claim 10  
Line 26, delete "5-(2" and replace it with --5-((2--.

Column 219, claim 13

Lines 29-41, delete " 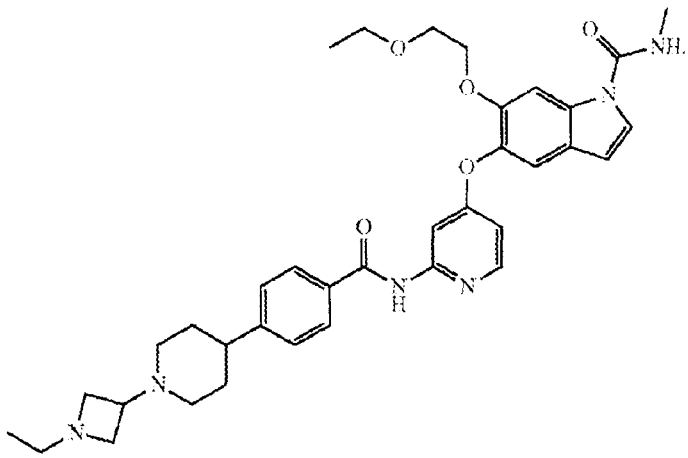 " and

Signed and Sealed this  
Eleventh Day of August, 2015

Michelle K. Lee  
*Director of the United States Patent and Trademark Office*

CERTIFICATE OF CORRECTION (continued)
U.S. Pat. No. 8,933,099 B2 replace it with

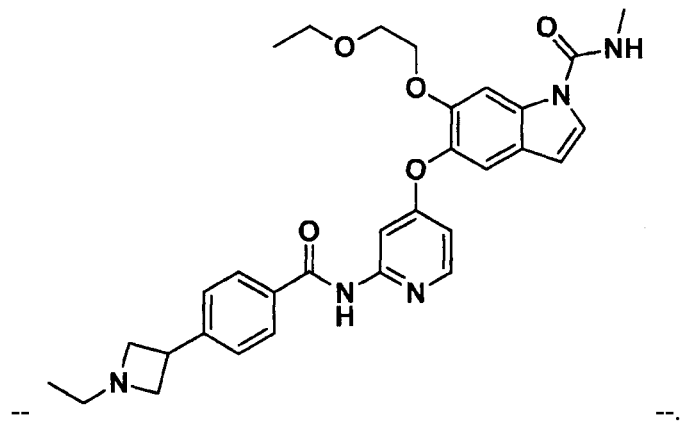

-- --.

Column 220, claim 20
Line 17, after "treating" delete "or".

Column 220, claim 21
Line 22, after "treating" delete "or".

Column 220, claim 22
Line 27, after "treating" delete "or".

Column 220, claim 23
Line 32, after "treating" delete "or".